US011633390B2

(12) United States Patent
Kristensen et al.

(10) Patent No.: US 11,633,390 B2
(45) Date of Patent: *Apr. 25, 2023

(54) 5-HT2A AGONISTS FOR USE IN TREATMENT OF DEPRESSION

(71) Applicant: Lophora ApS, Copenhagen (DK)

(72) Inventors: Jesper Langgaard Kristensen, Copenhagen (DK); Anders Asbjørn Jensen, Copenhagen (DK); Emil Märcher-Rørsted, Copenhagen (DK); Sebastian Leth-Petersen, Copenhagen (DK)

(73) Assignee: LOPHORA APS, Charlottenlund (DK)

( * ) Notice: Subject to any disclaimer, the term of this patent is extended or adjusted under 35 U.S.C. 154(b) by 2 days.

This patent is subject to a terminal disclaimer.

(21) Appl. No.: 17/349,255

(22) Filed: Jun. 16, 2021

(65) Prior Publication Data

US 2022/0062257 A1    Mar. 3, 2022

Related U.S. Application Data

(62) Division of application No. 17/090,457, filed on Nov. 5, 2020, now Pat. No. 11,246,860.

(30) Foreign Application Priority Data

Nov. 7, 2019 (EP) ..................................... 19207578

(51) Int. Cl.
| | | |
|---|---|---|
| *A61K 31/452* | (2006.01) | |
| *A61P 25/24* | (2006.01) | |
| *A61K 31/397* | (2006.01) | |
| *A61K 31/40* | (2006.01) | |
| *A61K 31/451* | (2006.01) | |
| *C07D 205/04* | (2006.01) | |
| *C07D 207/08* | (2006.01) | |
| *C07D 211/22* | (2006.01) | |
| *C07D 211/34* | (2006.01) | |

(52) U.S. Cl.
CPC .......... *A61K 31/452* (2013.01); *A61K 31/397* (2013.01); *A61K 31/40* (2013.01); *A61K 31/451* (2013.01); *A61P 25/24* (2018.01); *C07D 205/04* (2013.01); *C07D 207/08* (2013.01); *C07D 211/22* (2013.01); *C07D 211/34* (2013.01)

(58) Field of Classification Search
CPC ............................ C07D 211/34; A61K 31/452
See application file for complete search history.

(56) References Cited

U.S. PATENT DOCUMENTS 11,246,860 B2 *  2/2022  Kristensen ............. A61K 31/40
2016/0185752 A1   6/2016  Bousba

OTHER PUBLICATIONS

Juncosa. Jr., Jose I., et al., "Extensive Rigid Analogue Design Maps the Binding Conformation of Potent N-Benzylphenethylamine 5-HT2A Serotonin Receptor Agonist Ligands," ACS Chem. Neurosci., 2013, 4, 96-109.
Hansen, M., et al., "Synthesis and Structure-Activity Relationships of N-Benzyl Phenethylamines as 5-HT2A/2C Agonists," ACS Chem. Neurosci., 2014, 5, 243-249.
Tupper, Ph.D., K.W., et al., "Psychedelic medicine: a re-emerging therapeutic program." CMAJ, Oct. 6, 2015, 187(14), 1054-1059.
Carhart-Harris, R.L., et al., "Psilocybin with psychological support for treatment-resistant depression: an open-label feasibility study," The Lancet/Psychiatry, Jul. 2016, vol. 3, issue 7, pp. 619-627.
Madsen, M.K., et al., "Psychedelic effects of psilocybin correlate with serotonin 2A receptor occupancy and plasma psilocin levels," Neuropsychopharmacol., Jan. 2019, 44, 1328-1334.
Leth-Petersen, S., et al., "Metabolic Fate of Hallucinogenic NBOMes," Chem. Res. Toxicol,. 2016, 29, 96-100.
Keary, M.D., C.J., et al., "Intoxications Associated With Agitation, Tachycardia, Hypertension, and Fever: Differential Diagnosis, Evaluation, and Management," Prim Care Companion CNS Disord. 2013; 15(3).
Halberstadt, A.L., et al., "Rote of the 5-HT2A receptor in the locomotor hyperactivity produced by phenylalkylamine hallucinogens in mice." Neuropharmacology, 2013, 70, 218-227.
Halberstadt, A.L., et al., "5-HT2A and 5-HT2C Receptors Exert Opposing Effects on Locomotor Activity in Mice," Neuropharmacology, 2009, 34, 1958-1967.
Overstreet, D.H., "The Flinders Sensitive Line Rat Model of Depression—25 Yeas and Still Producing." Pharmacol Rev., Jan. 2013, 65, 143-155.
Kitamura, Y., et al., "Influence of ACTH on the effects of imipramine, desipramine and lithium on duration of immobility of rats in the forced swim test," Pharmacol Biochem Behav., Jan.-Feb. 2002;71(1-2):63-9.
Jensen, A.A., et al., "Design, Synthesis, and Pharmacological Characterization of N- and O-Substituted 5,6,7,8-Tetrahydro-4H-isoxazolo[4,5-d]azepin-3-ol Analogues: Novel 5-HT2A/5-HT2C Receptor Agonists with Procognitive Properties," J. Med. Chem., 2013, 56, 1211-1227.
Roth, MD, PhD, B.L, "National Institute of Mental Health Psychoactive Drug Screening Program (NIMH PDSP), Assay Protocol Book, Version III." Dept. of Pharmacology, University of North Carolina at Chapel Hill, Mar. 2018.
Canal, C.E., et al., "Head-twitch response in rodents induced by the hallucinogen 2, 5-dimethoxy-4-iodamphetamine: a comprehensive history, a re-evaluation of mechanisms, and its utility as a model," Drug Test Anal., 2012, 4(0), 556-576.
Detke, M.J., et al., "Active behaviors in the rat forced swimming test differentially produced by serotonergic and noradrenergic antidepressants," Psychopharmacology, 1995, 121, 66-72.

(Continued)

*Primary Examiner* — Golam M Shameem
(74) *Attorney, Agent, or Firm* — Duane Morris, LLP; Gregory M. Lefkowitz; Brandon A. Chan

(57) ABSTRACT

The present invention relates to agonists of the 5-HT$_{2A}$ serotonin receptors and their medical uses. In one aspect the invention relates to 5-HT$_{2A}$ agonists of formula (I). In second aspect, the invention relates to selective 5-HT$_{2A}$ agonists of formula (II). In another aspect, the invention relates to mixed 5-HT$_{2A}$/5-HT$_{2C}$ agonists of formula (III). In yet another aspect, the invention relates to 5-HT$_{2A}$ agonists for use in the treatment of a depressive disorder, more particular a 5-HT$_{2A}$ agonist for the use in the treatment of treatment-resistant depression.

15 Claims, 7 Drawing Sheets

(56) References Cited

OTHER PUBLICATIONS

Pereira, V.S., et al., "Esketamine and rapastinel, but not imipramine, have antidepressant-like effect in a treatmentresistant animal model of depression," Acta Neuropsychiatrica, 31:258-265.
Sard. H., et al., "SAR of psilocybin analogs: Discovery of a selective 5-HT2C Agonist," J. Bioorg. Med. Chem. Lett., 2005, 15, 4555-4559.
Besnard, J., et al., "Automated design of ligands to polypharmacological profiles," Nature, Dec. 3, 2012, vol. 492, pp. 215-220.
Sheldrick, G.M., "SHELXT—Integrated space-group and crystal-structure determination." Acta Cryst., 2015, A71, 3-8.
Dolomanov, O.V., "OLEX2: a complete structure solution, refinement and analysis program," J. Appl. Cryst., 2009, 42, 339-341.
Suzuki, MD, J., et al., "Toxicities associated with NBOMe ingestion, a novel class of potent hallucinogens: A review of the literature," Psychosomatics., 2015, 56(2): 129-139.
Porter, R.H.P., et al., "Functional characterization of agonists at recombinant human 5-HT2A, 5-HT2B and 5-HT2C receptors in CHO-K1 cells," Br J Pharmacol., Sep. 1999 128(1):13-20.
Jademyr. S., "Synthesis of Conformationally Restrained Serotonin 2 Agonists, Probing for Functional Selectivity," Department of Chemistry and Molecular Biology, University of Gothenburg, Degree project for Master of Science with a major in Organic Chemistry, 60 hec, 2018:23 (Apr. 6, 2019).

\* cited by examiner

5-HT2A AGONISTS FOR USE IN TREATMENT OF DEPRESSION

CROSS REFERENCE TO RELATED APPLICATION

This application is a divisional of U.S. Utility patent application Ser. No. 17/090,457, filed on Nov. 5, 2020, which claims priority to European Patent Application No. 19207578.6, filed on Nov. 7, 2019, the entire contents of which are incorporated herein by reference.

FIELD OF THE INVENTION

The present invention relates to agonists of the $5\text{-}HT_{2A}$ serotonin receptors. In a one aspect, the invention relates to $5\text{-}HT_{2A}$ agonists. In another aspect, the invention relates to selective $5\text{-}HT_{2A}$ agonists. In yet another aspect, the invention relates to mixed $5\text{-}HT_{2A}/5\text{-}HT_{2C}$ agonists. In yet another aspect, the invention relates to $5\text{-}HT_{2A}$ agonists for use as medicament in particular for use in the treatment of a depressive disorder, more particular a $5\text{-}HT_{2A}$ agonist for the use in the treatment of treatment-resistant depression.

BACKGROUND OF THE INVENTION

Depression was for a long time considered an illness of the soul but it is currently viewed as a disorder of the brain. A shift in paradigm began more than 50 years ago, following the discovery that biogenic amines, notably norepinephrine (also called noradrenaline (NA)) and serotonin (5-hydroxytryptamine, 5-HT), act as neurotransmitters in the brain. The monoamine hypothesis of depression was first proposed, referring essentially to the monoamines (NA, 5-HT and dopamine), and later the possible role of serotonin was emphasized. Serotonin is involved in and regulates diverse biological functions in the brain, such as e.g. mood, emotion and sleep. Thus, the serotonergic system and serotonin receptors have been investigated for several decades in relation to treatment of depression as well as in relation to other psychiatric disorders. In its original formulation, the 5-HT hypothesis for depression postulated a deficit in brain 5-HT levels as a primary cause, reversed by antidepressants, which would restore normal function in depressed patients.

The current "first-line" therapies for major depressive disorder (MDD) can be grouped into three classes: the selective serotonin reuptake inhibitors (SSRIs), the serotonin and norepinephrine reuptake inhibitors (SNRIs), and the norepinephrine-dopamine reuptake inhibitors (NDRIs). These reuptake inhibitors show varying degrees of selectivity for the three transporters mediating uptake of the three monoamines, with SSRIs having negligible affinities for the norepinephrine and dopamine transporters. The primary medications used in the treatment of depression today are the SSRIs that largely have replaced older generations of antidepressants, such as tricyclic antidepressants (TCAs) and monoamine oxidase inhibitors. Several SSRIs exist, such as sertraline (Zoloft, Lustral), escitalopram (Lexapro, Cipralex), fluoxetine (Prozac), paroxetine (Seroxat) and citalopram (Celexa). The SSRIs are believed to exert their effects via an increase in the extracellular level of serotonin by limiting its reuptake into the presynaptic cell, thereby increasing the level of serotonin in the synaptic cleft available to bind to and activate presynaptic and postsynaptic serotonin receptors. While the modern classes of antidepressants offer superior tolerability and safety over older medications such as the TCAs, presently there is no universally effective pharmacologic treatment for MDD. Hence, effective disease management requires careful attention and continuous assessment of medication response and management of side effects. Thus, the SSRI class of medications is not without drawbacks, the most notable of these being the slow on-set of the antidepressant effects of the drugs (weeks-to-months) and the fact that approximately one half of patients are "non-responders", i.e. do not respond significantly to the SSRI at all. Moreover, administration of SSRIs is associated with adverse effects such as nausea, weight gain and reduced libido. Nevertheless, the significant safety and tolerability advantages of SSRIs compared to the TCAs and their modest but real tolerability advantages compared to the SNRIs justify considering this class of medications first when selecting an antidepressant for a mild-to-moderately severe episode of MDD.

Several addition therapies with non-antidepressant medication have been investigated within depression. These addition therapies have been shown to increase the effectiveness of the antidepressant and to be effective in people with treatment-resistant depression in some cases. Such addition therapies include benzodiazepines, atypical antipsychotics, and stimulants such as amphetamines and methylphenidate (Ritalin). As an example, the atypical antipsychotic aripiprazole has been approved by the US Food and Drug Administration as adjunct to antidepressants for the treatment of MDD. Furthermore, the NMDA receptor antagonist ketamine has shown effect as a rapid-acting antidepressant for treatment-resistant depression. However, several of these therapies come with serious side effects and in the case of the stimulants also have the potential of drug abuse. Thus, there is still an unmet need for further development of new medications for the treatment of depression, in particular new medications effective for use in treatment-resistant depression.

Recent research efforts have shown that classical psychedelics may be useful for the treatment of psychiatric disorders, e.g. major depression, severe depression, treatment-resistant depression, alcohol dependence, alcohol use disorder, nicotine dependence, cocaine-related disorders, heroin dependence, obsessive compulsive disorder, eating disorders, general anxiety, death-related anxiety in terminal cancer patients, PTSD, Alzheimer's disease, mild cognitive impairment, distress, grief, migraine headache, post traumatic headache, cluster headache, Parkinson's disease, and psychosis.[1,2] The psychedelics are a class of drugs whose primary action is to trigger psychedelic experiences via serotonin receptor agonism, producing thought and visual/auditory changes and an altered state of consciousness. Classical psychedelics include mescaline (the active constituent of the peyote cactus), lysergic acid diethylamide (LSD), psilocybin (the active constituent of psilocybin mushrooms commonly known as "magic mushrooms") and N,N-dimethyltryptamine (DMT) (the active component in ayahuasca). Most classical psychedelic drugs fall into one of three families: the tryptamines, phenethylamines or ergolines. Although ergolines constitute their own group, they are in fact both tryptamines and phenethylamines.

The classical psychedelics exhibit polypharmacology, i.e. mediate effects on numerous neurotransmitter receptors. For example, LSD acts as a full agonist/partial agonist at a plethora of monoaminergic receptors, and psilocin (active metabolite of psilocybin) acts as agonist/partial agonist on numerous 5-HT receptors. However, the rapid antidepressant effects of these classical psychedelics have primarily been ascribed to their activation of $5\text{-}HT_{2A}$ receptors.[3]

The serotonin receptor family comprises at least 14 different receptor subtypes divided into subfamilies (5-HT$_1$ to 5-HT$_7$). The 5-HT$_2$ receptor family is composed by the subtypes 5-HT$_{2A}$, 5-HT$_{2B}$ and 5-HT$_{2C}$. As mentioned above, 5-HT$_{2A}$ is thought to be the primary target mediating the antidepressant effects of classical psychedelics. In contrast, 5-HT$_{2B}$ is mainly expressed in peripheral tissues, and it is known to mediate cardiac side effects of non-selective serotonin receptor agonists. Thus, research efforts aimed at exploring the potential of 5-HT$_{2A}$ as a putative target in depression have focused on developing 5-HT$_{2A}$/5-HT$_{2C}$ agonists that do not target 5-HT$_{2B}$, in particular 5-HT$_{2A}$ selective agonists that target neither 5-HT$_{2B}$ nor 5-HT$_{2C}$. However, this has proven difficult, since 5-HT$_{2B}$ and 5-HT$_{2C}$ are closely homologous to 5-HT$_{2A}$. Furthermore, discovery of truly selective agonists requires determination of agonist potency and efficacy in functional assays, as selectivity in terms of binding affinities (K$_i$ or IC$_{50}$) determined in radioligand competition binding assays may not translate into the same selectivity in functional assays. One disclosure of agonists that displays 5-HT$_{2A}$-over-5-HT$_{2C}$ selectivity has been reported in *J. Pharmacol. Exp. Ther.* 2017, 361, 441-453, using the 4-(2-(benzylamino)ethyl)-2,5-dimethoxybenzonitrile scaffold. As an example, the compound 25CN—NBOH exhibited a functional selectivity for 5-HT$_{2A}$ over 5-HT$_{2C}$ (20-fold or 127-fold) when measured in two fluorescence-based Ca$^{2+}$ imaging assays. However, these compounds are generally less suited in terms of drug-like properties, and they are metabolically unstable and/or toxic.[4-5] Another disclosure of agonists that display 5-HT$_{2A}$-over-5-HT$_{2C}$ selectivity has been reported in ACS Chem. Neurosci. 2013, 4, 96-109, using 2,5-diaryl-piperidine scaffolds, 4-aryl-1,2,3,4-tetrahydroisoquinoline scaffolds and 2-benzyl-6-arylpiperidine scaffolds. One of the 2-benzyl-6-arylpiperidine scaffolds in the series exhibited a reasonable selectivity for 5-HT$_{2A}$ over 5-HT$_{2C}$ (124-fold) in terms of binding affinity, and the racemic mixture of the compound displayed 5-HT$_{2A}$ agonism in a functional inositol phosphate (IP) assay. However, the compound was not tested functionally at 5-HT$_{2C}$, and its 5-HT$_{2A}$-over-5-HT$_{2C}$ selectivity in the binding assays does not necessarily translate into a similar degree of selectivity in a functional assay.

The 2-benzyl-6-arylpiperidine scaffolds 8a and 8b reported in ACS Chem. Neurosci. 2013, 4, 96-109, showed moderate 5-HT$_{2A}$-over-5-HT$_{2C}$ selectivity in terms of binding affinity (13-fold and 27-fold, respectively) and were further characterized by the inventors due to some structural similarity with the scaffolds of the present invention. The inventors have demonstrated that only compound 8a evoked significant agonist responses at 5-HT$_{2A}$ in the functional Ca$^{2+}$/Fluo-4 assay and in the functional inositol phosphate (IP) assay at concentrations up to 50 µM and 100 µM, respectively, and that compound 8b exhibited no agonist response in these assays at all (see table 1a and 4). Thus, compound 8b is not a 5-HT$_{2A}$ agonist. Furthermore, compound 8a showed selectivity towards 5-HT$_{2C}$ and 5-HT$_{2B}$ over 5-HT$_{2A}$, in the IP assay and only slight selectivity towards 5-HT$_{2A}$ over 5-HT$_{2C}$ in the Ca$^{2+}$/Fluo-4 assay (see table 1a and 4). Furthermore, both of these scaffolds may also suffer from the same drawbacks in terms of being metabolically unstable and/or toxic as the 4-(2-(benzylamino)ethyl)-2,5-dimethoxybenzonitrile scaffold as they also comprises an N-benzylated amine.

Since the effects of psilocin and other classical psychedelics on various psychiatric conditions have been proposed to arise mainly from their 5-HT$_{2A}$ agonist component, the inventors hypothesized that it may suffice to activate these receptors alone to obtain the rapid anti-depressant effect exhibited by these drugs. The lack of selective 5-HT$_{2A}$ agonists with CNS drug-like properties has so far hampered the exploration of the therapeutic potential in such drugs. Moreover, in the light of the diversity and complexity of depression disorders, it may be hypothesized that some patient groups could benefit from a mixed 5-HT$_{2A}$/5-HT$_{2C}$ agonist, whereas in other patient groups, a selective 5-HT$_{2A}$ agonist may be sufficient or even better than mixed 5-HT$_{2A}$/5-HT$_{2C}$ agonists. Accordingly, a first object of the invention is to provide 5-HT$_{2A}$ agonists. A second object of the invention is to provide selective 5-HT$_{2A}$ agonists that are selective over 5-HT$_{2C}$ and/or 5-HT$_{2B}$. Another object of the invention is to provide mixed 5-HT$_{2A}$/5-HT$_{2C}$ agonists. Even further, an object of the invention is to provide compounds for use in the treatment of depression, in particular for use in the treatment of treatment-resistant depression. The inventors have surprisingly found a new class of compounds comprising a 3-(2,4,5-trisubstituted-phenyl)piperidine, a 3-(2,4-disubstituted-phenyl)piperidine or a 3-(3,4-disubstituted-phenyl)piperidine that all act as 5-HT$_{2A}$ agonists, wherein a subgroup (i.e. the (S)-enantiomers) of these compounds act as selective 5-HT$_{2A}$ agonists (particularly in regard to 5-HT$_{2C}$ and/or 5-HT$_{2B}$). Further, the inventors surprisingly found yet another class of compounds comprising a 3-(2,4,5-trisubstituted-phenyl)azetidine or a 3-(2,4,5-trisubstituted-phenyl)pyrrolidine that act as very potent agonists with roughly equipotent activity at 5-HT$_{2A}$ and 5-HT$_{2C}$. All of these compounds may be beneficial in the treatment of depression, in particular in the treatment of individuals suffering from treatment-resistant depression.

Thus, in a first aspect, the invention relates to 5-HT$_{2A}$ agonists comprising a 3-(2,4,5-trisubstituted-phenyl)piperidine, a 3-(2,4-disubstituted-phenyl)piperidine or a 3-(3,4-disubstituted-phenyl)piperidine. In a second aspect, the invention relates to a subgroup (i.e. the (S)-enantiomers) of the compounds according to the first aspect, that are selective for 5-HT$_{2A}$ over 5-HT$_{2C}$ and/or 5-HT$_{2B}$. In a third aspect, the invention relates to 5-HT$_{2A}$/5-HT$_{2C}$ agonists, preferably 5-HT$_{2A}$/5-HT$_{2C}$ agonists that are selective over 5-HT$_{2B}$. Further aspects of the invention includes the compounds in the first, second and/or third aspect for use as a medicament, in particular for use as a medicament in the treatment of a depressive disorder, more particular for use as a medicament in the treatment of treatment-resistant depression.

Definitions:

According to the present invention, C$_1$-C$_5$ alkyl is to be understood as univalent groups derived from alkanes (C$_n$H$_{2n+2}$) by removal of a hydrogen atom from any carbon atom where n is 1-5, i.e. 1-5 carbon atoms are comprised. C$_1$-C$_5$ alkyls may be linear (—C$_n$H$_{2n+1}$) or branched (—C$_n$H$_{2n+1}$). Likewise, C$_3$-C$_5$ cycloalkyl (—C$_n$H$_{2n+1}$) is to be understood as univalent groups derived from cycloalkanes (—C$_n$H$_{2n}$) by removal of a hydrogen atom from any carbon atom where n is 3-5, i.e. 3-5 carbon atoms are comprised. C$_x$-C$_y$, such as C$_1$-C$_5$, generally refers to the total number of carbon atoms also for alkenyls and alkynyls. C$_2$-C$_5$ alkenyls and C$_2$-C$_5$ alkynyls may be linear or branched. Furthermore, C$_2$-C$_5$ alkenyls or alkynyls may contain one or more alkene(s) or alkyne(s).

According to the present invention, fluoroalkyl should be understood as an alkyl group wherein, one or more hydrogen (—H) atom(s) has/have been replaced by (a) fluorine (—F) atom(s). Thus, in the present context, a fluoroalkyl may be fully fluorinated, mono-fluorinated or anything in between. As a non-limiting example, C$_2$-fluoroalkyl may refer to e.g.

—CF$_2$CF$_3$, —CF$_2$CHF$_2$, —CF$_2$CH$_2$F, —CF$_2$CH$_3$, —CHFCF$_3$, —CHFCHF$_2$, —CHFCH$_2$F, —CHFCH$_3$, —CH$_2$CF$_3$, —CH$_2$CHF$_2$, —CH$_2$CH$_2$F. As another non-limiting example, C$_1$-fluoroalkyl may refer to —CF$_3$, —CF$_2$H or —CFH$_2$. Fluoroalkenyl and fluoroalkynyl should be understood in a similar way. Flourination may be suitable to e.g. prevent sites from being metabolized.

According to aspects 1 and 3 of the present invention, a 5-HT$_{2A}$ agonist should be understood as an agonist activating 5-HT$_{2A}$ receptors with an EC$_{50}$ below 12 µM, such as below 10 µM, such as below 5 µM, preferably below 3 µM, such as below 2 µM, more preferably below 1 µM, even more preferably below 0.5 µM when measured in the functional Ca$^{2+}$/Fluo-4 assay as described in the experimental section.

According to aspects 2 and 4 of the present invention, a 5-HT$_{2A}$ selective agonist should be understood as an agonist activating 5-HT$_{2A}$ receptors with an EC$_{50}$ below 5 µM, such as below 3 µM, preferably below 2 µM, more preferably below 1 µM, even more preferably below 0.5 µM, such as below 0.25 µM, more preferably below 0.15 µM, such as below 0.12 µM, even more preferably below 0.1 µM, such as below 90 nM, most preferably below 80 nM, such as below 70 nM, when measured in the Ca$^{2+}$/Fluo-4 functional assay and in addition displays selectivity towards 5-HT$_{2A}$ over 5-HT$_{2C}$ when measured in the functional Ca$^{2+}$/Fluo-4 assay (as described in the experimental section) and/or selectivity towards 5-HT$_{2A}$ over 5-HT$_{2B}$ when measured in the functional inositol phosphate (IP) assay (as described in the experimental section). The lack of significant agonist activity exhibited by a compound at the 5-HT$_{2C}$ receptor at the concentration ranges tested in the functional Ca$^{2+}$/Fluo-4 assay may either be the result of very low agonist potency at the receptor, of the compound possessing so low agonist efficacy at the receptor that it cannot be detected in the assay, or of the compound being a competitive antagonist and thus per definition having no agonist efficacy at the receptor. Most preferably, the 5-HT$_{2A}$ selective agonists do not show any agonist activity (efficacy) in the Ca$^{2+}$/Fluo-4 functional assay. Thus, preferably, the selectivity for 5-HT$_{2A}$ towards 5-HT$_{2C}$ (i.e. EC$_{50}^{5\text{-}HT2C}$/EC$_{50}^{5\text{-}HT2A}$) is at least a factor of 2, such as at least a factor of 3, such as at least a factor of 4, more preferably at least a factor 5, such as at least a factor of 6, such as at least a factor of 7, even more preferably at least a factor of 8, such as at least a factor of 9, yet more preferably at least a factor of 10, such as at least a factor of 11, such as at least a factor of 12, yet more preferably at least a factor of 20, such as at least a factor of 30, most preferably at least a factor of 100 when the 5-HT$_{2A}$ and 5-HT$_{2C}$ EC$_{50}$ values are measured in the Ca$^{2+}$/Fluo-4 functional assay as described in the experimental section. Preferably, the selective 5-HT$_{2A}$ agonists do not activate 5-HT$_{2B}$ significantly. Therefore, preferably the selectivity towards 5-HT$_{2B}$ (i.e. EC$_{50}^{5\text{-}HT2B}$/EC$_{50}^{5\text{-}HT2A}$) is at least a factor of 2, such as a factor of 3, such as a factor of 4, more preferably a factor of at least 5, such as a factor of 6, such as a factor of 7, even more preferably at least a factor of 8 when the 5-HT$_{2A}$ and 5-HT$_{2B}$ EC$_{50}$ values are measured in the functional IP assay described in the experimental section.

According to aspects 3 and 6 of the present invention, a mixed 5-HT$_{2A}$/5-HT$_{2C}$ agonist should be understood as an agonist activating both 5-HT$_{2A}$ and 5-HT$_{2C}$ with a 5-HT$_{2A}$ EC$_{50}$ value below 5 µM, such as below 3 µM, such as below 2 µM, preferably below 1 µM, such as below 0.5 µM, more preferably below 0.25 µM, yet more preferably below 100 nM and a 5-HT$_{2C}$ EC$_{50}$ value below 3 µM, such as below 2 µM, preferably below 1 µM, such as below 0.5 µM, more preferably below 0.25 µM, yet more preferably below 100 nM when measured in the functional Ca$^{2+}$/Fluo-4 assay described in the experimental section. Preferably, the 5-HT$_{2A}$ EC$_{50}$ value is below 90 nM, such below 80 nM, such as below 70 nM, more preferably below 60 nM, such as below 50 nM, even more preferably below 40 nM, such as below 30 nM, most preferably below 20 nM, such as below 10 nM. Preferably, the 5-HT$_{2C}$ EC$_{50}$ value is below 90 nM, such below 80 nM, preferably below 70 nM, more preferably below 60 nM, most preferably below 50 nM. Preferably the selectivity between 5-HT$_{2A}$ and 5-HT$_{2C}$ (i.e. EC$_{50}^{5\text{-}HT2C}$/EC$_{50}^{5\text{-}HT2A}$) is less than a factor of 20, such as less than a factor of 15, more preferably less than a factor of 10, such as a factor of less than 8, most preferably less than a factor of 7, such as a factor less than 6. Preferably, the mixed 5-HT$_{2A}$/5-HT$_{2C}$ agonists do not activate 5-HT$_{2B}$. Likewise, preferably the selectivity for 5-HT$_{2A}$ towards 5-HT$_{2B}$ (i.e. EC$_{50}^{5\text{-}HT2B}$/EC$_{50}^{5\text{-}HT2A}$) is at least a factor of 2, such as a factor of 3, such as a factor of 4, more preferably a factor of at least 5, such as a factor of 6, such as a factor of 7, even more preferably at least a factor of 8 when the 5-HT$_{2A}$ and 5-HT$_{2B}$ EC$_{50}$ values are measured in IP assay described in the experimental section.

The compounds according to the present invention have also shown to possess high selectivity in terms of binding affinity (lower K$_i$ values) at 5-HT$_2$ receptors as exemplified for compound 8 compared to other monoaminergic receptors such as members of the other serotonin receptor subfamilies (5-HT$_1$, 5-HT$_3$, 5-HT$_5$, 5-HT$_6$ and 5-HT$_7$), members of the norepinephrine receptor families (a$_{1A}$, a$_{1B}$, a$_{1C}$, a$_{2A}$, a$_{2B}$, a$_{2C}$) and the dopamine receptors (D$_1$, D$_2$, D$_3$, D$_4$, D$_5$) (see Table 3), when measured in the binding assays described in the experimental section. Thus, according to the invention a 5-HT$_{2A}$ agonist should preferably have a K$_i$ value on D$_1$-D$_5$ above 1000 nM, such as above 2000 nM, preferably above 3000 nM, such as above 4000 nM, more preferably above 5000 nM, such as above 6000 nM, even more preferably above 7000 nM, such as above 8000 nM, most preferably above 9000 nM, such as above 10000 nM when measured in the dopamine receptor binding assays described in the experimental section. Likewise, according to the invention, a 5-HT$_{2A}$ agonist should preferably have a K$_i$ on a$_{1A}$, a$_{1B}$ and a$_{2C}$, above 1000 nM, such as above 2000 nM, preferably above 3000 nM, such as above 4000 nM, more preferably above 5000 nM, such as above 6000 nM, even more preferably above 7000 nM, such as above 8000 nM, most preferably above 9000 nM, such as above 10000 nM and a K$_i$ value on a$_{2A}$ and a$_{2B}$ above 200 nM, such as above 250 nM, preferably above 300 nM, such as above 350 nM, more preferably above 400 nM, such as above 450 nM, even more preferably above 500 nM, such as above 550 nM, most preferably above 550 nM, such as above 600 nM when measured in the norepinephrine receptor binding assays described in the experimental section. Likewise, a 5-HT$_{2A}$ agonist should preferably have a K$_i$ value on 5-HT$_3$ and 5-HT$_{5A}$ above 1000 nM, such as above 2000 nM, preferably above 3000 nM, such as above 4000 nM, more preferably above 5000 nM, such as above 6000 nM, even more preferably above 7000 nM, such as above 8000 nM, most preferably above 9000 nM, such as above 10000 nM and preferably a K$_i$ value on 5-HT$_{1A}$, 5-HT$_6$ and 5-HT$_7$ above 100 nM, such as above 150 nM, preferably above 200 nM, such as above 250 nM, more preferably above 300 nM when measured in the serotonin receptor binding assay described in the experimental section.

According to the present invention treatment-resistant depression (TRD) should be understood as a depressive disorder, preferably major depressive disorder (MDD), that cannot be treated adequately with known antidepressants and/or psychotherapy, such that a desired clinical outcome can be reached (i.e. inadequate response observed). An inadequate response should be understood as no clinical response (e.g. no improvement in depressive symptoms) or a person who does not achieve full remission of depressive symptoms.

SUMMARY OF THE INVENTION

In the first aspect the invention relates to 5-$HT_{2A}$ agonists of the general formula (I)

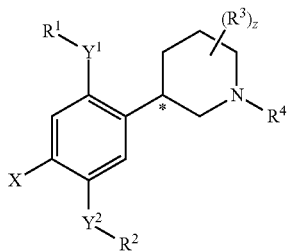

(I)

or a pharmaceutically acceptable salt thereof wherein:

\* denotes the (R) or (S) stereoisomer or any mixture thereof;

X is selected from the group consisting of I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_2$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl and $C_3$-$C_5$ fluorocycloalkyl;

z denotes the number of $R^3$ groups and is an integer with a value of 0, 1, 2, 3 or 4;

$R^3$ is/are independently selected from the group consisting of F, $C_1$-$C_3$ alkyl, $C_1$-$C_3$ fluoroalkyl, $C_2$-$C_3$ alkenyl and $C_1$-$C_3$ alkynyl;

$R^4$ is selected from H or $CH_3$;

with the proviso that at least one of $Y^1$ or $Y^2$ is selected as O or S.

In a second aspect, the invention relates to selective 5-$HT_{2A}$ agonists of the general formula (II)

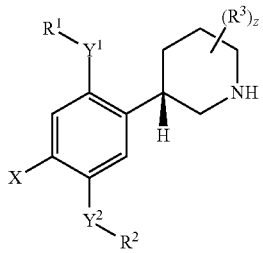

(II)

or a pharmaceutically acceptable salt thereof wherein:

X is selected from the group consisting of I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_2$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl and $C_3$-$C_5$ fluorocycloalkyl;

z denotes the number of $R^3$ groups and is an integer with a value of 0, 1, 2, 3 or 4;

$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;

with the proviso that at least one of $Y^1$ or $Y^2$ is selected as O or S.

In a third aspect, the invention relates to mixed 5-$HT_{2A}$/5-$HT_{2C}$ agonists of the general formula (III)

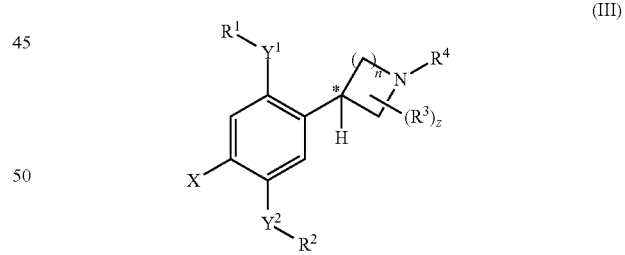

(III)

or a pharmaceutically acceptable salt thereof wherein:

X is selected from the group consisting of I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_2$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;

$Y^1$ and $Y^2$ are independently selected from the group consisting of O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl and $C_3$-$C_5$ fluorocycloalkyl;

* denotes the (R) or (S) stereoisomer or any mixture thereof if a chiral center is present;

n is an integer with a value of 1, 2, 3 or 4 to form an azetidine, pyrrolidine, piperidine or azepane ring system;

z denotes the number of $R^3$ groups and is an integer with a value of 0, 1, 2, 3 or 4;

$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;

$R^4$ is selected from H or $CH_3$;

with the proviso that when n=3, * denotes the (R) stereoisomer and further with the proviso that at least one of $Y^1$ or $Y^2$ is selected as O or S.

In a fourth aspect, the invention relates to 5-$HT_{2A}$ agonists of the general formula (I) or a pharmaceutically acceptable salt thereof for use as a medicament

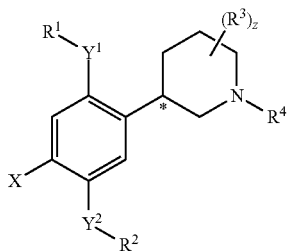

(I)

wherein:

* denotes the (R) or (S) stereoisomer or any mixture thereof;

X is selected from the group consisting of F, Cl, Br, I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, or halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl and $C_3$-$C_5$ fluorocycloalkyl;

z denotes the number of $R^3$ groups and is an integer with a value of 0, 1, 2, 3 or 4;

$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;

$R^4$ is selected from H or $CH_3$;

with the proviso that at least one of $Y^1$ or $Y^2$ are selected as O or S.

In a fifth aspect, the invention relates to selective 5-$HT_{2A}$ agonists of the general formula (II) or a pharmaceutically acceptable salt thereof for use as a medicament

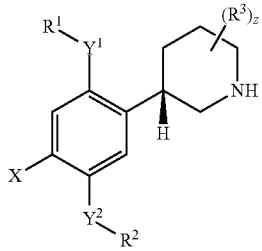

(II)

wherein:

X is selected from the group consisting of F, Cl, Br, I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl and $C_3$-$C_5$ fluorocycloalkyl;

z denotes the number of $R^3$ groups and is an integer with a value of 0, 1, 2, 3 or 4;

$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;

with the proviso that at least one of $Y^1$ or $Y^2$ are selected as O or S.

In a sixth aspect, the invention relates to mixed 5-$HT_{2A}$/5-$HT_{2C}$ agonists or a pharmaceutically acceptable salt thereof of the general formula (III) for use as a medicament

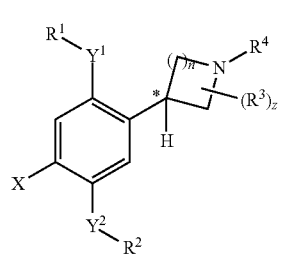

(III)

wherein:

X is selected from the group consisting of F, Cl, Br, I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl and $C_3$-$C_5$ fluorocycloalkyl;

* denotes the (R) or (S) stereoisomer or any mixture thereof if a chiral center is present;

n is an integer with a value of 1, 2, 3 or 4 to form an azetidine, pyrrolidine, piperidine or azepane ring system;

z denotes the number of $R^3$ groups and is an integer with a value of 0, 1, 2, 3 or 4;

$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;

$R^4$ is selected from H or $CH_3$;

with the proviso that when n=3, * denotes the (R) stereoisomer and further with the proviso that at least one of $Y^1$ or $Y^2$ is selected as O or S.

A seventh aspect of the invention relates to a method of synthesis of the compounds according to any of the preceding aspects of the invention.

An eighth aspect relates to particular medical uses of the compounds according to the invention.

A ninth aspect relates to pharmaceutical compositions comprising one or more compounds according to the invention.

The invention will now be described in more detail in the following embodiments.

BRIEF DESCRIPTION OF THE FIGURES

FIG. 2A shows the dose-dependent increase of HTR mediated by compound 8 (subcutaneous administration) in male C57BL/6J mice. FIG. 2B shows the dose-dependent increase of HTR mediated by compound 8 (intraperitoneal administration) in Sprague Dawley male rats.

DETAILED DESCRIPTION OF THE INVENTION

Figure 1A:
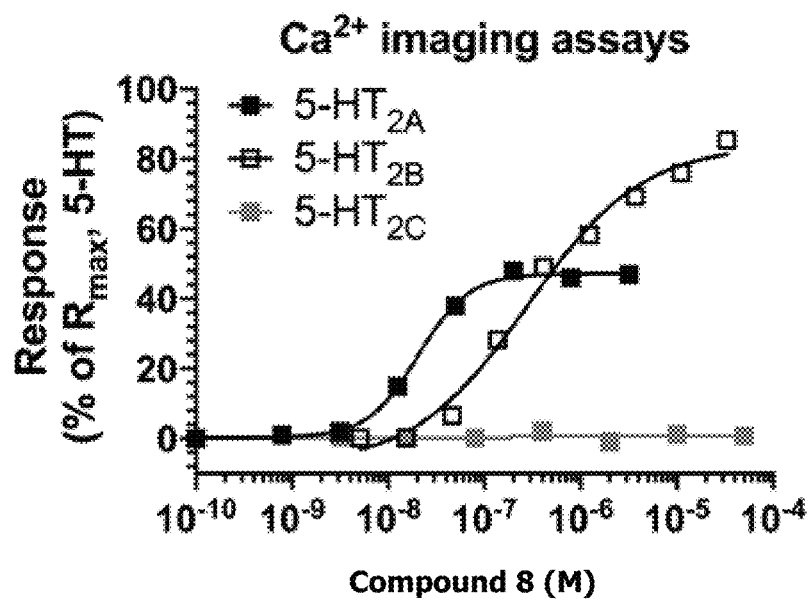
FIG. 1A shows the concentration-dependent responses elicited by compound 8 in $5\text{-}HT_{2A}$-, $5\text{-}HT_{2B}$- and $5\text{-}HT_{2C}$-expressing cell lines in the functional $Ca^{2+}$/Fluo-4 assay when tested as agonist.

Aspect 1—$5\text{-}HT_{2A}$ Agonists of the General Formula (I)

The inventors found that compounds comprising a 3-(2,4,5-trisubstituted-phenyl)piperidine, a 3-(2,4-disubstituted-phenyl)piperidine or a 3-(3,4-disubstituted-phenyl)piperidine act as potent $5\text{-}HT_{2A}$ agonists and show promising results as anti-depressants. Thus, one overall inventive concept relates to $5\text{-}HT_{2A}$ agonists and their use as medicaments, preferably their use as anti-depressant medicaments, wherein the $5\text{-}HT_{2A}$ agonists comprise a 3-(2,4,5-trisubstituted-phenyl)piperidine, a 3-(2,4-disubstituted-phenyl)piperidine or a 3-(3,4-disubstituted-phenyl)piperidine.

In the first aspect the invention relates to $5\text{-}HT_{2A}$ agonists of the general formula (I)

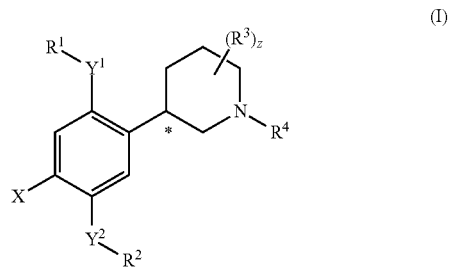

(I)

or a pharmaceutically acceptable salt thereof wherein:

* denotes the (R) or (S) stereoisomer or any mixture thereof;

X is selected from the group consisting of I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_2$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl or $C_3$-$C_5$ fluorocycloalkyl;

z denotes the number of $R^3$ groups and is an integer with a value of 0, 1, 2, 3 or 4;

$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;

$R^4$ is selected from H or $CH_3$ with the proviso that at least one of $Y^1$ or $Y^2$ is selected as O or S.

Substituent X

The inventors found that the substituent X in Formula (I) was important for the potency of the 5-HT$_{2A}$ agonists and that X tolerated a variety of lipophilic substituents. The skilled person is aware of a range of substituents that are suitable to fulfill the role as a lipophilic substituent. Thus, in an embodiment of the invention, X is selected from I, CN, S—(C$_1$-C$_5$ alkyl), S—(C$_1$-C$_5$ fluoroalkyl), C$_2$-C$_5$ alkyl, C$_1$-C$_5$ fluoroalkyl. In a preferred embodiment, X is selected from I, CN, S—(C$_1$-C$_3$ alkyl), S—(C$_1$-C$_3$ fluoroalkyl), C$_2$-C$_5$ alkyl, C$_1$-C$_5$ fluoroalkyl. In a more preferred embodiment, X is selected from I, CN, S—(C$_1$-C$_3$ alkyl), S—(C$_1$-C$_3$ fluoroalkyl), C$_2$-C$_4$ alkyl, C$_1$-C$_4$ fluoroalkyl. In yet a more preferred embodiment, X is selected from I, CN, S—CH$_3$, S—CF$_3$, C$_2$-C$_3$ alkyl, C$_1$-C$_3$ fluoroalkyl. In an even more preferred embodiment of the invention, X is selected from I, CF$_3$, CN, S—CH$_3$, S—CF$_3$. In a yet an even more preferred embodiment, X is selected from I, CF$_3$, CN, S—CH$_3$. In a highly preferred embodiment, X is selected from I, CF$_3$, S—CH$_3$. In an even more highly preferred embodiment of the invention, X is selected from I or CF$_3$. In the most preferred embodiment of the invention, X is CF$_3$.

Substituents Y$^1$ and Y$^2$

The inventors further found that Y$^1$ and Y$^2$ could be selected from H, O, S, C$_1$-C$_3$ alkyl, C$_1$-C$_3$ fluoroalkyl, or halogen with the proviso that at least one of Y$^1$ or Y$^2$ are selected as O or S. It follows that when Y$^1$ is H, halogen, C$_1$-C$_3$ fluoroalkyl, or C$_1$-C$_3$ alkyl, R$^1$ is not present (deleted). Likewise, when Y$^2$ is H, halogen, C$_1$-C$_3$ fluoroalkyl, or C$_1$-C$_3$ alkyl, R$^2$ is not present (deleted). In an embodiment of the invention Y$^1$ is selected from O, S, CH$_3$ or halogen and Y$^2$ is selected from O, S, CH$_3$ or halogen. In a preferred embodiment of the invention Y$^1$ is selected from O, S, H or halogen and Y$^2$ is selected from O, S, H or halogen. In yet a preferred embodiment Y$^1$ is selected from O, S, or CH$_3$ and Y$^2$ is selected from O, S, or CH$_3$. In a more preferred embodiment of the invention Y$^1$ is selected from O, S or H and Y$^2$ is selected from O, S or H. In yet a more preferred embodiment Y$^1$ is selected from O or S and Y$^2$ is selected from O or S. In yet a preferred embodiment, Y$^1$ is O or S, and Y$^2$ is selected from H, halogen, O or S. In particular, the presence of a heteroatom in Y$^1$ and Y$^2$ provided potent 5-HT$_{2A}$ compounds. Thus, in an embodiment of the invention, Y$^1$ is O, and Y$^2$ is S. In another embodiment of the invention, Y$^1$ is S, and Y$^2$ is O. In yet another embodiment, Y$^1$ and Y$^2$ are S. In the most preferred embodiment of the invention, Y$^1$ and Y$^2$ are O.

Substituent R$^1$ and R$^2$

The inventors surprisingly found that the pharmacophore occupied by R$^1$ and R$^2$ in formula (I) allowed small lipophilic substituents while maintaining 5-HT$_{2A}$ activity and potency of the compounds. Thus, in an embodiment of the invention, R$^1$ and R$^2$ are independently selected from the group consisting of not present (R$^1$ not present if Y$^1$ is H, C$_1$-C$_3$ alkyl, C$_1$-C$_3$ fluoroalkyl, or halogen, R$^2$ not present if Y$^2$ is H, C$_1$-C$_3$ alkyl, C$_1$-C$_3$ fluoroalkyl or halogen), C$_1$-C$_5$ alkyl, C$_1$-C$_5$ fluoroalkyl, C$_3$-C$_5$ cycloalkyl or C$_3$-C$_5$ fluorocycloalkyl. In a preferred embodiment of the invention, R$^1$ and R$^2$ are independently selected from the group consisting of C$_1$-C$_3$ alkyl, C$_1$-C$_3$ fluoroalkyl, C$_3$-C$_5$ cycloalkyl or C$_3$-C$_5$ fluorocycloalkyl. In yet a more preferred embodiment, R$^1$ and R$^2$ are independently selected from the group consisting of C$_1$-C$_3$ alkyl, C$_1$-C$_3$ fluoroalkyl, C$_3$-C$_5$ cycloalkyl. In yet an even more preferred embodiment of the invention, R$^1$ and R$^2$ are independently selected from the group consisting of C$_1$-C$_3$ alkyl, C$_1$-C$_3$ fluoroalkyl, and cyclopropyl. In an even more preferred embodiment, R$^1$ and R$^2$ are independently selected from the group consisting of C$_1$-C$_3$ alkyl and C$_1$-C$_3$ fluoroalkyl. In a highly preferred embodiment, R$^1$ and R$^2$ are independently selected from the group consisting of C$_1$-C$_2$ alkyl and C$_1$-C$_2$ fluoroalkyl. In another highly preferred embodiment, R$^1$ and R$^2$ are independently selected from the group consisting of C$_1$-C$_2$ alkyl. In an even more preferred embodiment, R$^1$ and R$^2$ are independently selected from the group consisting of methyl (CH$_3$) and trifluoromethyl (CF$_3$). In the most preferred embodiment of the invention, R$^1$ and R$^2$ are both methyl (CH$_3$).

Type of R$^3$ Substituent(s)

In an embodiment of the invention, the R$^3$ group(s) is/are independently selected from the group consisting of F, C$_1$-C$_3$ alkyl and C$_1$-C$_3$ fluoroalkyl. In a preferred embodiment of the invention, the R$^3$ group(s) is/are independently selected from the group consisting of F, C$_1$-C$_2$ alkyl and C$_1$-C$_2$ fluoroalkyl. In the highly preferred embodiment of the invention, the R$^3$ group(s) is/are independently selected from the group consisting of F, methyl (CH$_3$) and trifluoromethyl (CF$_3$). In the most preferred embodiment of the invention, the R$^3$ group(s) is/are independently selected from the group consisting of F and methyl (CH$_3$).

Number (z) of R$^3$ Substituent(s) and Preferred Positions

The inventors further found that the carbon atoms in the piperidine ring system could be substituted with small lipophilic substituents (R$^3$). Thus, according to the present invention, the one or more R$^3$ substituent(s) (if present) is/are present at any of the positions (2), (3), (4), (5) and/or (6) as shown in formula (I) below. More preferably, one or more R$^3$ substituent(s) (if present) is/are present at any of the positions (2), (3) and/or (6) as shown in in formula (I) below, most preferably at position (2) or (3) as shown in in formula (I) below. It follows that two R$^3$ substituents may be present on the same position (carbon atom). The inventors found that the secondary amine (free NH) in the piperidine ring system was highly important for maintaining high agonist activity at the 5-HT$_{2A}$ receptor, whereas nitrogen substituents (tertiary amines) led to a significant loss of potency at 5-HT$_{2A}$ (factor ~80 for compound 59 (N-Et) and a factor ~20 for compound 61 (N-Me) compared to compound 8). In some less preferred embodiments, the piperidine may be N-methylated despite the loss of potency in order to change other properties, e.g. ADME properties.

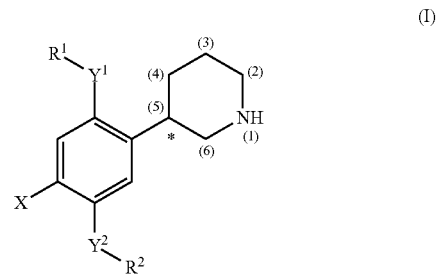

(I)

Thus, in an embodiment of the invention, z is 0-4 such that the piperidine is unsubstituted or substituted with 1-4 R$^3$ groups. In a preferred embodiment of the invention, z is 0-3 such that the piperidine is unsubstituted or substituted with 1-3 R$^3$ groups. In a more preferred embodiment of the invention, z is 0-2 such that the piperidine is unsubstituted or substituted with 1-2 R$^3$ groups. In an even more preferred embodiment of the invention, z is 0-1 such that the piperidine is unsubstituted or substituted with one R$^3$ group. In the most preferred embodiment of the invention z is 0, such that no $R^3$ substituents are present.

In a highly preferred embodiment of the invention, z is 0 or 1, such that the piperidine is unsubstituted or substituted with one $R^3$ group, a wherein the one $R^3$ group is present in any of the positions indicated as (2), (3), (4), (5) or (6) in formula (I) above, preferably in any of the positions indicated (2), (3) or (6) in formula (I) above, most preferably in the position indicated as (2) or (3) in formula (I) above.

Stereochemistry

In the first aspect, the compounds of formula (I) comprise both the (R) and (S) stereoisomers at the chiral center denoted *. The compounds may therefore be a single stereoisomer or a mixture of the (R) and (S) stereoisomers in any ratio such as a 1:1 mixture of stereoisomers on the center denoted * (i.e. racemate if no $R^3$ groups are present). It is evident to the skilled person that in case of $R^3$ substituents on the piperidine, one or more additional chiral centers may be present in the molecule. These other chiral centers may also be either in the (R) and (S) configuration in accordance with Cahn-Ingold-Prelog priority rules. The number of stereoisomers possible depends on the number of chiral centers present and can be calculated as $2^n$, where n is the number of additional chiral centers. In the present context, the invention is intended to cover all the single stereoisomers possible as well as any mixture thereof. The stereoisomers according to the present invention may be separated using conventional methods in the art. Thus, diastereomers may be separated by selective crystallization, liquid column chromatography, such as conventional silica gel chromatography or High Performance Liquid Chromatography (HPLC) (reverse and normal-phase). Furthermore, enantiomers may be separated using chiral resolution, such as chiral HPLC, chiral SFC or by chiral derivatizing agents to form diastereomers that may be separated with any of the above-mentioned conventional methods.

Preferred Embodiments

In a preferred embodiment of the invention, X is selected from I, CN, S—($C_1$-$C_3$ alkyl), S—($C_1$-$C_3$ fluoroalkyl), $C_2$-$C_3$ alkyl, $C_1$-$C_3$ fluoroalkyl; $Y^1$ is selected from H, O, S, $CH_3$ or halogen; $Y^2$ is selected from H, O, S, $CH_3$ or halogen. $R^1$ and $R^2$ are independently selected from the group consisting of not present ($R^1$ not present if $Y^1$ is H, $CH_3$ or halogen, $R^2$ not present if $Y^2$ is H, $CH_3$ or halogen), $C_1$-$C_3$ alkyl, $C_1$-$C_3$ fluoroalkyl, cyclopropyl; z is 0, 1, 2 or 3; and $R^3$ is/are independently selected from F, $CH_3$ or $CF_3$; with the proviso that at least one of $Y^1$ or $Y^2$ are selected as O or S.

In another preferred embodiment of the invention, X is selected from I, CN, S—($C_1$-$C_3$ alkyl), S—($C_1$-$C_3$ fluoroalkyl), $C_2$-$C_3$ alkyl, $C_1$-$C_3$ fluoroalkyl; $Y^1$ is selected from H, O, or S; $Y^2$ is selected from H, O, or S. $R^1$ and $R^2$ are independently selected from the group consisting of not present ($R^1$ not present if $Y^1$ is H, $R^2$ not present if $Y^2$ is H), $C_1$-$C_3$ alkyl, $C_1$-$C_3$ fluoroalkyl, cyclopropyl; z is 0, 1, 2 or 3; and $R^3$ is/are independently selected from F, $CH_3$ or $CF_3$; with the proviso that at least one of $Y^1$ or $Y^2$ are selected as O or S.

In yet a preferred embodiment of the invention, X is selected from I, CN, S—($C_1$-$C_2$ alkyl), S—($C_1$-$C_2$ fluoroalkyl), $C_2$-$C_3$ alkyl, $C_1$-$C_3$ fluoroalkyl; $Y^1$ is selected from H, O, S, $CH_3$ or halogen; $Y^2$ is selected from H, O, S, $CH_3$ or halogen. $R^1$ and $R^2$ are independently selected from the group consisting of not present ($R^1$ not present if $Y^1$ is H, $CH_3$ or halogen, $R^2$ not present if $Y^2$ is H, $CH_3$ or halogen), $C_1$-$C_3$ alkyl, $C_1$-$C_3$ fluoroalkyl, $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ are selected as O or S.

In another preferred embodiment of the invention, X is selected from I, CN, S—($C_1$-$C_2$ alkyl), S—($C_1$-$C_2$ fluoroalkyl), $C_2$-$C_3$ alkyl, $C_1$-$C_3$ fluoroalkyl; $Y^1$ is selected from H, O or S; $Y^2$ is selected from H, O, or S. $R^1$ and $R^2$ are independently selected from the group consisting of not present ($R^1$ not present if $Y^1$ is H, $R^2$ not present if $Y^2$ is H), $C_1$-$C_3$ alkyl, $C_1$-$C_3$ fluoroalkyl, $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ are selected as O or S.

In yet a preferred embodiment of the invention, X is selected from I, CN, S—($C_1$-$C_2$ alkyl), S—($C_1$-$C_2$ fluoroalkyl), $C_2$-$C_3$ alkyl, $C_1$-$C_3$ fluoroalkyl; $Y^1$ is selected from O, S, $CH_3$ or halogen; $Y^2$ is selected from H, O, S, $CH_3$ or halogen. $R^1$ and $R^2$ are independently selected from the group consisting of not present ($R^1$ not present if $Y^1$ is $CH_3$ or halogen, $R^2$ not present if $Y^2$ is H, $CH_3$ or halogen), $C_1$-$C_3$ alkyl, $C_1$-$C_3$ fluoroalkyl, $C_3$-$C_5$ cycloalkyl; z is 0 or 1; and $R^3$ is selected from F, $C_1$-$C_2$ alkyl or $C_1$-$C_2$ fluoroalkyl; with the proviso that at least one of $Y^1$ or $Y^2$ are selected as O or S.

In yet a preferred embodiment of the invention, X is selected from I, CN, S—($C_1$-$C_2$ alkyl), S—($C_1$-$C_2$ fluoroalkyl), $C_2$-$C_3$ alkyl, $C_1$-$C_3$ fluoroalkyl; $Y^1$ is selected from O, S, $CH_3$ or halogen; $Y^2$ is selected from H, O, S, $CH_3$ or halogen. $R^1$ and $R^2$ are independently selected from the group consisting of not present ($R^1$ not present if $Y^1$ is $CH_3$ or halogen, $R^2$ not present if $Y^2$ is H, $CH_3$ or halogen), $C_1$-$C_3$ alkyl, $C_1$-$C_3$ fluoroalkyl, cyclopropyl; z is 0 or 1; and $R^3$ is selected from F, $C_1$-$C_2$ alkyl or $C_1$-$C_2$ fluoroalkyl; with the proviso that at least one of $Y^1$ or $Y^2$ are selected as O or S.

In yet a preferred embodiment of the invention, X is selected from I, CN, S—($C_1$-$C_2$ alkyl), S—($C_1$-$C_2$ fluoroalkyl), $C_2$-$C_3$ alkyl, $C_1$-$C_3$ fluoroalkyl; $Y^1$ is selected from O, S, $CH_3$ or halogen; $Y^2$ could be selected from H, O, S, $CH_3$ or halogen. $R^1$ and $R^2$ are independently selected from the group consisting of not present ($R^1$ not present if $Y^1$ is $CH_3$ or halogen, $R^2$ not present if $Y^2$ is H, $CH_3$ or halogen), $C_1$-$C_3$ alkyl, $C_1$-$C_3$ fluoroalkyl, $C_3$-$C_5$ cycloalkyl; z is 0 or 1; and $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated (2) or (3) in formula (I) above; with the proviso that at least one of $Y^1$ or $Y^2$ are selected as O or S.

In yet a preferred embodiment of the invention, X is selected from I, CN, S—$CH_3$, S—$CF_3$, $C_2$-$C_3$ alkyl, $C_1$-$C_3$ fluoroalkyl; $Y^1$ is selected from O or S; $Y^2$ is selected from H, O, S, $CH_3$ or halogen. $R^1$ are selected from the group consisting of $C_1$-$C_3$ alkyl, $C_1$-$C_3$ fluoroalkyl, $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; $R^2$ are selected from the group consisting of not present ($R^2$ not present if $Y^2$ is H, $CH_3$ or halogen), $C_1$-$C_3$ alkyl, $C_1$-$C_3$ fluoroalkyl, $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ are selected as O or S.

In yet a preferred embodiment of the invention, X is selected from I, CN, S—$CH_3$, S—$CF_3$, $C_2$-$C_3$ alkyl, $C_1$-$C_3$ fluoroalkyl; $Y^1$ is selected from O or S; $Y^2$ is selected from H, O, S, $CH_3$ or halogen; $R^1$ is selected from $C_1$-$C_3$ alkyl, $C_1$-$C_3$ fluoroalkyl or $C_3$-$C_5$ cycloalkyl; z is 0 or 1; $R^3$ is selected from F, $C_1$-$C_2$ alkyl or $C_1$-$C_2$ fluoroalkyl; $R^2$ is selected from the group consisting of not present ($R^2$ not present if $Y^2$ is H, $CH_3$ or halogen), $C_1$-$C_3$ alkyl, $C_1$-$C_3$ fluoroalkyl, $C_3$-$C_5$ cycloalkyl; z is 0 or 1; $R^3$ is selected from F, $C_1$-$C_2$ alkyl or $C_1$-$C_2$ fluoroalkyl.

In yet a preferred embodiment of the invention, X is selected from I, CN, S—$CH_3$, S—$CF_3$, $C_2$-$C_3$ alkyl, $C_1$-$C_3$ fluoroalkyl; $Y^1$ is selected from O or S; $Y^2$ is selected from H, O or S; $R^1$ is selected from the group consisting of $C_1$-$C_3$ alkyl, $C_1$-$C_3$ fluoroalkyl, $C_3$-$C_5$ cycloalkyl; z is 0 or 1; $R^3$ is selected from F, $C_1$-$C_2$ alkyl or $C_1$-$C_2$ fluoroalkyl; $R^2$ is selected from the group consisting of not present ($R^2$ not present if $Y^2$ is H), $C_1$-$C_3$ alkyl, $C_1$-$C_3$ fluoroalkyl, $C_3$-$C_5$ cycloalkyl; z is 0 or 1; $R^3$ is selected from F, $C_1$-$C_2$ alkyl or $C_1$-$C_2$ fluoroalkyl.

In yet a preferred embodiment of the invention, X is selected from I, CN, S—$CH_3$, S—$CF_3$, $C_2$-$C_3$ alkyl, $C_1$-$C_3$ fluoroalkyl; $Y^1$ is selected from O or S; $Y^2$ is selected from H, O, S, $CH_3$ or halogen. $R^1$ is selected from the group consisting of $C_1$-$C_3$ alkyl, $C_1$-$C_3$ fluoroalkyl, $C_3$-$C_5$ cycloalkyl; $R^2$ is selected from the group consisting of not present ($R^2$ not present if $Y^2$ is H, $CH_3$ or halogen), $C_1$-$C_3$ alkyl, $C_1$-$C_3$ fluoroalkyl, $C_3$-$C_5$ cycloalkyl; z is 0 or 1; $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet a preferred embodiment of the invention, X is selected from I, CN, S—$CH_3$, S—$CF_3$, $C_2$-$C_3$ alkyl, $C_1$-$C_3$ fluoroalkyl; $Y^1$ is selected from O or S; $Y^2$ is selected from H, O, or S; $R^1$ is selected from the group consisting of, $C_1$-$C_3$ alkyl, $C_1$-$C_3$ fluoroalkyl, $C_3$-$C_5$ cycloalkyl; $R^2$ is selected from the group consisting of not present ($R^2$ not present if $Y^2$ is H), $C_1$-$C_3$ alkyl, $C_1$-$C_3$ fluoroalkyl, $C_3$-$C_5$ cycloalkyl; z is 0 or 1; $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a more preferred embodiment of the invention, X is selected from I, CN, S—$CH_3$, S—$CF_3$, $C_2$-$C_3$ alkyl, $C_1$-$C_3$ fluoroalkyl; $Y^1$ and $Y^2$ are independently selected from O or S; $R^1$ and $R^2$ are independently selected from the group consisting of $C_1$-$C_3$ alkyl, $C_1$-$C_3$ fluoroalkyl, $C_3$-$C_5$ cycloalkyl; z is 0, 1, 2 or 3; and $R^3$ is/are independently selected from F, $C_1$-$C_2$ alkyl or $C_1$-$C_2$ fluoroalkyl.

In yet a more preferred embodiment of the invention, X is selected from I, $CF_3$, $C_2$-$C_3$ alkyl, $C_1$-$C_3$ fluoroalkyl; $Y^1$ and $Y^2$ are independently selected from O or S; $R^1$ and $R^2$ are independently selected from $C_1$-$C_3$ alkyl, $C_1$-$C_3$ fluoroalkyl or $C_3$-$C_5$ cycloalkyl; z is 0 or 1; and $R^3$ is selected from F, $C_1$-$C_2$ alkyl or $C_1$-$C_2$ fluoroalkyl.

In yet a more preferred embodiment of the invention, X is selected from I, CN, S—$CH_3$, S—$CF_3$, $C_2$-$C_3$ alkyl, $C_1$-$C_3$ fluoroalkyl; $Y^1$ and $Y^2$ are independently selected from O or S; $R^1$ and $R^2$ are independently selected from $C_1$-$C_3$ alkyl, $C_1$-$C_3$ fluoroalkyl or $C_3$-$C_5$ cycloalkyl; z is 0 or 1; and $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In an even more preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_3$ alkyl, $C_1$-$C_3$ fluoroalkyl, $C_3$-$C_5$ cycloalkyl; z is 0, 1 or 2; and $R^3$ is/are independently selected from F, $C_1$-$C_2$ alkyl or $C_1$-$C_2$ fluoroalkyl.

In yet an even more preferred embodiment of the invention, X is selected from I, $CF_3$, CN, S—$CH_3$, S—$CF_3$; $Y^1$ and $Y^2$ are independently selected from O or S; $R^1$ and $R^2$ are independently selected from the group consisting of $C_1$-$C_3$ alkyl, $C_1$-$C_3$ fluoroalkyl, $C_3$-$C_5$ cycloalkyl; z is 0, 1 or 2; and $R^3$ is/are independently selected from F, $C_1$-$C_2$ alkyl or $C_1$-$C_2$ fluoroalkyl.

In yet an even more preferred embodiment of the invention, X is selected from I, $CF_3$, CN, S—$CH_3$, S—$CF_3$; $Y^1$ and $Y^2$ are independently selected from O or S; $R^1$ and $R^2$ are independently selected from the group consisting of $C_1$-$C_3$ alkyl, $C_1$-$C_3$ fluoroalkyl, $C_3$-$C_5$ cycloalkyl; z is 0 or 1; and $R^3$ is/are independently selected from F, $C_1$-$C_2$ alkyl or $C_1$-$C_2$ fluoroalkyl.

In yet an even more preferred embodiment of the invention, X is selected from I, $CF_3$, CN, S—$CH_3$, S—$CF_3$; $Y^1$ and $Y^2$ are independently selected from O or S; $R^1$ and $R^2$ are independently selected from the group consisting of $C_1$-$C_3$ alkyl, $C_1$-$C_3$ fluoroalkyl, $C_3$-$C_5$ cycloalkyl; z is 0 or 1; and $R^3$ is/are independently selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet an even more preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_3$ alkyl, $C_1$-$C_3$ fluoroalkyl, $C_3$-$C_5$ cycloalkyl; z is 0 or 1; and $R^3$ is selected from F, $C_1$-$C_2$ alkyl or $C_1$-$C_2$ fluoroalkyl.

In yet an even more preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_3$ alkyl, $C_1$-$C_3$ fluoroalkyl, $C_3$-$C_5$ cycloalkyl; z is 0 or 1; and $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a yet a more preferred embodiment of the invention, X is selected from I, $CF_3$, CN, S—$CH_3$, S—$CF_3$; $Y^1$ and $Y^2$ are independently selected from O or S; $R^1$ and $R^2$ are independently selected from the group consisting of $C_1$-$C_3$ alkyl, $C_1$-$C_3$ fluoroalkyl, cyclopropyl; z is 0, 1 or 2; and $R^3$ is/are independently selected from F, $C_1$-$C_2$ alkyl or $C_1$-$C_2$ fluoroalkyl.

In a yet a more preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_3$ alkyl, $C_1$-$C_3$ fluoroalkyl, cyclopropyl; z is 0 or 1; and $R^3$ is independently selected from F, $C_1$-$C_2$ alkyl or $C_1$-$C_2$ fluoroalkyl.

In a yet a more preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_3$ alkyl, $C_1$-$C_3$ fluoroalkyl, cyclopropyl; z is 0 or 1; and $R^3$ is independently selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a yet a more preferred embodiment of the invention, X is selected from I, $CF_3$, CN, S—$CH_3$, S—$CF_3$; $Y^1$ and $Y^2$ are independently selected from O or S; $R^1$ and $R^2$ are independently selected from the group consisting of $C_1$-$C_2$ alkyl; z is 0 or 1; and $R^3$ is selected from F, $CH_3$, $CF_3$.

In a yet a more preferred embodiment of the invention, X is selected from I, $CF_3$, CN, S—$CH_3$, S—$CF_3$; $Y^1$ and $Y^2$ are independently selected from O or S; $R^1$ and $R^2$ are independently selected from the group consisting of $C_1$-$C_2$ alkyl; z is 0 or 1; and $R^3$ is selected from F, $CH_3$, $CF_3$ and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a highly preferred embodiment of the invention, X is selected from I, $CF_3$, CN, S—($C_1$-$C_2$ alkyl), S—$CF_3$; $Y^1$ and $Y^2$ are independently selected as O or S; $R^1$ and $R^2$ are independently selected from the group consisting of $C_1$-$C_3$ alkyl, $C_1$-$C_3$ fluoroalkyl, cyclopropyl; z is 0, 1, 2 or 3; and $R^3$ is/are independently selected from F, methyl ($CH_3$) or trifluoromethyl ($CF_3$).

In yet a highly preferred embodiment of the invention, X is selected from I, $CF_3$, CN, S—($C_1$-$C_2$ alkyl), 5-$CF_3$; $Y^1$ and $Y^2$ are independently selected as O or S; $R^1$ and $R^2$ are independently selected from the group consisting of $C_1$-$C_3$ alkyl, $C_1$-$C_3$ fluoroalkyl, cyclopropyl; z is 0 or 1; and $R^3$ is/are independently selected from F, methyl ($CH_3$) or trifluoromethyl ($CF_3$).

In yet a highly preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_2$ alkyl; z is 0 or 1; and $R^3$ is selected from F, methyl ($CH_3$) or trifluoromethyl ($CF_3$).

In yet a highly preferred embodiment of the invention, X is selected from I, $CF_3$, CN, S—$CH_3$, S—$CF_3$; $Y^1$ and $Y^2$ are independently selected from O or S; $R^1$ and $R^2$ are independently selected from the group consisting of $C_1$-$C_2$ alkyl; z is 0 or 1; and $R^3$ is selected from F, methyl ($CH_3$) or trifluoromethyl ($CF_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a more highly preferred embodiment of the invention, X is selected from I, $CF_3$, CN, S—$CH_3$, S—$CF_3$; $Y^1$ and $Y^2$ are independently selected from O or S; $R^1$ and $R^2$ are independently selected from the group consisting of $C_1$-$C_3$ alkyl; z is 0 or 1; and $R^3$ is selected from methyl ($CH_3$) or trifluoromethyl ($CF_3$).

In yet a more highly preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_3$ alkyl, $C_1$-$C_3$ fluoroalkyl; z is 0 or 1; and $R^3$ is selected from F, methyl ($CH_3$) or trifluoromethyl ($CF_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet a more highly preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_2$ alkyl, $C_1$-$C_2$ fluoroalkyl; z is 0 or 1; and $R^3$ is selected from F, methyl ($CH_3$) or trifluoromethyl ($CF_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet a more highly preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_2$ alkyl; z is 0 or 1; and $R^3$ is selected from F, methyl ($CH_3$) or trifluoromethyl ($CF_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet a more highly preferred embodiment of the invention, X is selected from I, $CF_3$, S—$CH_3$, S—$CF_3$, $Y^1$ is O and $Y^2$ is selected from O or S; $R^1$ and $R^2$ are independently selected from the group consisting of $C_1$-$C_2$ alkyl, z is 0 or 1, and $R^3$ is/are selected from F, methyl ($CH_3$) or trifluoromethyl ($CF_3$).

In yet a more highly preferred embodiment of the invention, X is selected from I or $CF_3$; $Y^1$ and $Y^2$ are O; $R^1$ and $R^2$ are methyl ($CH_3$); z is 0 or 1, and $R^3$ is independently selected from F, methyl ($CH_3$) or trifluoromethyl ($CF_3$), most preferably methyl ($CH_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In the most preferred embodiment of the invention, X is $CF_3$; $Y^1$ and $Y^2$ are O; $R^1$ and $R^2$ are methyl ($CH_3$) and z is 0.

In any of the above-mentioned embodiments $R^4$ is most preferably selected as H. In any of the above-mentioned embodiments $Y^1$ and $Y^2$ are most preferably selected as O. In any of the above-mentioned embodiments z is most preferably 0 or 1. In any of the above-mentioned embodiments $R^3$ is most preferably methyl ($CH_3$).

Aspect 2—Selective 5-$HT_{2A}$ Agonists

In the second aspect the invention relates to selective 5-$HT_{2A}$ agonists of the general formula (II)

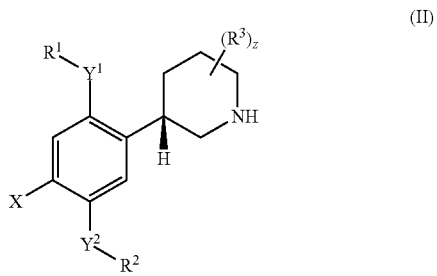

or a pharmaceutically acceptable salt thereof wherein:
X is selected from the group consisting of I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_2$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_{z-o5}$ fluoroalkenyl, $C_{z-o5}$ alkynyl, $C_2$-$C_5$ fluoroalkynyl, $C_3$-$C_5$ cycloalkyl and $C_3$-$C_5$ fluorocycloalkyl;

z denotes the number of $R^3$ groups and is an integer with a value of 0, 1, 2, 3 or 4;

$R^3$ is/are independently selected from the group consisting of F, $C_1$-$C_3$ alkyl, $C_1$-$C_3$ fluoroalkyl, $C_2$-$C_3$ alkenyl or $C_2$-$C_3$ alkynyl;

with the proviso that at least one of $Y^1$ or $Y^2$ are selected as O or S.

Substituent X

The inventors found that the substituent X in Formula (II) was important for the potency of the 5-$HT_{2A}$ agonists and that X tolerated a variety of lipophilic substituents. The skilled person is aware of a range of substituents that are suitable to fulfill the role as a lipophilic substituent. Thus, in an embodiment of the invention, X is selected from I, CN, S—($C_1$-$C_5$ alkyl), S—($C_1$-$C_5$ fluoroalkyl), $C_2$-$C_5$ alkyl, $C_1$-$C_5$ fluoroalkyl. In a preferred embodiment, X is selected from I, CN, S—($C_1$-$C_4$ alkyl), S—($C_1$-$C_4$ fluoroalkyl), $C_2$-$C_4$ alkyl, $C_1$-$C_4$ fluoroalkyl. In yet a preferred embodiment, X is selected from I, CN, S—($C_1$-$C_3$ alkyl), S—($C_1$-$C_3$ fluoroalkyl), $C_2$-$C_3$ alkyl, $C_1$-$C_3$ fluoroalkyl. In yet a preferred embodiment, X is selected from I, CN, S—($C_1$-$C_3$ alkyl), S—($C_1$-$C_3$ fluoroalkyl), $C_2$-$C_5$ alkyl, $C_1$-$C_5$ fluoroalkyl. In a more preferred embodiment, X is selected from I, CN, S—$CH_3$, S—$CF_3$, $C_2$-$C_3$ alkyl, $C_1$-$C_3$ fluoroalkyl. In an even more preferred embodiment of the invention, X is selected from I, $CF_3$, CN, S—$CH_3$, S—$CF_3$. In a yet an even more preferred embodiment, X is selected from I, $CF_3$, CN, S—$CH_3$. In a highly preferred embodiment, X is selected from I, $CF_3$, S—$CH_3$. In an even more highly preferred embodiment of the invention, X is selected from I or $CF_3$. In the most preferred embodiment of the invention, X is selected from $CF_3$.

Substituents $Y^1$ and $Y^2$

The inventors further found that $Y^1$ and $Y^2$ could independently be selected from H, O, S, $C_1$-$C_3$ alkyl, $C_1$-$C_3$ fluoroalkyl, or halogen with the proviso that at least one of $Y^1$ or $Y^2$ is selected as O or S. It follows that when $Y^1$ is H, halogen, $C_1$-$C_3$ fluoroalkyl or $C_1$-$C_3$ alkyl, $R^1$ is not present (deleted). Likewise, when $Y^2$ is H, halogen, $C_1$-$C_3$ fluoroalkyl, or $C_1$-$C_3$ alkyl, $R^2$ is not present (deleted). In an embodiment of the invention $Y^1$ is selected from O, S, $CH_3$ or halogen and $Y^2$ is selected from O, S, $CH_3$ or halogen. In a preferred embodiment of the invention $Y^1$ is selected from O, S, H or halogen and $Y^2$ is selected from O, S, H or halogen. In yet a preferred embodiment $Y^1$ is selected from O, S, or $CH_3$ and $Y^2$ is selected from O, S, or $CH_3$. In a more preferred embodiment of the invention $Y^1$ is selected from O, S or H and $Y^2$ is selected from O, S or H. In yet a more preferred embodiment $Y^1$ is selected from O or S and $Y^2$ is selected from O or S. In yet a preferred embodiment, $Y^1$ is selected from O or S, and $Y^2$ is selected from H, halogen, O or S. In particular, the presence of a heteroatom in $Y^1$ and $Y^2$ provided potent 5-$HT_{2A}$ agonists. Thus, in an embodiment of the invention, $Y^1$ is O, and $Y^2$ is S. In another embodiment of the invention, $Y^1$ is S, and $Y^2$ is O. In yet another embodiment, $Y^1$ and $Y^2$ are S. In the most preferred embodiment of the invention, $Y^1$ and $Y^2$ are O.

Substituent $R^1$ and $R^2$

The inventors surprisingly found that the pharmacophore occupied by $R^1$ and $R^2$ in formula (II) allowed small lipophilic substituents while maintaining 5-$HT_{2A}$ activity and potency of the compounds. Thus, in an embodiment of the invention, $R^1$ and $R^2$ are independently selected from the group consisting of not present ($R^1$ not present if $Y^1$ is H, $C_1$-$C_3$ alkyl, $C_1$-$C_3$ fluoroalkyl or halogen, $R^2$ not present if $Y^2$ is H, $C_1$-$C_3$ alkyl, $C_1$-$C_3$ fluoroalkyl or halogen), $C_1$-$C_5$ alkyl, $C_1$-$C_5$ fluoroalkyl, $C_3$-$C_5$ cycloalkyl and $C_3$-$C_5$ fluorocycloalkyl. In a preferred embodiment of the invention, $R^1$ and $R^2$ are independently selected from the group consisting of $C_1$-$C_3$ alkyl, $C_1$-$C_3$ fluoroalkyl, $C_3$-$C_5$ cycloalkyl and $C_3$-$C_5$ fluorocycloalkyl. In yet a more preferred embodiment, $R^1$ and $R^2$ are independently selected from the group consisting of $C_1$-$C_3$ alkyl, $C_1$-$C_3$ fluoroalkyl and $C_3$-$C_5$ cycloalkyl. In yet an even more preferred embodiment of the invention, $R^1$ and $R^2$ are independently selected from the group consisting of $C_1$-$C_3$ alkyl, $C_1$-$C_3$ fluoroalkyl and cyclopropyl. In an even more preferred embodiment, $R^1$ and $R^2$ are independently selected from the group consisting of $C_1$-$C_3$ alkyl and $C_1$-$C_3$ fluoroalkyl. In a highly preferred embodiment, $R^1$ and $R^2$ are independently selected from the group consisting of $C_1$-$C_2$ alkyl and $C_1$-$C_2$ fluoroalkyl. In another highly preferred embodiment, $R^1$ and $R^2$ are independently selected from $C_1$-$C_2$ alkyl. In an even more preferred embodiment, $R^1$ and $R^2$ are independently selected from the group consisting of methyl ($CH_3$) and trifluoromethyl ($CF_3$). In the most preferred embodiment of the invention, $R^1$ and $R^2$ are both methyl ($CH_3$).

Number (z) of $R^3$ Substituent(s) and Preferred Positions

The inventors further found that the carbon atoms in the piperidine ring system could be substituted with small lipophilic substituents ($R^3$). Thus, according to the present invention, the one or more $R^3$ substituent(s) (if present) is/are present at any of the positions (2), (3), (4), (5) and/or (6) as shown in formula (II) below. More preferably, one or more $R^3$ substituent(s) (if present) is/are present at any of the positions (2), (3) and/or (6) as shown in in formula (II) below, most preferably at position (2) or (3) as shown in in formula (II) below. It follows that two $R^3$ substituents may be present on the same position (carbon atom). The inventors found that the secondary amine (free NH) in the piperidine ring system was highly important for maintaining high agonist activity at the 5-$HT_{2A}$ receptor, whereas nitrogen substituents (tertiary amines) led to a significant loss of potency at 5-$HT_{2A}$ (factor ~80 for compound 59 (N-Et) and a factor ~20 for compound 61 (N-Me) compared to compound 8). Furthermore, N-methylation of the piperidine resulted in a loss of selectivity for 5-$HT_{2A}$ over 5-$HT_{2C}$ as shown for compound 61 in comparison with compound 8. Thus, in the second aspect the piperidine comprises a secondary amine (free NH) (i.e. the piperidine is not N-methylated).

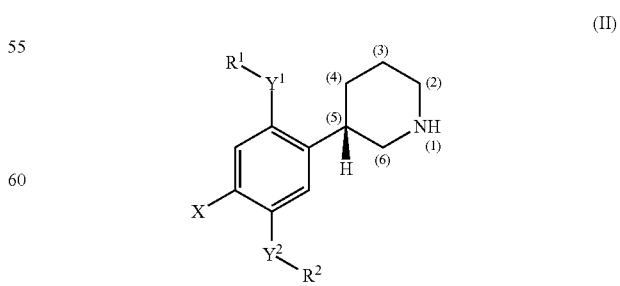

(II)

Thus, in an embodiment of the invention, z is 0-4 such that the piperidine is unsubstituted or substituted with 1-4 $R^3$ groups. In a preferred embodiment of the invention, z is 0-3 such that the piperidine is unsubstituted or substituted with 1-3 $R^3$ groups. In a more preferred embodiment of the invention, z is 0-2 such that the piperidine is unsubstituted or substituted with 1-2 $R^3$ groups. In an even more preferred embodiment of the invention, z is 0-1 such that the piperidine is unsubstituted or substituted with one $R^3$ group. In the most preferred embodiment of the invention z is 0, such that no $R^3$ substituents are present.

In a preferred embodiment of the invention, z is 0 or 1, such that the piperidine is unsubstituted or substituted with one $R^3$ group, and wherein the one $R^3$ group is present in the positions (2), (3), (4), (5) or (6) as shown in formula (II) above, preferably in the any of the positions indicated as (2), (3) or (6) as shown in formula (II) above, most preferably in any of the position indicated as (2) or (3) in formula (II) above.

Type of $R^3$ Substituent(s)

In an embodiment of the invention, the $R^3$ group(s) is/are independently selected from the group consisting of F, $C_1$-$C_3$ alkyl or $C_1$-$C_3$ fluoroalkyl. In a preferred embodiment of the invention, the $R^3$ group(s) is/are independently selected from the group consisting of F, $C_1$-$C_2$ alkyl or $C_1$-$C_2$ fluoroalkyl. In the highly preferred embodiment of the invention, the $R^3$ group(s) is/are independently selected from the group consisting of F, methyl ($CH_3$) or trifluoromethyl ($CF_3$). In the most preferred embodiment of the invention, the $R^3$ group(s) is/are independently selected from the group consisting of F, methyl ($CH_3$), most preferably methyl ($CH_3$).

Stereochemistry

In the second aspect, the compound is a stereoisomer with the absolute stereochemistry at the chiral center as drawn in Formula (II) (i.e. (S)-stereoisomer). It is evident to the skilled person that in case of $R^3$ substituents on the piperidine, one or more additional chiral centers may be present in the molecule. These other chiral centers may be either in the (R) and (S) configuration in accordance with Cahn-Ingold-Prelog priority rules. The number of stereoisomers possible depends on the number of chiral centers present and can be calculated as $2^n$, where n is the number of additional chiral centers. In the present context, the invention is intended to cover all the single stereoisomers possible as well as any mixture thereof. The stereoisomers according to the present invention may be separated using conventional methods in the art. Thus, diastereomers may be separated by selective crystallization, liquid column chromatography, such as conventional silica gel chromatography or High Performance Liquid Chromatography (HPLC) (reverse and normal-phase). Furthermore, enantiomers may be separated using chiral resolution, such as chiral HPLC, chiral SFC or chiral derivatizing agents to form diastereomers that may be separated with any of the above-mentioned conventional methods.

Preferred Embodiments

In a preferred embodiment of the invention, X is selected from I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_2$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl or $C_2$-$C_5$ fluoroalkynyl; $Y^1$ and $Y^2$ are independently selected from H, O, S, $CH_3$ or halogen; $R^1$ and $R^2$ are independently selected from the not present ($R^1$ not present if $Y^1$ is H, $CH_3$ or halogen, $R^2$ not present if $Y^2$ is H, $CH_3$ or halogen), $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl or $C_3$-$C_5$ fluorocycloalkyl; z denotes the number of $R^3$ groups and is an integer with a value of 0, 1, 2, 3 or 4; $R^3$ is/are independently selected from F, $C_1$-$C_3$ alkyl, $C_1$-$C_3$ fluoroalkyl, $C_2$-$C_3$ alkenyl or $C_2$-$C_3$ alkynyl; with the proviso that at least one of $Y^1$ or $Y^2$ is selected as O or S.

In yet a preferred embodiment of the invention, X is selected from I, CN, S—$CH_3$, S—$CF_3$, $C_2$-$C_3$ alkyl, $C_1$-$C_3$ fluoroalkyl; $Y^1$ and $Y^2$ are independently selected from O, S, $CH_3$ or halogen; $R^1$ and $R^2$ are independently selected from not present ($R^1$ not present if $Y^1$ is $CH_3$ or halogen, $R^2$ not present if $Y^2$ is $CH_3$ or halogen), $C_1$-$C_3$ alkyl, $C_1$-$C_3$ fluoroalkyl or $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ is selected as O or S.

In yet a preferred embodiment of the invention, X is selected from I, CN, S—$CH_3$, S—$CF_3$, $C_2$-$C_3$ alkyl or $C_1$-$C_3$ fluoroalkyl; $Y^1$ and $Y^2$ are independently selected from O, $CH_3$, or S; $R^1$ and $R^2$ are independently selected from not present ($R^1$ not present if $Y^1$ is $CH_3$, $R^2$ not present if $Y^2$ is $CH_3$), $C_1$-$C_3$ alkyl, $C_1$-$C_3$ fluoroalkyl or $C_3$-$C_5$ cycloalkyl; z is 0, 1, 2 or 3; and $R^3$ is/are independently selected from F, $C_1$-$C_2$ alkyl or $C_1$-$C_2$ fluoroalkyl.

In a more preferred embodiment of the invention, X is selected from I, CN, S—$CH_3$, S—$CF_3$, $C_2$-$C_3$ alkyl or $C_1$-$C_3$ fluoroalkyl; $Y^1$ and $Y^2$ are independently selected from O or S; $R^1$ and $R^2$ are independently selected from $C_1$-$C_3$ alkyl, $C_1$-$C_3$ fluoroalkyl or $C_3$-$C_5$ cycloalkyl; z is 0, 1, 2 or 3; and $R^3$ is/are independently selected from F, $C_1$-$C_2$ alkyl or $C_1$-$C_2$ fluoroalkyl.

In an even more preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_3$ alkyl, $C_1$-$C_3$ fluoroalkyl, $C_3$-$C_5$ cycloalkyl; z is 0, 1 or 2; and $R^3$ is/are independently selected from F, $C_1$-$C_2$ alkyl or $C_1$-$C_2$ fluoroalkyl.

In a yet more preferred embodiment of the invention, X is selected from I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or cyclopropyl; z is 0, 1 or 2; and $R^3$ is/are independently selected from F, $C_1$-$C_2$ alkyl or $C_1$-$C_2$ fluoroalkyl.

In a highly preferred embodiment of the invention, X is selected from I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or cyclopropyl; z is 0, 1, 2 or 3; and $R^3$ is/are independently selected from F, methyl ($CH_3$) or trifluoromethyl ($CF_3$).

In more highly preferred embodiment of the invention, X is selected from I, $CF_3$, CN, S—$CH_3$, S—$CF_3$; $Y^1$ and $Y^2$ are O; $R^1$ and $R^2$ are independently selected from the group consisting of $C_1$-$C_3$ alkyl, $C_1$-$C_3$ fluoroalkyl; z is 0, 1 or 2; and $R^3$ is/are independently selected from F, methyl ($CH_3$) or trifluoromethyl ($CF_3$).

In yet a more highly preferred embodiment of the invention, X is selected from I, $CF_3$, CN, S—$CH_3$ or S—$CF_3$; $Y^1$ and $Y^2$ are O; $R^1$ and $R^2$ are independently selected from $C_1$-$C_2$ alkyl or $C_1$-$C_2$ fluoroalkyl; z is 0, 1 or 2; and $R^3$ is/are independently selected from F, methyl ($CH_3$) or trifluoromethyl ($CF_3$).

In yet a more highly preferred embodiment of the invention, X is selected from I, $CF_3$, CN, S—$CH_3$ or S—$CF_3$; $Y^1$ and $Y^2$ are O; $R^1$ and $R^2$ are independently selected from $C_1$-$C_2$ alkyl or $C_1$-$C_2$ fluoroalkyl; z is 0 or 1; and $R^3$ is/are selected from F, methyl ($CH_3$) or trifluoromethyl ($CF_3$).

In yet a more highly preferred embodiment of the invention, X is selected from I, $CF_3$, CN, S—$CH_3$ or S—$CF_3$; $Y^1$ and $Y^2$ are O; $R^1$ and $R^2$ are independently selected from $C_1$-$C_2$ alkyl; z is 0 or 1; and $R^3$ is/are selected from F, methyl ($CH_3$) or trifluoromethyl ($CF_3$).

In yet a more highly preferred embodiment of the invention, X is selected from I or $CF_3$; $Y^1$ and $Y^2$ are O; $R^1$ and $R^2$ are methyl ($CH_3$); z is 0, 1 or 2, and $R^3$ is/are independently selected from F, methyl ($CH_3$) or trifluoromethyl ($CF_3$).

In the most preferred embodiment of the invention, X is $CF_3$; $Y^1$ and $Y^2$ are O; $R^1$ and $R^2$ are methyl ($CH_3$) and z is 0.

Furthermore, any preferred embodiments mentioned under aspect 1 apply equally well to aspect 2 for the compounds of formula (II).

Aspect 3—Mixed 5-$HT_{2A}$/5-$HT_{2C}$ Agonists

In the third aspect, the invention relates to 5-$HT_{2A}$/5-$HT_{2C}$ agonists of the general formula (III)

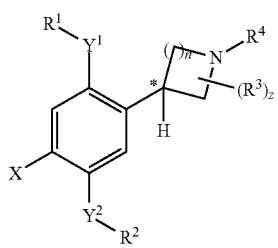

(III)

or a pharmaceutically acceptable salt thereof wherein:
X is selected from the group consisting of I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_2$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;
$Y^1$ and $Y^2$ are independently selected from the group consisting of H, O, S, $C_1$-$C_3$ alkyl, $C_1$-$C_3$ fluoroalkyl, and halogen;
$R^1$ is not present when $Y^1$ is H, $C_1$-$C_3$ alkyl, $C_1$-$C_3$ fluoroalkyl, or halogen;
$R^2$ is not present when $Y^2$ is H, $C_1$-$C_3$ alkyl, $C_1$-$C_3$ fluoroalkyl, or halogen;
when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl or $C_3$-$C_5$ fluorocycloalkyl;
* denotes the (R) or (S) stereoisomer or any mixture thereof if a chiral center is present;
n is an integer with a value of 1, 2, 3 or 4 to form an azetidine, pyrrolidine, piperidine or azepane ring system;
z denotes the number of $R^3$ groups and is an integer with a value of 0, 1, 2, 3 or 4;
$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;
$R^4$ is selected from H or $CH_3$;
with the proviso that when n=3, * denotes the (R) stereoisomer and further with the proviso that at least one of $Y^1$ or $Y^2$ are selected as O or S.

In the third aspect, X, Y', $Y^2$, $R^1$, $R^2$, z and $R^3$ are selected with the same preference as in aspect 1 or 2. Thus, the embodiments under all the headings "Substituent X", "Substituents $Y^1$ and $Y^2$", "Substituents $R^1$ and $R^2$", "Number (z) of $R^3$ substituents and preferred positions" and "Type of $R^3$ substituent(s)" apply equally to aspect 3. Likewise, the preferred embodiments described under aspect 1 and 2 apply equally to aspect 3 for all the ring systems (i.e. the azetidine, pyrrolidine, piperidine or azepane ring system).

In the most preferred embodiments $R^4$ is H.

Stereochemistry (*)

The inventors surprisingly found that both the (R) and (S)-stereoisomers of Formula (IV), (V) and (VI) shown below resulted in potent 5-$HT_{2A}$/5-$HT_{2C}$ agonists with minor selectivity towards the 5-$HT_{2A}$ receptor over 5-$HT_{2C}$ receptor (approximately a factor 2-5 in $EC_{50}$ values), when measured in the $Ca^{2+}$/Fluo-4 functional assay as described herein. It should be noted that in some cases, no chiral center is present (e.g. when n=1 to form an azetidine with no $R^3$ substituents). Likewise, the (R)-stereoisomers shown in Formula (VII) (i.e. (R)-piperidines) also provided 5-$HT_{2A}$ agonists with mixed 5-$HT_{2A}$/5-$HT_{2C}$ agonist profiles and with minor selectivity towards the 5-$HT_{2A}$ receptor over 5-$HT_{2C}$ receptor (approximately a factor 2-10 in $EC_{50}$), when measured in the $Ca^{2+}$/Fluo-4 functional assay. However, these agonists had a significant loss of potency (approximately 13-70-fold on 5-$HT_{2A}$ and a 20-70-fold on 5-$HT_{2C}$ when compared with the (R)-pyrrolidines). Thus, in a preferred embodiment of aspects 3 and 6, n is an integer with a value of 1, 2 or 4, more preferably n is an integer with a value of 1 or 2, most preferably n is an integer with a value of 1.

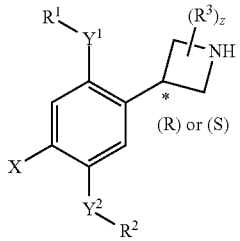

(IV)

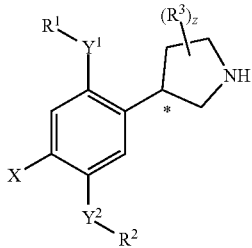

(V)

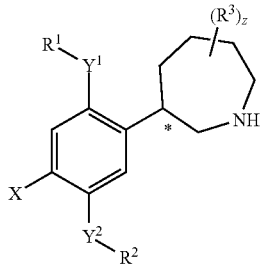

(VI)

-continued

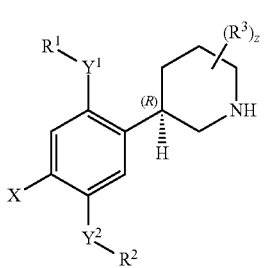
(VII)

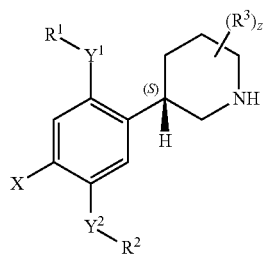
(II)

In aspects 3 and 6 of the invention, (*) is intended to cover both the (R) and (S)-stereoisomers of Formula (IV), (V), (VI) shown above (i.e. the enantiomers when no other chiral centers are present) as well as any mixture thereof and the (R)-stereoisomers of Formula (VII). It is evident to the skilled person that in case of $R^3$ substituents on the saturated heterocycle (i.e. the azetidine, pyrrolidine, piperidine or azepane ring system) one or more additional chiral centers may be present in the molecule. The number of stereoisomers possible depends on the number of chiral centers present and can be calculated as $2^n$, where n is the number of chiral centers. In the present context, the invention is intended to cover all the single stereoisomers possible as well as any mixture thereof. The stereoisomers according to the present invention may be separated using conventional methods in the art as described under aspect 1.

Aspect 4—Medical Use of 5-HT$_{2A}$ Agonists

In the fourth aspect, the invention relates to 5-HT$_{2A}$ agonists of the general formula (I) or a pharmaceutically acceptable salt thereof for use as a medicament

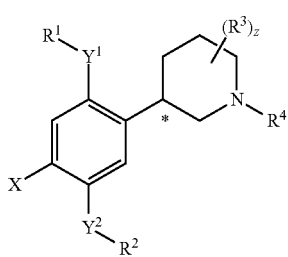
(I)

wherein:
* denotes the (R) or (S) stereoisomer or any mixture thereof;
X is selected from the group consisting of F, Cl, Br, I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;
$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;
$R^2$ is not present when $Y^2$ is H, $C_1$-$C_3$ alkyl, $C_1$-$C_3$ fluoroalkyl, or halogen;
when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl and $C_3$-$C_5$ fluorocycloalkyl;
z denotes the number of $R^3$ groups and is an integer with a value of 0, 1, 2, 3 or 4;
$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;
$R^4$ is selected from H or $CH_3$;
with the proviso that at least one of $Y^1$ or $Y^2$ are selected as O or S.

In the fourth aspect, $Y^1$, $Y^2$, $R^1$, $R^2$, z, and $R^3$ are selected with the same preference as in aspects 1 and 2. Thus, the embodiments under the headings "Substituents $Y^1$ and $Y^2$", "Substituents $R^1$ and $R^2$", "Number (z) of $R^3$ substituents and preferred positions" and "Type of $R^3$ substituent(s)" in aspects 1 and 2 apply equally well to aspect 4. Furthermore, the preferred embodiments in aspects 1 and 2 also apply to aspect 4. In addition, the description under the heading "Stereochemistry" in aspect 1 applies equally to aspect 4.

Substituent X on the Aromatic Ring

For aspects 4, 5 and 6 (i.e. medical use aspects/method of treatment aspects), X further includes $CH_3$, F, Cl and Br. Thus, in an embodiment of aspects 4, 5 or 6, X is selected from F, Cl, Br, I, CN, S—($C_1$-$C_5$ alkyl), S—($C_1$-$C_5$ fluoroalkyl), $C_1$-$C_5$ alkyl or $C_1$-$C_5$ fluoroalkyl. In a preferred embodiment, X is selected from F, Cl, Br, I, CN, S—($C_1$-$C_3$ alkyl), S—($C_1$-$C_3$ fluoroalkyl), $C_1$-$C_5$ alkyl or $C_1$-$C_5$ fluoroalkyl. In yet a preferred embodiment, X is selected from F, Cl, Br, I, CN, S—($C_1$-$C_4$ alkyl), S—($C_1$-$C_4$ fluoroalkyl), $C_1$-$C_4$ alkyl or $C_1$-$C_4$ fluoroalkyl. In yet a preferred embodiment, X is selected from F, Cl, Br, I, CN, S—($C_1$-$C_3$ alkyl), S—($C_1$-$C_3$ fluoroalkyl), $C_1$-$C_3$ alkyl or $C_1$-$C_3$ fluoroalkyl. In yet a preferred embodiment, X is selected from F, Cl, Br, I, CN, S—($C_1$-$C_2$ alkyl), S—($C_1$-$C_2$ fluoroalkyl), $C_1$-$C_2$ alkyl or $C_1$-$C_2$ fluoroalkyl. In yet a preferred embodiment, X is selected from F, Cl, Br, I, CN, S—($C_1$-$C_2$ alkyl), $C_1$-$C_2$ alkyl or $C_1$-$C_2$ fluoroalkyl. In a more preferred embodiment, X is selected from Cl, Br, I, CN, S—$CH_3$, S—$CF_3$, $C_1$-$C_3$ alkyl or $C_1$-$C_3$ fluoroalkyl. In an even more preferred embodiment of the invention, X is selected from Cl, Br, I, $CH_3$, $CF_3$, CN, S—$CH_3$ or S—$CF_3$. In a yet an even more preferred embodiment, X is selected from Cl, Br, I, $CF_3$, CN or S—$CH_3$. In a highly preferred embodiment, X is selected from Cl, Br, I, $CF_3$ or S—$CH_3$. In another highly preferred embodiment, X is selected from Cl, Br, I, or $CF_3$. In an even more highly preferred embodiment, X is selected from Cl, I, or $CF_3$. In a yet even more highly preferred embodiment, X is selected from I or $CF_3$. In the most preferred embodiment of the invention, X is selected from $CF_3$.

Preferred Embodiments

In a preferred embodiment of the invention, X is selected from F, Cl, Br, I, CN, S—($C_1$-$C_3$ alkyl), S—($C_1$-$C_3$ fluoroalkyl), $C_1$-$C_3$ alkyl, $C_1$-$C_3$ fluoroalkyl; $Y^1$ is selected from H, O, S, $CH_3$ or halogen; $Y^2$ is selected from H, O, S, $CH_3$ or halogen. $R^1$ and $R^2$ are independently selected from not present ($R^1$ not present if $Y^1$ is H, $CH_3$ or halogen, $R^2$ not present if $Y^2$ is H, $CH_3$ or halogen), $C_1$-$C_3$ alkyl, $C_1$-$C_3$ fluoroalkyl or cyclopropyl; z is 0, 1, 2 or 3; and $R^3$ is/are independently selected from F, $CH_3$ or $CF_3$; with the proviso that at least one of $Y^1$ or $Y^2$ is selected as O or S.

In yet a preferred embodiment of the invention, X is selected from F, Cl, Br, I, CN, S—($C_1$-$C_3$ alkyl), S—($C_1$-$C_3$ fluoroalkyl), $C_1$-$C_3$ alkyl or $C_1$-$C_3$ fluoroalkyl; $Y^1$ is selected from H, O, or S; $Y^2$ is selected from H, O, or S. $R^1$ and $R^2$ are independently selected from the group consisting of not present ($R^1$ not present if $Y^1$ is H, $R^2$ not present if $Y^2$ is H), $C_1$-$C_3$ alkyl, $C_1$-$C_3$ fluoroalkyl, cyclopropyl; z is 0, 1, 2 or 3; and $R^3$ is/are independently selected from F, $CH_3$ or $CF_3$; with the proviso that at least one of $Y^1$ or $Y^2$ is selected as O or S.

In yet a preferred embodiment of the invention, X is selected from F, Cl, Br, I, CN, S—($C_1$-$C_2$ alkyl), 5-$CF_3$, $C_1$-$C_3$ alkyl or $C_1$-$C_3$ fluoroalkyl; $Y^1$ is selected from O, S, $CH_3$ or halogen; $Y^2$ could be selected from H, O, S, $CH_3$ or halogen. $R^1$ and $R^2$ are independently selected from not present ($R^1$ not present if $Y^1$ is $CH_3$ or halogen, $R^2$ not present if $Y^2$ is H, $CH_3$ or halogen), $C_1$-$C_3$ alkyl, $C_1$-$C_3$ fluoroalkyl or $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ is selected as O or S.

In yet a preferred embodiment of the invention, X is selected from F, Cl, Br, I, CN, S—($C_1$-$C_2$ alkyl), 5-$CF_3$, $C_1$-$C_3$ alkyl, $C_1$-$C_3$ fluoroalkyl; $Y^1$ is selected from O, S, $CH_3$ or halogen; $Y^2$ is selected from H, O, S, $CH_3$ or halogen. $R^1$ and $R^2$ are independently selected from the group consisting of not present ($R^1$ not present if $Y^1$ is $CH_3$ or halogen, $R^2$ not present if $Y^2$ is H, $CH_3$ or halogen), $C_1$-$C_3$ alkyl, $C_1$-$C_3$ fluoroalkyl, $C_3$-$C_5$ cycloalkyl; z is 0 or 1; and $R^3$ is selected from F, $C_1$-$C_2$ alkyl or $C_1$-$C_2$ fluoroalkyl.

In yet a preferred embodiment of the invention, X is selected from F, Cl, Br, I, CN, S—($C_1$-$C_2$ alkyl), 5-$CF_3$, $C_1$-$C_3$ alkyl, $C_1$-$C_3$ fluoroalkyl; $Y^1$ is selected from O, S, $CH_3$ or halogen; $Y^2$ is selected from H, O, S, $CH_3$ or halogen. $R^1$ and $R^2$ are independently selected from not present ($R^1$ not present if $Y^1$ is $CH_3$ or halogen, $R^2$ not present if $Y^2$ is H, $CH_3$ or halogen), $C_1$-$C_3$ alkyl, $C_1$-$C_3$ fluoroalkyl or $C_3$-$C_5$ cycloalkyl; z is 0 or 1; and $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a preferred embodiment of the invention, X is selected from F, Cl, Br, I, CN, S—$CH_3$, S—$CF_3$, $C_1$-$C_3$ alkyl, $C_1$-$C_3$ fluoroalkyl; $Y^1$ is selected from O or S; $Y^2$ could be selected from H, O, S, $CH_3$ or halogen. $R^1$ is selected from $C_1$-$C_3$ alkyl, $C_1$-$C_3$ fluoroalkyl or $C_3$-$C_5$ cycloalkyl; $R^2$ is selected from not present ($R^2$ not present if $Y^2$ is H, $CH_3$ or halogen), $C_1$-$C_3$ alkyl, $C_1$-$C_3$ fluoroalkyl or $C_3$-$C_5$ cycloalkyl; z is 0, 1, 2 or 3; and $R^3$ is/are independently selected from F, $C_1$-$C_2$ alkyl or $C_1$-$C_2$ fluoroalkyl.

In yet a preferred embodiment of the invention, X is selected from F, Cl, Br, I, CN, S—$CH_3$, S—$CF_3$, $C_1$-$C_3$ alkyl, $C_1$-$C_3$ fluoroalkyl; $Y^1$ is selected from O or S; $Y^2$ is selected from H, O, S, $CH_3$ or halogen. $R^1$ is selected from $C_1$-$C_3$ alkyl, $C_1$-$C_3$ fluoroalkyl or $C_3$-$C_5$ cycloalkyl; $R^2$ is selected from not present ($R^2$ not present if $Y^2$ is H, $CH_3$ or halogen), $C_1$-$C_3$ alkyl, $C_1$-$C_3$ fluoroalkyl or $C_3$-$C_5$ cycloalkyl; z is 0 or 1; $R^3$ is selected from F, $C_1$-$C_2$ alkyl or $C_1$-$C_2$ fluoroalkyl.

In yet a preferred embodiment of the invention, X is selected from F, Cl, Br, I, CN, S—$CH_3$, S—$CF_3$, $C_1$-$C_3$ alkyl, $C_1$-$C_3$ fluoroalkyl; $Y^1$ is selected from O or S; $Y^2$ is selected from H, O, S, $CH_3$ or halogen. $R^1$ is selected from $C_1$-$C_3$ alkyl, $C_1$-$C_3$ fluoroalkyl or $C_3$-$C_5$ cycloalkyl; $R^2$ is selected from not present ($R^2$ not present if $Y^2$ is H, $CH_3$ or halogen), $C_1$-$C_3$ alkyl, $C_1$-$C_3$ fluoroalkyl or $C_3$-$C_5$ cycloalkyl; z is 0 or 1; $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a more preferred embodiment of the invention, X is selected from F, Cl, Br, I, CN, S—$CH_3$, S—$CF_3$, $C_1$-$C_3$ alkyl, $C_1$-$C_3$ fluoroalkyl; $Y^1$ and $Y^2$ are independently selected from O or S; $R^1$ and $R^2$ are independently selected from $C_1$-$C_3$ alkyl, $C_1$-$C_3$ fluoroalkyl or $C_3$-$C_5$ cycloalkyl; z is 0, 1, 2 or 3; and $R^3$ is/are independently selected from F, $C_1$-$C_2$ alkyl or $C_1$-$C_2$ fluoroalkyl.

In yet a more preferred embodiment of the invention, X is selected from F, Cl, Br, I, CN, S—$CH_3$, S—$CF_3$, $C_1$-$C_3$ alkyl, $C_1$-$C_3$ fluoroalkyl; $Y^1$ and $Y^2$ are independently selected from O or S; $R^1$ and $R^2$ are independently selected from the group consisting of $C_1$-$C_3$ alkyl, $C_1$-$C_3$ fluoroalkyl, $C_3$-$C_5$ cycloalkyl; z is 0 or 1; and $R^3$ is selected from F, $C_1$-$C_2$ alkyl or $C_1$-$C_2$ fluoroalkyl.

In yet a more preferred embodiment of the invention, X is selected from F, Cl, Br, I, CN, S—$CH_3$, S—$CF_3$, $C_1$-$C_3$ alkyl or $C_1$-$C_3$ fluoroalkyl; $Y^1$ and $Y^2$ are independently selected from O or S; $R^1$ and $R^2$ are independently selected from $C_1$-$C_3$ alkyl, $C_1$-$C_3$ fluoroalkyl or $C_3$-$C_5$ cycloalkyl; z is 0 or 1; and $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In an even more preferred embodiment of the invention, X is selected from F, Cl, Br, I, $CH_3$, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or $C_3$-$C_5$ cycloalkyl; z is 0, 1 or 2; and $R^3$ is/are independently selected from F, $C_1$-$C_2$ alkyl or $C_1$-$C_2$ fluoroalkyl.

In yet an even more preferred embodiment of the invention, X is selected from F, Cl, Br, I, $CH_3$, $CF_3$, CN, S—$CH_3$, S—$CF_3$; $Y^1$ and $Y^2$ are independently selected from O or S; $R^1$ and $R^2$ are independently selected from the group consisting of $C_1$-$C_3$ alkyl, $C_1$-$C_3$ fluoroalkyl, $C_3$-$C_5$ cycloalkyl; z is 0, 1 or 2; and $R^3$ is/are independently selected from F, $C_1$-$C_2$ alkyl or $C_1$-$C_2$ fluoroalkyl.

In yet an even more preferred embodiment of the invention, X is selected from Cl, Br, I, $CH_3$, $CF_3$, CN, S—$CH_3$, S—$CF_3$; $Y^1$ and $Y^2$ are independently selected from O or S; $R^1$ and $R^2$ are independently selected from $C_1$-$C_3$ alkyl, $C_1$-$C_3$ fluoroalkyl or $C_3$-$C_5$ cycloalkyl; z is 0 or 1; and $R^3$ is selected from F, $C_1$-$C_2$ alkyl or $C_1$-$C_2$ fluoroalkyl.

In yet an even more preferred embodiment of the invention, X is selected from Cl, Br, I, $CH_3$, $CF_3$, CN, S—$CH_3$ or S—$CF_3$; $Y^1$ and $Y^2$ are independently selected from O or S; $R^1$ and $R^2$ are independently selected from $C_1$-$C_3$ alkyl, $C_1$-$C_3$ fluoroalkyl or $C_3$-$C_5$ cycloalkyl; z is 0 or 1; and $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet an even more preferred embodiment of the invention, X is selected from Cl, Br, I, $CH_3$, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or $C_3$-$C_5$ cycloalkyl; z is 0 or 1; and $R^3$ is selected from F, $C_1$-$C_2$ alkyl or $C_1$-$C_2$ fluoroalkyl.

In yet an even more preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or $C_3$-$C_5$ cycloalkyl; z is 0 or 1; and $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a yet a more preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or cyclopropyl; z is 0, 1 or 2; and $R^3$ is/are independently selected from F, $C_1$-$C_2$ alkyl or $C_1$-$C_2$ fluoroalkyl.

In a yet a more preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or cyclopropyl; z is 0 or 1; and $R^3$ is selected from F, $C_1$-$C_2$ alkyl or $C_1$-$C_2$ fluoroalkyl.

In a yet a more preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or cyclopropyl; z is 0 or 1; and $R^3$ is selected from F, $C_1$-$C_2$ alkyl or $C_1$-$C_2$ fluoroalkyl and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a yet a more preferred embodiment of the invention, X is selected from Cl, Br, I, $CF_3$, CN, S—$CH_3$ or S—$CF_3$; $Y^1$ and $Y^2$ are independently selected from O or S; $R^1$ and $R^2$ are independently selected from $C_1$-$C_2$ alkyl; z is 0 or 1; and $R^3$ is selected from F, $CH_3$ or $CF_3$.

In a yet a more preferred embodiment of the invention, X is selected from Cl, Br, I, $CF_3$, CN, S—$CH_3$, S—$CF_3$; $Y^1$ and $Y^2$ are independently selected from O or S; $R^1$ and $R^2$ are independently selected from $C_1$-$C_2$ alkyl; z is 0 or 1; and $R^3$ is selected from F, $CH_3$, $CF_3$ and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a highly preferred embodiment of the invention, X is selected from Cl, Br, I, $CF_3$, CN, S—($C_1$-$C_2$ alkyl) or S—$CF_3$; $Y^1$ and $Y^2$ are independently selected from O or S; $R^1$ and $R^2$ are independently selected from $C_1$-$C_3$ alkyl, $C_1$-$C_3$ fluoroalkyl, cyclopropyl; z is 0, 1, 2 or 3; and $R^3$ is/are independently selected from F, methyl ($CH_3$) or trifluoromethyl ($CF_3$).

In yet a highly preferred embodiment of the invention, X is selected from Cl, Br, I, $CF_3$, CN, S—($C_1$-$C_2$ alkyl) or S—$CF_3$; $Y^1$ and $Y^2$ are independently selected from O or S; $R^1$ and $R^2$ are independently selected from $C_1$-$C_3$ alkyl, $C_1$-$C_3$ fluoroalkyl or cyclopropyl; z is 0 or 1; and $R^3$ is selected from F, methyl ($CH_3$) or trifluoromethyl ($CF_3$).

In yet a highly preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_2$ alkyl; z is 0 or 1; and $R^3$ is selected from F, methyl ($CH_3$) or trifluoromethyl ($CF_3$).

In yet a highly preferred embodiment of the invention, X is selected from Cl, Br, I, $CF_3$, CN, S—$CH_3$ or S—$CF_3$; $Y^1$ and $Y^2$ are independently selected from O or S; $R^1$ and $R^2$ are independently selected $C_1$-$C_2$ alkyl; z is 0 or 1; and $R^3$ is selected from F, methyl ($CH_3$) or trifluoromethyl ($CF_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In a more highly preferred embodiment of the invention, X is selected from Cl, Br, I, $CF_3$, CN, S—$CH_3$ or S—$CF_3$; $Y^1$ and $Y^2$ are independently selected from O or S; $R^1$ and $R^2$ are independently selected from $C_1$-$C_3$ alkyl; z is 0 or 1; and $R^3$ is selected from methyl ($CH_3$) or trifluoromethyl ($CF_3$).

In yet a more highly preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl; z is 0 or 1; and $R^3$ is selected from F, methyl ($CH_3$) or trifluoromethyl ($CF_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet a more highly preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_2$ alkyl or $C_1$-$C_2$ fluoroalkyl; z is 0 or 1; and $R^3$ is selected from F, methyl ($CH_3$) or trifluoromethyl ($CF_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet a more highly preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_2$ alkyl; z is 0 or 1; and $R^3$ is selected from F, methyl ($CH_3$) or trifluoromethyl ($CF_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet a more highly preferred embodiment of the invention, X is selected from Cl, Br, I, $CF_3$, S—$CH_3$ or S—$CF_3$; $Y^1$ is O and $Y^2$ is selected from O or S; $R^1$ and $R^2$ are independently selected from $C_1$-$C_2$ alkyl; z is 0 or 1, and $R^3$ is/are selected from F, methyl ($CH_3$) or trifluoromethyl ($CF_3$).

In yet a more highly preferred embodiment of the invention, X is selected from Cl, Br, I or $CF_3$; $Y^1$ and $Y^2$ are O; $R^1$ and $R^2$ are methyl ($CH_3$); z is 0 or 1; $R^3$ is independently selected from F, methyl ($CH_3$) or trifluoromethyl ($CF_3$), most preferably methyl ($CH_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In yet a more highly preferred embodiment of the invention, X is selected from I or $CF_3$; $Y^1$ and $Y^2$ are O; $R^1$ and $R^2$ are methyl ($CH_3$); z is 0 or 1; $R^3$ is selected from methyl ($CH_3$) or trifluoromethyl ($CF_3$), most preferably methyl ($CH_3$) and wherein the $R^3$ group is present in any of the positions indicated as (2), (3), (4), (5) or (6) in formula (I) above, preferably in any of the positions indicated as (2), (3) or (6) in formula (I) above, most preferably in any of the positions indicated as (2) or (3) in formula (I) above.

In the most preferred embodiment of the invention, X is $CF_3$; $Y^1$ and $Y^2$ are O; $R^1$ and $R^2$ are methyl ($CH_3$) and z is 0.

In any of the above embodiments $R^4$ is most preferably selected as H.

Aspect 5—Medical Use of Selective 5-$HT_{2A}$ Agonists

In the fifth aspect, the invention relates to selective 5-$HT_{2A}$ agonists of the general formula (II) or a pharmaceutically acceptable salt thereof for use as a medicament

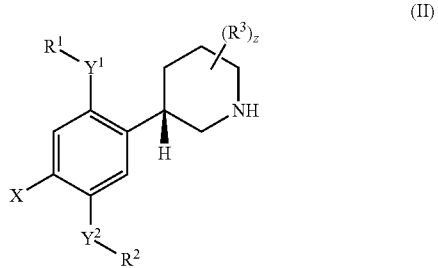

(II)

wherein:
X is selected from the group consisting of F, Cl, Br, I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl and $C_2$-$C_5$ fluoroalkynyl;
$Y^1$ and $Y^2$ are independently selected from the group consisting of H, O, S, $C_1$-$C_3$ alkyl, $C_1$-$C_3$ fluoroalkyl, and halogen;
$R^1$ is not present when $Y^1$ is H, $C_1$-$C_3$ alkyl, $C_1$-$C_3$ fluoroalkyl, or halogen;
$R^2$ is not present when $Y^2$ is H, $C_1$-$C_3$ alkyl, $C_1$-$C_3$ fluoroalkyl, or halogen;
when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl or $C_3$-$C_5$ fluorocycloalkyl;
z denotes the number of $R^3$ groups and is an integer with a value of 0, 1, 2, 3 or 4;
$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;
with the proviso that at least one of $Y^1$ or $Y^2$ are selected as O or S.

In the fifth aspect, $Y^1$, $Y^2$, $R^1$, $R^2$, z, and $R^3$ are selected with the same preference as in aspects 1 and 2. Thus, the embodiments under the headings "Substituents $Y^1$ and $Y^2$", "Substituents $R^1$ and $R^2$", "Number (z) of $R^3$ substituents and preferred positions" and "Type of $R^3$ substituent(s)" in aspects 1 and 2 apply equally well to aspect 5. Furthermore, the preferred embodiments in aspects 1, 2 and 4 also apply to aspect 5. In addition, the description under the heading "Stereochemistry" in aspect 2 applies equally to aspect 5.

Substituent X on the Aromatic Ring

For aspects 4, 5 and 6 (i.e. medical use aspects), X also includes $CH_3$, F, Cl and Br. Thus, in an embodiment of aspects 4, 5 or 6, X is selected from F, Cl, Br, I, CN, S—($C_1$-$C_5$ alkyl), S—($C_1$-$C_5$ fluoroalkyl), $C_1$-$C_5$ alkyl or $C_1$-$C_5$ fluoroalkyl. In a preferred embodiment, X is selected from F, Cl, Br, I, CN, S—($C_1$-$C_3$ alkyl), S—($C_1$-$C_3$ fluoroalkyl), $C_1$-$C_5$ alkyl or $C_1$-$C_5$ fluoroalkyl. In a more preferred embodiment, X is selected from Cl, Br, I, CN, S—$CH_3$, S—$CF_3$, $C_1$-$C_3$ alkyl or $C_1$-$C_3$ fluoroalkyl. In yet a more preferred embodiment, X is selected from Cl, Br, I, S—$CH_3$, S—$CF_3$, $C_1$-$C_3$ alkyl or $C_1$-$C_3$ fluoroalkyl. In an even more preferred embodiment of the invention, X is selected from Cl, Br, I, $CF_3$, CN, S—$CH_3$ or S—$CF_3$. In yet an even more preferred embodiment of the invention, X is selected from Cl, Br, I, $CF_3$, S—$CH_3$ or S—$CF_3$. In a yet an even more preferred embodiment, X is selected from Cl, Br, I, $CF_3$, CN or S—$CH_3$. In a highly preferred embodiment, X is selected from Cl, Br, I, $CF_3$ or S—$CH_3$. In another highly preferred embodiment, X is selected from Cl, Br, I, or $CF_3$. In an even more highly preferred embodiment, X is selected from Cl, I, or $CF_3$. In a yet even more highly preferred embodiment, X is selected from I or $CF_3$. In the most preferred embodiment of the invention, X is selected from $CF_3$.

Preferred Embodiments

In a preferred embodiment of the invention, X is selected from F, Cl, Br, I, CN, S—($C_1$-$C_3$ alkyl), S—($C_1$-$C_3$ fluoroalkyl), $C_1$-$C_3$ alkyl or $C_1$-$C_3$ fluoroalkyl; $Y^1$ and $Y^2$ are independently selected from O, $CH_3$, or S; $R^1$ and $R^2$ are independently selected from not present ($R^1$ not present if $Y^1$ is $CH_3$, $R^2$ not present if $Y^2$ is $CH_3$), $C_1$-$C_3$ alkyl, $C_1$-$C_3$ fluoroalkyl, $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ is selected as O or S.

In yet a preferred embodiment of the invention, X is selected from F, Cl, Br, I, CN, S—($C_1$-$C_3$ alkyl), S—($C_1$-$C_3$ fluoroalkyl), $C_1$-$C_3$ alkyl or $C_1$-$C_3$ fluoroalkyl; $Y^1$ and $Y^2$ are independently selected from H, O, or S; $R^1$ and $R^2$ are independently selected from not present ($R^1$ not present if $Y^1$ is H, $R^2$ not present if $Y^2$ is H), $C_1$-$C_3$ alkyl, $C_1$-$C_3$ fluoroalkyl or $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ is selected as O or S.

In yet a preferred embodiment of the invention, X is selected from F, Cl, Br, I, CN, S—($C_1$-$C_3$ alkyl), S—($C_1$-$C_3$ fluoroalkyl), $C_1$-$C_3$ alkyl or $C_1$-$C_3$ fluoroalkyl; $Y^1$ and $Y^2$ are independently selected from halogen, O or S; $R^1$ and $R^2$ are independently selected from not present ($R^1$ not present if $Y^1$ is halogen, $R^2$ not present if $Y^2$ is halogen), $C_1$-$C_3$ alkyl, $C_1$-$C_3$ fluoroalkyl, $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ is selected as O or S.

In a preferred embodiment of the invention, X is selected from F, Cl, Br, I, CN, S—$CH_3$, S—$CF_3$, $C_1$-$C_3$ alkyl or $C_1$-$C_3$ fluoroalkyl; $Y^1$ and $Y^2$ are independently selected from O, $CH_3$ or S; $R^1$ and $R^2$ are independently selected from not present ($R^1$ not present if $Y^1$ is $CH_3$, $R^2$ not present if $Y^2$ is $CH_3$), $C_1$-$C_3$ alkyl, $C_1$-$C_3$ fluoroalkyl, $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ are selected as O or S.

In yet a preferred embodiment of the invention, X is selected from F, Cl, Br, I, CN, S—$CH_3$, S—$CF_3$, $C_1$-$C_3$ alkyl or $C_1$-$C_3$ fluoroalkyl; $Y^1$ and $Y^2$ are independently selected from H, O or S; $R^1$ and $R^2$ are independently selected from not present ($R^1$ not present if $Y^1$ is H, $R^2$ not present if $Y^2$ is H), $C_1$-$C_3$ alkyl, $C_1$-$C_3$ fluoroalkyl or $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ is selected as O or S.

In yet a preferred embodiment of the invention, X is selected from F, Cl, Br, I, CN, S—$CH_3$, S—$CF_3$, $C_1$-$C_3$ alkyl, $C_1$-$C_3$ fluoroalkyl; $Y^1$ and $Y^2$ are independently selected from halogen, O or S; $R^1$ and $R^2$ are independently selected from not present ($R^1$ not present if $Y^1$ is halogen, $R^2$ not present if $Y^2$ is halogen), $C_1$-$C_3$ alkyl, $C_1$-$C_3$ fluoroalkyl or $C_3$-$C_5$ cycloalkyl; z is 0, 1, 2 or 3; and $R^3$ is/are independently selected from F, $C_1$-$C_2$ alkyl or $C_1$-$C_2$ fluoroalkyl; with the proviso that at least one of $Y^1$ or $Y^2$ is selected as O or S.

In a more preferred embodiment of the invention, X is selected from Cl, Br, I, CN, S—$CH_3$, S—$CF_3$, $C_1$-$C_3$ alkyl or $C_1$-$C_3$ fluoroalkyl; $Y^1$ and $Y^2$ are independently selected from O or S; $R^1$ and $R^2$ are independently selected from $C_1$-$C_3$ alkyl, $C_1$-$C_3$ fluoroalkyl or $C_3$-$C_5$ cycloalkyl; z is 0, 1 or 2; and $R^3$ is/are independently selected from F, $C_1$-$C_2$ alkyl or $C_1$-$C_2$ fluoroalkyl.

In an even more preferred embodiment of the invention, X is selected from Cl, Br, I, $CF_3$, CN, S—$CH_3$ or S—$CF_3$; $Y^1$ and $Y^2$ are independently selected from O or S; $R^1$ and $R^2$ are independently selected from $C_1$-$C_3$ alkyl, $C_1$-$C_3$ fluoroalkyl or $C_3$-$C_5$ cycloalkyl; z is 0, 1 or 2; and $R^3$ is/are independently selected from F, $C_1$-$C_2$ alkyl or $C_1$-$C_2$ fluoroalkyl.

In a yet more preferred embodiment of the invention, X is selected from Cl, Br, I, $CF_3$, CN, S—$CH_3$ or S—$CF_3$; $Y^1$ and $Y^2$ are independently selected from O or S; $R^1$ and $R^2$ are independently selected from $C_1$-$C_3$ alkyl, $C_1$-$C_3$ fluoroalkyl or cyclopropyl; z is 0, 1, 2; and $R^3$ is/are independently selected from F, $C_1$-$C_2$ alkyl or $C_1$-$C_2$ fluoroalkyl.

In a highly preferred embodiment of the invention, X is selected from Cl, Br, I, $CF_3$, CN, S—$CH_3$ or S—$CF_3$; $Y^1$ and $Y^2$ are independently selected from O or S; $R^1$ and $R^2$ are independently selected from $C_1$-$C_3$ alkyl, $C_1$-$C_3$ fluoroalkyl or cyclopropyl; z is 0, 1 or 2; and $R^3$ is/are independently selected from F, methyl ($CH_3$) or trifluoromethyl ($CF_3$).

In yet another highly preferred embodiment of the invention, X is selected from Cl, Br, I, $CF_3$, CN, S—$CH_3$ or S—$CF_3$; $Y^1$ and $Y^2$ are independently selected from O or S; $R^1$ and $R^2$ are independently selected from $C_1$-$C_2$ alkyl or $C_1$-$C_2$ fluoroalkyl; z is 0, 1, 2 or 3; and $R^3$ is/are independently selected from F, methyl ($CH_3$) or trifluoromethyl ($CF_3$).

In yet another highly preferred embodiment of the invention, X is selected from Cl, Br, I, $CF_3$, CN, S—$CH_3$ or S—$CF_3$; $Y^1$ and $Y^2$ are independently selected from O or S; $R^1$ and $R^2$ are independently selected from $C_1$-$C_2$ alkyl or $C_1$-$C_2$ fluoroalkyl; z is 0, 1 or 2; and $R^3$ is/are selected from F, methyl ($CH_3$) or trifluoromethyl ($CF_3$).

In a more highly preferred embodiment of the invention, X is selected from Cl, Br, I or $CF_3$; $Y^1$ and $Y^2$ are independently selected from O or S, $R^1$ and $R^2$ are independently selected from $C_1$-$C_2$ alkyl or $C_1$-$C_2$ fluoroalkyl; z is 0, 1 or 2; and $R^3$ is/are selected from F, methyl ($CH_3$) or trifluoromethyl ($CF_3$).

In yet a more highly preferred embodiment of the invention, X is selected from Cl, Br, I or $CF_3$; $Y^1$ and $Y^2$ are independently selected from O or S; $R^1$ and $R^2$ are independently selected from methyl ($CH_3$) or trifluoromethyl ($CF_3$); z is 0, 1 or 2; and $R^3$ is/are selected from F, methyl ($CH_3$) or trifluoromethyl ($CF_3$).

In an even more preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or $C_3$-$C_5$ cycloalkyl; z is 0, 1 or 2; and $R^3$ is/are independently selected from F, $C_1$-$C_2$ alkyl or $C_1$-$C_2$ fluoroalkyl.

In a yet more preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or cyclopropyl; z is 0, 1, 2; and $R^3$ is/are independently selected from F, $C_1$-$C_2$ alkyl or $C_1$-$C_2$ fluoroalkyl.

In a highly preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_3$ alkyl, $C_1$-$C_3$ fluoroalkyl or cyclopropyl; z is 0, 1 or 2; and $R^3$ is/are independently selected from F, methyl ($CH_3$) or trifluoromethyl ($CF_3$).

In yet another highly preferred embodiment of the invention, X is selected from Cl, Br, I, $CF_3$, CN, S—$CH_3$ or S—$CF_3$; $Y^1$ and $Y^2$ are O; $R^1$ and $R^2$ are independently selected from $C_1$-$C_2$ alkyl or $C_1$-$C_2$ fluoroalkyl; z is 0, 1, 2 or 3; and $R^3$ is/are independently selected from F, methyl ($CH_3$) or trifluoromethyl ($CF_3$).

In yet another highly preferred embodiment of the invention, X is selected from Cl, Br, I, $CF_3$, CN, S—$CH_3$, S—$CF_3$; $Y^1$ and $Y^2$ are O; $R^1$ and $R^2$ are independently selected from $C_1$-$C_2$ alkyl or $C_1$-$C_2$ fluoroalkyl; z is 0, 1 or 2; and $R^3$ is/are selected from F, methyl ($CH_3$) or trifluoromethyl ($CF_3$).

In a more highly preferred embodiment of the invention, X is selected from Cl, Br, I or $CF_3$; $Y^1$ and $Y^2$ are O; $R^1$ and $R^2$ are independently selected from $C_1$-$C_2$ alkyl or $C_1$-$C_2$ fluoroalkyl; z is 0, 1 or 2; and $R^3$ is/are selected from F, methyl ($CH_3$) or trifluoromethyl ($CF_3$).

In yet a more highly preferred embodiment of the invention, X is selected from Cl, Br, I or $CF_3$; $Y^1$ and $Y^2$ are O; $R^1$ and $R^2$ are independently selected from methyl ($CH_3$) or trifluoromethyl ($CF_3$); z is 0, 1 or 2; and $R^3$ is/are selected from F, methyl ($CH_3$) or trifluoromethyl ($CF_3$).

In yet a more highly preferred embodiment of the invention, X is selected from Cl, Br, I or $CF_3$; $Y^1$ and $Y^2$ are O; $R^1$ and $R^2$ are methyl ($CH_3$); z is 0, 1 or 2; and $R^3$ is/are selected from F, methyl ($CH_3$) or trifluoromethyl ($CF_3$).

In yet a more highly preferred embodiment of the invention, X is selected from I or $CF_3$; $Y^1$ and $Y^2$ are O; $R^1$ and $R^2$ are methyl ($CH_3$); z is 0, 1 or 2; and $R^3$ is/are selected from F, methyl ($CH_3$) or trifluoromethyl ($CF_3$).

In yet a more highly preferred embodiment of the invention, X is selected from I or $CF_3$; $Y^1$ and $Y^2$ are O; $R^1$ and $R^2$ are methyl ($CH_3$); z is 0, 1 or 2; and $R^3$ is/are selected from F or methyl ($CH_3$).

In the most preferred embodiment of the invention, X is $CF_3$; $Y^1$ and $Y^2$ are O, $R^1$ and $R^2$ are methyl ($CH_3$); and z is 0.

Furthermore, any preferred embodiments mentioned under aspects 1, 2 or 4 apply equally well to aspect 5.

Aspect 6—Medical Use of 5-$HT_{2A}$/5-$HT_{2C}$ Agonists

In the sixth aspect, the invention relates to 5-$HT_{2A}$/5-$HT_{2C}$ agonists of the general formula (III) or a pharmaceutically acceptable salt thereof for use as a medicament

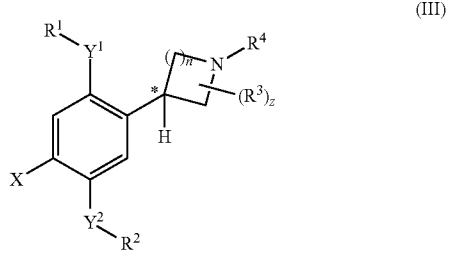

(III)

wherein:
X is selected from the group consisting of F, Cl, Br, I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl and $C_3$-$C_5$ fluorocycloalkyl;

* denotes the (R) or (S) stereoisomer or any mixture thereof if a chiral center is present;

n is an integer with a value of 1, 2, 3 or 4 to form an azetidine, pyrrolidine, piperidine or azepane ring system;

z denotes the number of $R^3$ groups and is an integer with a value of 0, 1, 2, 3 or 4;

$R^3$ is/are independently selected from the group consisting of F, $C_1$-$C_3$ alkyl, $C_1$-$C_3$ fluoroalkyl, $C_2$-$C_3$ alkenyl and $C_2$-$C_3$ alkynyl;

$R^4$ is selected from H or $CH_3$;

with the proviso that when n=3, * denotes the (R) stereoisomer and further with the proviso that at least one of $Y^1$ or $Y^2$ are selected as O or S.

In the sixth aspect, $Y^1$, $Y^2$, $R^1$, $R^2$, z, $R^3$ are selected with the same preference as in aspects 1, 2 and 3. Thus, the embodiments under the headings "Substituents $Y^1$ and $Y^2$", "Substituent $R^1$ and $R^2$", "Number (z) of $R^3$ substituents" and "Type of $R^3$ substituent(s)" in aspects 1 and 2 apply equally to aspect 6. Furthermore, in the sixth aspect, X is selected with the same preference as in aspects 4 and 5. Thus, the embodiments under the heading "Substituent X" in aspects 4 and 5 apply equally to aspect 6. In addition the description under the heading "Stereochemistry" in aspect 3 apply equally to aspect 6. Finally, the preferred embodiments described under aspects 1-5 apply equally to aspect 6 for all the ring systems (i.e. the azetidine, pyrrolidine, piperidine or azepane ring system). Most preferably, $R^4$ is selected as H in any of the embodiments.

Aspect 7—Synthesis of Compounds According to the Invention

The compounds according to aspect 3 or 6 comprising an azetidine or pyrrolidine were synthesized by a metal free reductive cross-coupling between a boronic acid and a diazo compound (generated in situ from arylsulfonylhydrazones) as illustrated in reaction scheme 1 below. The arylhydrazones was prepared by condensation between the arylsulfonylhydrazide and the appropriate 3-oxo-heterocycle. A large amount of aryl boronic acids are commercially available or may be prepared from aryl halides using conventional chemistry, such as e.g. halogen metal exchange followed by quenching with a borate or cross-coupling reactions between an aryl halide with e.g. bis(pinacolato)diboron in the presence of transition metal catalysis. Likewise, heterocycles comprising the ketone such as azetidin-3-one, pyrrolidin-3-one, piperidin-3-one or azepan-3-one are commercially available or may be prepared in few steps using conventional chemistry.

Reaction scheme 1

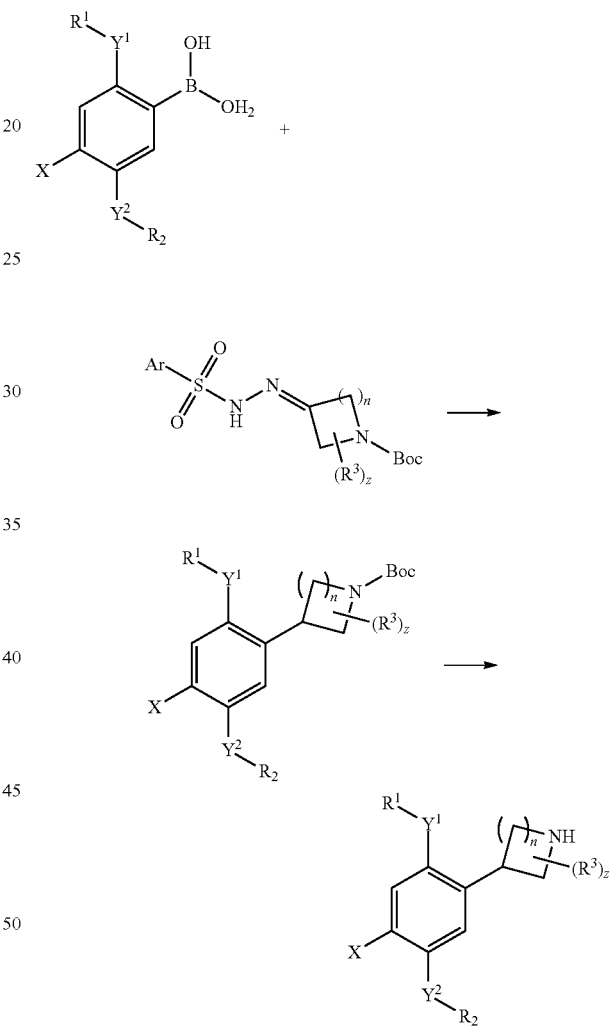

The compounds according to aspects 1-6 comprising a piperidine was synthesized readily using e.g. an appropriate cross-coupling reaction such as a Suzuki-cross coupling between a 3-halo-pyridine and an aryl boronic acid or vice versa (i.e. a pyridine-3-yl boronic acid and an aryl halide). The pyridine in the cross-coupling product may subsequently be reduced to the piperidine by hydrogenation using an appropriate catalyst such as Adams catalyst ($PtO_2$). Reaction scheme 2 below illustrates one way of synthesizing compounds comprising a piperidine according to aspects 1-6 of the invention using a 3-halo-pyridine and a boronic acid.

Reaction scheme 2

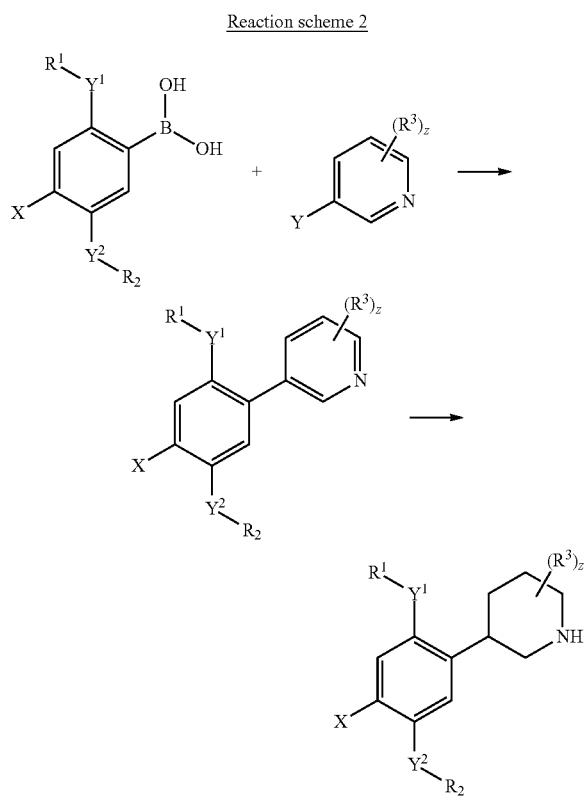

The substituent X may be present in the boronic acid building block during the cross-coupling if it does not interfere with the chemoselectivity of the reaction and tolerates hydrogenation or alternatively, the desired X may be installed subsequently by e.g. electrophilic aromatic substitution (halogenation), optionally followed by further reactions, e.g. a Ullmann type cross-coupling with an alkylthiol or a Rosenmund-von Braun reaction.

A large amount of substituted 3-halo-pyridines and substituted aryl halides as building blocks are commercially available and may be used directly. Alternatively, such building blocks may be prepared from commercially available building blocks in few steps using conventional chemistry well known to the skilled person. Such chemistry may include e.g. electrophilic aromatic substitutions, $S_NAR$, cross-couplings, halogen-metal exchange and Sandmeyer chemistry etc. Likewise, a large amount of aryl boronic acids are commercially available or may be prepared from aryl halides using conventional chemistry such as e.g. halogen metal exchange and quenching with a borate or cross-coupling reactions with e.g. bis(pinacolato)diboron.

Aspect 8—Medical Use of Compounds According to the Invention

The compounds according to the invention are for use as a medicament, more particularly for use in the treatment of a depressive disorder. The depressive disorder may be selected from a list consisting of major depressive disorder (MDD) (also known as clinical depression, unipolar depression), treatment resistant depression disorder (TRD), severe treatment resistant depression disorder, melancholia, psychotic depression, antenatal depression, postnatal depression, bipolar disorder, bipolar type I disorder, bipolar type II disorder, cyclothymic disorder, dysthymic disorder or seasonal affective disorder. In a highly preferred embodiment of the invention, the compounds according to the invention are for use in the treatment of TRD or severe treatment-resistant depression in any of the above depressive disorders. In another highly preferred embodiment of the invention, the compounds according to the invention are for use in the treatment of MDD, treatment-resistant depression disorder (TRD), or severe treatment-resistant depression disorder. In the most preferred embodiment, the compounds according to the invention are for use in the treatment of MDD or TRD in MDD.

Furthermore, 5-HT$_{2A}$ agonists, such as psilocybin, have shown to be useful in the treatment of a number of diseases, disorders and addictions besides the above depressive disorders. Thus, in another preferred embodiment the compounds according to aspects 4-6 are for use in the treatment of a disease, a disorder, an addiction or an abuse selected from the list consisting of Alzheimer's disease, Parkinson's disease, autism, general anxiety, existential anxiety, end of life anxiety, terminal cancer related end of life anxiety, epilepsy, sleep-wake disorders, neurocognitive disorders, obsessive compulsive disorder (OCD), attention deficit disorder (ADD), attention deficit hyperactivity disorder (ADHD), post-traumatic stress disorder (PTSD), stress, acute stress disorder, Horton's headache, chronic cluster headache, migraine, general local inflammation, muscle inflammation, joint inflammation, pulmonary inflammation, asthma, arthritis, smoking cessation, alcohol cessation, cocaine cessation, heroin cessation, opioid cessation, methamphetamine cessation, general addiction therapy, eating disorders such as compulsive eating disorders, anorexia nervosa, bulimia nervosa, binge eating disorder, Pica, Rumination disorder, avoidant/restrictive food intake disorder, night eating syndrome, other specified feeding or eating disorder (OSFED), body dysmorphic disorder, purging disorder, pain, chronic pain disorders, sleep wake disorders or physical rehabilitation. In a highly preferred embodiment, the compounds according to the aspects 4-6 are for use in the treatment of chronic cluster headache, bipolar type II disorder, body dysmorphic disorder.

Figure 4A:
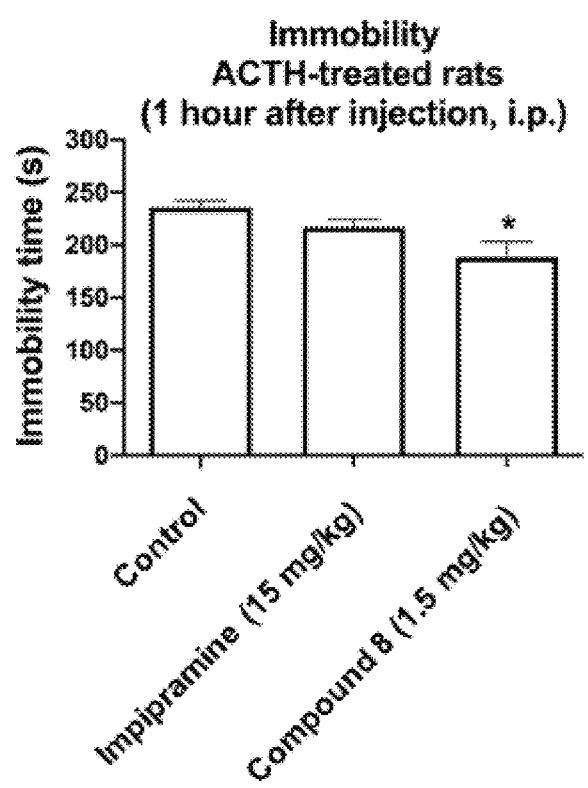
FIG. 4A shows the effects of compound 8 and the TCA imipramine on immobility time of rats treated with adrenocorticotropic hormone (ACTH) in the forced swim test. Chronic administration of rats with ACTH abrogates the antidepressant effect of TCAs, such as imipramine, and it is thus a validated stress-induced rodent model of treatment-resistant depression.[9]
Figure 4B:
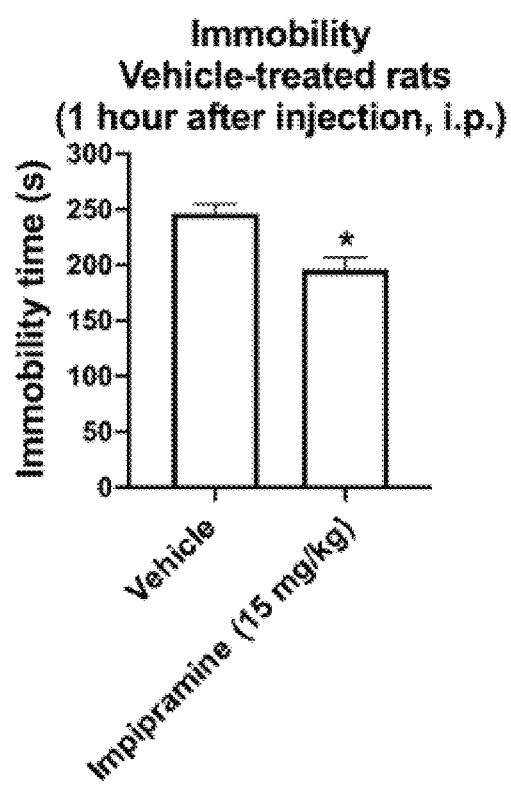
FIG. 4B shows the significant antidepressant-like effect of imipramine (15 mg/kg, i.p.) in vehicle-treated rats (positive control), which contrasts the lack of effect of the same dose of imipramine in ACTH-treated rats (FIG. 4A).
Figure 5:
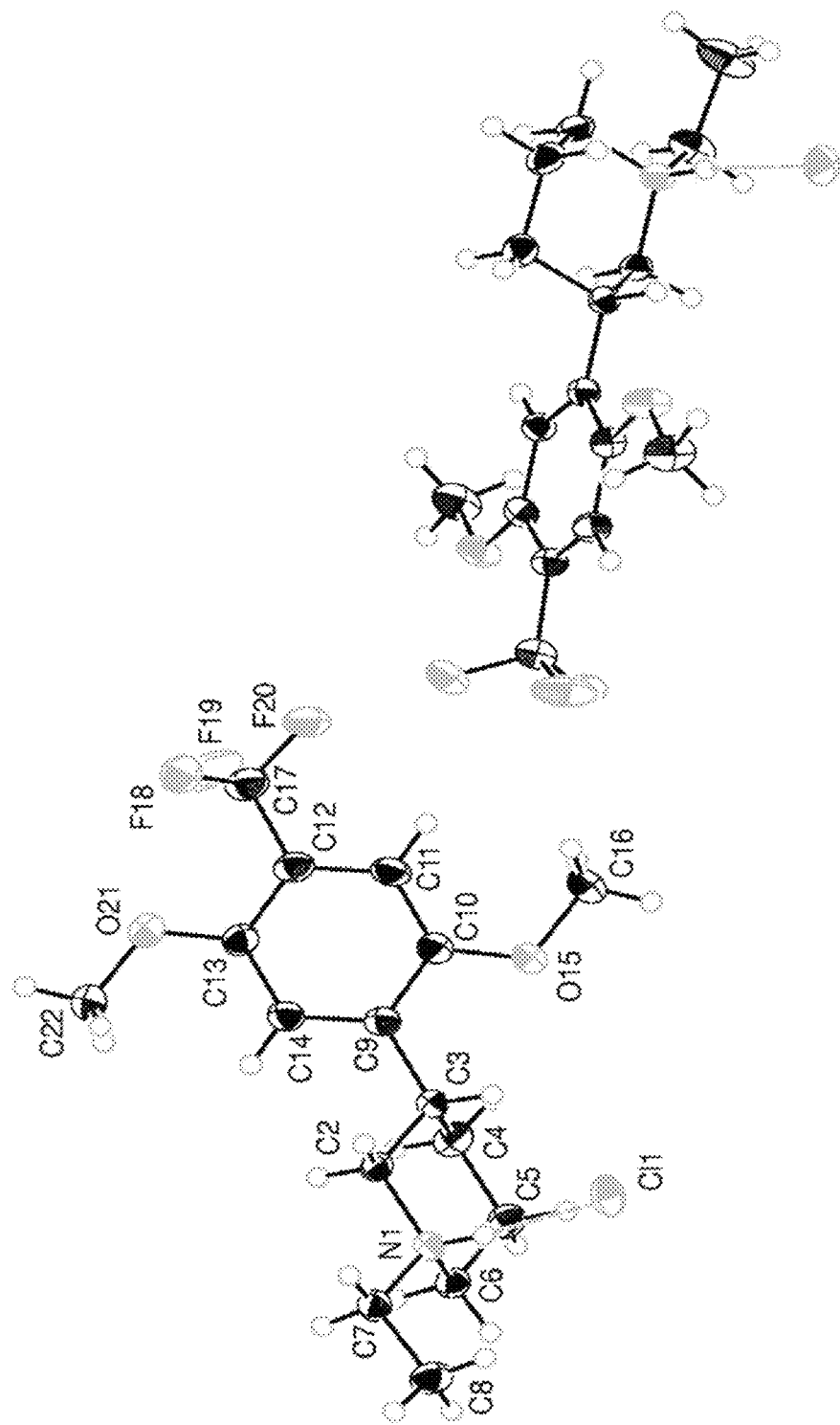
FIG. 5 shows the x-ray structure of compound 59.
Figure 6:
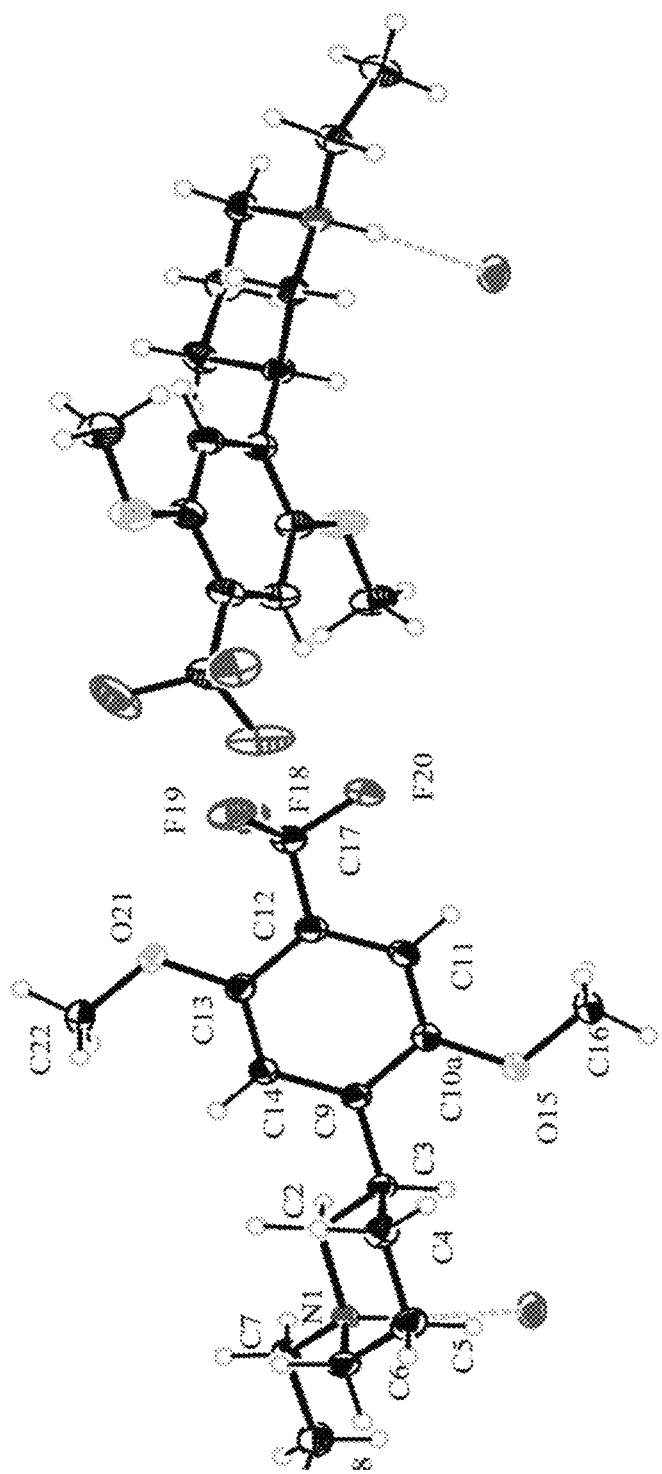
FIG. 6 shows the x-ray structure of compound 58.

The results in FIGS. 4A and 4B demonstrate the effect compound 8 in rodent models for depression and treatment-resistant depression. Thus, in a highly preferred embodiment, the invention relates to the use of selective 5-HT$_{2A}$ agonists of aspect 3 for use in the treatment of treatment-resistant depression in any depressive disorder, most preferably MDD. Thus, the compounds of the invention are particularly intended for use in the treatment of an individual who does not respond adequately to current anti-depressive treatments, such as SSRIs. In one embodiment of the invention, the treatment of treatment-resistant depression may involve an initial co-administration of a compound according to the present invention as a rapid-acting antidepressant to circumvent the slow on-set of the SSRIs. In another embodiment of the invention, the treatment of treatment-resistant depression may involve substitution of an antidepressant with a compound according to the present invention.

Aspect 9—Pharmaceutical Compositions

Another aspect of the invention relates to a pharmaceutical composition comprising a compound according to aspects 1-6 of the invention, a pharmaceutical acceptable carrier and optionally one or more pharmaceutically acceptable excipients. In the present context, a pharmaceutical composition should be understood as any conventional type of formulation intended for e.g. parental, oral, inhalation or topical administration. Parental formulations may be intended for intravenous, subcutaneous or intramuscular administration. Suitable oral formulations may include tablets, capsules, powders, solutions, suspensions or a sustained release formulation for oral administration. Other suitable formulations may include creams, ointments, gels, pastes or patches for topical administration. Suitable parental formulations may include liquids, lyophilized or spray dried powders for dissolution prior to parental administration. Preferably, the formulation is an oral formulation such as a tablet or a parental formulation such as a liquid. The skilled person is familiar with the manufacture of different types of formulations and suitable excipients to use in the different formulation types can be found in e.g. Handbook of Pharmaceutical Excipients. In a pharmaceutical composition, comprising a compound according to aspects 2 or 4 of the invention, the (S)-stereoisomer should preferably be present in at least 80% ee, such as 85% ee, such 90% ee, such as 95% ee, such as 96% ee, preferably 97% ee, more preferably 98% ee, even more preferably at least 99% ee, most preferably only the (5)-stereoisomer.

Pharmaceutically Acceptable Salts

Any of the compounds according to the invention, exemplified with the list of compounds 1-57, may be in the form of a pharmaceutically acceptable salt since they all comprise a basic moiety (i.e. a secondary amine in the azetidine, pyrrolidine, piperidine or azepane). Thus, the compound may be in the form of a pharmaceutically acceptable acid addition salt. The salts may be either amorphous or crystalline products and a salt may exist as different polymorphs. The skilled person is aware of a large number of acids suitable for formation of a pharmaceutically acceptable salt as can be found in e.g. Handbook of Pharmaceutical Salts. Typical, pharmaceutical acceptable acid addition salts may be formed between a compound according to the invention and an acid selected from group consisting of but not limited to e.g. acetic acid, aspartic acid, benzenesulfonic acid, benzoic acid, carbonic acid, camphorsulfonic acid, HCl, HBr, HI, citric acid, decanoic acid, ethylenediaminetetraacetic acid, gluconic acid, fumaric acid, lactic acid, maleic acid, malic acid, methanesulfonic acid, nitric acid, phosphoric acid, propionic acid, tartaric acid, tosylic acid, sulfuric acid, salicylic acid or succinic acid. The skilled person is well aware of the importance of pharmaceutical salts. Salt screens are therefore often performed to identify suitable crystalline products with advantageous properties. Different salts or crystal forms of the product may influence the physiochemical properties of the compound. Thus, salts may have influence on e.g. the chemical and physical stability, hygroscopicity, melting point, solubility, dissolution rate and bioavailability. Thus, in the present context, a pharmaceutically acceptable salt is intended to include all suitable acid addition salts in both amorphous and crystalline forms as well as different polymorphs thereof.

Combination Therapy

The compounds according to the present invention may be used alone (i.e. in mono-therapy) or in combination with one or more known anti-depressants (i.e. in combination therapy). Thus, combination therapy may include but are not limited to combinations with other therapeutically active ingredients such as SSRIs, SNRIs, NDRIs, TCAs, benzodiazepines, atypical antipsychotics, stimulants such as amphetamines and methylphenidate, ketamine, classical psychedelics such as mescaline, lysergic acid diethylamide (LSD), psilocybin and N,N-dimethyltryptamine (DMT). In case of combination therapy the other therapeutically active ingredients may be administered in separate dosage forms or as a single dosage form comprising one or more compounds according to the invention in combination with one or more other therapeutically active ingredients. In particular, due to the slow on-set of e.g. SSRI as described above, it might be beneficial in some instances to initiate the treatment with one or more compounds according to the invention together with or followed by e.g. a SSRI to avoid any delay in anti-depressant effect.

EXAMPLES

In Vitro Pharmacology General Information

The $Ca^{2+}$/Fluo-4 Assay

The functional properties of the compounds were characterised at stable HEK293 cell lines stably expressing the human $5\text{-}HT_{2A}$ receptor or human $5\text{-}HT_{2C}$ receptor in the $Ca^{2+}$/Fluo-4 assay essentially as previously described.[10] Briefly, the cells were split into poly-D-lysine-coated black 96-well plates with clear bottoms ($6\times10^4$ cells/well). The following day the culture medium was aspirated and the cells were incubated in 50 µl assay buffer [Hanks Buffered Saline Solution containing 20 mM HEPES, 1 mM $CaCl_2$, 1 mM $MgCl_2$, 2.5 mM probenecid, pH 7.4] supplemented with 6 mM Fluo-4/AM at 37° C. for 1 hour. Next, the buffer was aspirated, the cells were washed once with 100 µl assay buffer, and then 100 µl assay buffer was added to the cells (in the antagonist experiments the compound was added at this point). The 96-well plate was assayed in FLEXStation[3] Plate Reader (Molecular Devices, Crawley, United Kingdom) measuring emission (in fluorescence units) at 525 nm caused by excitation at 485 nm before and up to 90 seconds after addition of 33.3 µl test compound solution in the assay buffer. The compounds were characterized in duplicate at least three times at each cell line. In the antagonist tests, 5-HT ($EC_{80}$) was used as agonist.

TABLE 1a

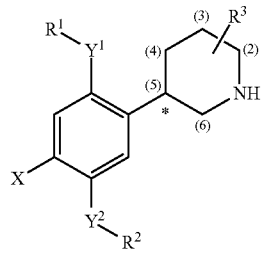

| Compound No. | * | X | $R^1$ | $R^2$ | $Y^1$ | $Y^2$ | $R^3$ | 5-$HT_{2A}$ $EC_{50}$ (nM) [$pEC_{50}$ ± S.E.M.] | $R_{max}$ ± S.E.M. | 5-$HT_{2C}$ $EC_{50}$ (nM) [$pEC_{50}$ ± S.E.M.] | $R_{max}$ ± S.E.M | Selectivity $EC_{50}^{5\text{-}HT2C}/EC_{50}^{5\text{-}HT2A}$ |
|---|---|---|---|---|---|---|---|---|---|---|---|---|
| 7 | (R) | $CF_3$ | Me | Me | O | O | — | 150 [6.82 ± 0.04] | 65 ± 5 | 860 [6.07 ± 0.06] | 26 ± 2 | 5.7 |
| 8 | (S) | $CF_3$ | Me | Me | O | O | — | 21 [7.67 ± 0.05] | 47 ± 3 | n.a. [@ 50 µM] [a] >50,000 [<4.3] | n.d. [d] | >1,000 [e] |

TABLE 1a-continued

| # | | | | | | | | | | | | |
|---|---|---|---|---|---|---|---|---|---|---|---|---|
| 9 | (R) | Cl | Me | Me | O | O | — | 690 [6.16 ± 0.11] | 61 ± 2 | 1,800 [5.75 ± 0.04] | 26 ± 2 | 2.6 |
| 10 | (S) | Cl | Me | Me | O | O | — | 66 [7.18 ± 0.05] | 32 ± 6 | n.a. [@ 50 μM] [a] >50,000 [<4.3] | n.d. [d] | >1,000 [e] |
| 11 | (R) | Br | Me | Me | O | O | — | 370 [6.43 ± 0.11] | 67 ± 6 | 1,900 >50,000 [<4.3] | 34 ± 4 | 5.1 |
| 12 | (S) | Br | Me | Me | O | O | — | 69 [7.16 ± 0.10] | 37 ± 4 | n.a. [@ 50 μM] [a] >50,000 [<4.3] | n.d. [d] | >1,000 [e] |
| 13 | (R) | I | Me | Me | O | O | — | 260 [6.58 ± 0.03] | 58 ± 4 | 2,800 [5.55 ± 0.08] | 20 ± 2 | 11 |
| 14 | (S) | I | Me | Me | O | O | — | 37 [7.43 ± 0.02] | 53 ± 3 | n.a. [@ 50 μM] [a] >50,000 [<4.3] | n.d. [d] | >1,000 [e] |
| 15 | (R) | CN | Me | Me | O | O | — | 2,200 [5.66 ± 0.06] | 41 ± 6 | ~10,000 [~5.0] [c] | ~13-17 [c] | 4.5 |
| 16 | (S) | CN | Me | Me | O | O | — | 270 [6.56 ± 0.13] | 25 ± 4 | n.a. [@ 50 μM] [a] >50,000 [<4.3] | n.d. [d] | >200 [e] |
| 17 | (R) | SMe | Me | Me | O | O | — | 180 [6.75 ± 0.06] | 85 ± 7 | 2,300 [5.63 ± 0.03] | 38 ± 5 | 13 |
| 18 | (S) | SMe | Me | Me | O | O | — | 26 [7.59 ± 0.11] | 84 ± 6 | 510 [6.29 ± 0.06] | 16 ± 2 | 20 |
| 19 | (R) | CF₃ | Me | Et | O | O | — | 320 [6.50 ± 0.10] | 86 ± 6 | w.a. [@ 2-10-50 μM] [b] | n.d. [d] | >30 [e] |
| 20 | (S) | CF₃ | Me | Et | O | O | — | 10 [7.99 ± 0.11] | 95 ± 1 | 290 [6.54 ± 0.04] | 44 ± 5 | 28 |
| 21 | (R) | CF₃ | Et | Et | O | O | — | 3,000 [5.52 ± 0.06] | 69 ± 4 | w.a. [@ 10-50 μM] [b] | n.d. [d] | >10 [e] |
| 22 | (S) | CF₃ | Et | Et | O | O | — | 100 [6.99 ± 0.07] | 47 ± 6 | w.a. [@ 10-50 μM] [b] | n.d. [d] | >300 [e] |
| 23 | (R) | Me | Me | Me | O | O | — | 260 [6.58 ± 0.06] | 89 ± 4 | 1,200 [5.92 ± 0.08] | 53 ± 6 | 4.6 |
| 24 | (S) | Me | Me | Me | O | O | — | 100 [6.98 ± 0.10] | 75 ± 3 | w.a. [@ 10-50 μM] [b] | n.d. [d] | >300 [e] |
| 25 | (R) | iPrS | Me | Me | O | O | — | 290 [6.54 ± 0.09] | 91 ± 4 | 2,300 [5.46 ± 0.05] | 50 ± 1 | 8.0 |
| 26 | (S) | iPrS | Me | Me | O | O | — | 160 [6.81 ± 0.09] | 92 ± 4 | w.a. [@ 2-10-50 μM] [b] | n.d. [d] | >30 [e] |
| 27 | (R) | SEt | Me | Me | O | O | — | 190 [6.73 ± 0.10] | 83 ± 6 | 780 [6.11 ± 0.08] | 52 ± 5 | 4.1 |
| 28 | (S) | SEt | Me | Me | O | O | — | 38 [7.42 ± 0.09] | 80 ± 6 | 570 [6.25 ± 0.08] | 8 ± 2 | 15 |
| 29 | (R) | CF₃ | Et | Me | O | O | — | 410 [6.39 ± 0.08] | 77 ± 7 | 2,700 [5.56 ± 0.02] | 34 ± 1 | 6.7 |
| 30 | (S) | CF₃ | Et | Me | O | O | — | 38 [7.42 ± 0.10] | 40 ± 3 | w.a. [@ 50 μM] [b] | n.d. [d] | >1,000 [e] |
| 31 | (R) | Et | Me | Me | O | O | — | 110 [6.94 ± 0.09] | 93 ± 5 | 640 [6.19 ± 0.12] | 44 ± 5 | 5.6 |
| 32 | (S) | Et | Me | Me | O | O | — | 41 [7.39 ± 0.11] | 79 ± 4 | 380 [6.42 ± 0.12] | 20 ± 4 | 9.3 |
| 33 | (R) | Et | Me | Et | O | O | — | 1,100 [5.95 ± 0.11] | 89 ± 4 | w.a. [@ 2-10-50 μM] [b] | n.d. [d] | >10 [e] |
| 34 | (S) | Et | Me | Et | O | O | — | 52 [7.29 ± 0.08] | 88 ± 4 | 840 [6.08 ± 0.02] | 28 ± 4 | 16 |
| 35 | — | CF₃ | Me | Me | O | O | 6'-Me | 73 [7.14 ± 0.11] | 75 ± 4 | 3,000 [5.53 ± 0.10] | 21 ± 2 | 41 |
| 36 | — | CF₃ | Me | Me | O | O | 3'-Me | 48 [7.32 ± 0.10] | 68 ± 2 | 400 [6.40 ± 0.09] | 43 ± 6 | 8.2 |
| 37 | — | CF₃ | Me | Me | O | O | 2'-Me | 270 [6.58 ± 0.11] | 90 ± 10 | 3,400 [5.47 ± 0.09] | 33 ± 5 | 13 |
| 38 | — | CF₃ | Me | Me | O | O | 2'-Me | 160 [6.81 ± 0.09] | 38 ± 4 | w.a. [@ 50 μM] [b] | n.d. [d] | >300 [e] |
| 39 | (S) | CF₃ | CH₂F | Me | O | O | — | 150 [6.82 ± 0.12] | 40 ± 5 | w.a. [@ 50 μM] [b] | n.d. [d] | >300 [e] |
| 40 | (R) | Et | Et | Et | O | O | — | ~7,000-10,000 [~5.15-5.00] [c] | ~61-74 [c] | w.a. [@ 10-50 μM] [b] | n.d. [d] | >3 [e] |
| 41 | (S) | Et | Et | Et | O | O | — | 380 [6.42 ± 0.09] | 44 ± 5 | w.a. [@ 50 μM] [b] | n.d. [d] | >100 [e] |
| 42 | (R) | Et | Et | Me | O | O | — | 1,500 [5.82 ± 0.07] | 80 ± 9 | w.a. [@ 2-10-50 μM] [b] | n.d. [d] | >10 [e] |
| 43 | (S) | Et | Et | Me | O | O | — | 140 [6.86 ± 0.11] | 42 ± 6 | n.a. [@ 50 μM] [a] >50,000 [<4.3] | n.d. [d] | >1,000 [e] |
| 44 | (R) | CF₃ | Me | Me | O | S | — | 71 [7.15 ± 0.11] | 96 ± 6 | 660 [6.18 ± 0.12] | 50 ± 2 | 9.3 |
| 45 | (S) | CF₃ | Me | Me | O | S | — | 9.1 [8.04 ± 0.02] | 82 ± 3 | 170 [6.78 ± 0.13] | 22 ± 4 | 18 |
| 46 | (R) | CF₃ | Me | Et | O | S | — | 150 [6.84 ± 0.05] | 97 ± 2 | 1,100 [5.97 ± 0.05] | 53 ± 5 | 7.4 |
| 47 | (S) | CF₃ | Me | Et | O | S | — | 26 [7.58 ± 0.11] | 96 ± 3 | 450 [6.34 ± 0.03] | 43 ± 6 | 17 |
| 48 | (R) | CF₃ | — | Me | H | O | — | 1,800 [5.74 ± 0.09] | 68 ± 7 | w.a. [@ 50 μM] [b] | n.d. [d] | >50 [e] |

TABLE 1a-continued

| | | | | | | | | | | | | |
|---|---|---|---|---|---|---|---|---|---|---|---|---|
| 49 | (S) | CF$_3$ | — | Me | H | O | — | 2,500 [5.61 ± 0.07] | 65 ± 3 | 1,300 [5.90 ± 0.10] | 35 ± 3 | 0.51 |
| 50 | (R) | CF$_3$ | Me | — | O | F | — | 640 [6.19 ± 0.10] | 78 ± 6 | 1,800 [5.75 ± 0.03] | 40 ± 8 | 2.8 |
| 51 | (S) | CF$_3$ | Me | — | O | F | — | 140 [6.85 ± 0.08] | 79 ± 5 | w.a. [@ 10-50 μM] [b] | n.d. [d] | >100 [e] |
| 52 | (R) | CF$_3$ | Me | — | O | H | — | 480 [6.32 ± 0.12] | 77 ± 2 | 1,400 [5.85 ± 0.05] | 38 ± 6 | 3.0 |
| 53 | (S) | CF$_3$ | Me | — | O | H | — | 69 [7.16 ± 0.05] | 68 ± 2 | w.a. [@ 2-10-50 μM] [b] | n.d. [d] | >100 [e] |
| 54 | (R) | CF$_3$ | Cyclopropyl | Me | O | O | — | 1,800 [5.75 ± 0.10] | 76 ± 4 | ~3,000~10,000 [~5.52-5.00] [c] | ~46-63 [c] | ~1.7-~5.6 |
| 55 | (S) | CF$_3$ | Cyclopropyl | Me | O | O | — | 1,100 [5.97 ± 0.06] | 30 ± 5 | w.a. [@ 50 μM] [b] | n.d. [d] | >50 [e] |
| 56 | (R) | n-Bu | Me | Me | O | O | — | 340 [6.46 ± 0.05] | 93 ± 5 | 1,600 [5.80 ± 0.07] | 68 ± 6 | 4.6 |
| 57 | (S) | n-Bu | Me | Me | O | O | — | 270 [6.57 ± 0.06] | 82 ± 2 | w.a. [@ 2-10-50 μM] [b] | n.d. [d] | >30 [e] |

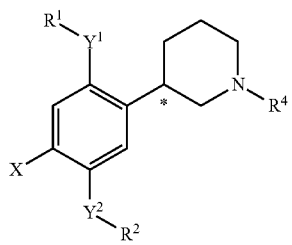

| | | | | | | | | 5-HT$_{2A}$ | | 5-HT$_{2C}$ | | Selectivity |
|---|---|---|---|---|---|---|---|---|---|---|---|---|
| Compound No. | * | X | R$^1$ | R$^2$ | Y$^1$ | Y$^2$ | R$^4$ | EC$_{50}$ (nM) [pEC$_{50}$ ± S.E.M.] | R$_{max}$ ± S.E.M. | EC$_{50}$ (nM) [pEC$_{50}$ ± S.E.M.] | R$_{max}$ ± S.E.M. | EC$_{50}^{5-HT2C}$/ EC$_{50}^{5-HT2A}$ |
| 58 | (R) | CF$_3$ | Me | Me | O | O | Et | w.a. [@ 2-10-50 μM] [b] | n.d. [d] | w.a. [@ 2-10-50 μM] [b] | n.d. [d] | n.d. [d] |
| 59 | (S) | CF$_3$ | Me | Me | O | O | Et | 1,500 [5.82 ± 0.09] | 44 ± 3 | w.a. [@ 10-50 μM] [b] | n.d. [d] | >30 [e] |
| 60 | (R) | CF$_3$ | Me | Me | O | O | Me | 1,100 [5.96 ± 0.09] | 53 ± 8 | w.a. [@ 2-10-50 μM] [b] | n.d. [d] | >5 [e] |
| 61 | (S) | CF$_3$ | Me | Me | O | O | Me | 390 [6.40 ± 0.07] | 19 ± 2 | 920 [6.04 ± 0.03] | 14 ± 2 | 2.2 |

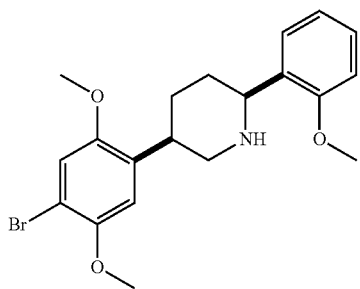

(8a)

| | | | | |
|---|---|---|---|---|
| 480 [6.32 ± 0.11] | 87 ± 4 | 2,000 [5.71 ± 0.03] | 82 ± 3 | 4.1 |

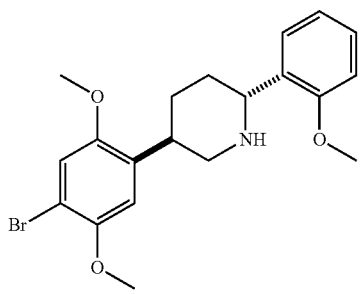

(8b)

| | | | | |
|---|---|---|---|---|
| w.a. [@ 10-50 μM] | n.d. [d] | w.a. [@ 10-50 μM] | n.d. [d] | n.d. [d] |

TABLE 1a-continued

| Structure | EC$_{50}$ (nM) [pEC$_{50}$ ± S.E.M.] 5-HT$_{2A}$ | R$_{max}$ ± S.E.M 5-HT$_{2A}$ | EC$_{50}$ (nM) [pEC$_{50}$ ± S.E.M.] 5-HT$_{2C}$ | R$_{max}$ ± S.E.M 5-HT$_{2C}$ | Selectivity EC$_{50}$$^{5-HT2C}$/EC$_{50}$$^{5-HT2A}$ |
|---|---|---|---|---|---|
| (DOI) | 0.44 [9.36 ± 0.06] | 88 ± 7 | 3.4 [8.47 ± 0.08] | 83 ± 8 | 7.8 |
| (25CN-NBOH) | 0.76 [9.12 ± 0.07] | 83 ± 6 | 47 [7.33 ± 0.10] | 96 ± 7 | 62 |

Agonist potencies (EC$_{50}$ values) and efficacies (maximal responses, R$_{max}$ values) exhibited by the compounds according to the invention when tested at stable h5-HT$_{2A}$- and h5-HT$_{2C}$-HEK293 cell lines in a Ca$^{2+}$ imaging assay using the calcium fluorophore Fluo-4.

EC$_{50}$ values are given in nM with pEC$_{50}$ values in brackets, and R$_{max}$ values are given in % as the R$_{max}$ of 5-HT at the respective receptors.

The EC$_{50}$$^{5-HT2C}$/EC$_{50}$$^{5-HT2A}$ ratios for the compounds are given as a measure of their 5-HT$_{2A}$-over-5-HT$_{2C}$ selectivity degrees.

The compounds are shown in comparison with the reference compounds 8a and 8b from ACS Chem. Neurosci. 2013, 4, 96-109 and the N-alkylated analogues 58-61.

The data are based on 3 or 4 individual experiments for all compounds performed at both receptors (n = 3-4).

[a] n.a., no agonist activity: the compound did not evoke significant responses at concentrations up to 50 μM.

[b] w.a., weak agonist activity: the compound only evoked significant response at the indicated concentrations.

Thus, a complete concentration-response curve could not be fitted, and EC$_{50}$ and R$_{max}$ values could not be determined.

[c] The agonist concentration-response relationship exhibited by the compound was not completely saturated at 50 μM.

Thus, EC$_{50}$ and R$_{max}$ values were estimated from the fitted curves and are given as intervals of the values obtained in the individual experiments.

[d] n.d., not determinable.

[e] Since the EC$_{50}$ value at 5-HT$_{2C}$ could not be determined, the EC$_{50}$$^{5-HT2C}$/EC$_{50}$$^{5-HT2A}$ ratio given for the compound is a conservative estimate based on the 5-HT$_{2A}$ EC$_{50}$ and the sizes of the agonist responses evoked by the effective concentrations of the compound at 5-HT$_{2C}$.

The compounds according to the invention were all 5-HT$_{2A}$ agonists with varying degree of potency in the low μM to low nM range.

Figure 1B:
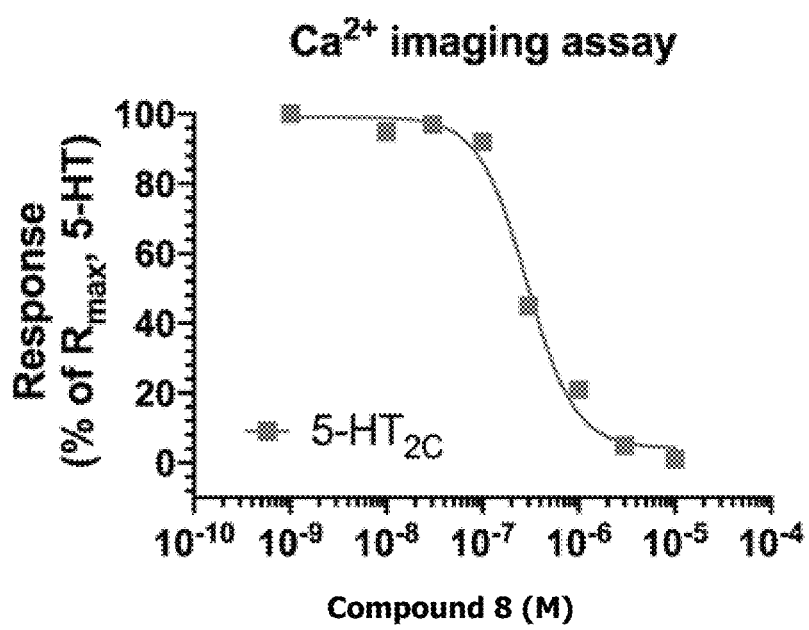
FIG. 1B shows the concentration-dependent inhibition of the 5-HT $EC_{80}$-induced response in the $5\text{-}HT_{2C}$-expressing cell line in the same assay mediated by compound 8 when tested as antagonist. The assay was performed as described in the experimental section.

In general, the (S)-enantiomers showed high selectivity towards 5-HT$_{2A}$ over 5-HT$_{2C}$, with some (S)-enantiomers not evoking significant agonist responses in the h5-HT$_{2C}$-HEK293 cells at concentrations up to 50 μM (exemplified for compound 8 in FIG. 1B).

TABLE 1b

| | | | | 5-HT$_{2A}$ | | 5-HT$_{2C}$ | | Selectivity |
|---|---|---|---|---|---|---|---|---|
| Compound No. | * | X | N | EC$_{50}$ (nM) [pEC$_{50}$ ± S.E.M.] | R$_{max}$ ± S.E.M | EC$_{50}$ (nM) [pEC$_{50}$ ± S.E.M.] | R$_{max}$ ± S.E.M | EC$_{50}$$^{5-HT2C}$/EC$_{50}$$^{5-HT2A}$ |
| 1 | — | Br | 1 | 1.6 [8.80 ± 0.10] | 97 ± 3 | 5.8 [8.24 ± 0.07] | 90 ± 3 | 3.6 |
| 2 | — | CF$_3$ | 1 | 1.0 [9.00 ± 0.10] | 95 ± 2 | 5.2 [8.28 ± 0.02] | 87 ± 4 | 5.2 |
| 3 | (R) | Br | 2 | 5.3 [8.11 ± 0.08] | 57 ± 3 | 26 [7.59 ± 0.03] | 73 ± 3 | 4.9 |
| 4 | (S) | Br | 2 | 7.7 [8.11 ± 0.08] | 39 ± 4 | 18 [7.75 ± 0.08] | 16 ± 3 | 2.3 |
| 5 | (R) | CF$_3$ | 2 | 11 [7.98 ± 0.08] | 45 ± 1 | 41 [7.39 ± 0.08] | 65 ± 4 | 3.7 |
| 6 | (S) | CF$_3$ | 2 | 5.4 [8.27 ± 0.09] | 35 ± 4 | 19 [7.72 ± 0.06] | 28 ± 2 | 3.5 |

Agonist potency (EC$_{50}$) and efficacy (R$_{max}$) of compounds according to the invention when tested at stable h5-HT$_{2A}$- and h5-HT$_{2C}$-HEK293 cell lines in a Ca$^{2+}$ imaging assay using the calcium fluorophore Fluo-4.
EC$_{50}$ values are given in nM with pEC$_{50}$ values in brackets, and R$_{max}$ values are given in % as the R$_{max}$ of 5-HT at the respective receptors.
The data are based on 3-4 experiments for all compounds at both receptors (n = 3-4).

The functional properties of compound 8 were characterized in a cell line stably expressing the human 5-HT$_{2B}$ receptor in a similar fluorescence-based Ca$^{2+}$ imaging assay (performed by Eurofins). Briefly, the cell line was expanded from a freezer stock according to standard procedures. Cells were seeded in a total volume of 20 μL into black-walled, clear-bottom, Poly-D-lysine coated 384-well microplates and incubated at 37° C. for the appropriate time prior to testing. The assay was performed in 1× Dye Loading Buffer consisting of 1× Dye, 1× Additive A and 2.5 mM Probenecid in HBSS/20 mM HEPES (pH 7.4). Cells were loaded with dye prior to testing. Media was aspirated from cells and replaced with 20 μL Dye Loading Buffer, and the cells were incubated for 30-60 minutes at 37° C. After dye loading, cells were removed from the incubator and 10 μL HBSS/20 mM HEPES was added. Cells were incubated for 30 minutes at room temperature in the dark to equilibrate plate temperature. Intermediate dilution of sample stocks was performed to generate 4× sample in assay buffer. Compound agonist activity was measured on a FLIPR Tetra (MDS). Calcium mobilization was monitored for 2 minutes and 10 μL 4× sample in HBSS/20 mM HEPES was added to the cells 5 seconds into the assay.

TABLE 2

| | | | | 5-HT$_{2A}$ | | 5-HT$_{2B}$ | | Selectivity |
|---|---|---|---|---|---|---|---|---|
| Com. No. | * | X | n | EC$_{50}$ (nM) [pEC$_{50}$ ± S.E.M.] | R$_{max}$ ± S.E.M. | EC$_{50}$ (nM) | R$_{max}$ | EC$_{50}$$^{5HT2B}$/ EC$_{50}$$^{5-HT2A}$ |
| 10 | (S) | CF$_3$ | 3 | 21 [7.67 ± 0.05] | 47 ± 3 | 280 | 84 | 13 |

Agonist potency (EC$_{50}$) and efficacy (R$_{max}$) of compound 8 according to the invention when tested at a stable h5-HT$_{2B}$ cell line in a fluorescence-based Ca$^{2+}$ imaging assay (performed by Eurofins).

The EC$_{50}$ value is given in nM, and the R$_{max}$ value is given in % as the R$_{max}$ of 5-HT at the receptor.

The pharmacological data for compound 8 at the 5-HT$_{2A}$-HEK293 cell line (from Table 1a) is given for comparison.

The IP Assay

The agonist properties of the compounds were characterized at HEK293 cell lines expressing the human 5-HT$_{2A}$, human 5-HT$_{2B}$ or human 5-HT$_{2C}$ receptors in an IP assay essentially as previously described.[19] The testing was performed by Eurofins. In the assay, the agonist activity of the compound at the receptors is investigated by measuring its effect on IP1 production in the cell using the Homogeneous Time Resolved Fluorescence (HTRF) detection method. Briefly, on the day of the assay the cells were suspended in a buffer containing 10 mM Hepes/NaOH (pH 7.4), 4.2 mM KCl, 146 mM NaCl, 1 mM CaCl$_2$, 0.5 mM MgCl$_2$, 5.5 mM glucose and 50 mM LiCl, then distributed in microplates at a density of 1.5×10$^4$ cells/well and incubated for 30 min at 37° C. in the presence of buffer (basal control), test compound or reference agonist. Separate assay wells containing 1 μM 5-HT (5-HT$_{2B}$ and 5-HT$_{2C}$) or 10 μM 5-HT (5-HT$_{2A}$) for stimulated control measurements were included. Following incubation, the cells were lysed, and the fluorescence acceptor (D2-labeled IP1) and fluorescence donor (anti-IP1 antibody labeled with europium cryptate) were added. After 60 min at room temperature, the fluorescence transfer was measured at $\lambda_{ex}$=337 nm and $\lambda_{em}$=620 and 665 nm using a microplate reader (Envision, Perkin Elmer). The test compounds were characterized in eight different concentrations in duplicate at each of the three cell lines. The reference agonist 5-HT was tested in each experiment. The IP1 concentrations in the different wells were determined by dividing the signal measured at 665 nm by that measured at 620 nm (ratio). The data for the test compounds were expressed as a percent of the control response to the 5-HT R$_{max}$.

TABLE 3

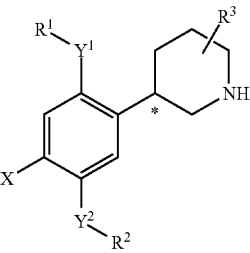

| Compound No. | * | X | $R^1$ | $R^2$ | $Y^1$ | $Y^2$ | $R^3$ | 5-HT$_{2A}$ EC$_{50}$ (nM) | $R_{max}$ | 5-HT$_{2B}$ EC$_{50}$ (nM) | $R_{max}$ | Selectivity EC$_{50}^{5\text{-}HT2B}$/EC$_{50}^{5\text{-}HT2A}$ |
|---|---|---|---|---|---|---|---|---|---|---|---|---|
| 8 | (S) | CF$_3$ | Me | Me | O | O | — | 20 | 74 | 150 | 60 | 7.5 |
| 10 | (S) | Cl | Me | Me | O | O | — | 380 | 62 | 240 | 50 | 0.63 |
| 12 | (S) | Br | Me | Me | O | O | — | 250 | 70 | 190 | 48 | 0.76 |
| 14 | (S) | I | Me | Me | O | O | — | 45 | 72 | 170 | 57 | 3.8 |
| 16 | (S) | CN | Me | Me | O | O | — | 980 | 77 | 5,000 | 45 | 5.1 |
| 18 | (S) | SMe | Me | Me | O | O | — | 270 | 72 | 180 | 64 | 0.67 |
| 20 | (S) | CF$_3$ | Me | Et | O | O | — | 36 | 79 | 580 | 57 | 16 |
| 22 | (S) | CF$_3$ | Et | Et | O | O | — | 170 | 54 | n.a. [@ 100 μM] $^a$ | n.d. $^b$ | >1,000 $^c$ |
| 24 | (S) | Me | Me | Me | O | O | — | 560 | 67 | 360 | 38 | 0.64 |
| 26 | (S) | iPrS | Me | Me | O | O | — | 1,100 | 72 | 1,200 | 43 | 1.1 |
| 28 | (S) | SEt | Me | Me | O | O | — | 180 | 62 | 240 | 55 | 1.3 |
| 30 | (S) | CF$_3$ | Et | Me | O | O | — | 140 | 35 | 1,200 | 26 | 8.6 |
| 32 | (S) | Et | Me | Me | O | O | — | 110 | 85 | 280 | 54 | 2.5 |
| 34 | (S) | Et | Me | Et | O | O | — | 160 | 78 | 860 | 50 | 5.4 |
| 35 | — | CF$_3$ | Me | Me | O | O | 6'-Me | 260 | 70 | 850 | 28 | 3.3 |
| 36 | — | CF$_3$ | Me | Me | O | O | 3'-Me | 41 | 61 | 120 | 39 | 2.9 |
| 37 | — | CF$_3$ | Me | Me | O | O | 2'-Me | 1,500 | 110 | 620 | 54 | 0.4 |
| 38 | — | CF$_3$ | Me | Me | O | O | 2'-Me | 120 | 60 | 2200 | 29 | 18 |
| 39 | (S) | CF$_3$ | CH$_2$F | Me | O | O | — | 300 | 60 | 1,100 | 54 | 3.6 |
| 41 | (S) | Et | Et | Et | O | O | — | 720 | 62 | n.a. [@ 100 μM] $^a$ >100,000 | n.d. $^b$ | >100 $^c$ |
| 43 | (S) | Et | Et | Me | O | O | — | 670 | 45 | 1,100 | 11 | 1.6 |
| 45 | (S) | CF$_3$ | Me | Me | O | S | — | 14 | 71 | 92 | 63 | 6.6 |
| 47 | (S) | CF$_3$ | Me | Et | O | S | — | 130 | 95 | 620 | 49 | 4.8 |
| 51 | (S) | CF$_3$ | Me | — | O | F | — | 260 | 59 | 740 | 37 | 2.8 |
| 53 | (S) | CF$_3$ | Me | — | O | H | — | 250 | 87 | 940 | 51 | 3.8 |
| 55 | (S) | CF$_3$ | Cyclopropyl | Me | O | O | — | 3,000 | 38 | n.a. [@ 100 μM] $^a$ >100,000 | n.d. $^b$ | >30 $^c$ |
| 57 | (S) | n-Bu | Me | Me | O | O | — | 190 | 62 | 350 | 18 | 1.8 |

Agonist potency (EC$_{50}$) and efficacy (R$_{max}$) exhibited by selected compounds according to the invention when tested at human 5-HT$_{2A}$ and human 5-HT$_{2B}$ receptors in the Eurofins functional IP assay.

EC$_{50}$ (in nM) and R$_{max}$ (in % of R$_{max}$ of 5-HT at the respective receptors) are based on duplicate determinations.

The EC$_{50}^{5\text{-}HT2B}$/EC$_{50}^{5\text{-}HT2A}$ ratios for the compounds are given as a measure of their 5-HT$_{2A}$-over-5-HT$_{2B}$ selectivity degrees.

$^a$ n.a., no agonist activity: the compound did not evoke significant responses at concentrations up to 100 μM.

$^b$ n.d., not determinable.

$^c$ Since the EC$_{50}$ value at 5-HT$_{2B}$ could not be determined, the EC$_{50}^{5\text{-}HT2B}$/EC$_{50}^{5\text{-}HT2A}$ ratio given for the compound is a conservative estimate based on its 5-HT$_{2A}$ EC$_{50}$ and the lack of significant agonist response at 5-HT$_{2B}$ at 100 μM.

As can be seen from table 3 the majority of compounds showed selectivity towards 5-HT$_{2A}$ over 5-HT$_{2B}$.

TABLE 4
| | 5-HT$_{2A}$ | | 5-HT$_{2B}$ | | 5-HT$_{2C}$ | | Selectivity |
|---|---|---|---|---|---|---|---|
| | EC$_{50}$ (nM) | R$_{max}$ (%) | EC$_{50}$ (nM) | R$_{max}$ (%) | EC$_{50}$ (nM) | R$_{max}$ (%) | EC$_{50}^{5\text{-}HT2C}$/EC$_{50}^{5\text{-}HT2A}$ |
| 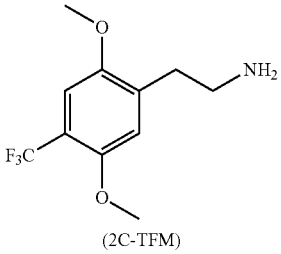 (2C-TFM) | 7.1 | 78 | 81 | 81 | 3.8 | 100 | 0.53 |
| 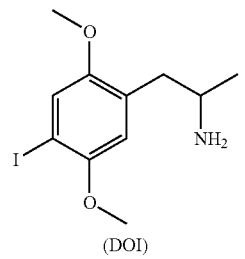 (DOI) | 7.3 | 89 | 13 | 79 | 9.1 | 89 | 1.3 |
| 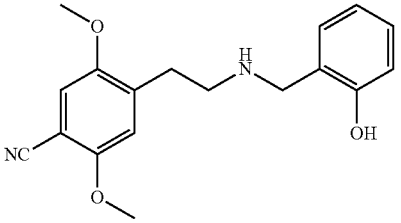 (25CN-NBOH) | 7.2 | 87 | 320 | 29 | 27 | 84 | 3.8 |
| 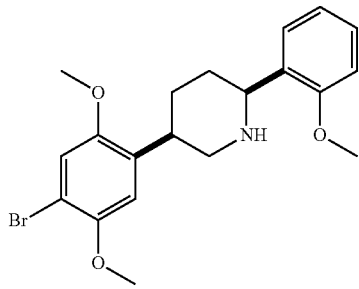 (8a) | 2,300 | 94 | 770 | 20 | 170 | 80 | 0.07 |

TABLE 4-continued

| | 5-HT$_{2A}$ | | 5-HT$_{2B}$ | | 5-HT$_{2C}$ | | Selectivity |
|---|---|---|---|---|---|---|---|
| | EC$_{50}$ (nM) | R$_{max}$ (%) | EC$_{50}$ (nM) | R$_{max}$ (%) | EC$_{50}$ (nM) | R$_{max}$ (%) | EC$_{50}^{5-HT2C}$/ EC$_{50}^{5-HT2A}$ |
| (8b) | n.a. [@ 100 µM] $^a$ >100,000 | n.d. $^c$ | n.a. [@ 100 µM] $^a$ >100,000 | n.d. $^c$ | w.a. [@ 100 µM] $^b$ >100,000 | n.d. $^c$ | n.d. $^c$ |

Functional properties of the known 5HT$_{2A}$ agonists 4-trifluoromethyl-2,5-dimethoxyphenethylamine (2C-TFM), 2,5-Dimethoxy-4-iodoamphetamine (DOI) and 4-(2-((2-hydroxybenzyl)amino)ethyl)-2,5-dimethoxybenzonitrile 25CN-NBOH in comparison with compound 8a and 8b from ACS Chem. Neurosci. 2013, 4, 96-109 at human 5-HT$_{2A}$, 5-HT$_{2B}$ and 5-HT$_{2C}$ in the Eurofins IP assay. EC$_{50}$ (in nM) and R$_{max}$ (in % of R$_{max}$ of 5-HT) are based on duplicate determinations. The EC$_{50}^{5-HT2C}$/EC$_{50}^{5-HT2A}$ ratios for the compounds are given as a measure of their 5-HT$_{2A}$-over-5-HT$_{2C}$ selectivity degrees.
$^a$ n.a., no agonist activity: the compound did not evoke significant responses at concentrations up to 100 µM.
$^b$ w.a., weak agonist activity: the compound only evoked a significant response at 100 µM.
Thus, a complete concentration-response curve could not be fitted, and EC$_{50}$ and R$_{max}$ values could not be determined.
$^c$ n.d., not determinable.
As can be seen from table 4 compound 8b does not act as an agonist at 5-HT$_{2A}$, 5-HT$_{2B}$ and 5-HT$_{2C}$.
Furthermore, compound 8a is an agonist at 5-HT$_{2A}$ and 5-HT$_{2C}$ but with high selectivity for 5-HT$_{2C}$ over 5-HT$_{2A}$.

Radioligand Binding Assays.

The binding affinities shown in table 5 of psilocin and compound 8 at various monoaminergic receptors were determined in radioligand competition binding assays by Psychiatric Drug Screening Program according to the experimental described in Assay Protocol Book, Version III.[11, 16] As shown compound 8 shows less affinity for various monoaminergic receptors compared to Psilocin.

TABLE 5

Binding affinities (K$_i$) exhibited by psilocin and compound 8 at various monoaminergic receptors in radioligand binding competition assays.

| Receptor | Psilocin K$_i$ (nM) | Comp. 8 K$_i$ (nM) | Receptor | Psilocin K$_i$ (nM) | Comp. 8 K$_i$ (nM) |
|---|---|---|---|---|---|
| 5-HT$_{1A}$ | 63 | 330 | D1 | 20 | >10,000 |
| 5-HT$_{1B}$ | 305 | n.t. | D2 | >10,000 | >10,000 |
| 5-HT$_{1D}$ | 19 | 663 | D3 | 100 | >10,000 |
| 5-HT$_{1e}$ | 44 | 762 | D4 | >10,000 | >10,000 |
| 5-HT$_{2A}$ | 340 | 16.5 | D5 | >10,000 | >10,000 |
| 5-HT$_{2B}$ | 4.7 | 85 | α$_{1A}$ | >10,000 | >10,000 |
| 5-HT$_{2C}$ | 140 | 42 | α$_{1B}$ | >10,000 | >10,000 |
| 5-HT$_3$ | n.t. | >10,000 | α$_{2A}$ | 2,000 | 1,400 |
| 5-HT$_{5A}$ | 70 | >10,000 | α$_{2B}$ | 1,300 | 820 |
| 5-HT$_6$ | 72 | 623 | α$_{2C}$ | 4,400 | >10,000 |
| 5-HT$_7$ | 72 | 2,360 | | | |

The binding data for psilocin and compound 8 were determined by Psychiatric Drug Screening Program.[11]

TABLE 6

Agonist potency (EC$_{50}$) and efficacy (R$_{max}$) of psilocin (the active metabolite of psilocybin) when tested at stable 5-HT$_{2A}$- and 5-HT$_{2C}$-cell lines and cells transiently transfected with 5-HT$_{2B}$ in a phosphoinositide hydrolysis assay.

| | Psilocin | |
|---|---|---|
| Receptor | EC$_{50}$ (nM) | R$_{max}$ (%) |
| 5-HT$_{2A}$ | 24 ± 2 | 43 ± 17 |
| 5-HT$_{2B}$ | 58 | 45 |
| 5-HT$_{2C}$ | 30 ± 18 | 51 ± 37 |

EC$_{50}$ ± S.D. values are given in nM and R$_{max}$ ± S.D. values are given in % of the R$_{max}$ of 5-HT at the respective receptors. Data are from Sard, H. et al.[15]

In Vivo Pharmacology General Information

The Head Twitch Response Model 1 (Mice)

Animals.

Male C57BL/6J mice (6-8 weeks old) obtained from Jackson Laboratories (Bar Harbor, Me., USA) were housed in a vivarium at an AAALAC-approved animal facility that meets all Federal and State requirements for care and treatment of laboratory animals. Mice were housed up to four per cage in a climate-controlled room on a reverse-light cycle (lights on at 1900 h, off at 0700 h) and were provided with ad libitum access to food and water, except during behavioral testing. Testing was conducted between 1000 and 1800 h. All animal experiments were carried out in accordance with NIH guidelines.

Head Twitch Response Studies.

The head twitch response (HTR) was assessed using a head-mounted magnet and a magnetometer detection coil 12. Briefly, mice were anesthetized, a small incision was made in the scalp, and a small neodymium magnet was attached to the dorsal surface of the cranium using dental cement. Following a two-week recovery period, HTR experiments were carried out in a well-lit room with at least 7 days between sessions to avoid carryover effects. Compound 8 was dissolved in isotonic saline solution (vehicle) in concentrations of 0.06 mg/mL, 0.2 mg/mL, 0.6 mg/mL, 2 mg/mL and 6 mg/mL and injected intraperiotoneally (IP) at a volume of 5 mL/kg. Mice were injected with compound 8 or vehicle and then HTR activity was recorded in a glass cylinder surrounded by a magnetometer coil for 30 min. Coil voltage was low-pass filtered (2-10 kHz cutoff frequency), amplified, and digitized (20 kHz sampling rate) using a Powerlab/8SP with LabChart v 7.3.2 (ADInstruments, Colorado Springs, Colo., USA), then filtered off-line (40-200 Hz band-pass). Head twitches were identified manually based on the following criteria: 1) sinusoidal wavelets; 2) evidence of at least three sequential head movements (usually exhibited as bipolar peaks) with frequency 40 Hz; 3) amplitude exceeding the level of background noise; 4) duration <0.15 s; and 5) stable coil voltage immediately preceding and following each response.

Data Analysis

Figure 2A:
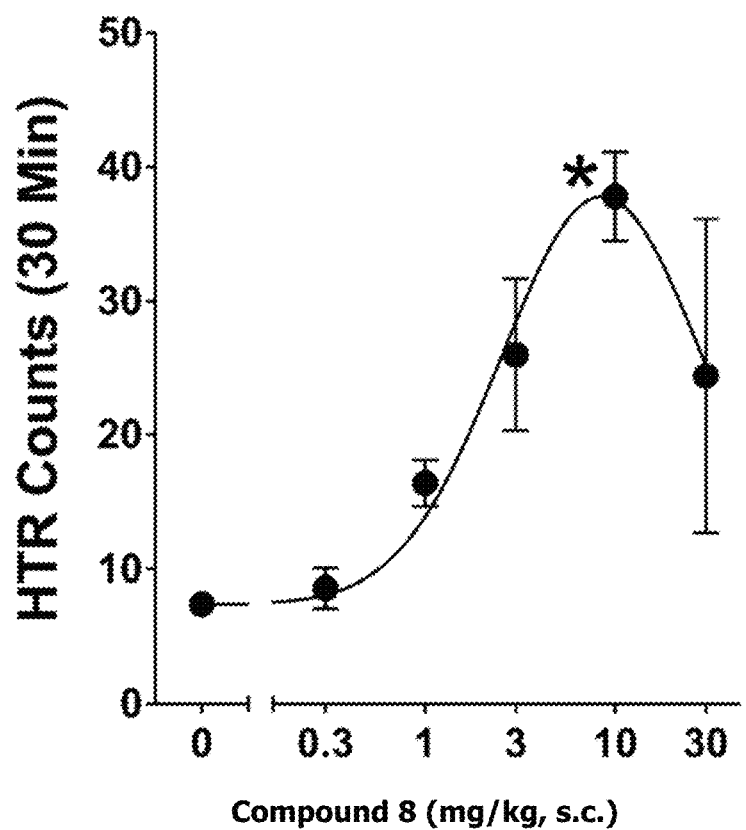
FIGS. 2A and 2B show the head twitch response (HTR) induced by compound 8 in mice and rats, respectively. It is well-established that $5\text{-}HT_{2A}$ agonists elicit this characteristic HTR in rodents, and the behavioural effect thus represents a demonstration of CNS exposure and $5\text{-}HT_{2A}$ agonism in vivo.[6, 7]

Head twitch counts were analysed using one-way analyses of variance (ANOVA). Post hoc pairwise comparisons between selected groups were performed using Tukey's studentized range method. Median effective doses (ED50 values) and 95% confidence intervals (95% CI) for HTR dose-response experiments were calculated by nonlinear regression (Prism 7.00, GraphPad Software). A gaussian distribution was used to fit biphasic HTR dose-response data (see FIG. 2A).

The Head Twitch Response Model 2 (Rats)

Animals

A total number of 8 male Sprague Dawley (SD) rats (9-10 weeks old, weighing 300-450 g) were used in a dose response HTR test of compound 8 (n=2 animals/dose). The rats were bred and housed at Translational Neuropsychiatry Unit (TNU), Aarhus University. They animals were housed in pairs (Cage 1291H Eurostandard Type III H, 425×266× 185 mm, Techniplast, Buguggiate, Italy) at 20±2° C. on a 12-h light/dark cycle (lights on at 07:00 am) and had ad libitum access to chow pellets and tap water. The animal colony was protected from outside noise, and all experimental procedures were performed in specially equipped rooms within the vivarium. The Danish National Committee for Ethics in Animal Experimentation had approved all animal procedures prior to initiation of the experiments (2016-15-0201-01105).

Drugs

The doses of compound 8 were established according the use of classical hallucinogen serotonergic psychedelics drugs in the class of phenylalkylamines described in the literature.[12] Concentrations of 0.375, 0.75, 1.5 and 3.0 mg/kg of compound 8 were tested in comparison with the administration of saline—NaCl solution—9 mg/mL (VEH) (Fresenius lab, Bad Homburg v.d.H, Germany).

The scale was calibrated and the compound was weighed inside an 1.5 mL eppendorf tube, diluted in NaCl solution—9 mg/mL (Fresenius lab, Bad Homburg v.d.H, Germany) and transferred for 15 mL tubes prior to the experiment day. The drug was stored in −4° C. for the use in the following day. All the doses were calculated and prepared for injection of a final volume of 1 mL/kg.

Procedure

The animals were randomized and weighed one day prior of the experiment. The cages were transferred from the vivarium to the experiment room 1 hour before the experiment start, to acclimate the animals. Before injections, the tubes containing the different doses of the drug were kept at room temperature. The set up was built using 2 cameras to record each animal. Camera 1 was located on top of the cage and recorded the animal from the above, while a frontal camera 2 was recording from the side. 29 G sterilized syringes of 0.5 mL (BD Ultra-fine insulin syringe, Beckton Dickinson, Franklin Lakes, N.J., USA) were filled with the volume calculated according to the individual animal weigh. The drug was administered i.p. The animal was transferred to the set up camera room and placed in a new transparent cage with no lid (482×267×210 mm). The animals were observed for 1 hour, while the vehicle group was observed for 30 min.

After the recording, the animals were placed in their original cages with water and food ad libitum where they remained for extra 30 min. At the endpoint 1.5 h, the animals were euthanized by decapitation. The brain structures of frontal cortex, hypothalamus and hippocampus were collected and frozen on powdered dry ice for further molecular analysis. The tissues were stored at −80° C.

HTR Score

Figure 2B:
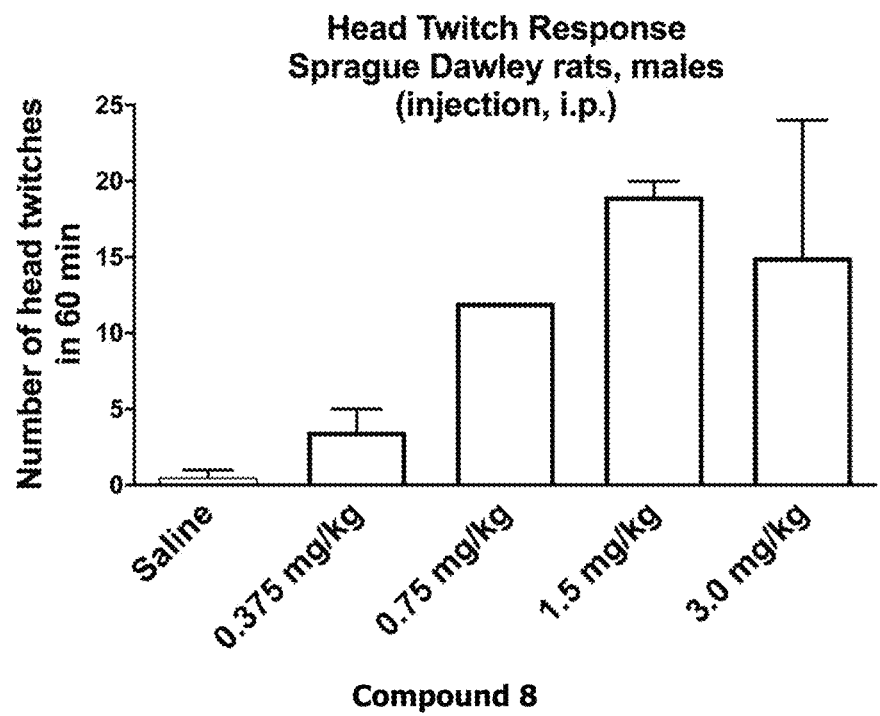

The MTS files from the video-recordings were transferred to the computer and analyzed. The responses producing head shakes were counted and reported in a timeline (see FIG. 2B).

The Hinders Sensitive Line (FSL) Model

Animals

Male Flinders line rats (Flinders Sensitive Line (FSL) and their control Flinders Resistant Line (FRL); 9-11 weeks of age; 228-336 g) from the colony maintained at (TNU), Aarhus University (originally derived from the colony at the University of North Carolina, USA) were housed in pairs (Cage 1291H Eurostandard Type III H, 425×266×185 mm, Techniplast, Buguggiate, Italy) at 20±2° C. on a 12-h light/dark cycle (lights on at 07:00 am). The animals had ad libitum access to chow pellets and tap water. The animal colony was protected from outside noise, and all experimental procedures were performed in specially equipped rooms within the vivarium. The Danish National Committee for Ethics in Animal Experimentation had approved all animal procedures prior to initiation of the experiments (2016-15-0201-01105).

Behavioural Tests

Open field test: Compound 8 was dissolved in saline and administered i.p. at 1.5 mg/kg. The following groups were included in the experiment: FRL-vehicle (n=10), FSL-vehicle (n=10), FSL-ketamine (15 mg/kg S-ketamine, Pfizer) (n=8), and FSL-compound 8 (1.5 mg/kg) (n=10). 50 minutes after injection of either vehicle or compound 8, locomotor activity was assessed in an open field in order to detect possible inhibitory or stimulatory drug effects that could confound the performance in the forced swim test (FST). A squared open field arena (plastic; 50×50×37 cm) with a light intensity of approximately 5 lux was used. Each rat was allowed to move freely for 5 min. The test arena was thoroughly cleaned with 70% ethanol between each rat to minimize the impact of olfactory cues. A camera, located directly above the center of the field, recorded the session and the total distance moved was quantified using EthoVision XT video tracking software (version 11.0.928; Noldus Information Technology, Wageningen, The Netherlands).

Forced swim test: After the open field test (OFT) and 60 minutes after injection of either vehicle or compound 8, the antidepressant potential was assessed in a modified FST.[13] Since FSL rats inherently show a depression-like phenotype, no pre-swim session was required. The rat was placed in an acrylic plastic cylinder (60 cm in height, 24 cm in diameter) containing 40 cm of water (25±1° C.) for 7 min. A camera, located directly in front of the cylinder, recorded the session.

Figure 3:
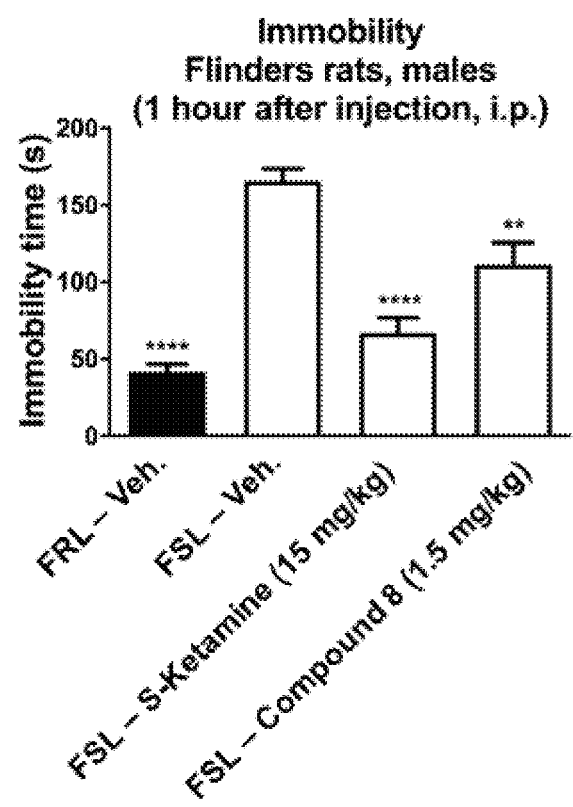
FIG. 3 shows the effects of compound 8 and (S)-ketamine (which belongs to another class of rapid antidepressant drugs) on immobility time of Flinders Sensitive Line (FSL) rats in the forced swim test. The FSL is a genetic rodent model for depression, as the animals exhibit reduced appetite, reduced mobility, anhedonia and sleep abnormalities.[8] The Flinders Resistant Line (FRL) is a control line that exhibits none of these depression-like symptoms. Both compound 8 (1.5 mg/kg, i.p.) and (S)-ketamine (15 mg/kg, i.p.) reduce the immobility time compared to the vehicle-treated FSL rats one hour after intraperitoneal administration.

An experienced investigator blinded to the treatments measured the time spent struggling (defined as attempts to climb the cylinder wall or diving), swimming (defined as a forward propulsion in the water surface), and being immobile (defined as the absence of movements except for the necessary activities to keep the head above water). Results are shown in FIG. 3.

The Adrenocorticotropic Hormone Model

The adrenocorticotropic hormone model (ACTH) model was conducted as previously described.[14] Male Sprague Dawley rats were used (age 7 weeks, N=50) (Taconic Biosciences A/S, Lille Skensved, Denmark). After 1 week habituation, the rats were given either 100 μg ACTH/animal/day s.c. (Adrenocorticotropic Hormone 1-24 (China Peptides, China)) at 10 a.m. for 14 days (n=30) or vehicle (VEH) consisting of 0.9% saline (n=20). At day 14, the rats were subjected to a pre-swim test (15 minutes). Following the pre-swim, the rats in the ACTH group (n=30) were administered with either 3 injections of imipramine (n=10) (IMI, 15 mg/kg (Sigma-Aldrich, Denmark, i.p.), 1 injection of compound 8 (n=10) (1.5 mg/kg i.p.), or vehicle (n=10). The rats in the VEH group (n=20) were administered with either 3 injections of imipramine (n=10) or vehicle (n=10), thus creating 5 groups with 10 animals in each group (VEH-VEH, VEH-IMI, ACTH-VEH, ACTH-IMI, ACTH-compound 8). The 3 IMI-injections were given at 24 hours, 18 hours, and 1 hour prior to the forced swim test (FST) at day 15. Compound 8 was given 1 hour prior to the FST. Preceding the FST, rat baseline mobility was determined in the (OFT). The OFT and the FST were conducted as described above. Results are shown in FIGS. 4A and 4B.

Chemical Synthesis General Experimental Details

All reactions were performed under an atmosphere of argon unless otherwise indicated. Reagents and starting materials were obtained from commercial sources and used as received. Solvents were of chromatography grade or dried either by an SG Water solvent purification system (DCM, DMF, THF) or with 3 Å molecular sieves (DMSO, toluene, MeCN, $Et_2O$, EtOH, DME and MeOH). Anhydrous reactions were run in flame- or oven-dried (150° C.) glassware under $N_2$ or argon. Purification by column chromatography and dry column vacuum chromatography (DCVC) was done following standard procedures using Merck Kieselgel 60 (40-63 μm or 15-40 μm mesh, respectively. Microwave assisted reactions were performed on a Biotage Initiator apparatus in a sealed vial using external surface sensor for temperature monitoring.

Thin-Layer Chromatography (TLC)

For TLC analysis, pre-coated silica gel 60 $F_{254}$ plates purchased from Merck were used. EtOAc, n-heptane, acetone, toluene, DCM, $Et_2O$, MeOH, $Et_3N$, and mixtures thereof were used as eluents. Visualization of the compounds was achieved with UV light (254 nm), iodine on silica or potassium permanganate, anisaldehyde, ninhydrin or ferric chloride stains. The denoted retention factors (Rf) were rounded to the nearest 0.05.

Liquid Chromatography Mass Spectrometry (LCMS)

LC/MS analyses were performed on Shimadzu Prominence chromatograph connected to Applied Biosystems API 2000 mass spectrometer, column Phenomenex Gemini 5 μm $C_{18}$; 50×2 mm, eluent MeCN (+0.1% HCOOH)/$H_2O$ (+0.1% HCOOH).

High Performance Liquid Chromatography Methods (HPLC)

HPLC retention times ($t_R$) are reported in minutes (min) and were determined by different methods, given in parenthesis.

Method A: HPLC was recorded on a Thermo Scientific Dionex 3000 UltiMate instrument connected to a Thermo Scientific Dionex 3000 Diode Array Detector by a Gemini-NX 3 μm C18 110A (250×4.6 mm) column with UV detection at 205, 210, 254 and 280 nm. Mobile phase (MP) A: 0.1% TFA in $H_2O$ (v/v). MP B: 0.1% TFA, 10% $H_2O$ in MeCN (v/v/v). Flow rate: 1.0 mL/min. Gradient: 0-30 min: 0-100% MP B.

Method B: HPLC was recorded on a Thermo Scientific Dionex 3000 UltiMate instrument connected to a Thermo Scientific Dionex 3000 Diode Array Detector using a Gemini-NX 3 μm C18 110A (250×4.6 mm) column with UV detection at 205, 210, 254 and 280 nm. MP A: 0.1% TFA in $H_2O$ (v/v). MP B: 0.1% TFA, 10% $H_2O$ in MeCN (v/v/v). Flow rate: 1.0 mL/min. Gradient: 0-20 min: 0-100% MP B.

Method C (Preparative HPLC): Preparative HPLC was performed on a Thermo Scientific Dionex 3000 ultimate instrument connected to a Thermo Scientific Dionex 3000 photodiode array detector using a Gemini-NX 5u RP C18 column (250×21.2 mm) with UV detection at 254 and 280 nm. MP A: 0.1% TFA, 100% $H_2O$ (v/v). MP B: 0.1% TFA, 10% $H_2O$, 90% MeCN (v/v/v). Flow rate 20 mL/min. Gradient: 0-25 min: 0-100% MP B, 25-30 min: 100% MP B.

Method D (Chiral HPLC): Enantiomeric excess (ee) of the desired enantiomers was determined using a Thermo Scientific Dionex 3000 UltiMate instrument connected to a Thermo Scientific Dionex 3000 Diode Array Detector using an analytical Phenomenex Lux 5 Amylose-2 (250×4.6 mm) chiral column with UV detection at 205, 210, 254 and 280 nm. MP A: 0.1% Diethylamine in Heptane (v/v). MP B: 0.1% Diethylamine in EtOH (v/v). Flow rate: 10.0 mL/min. using an isocratic gradient: 10% MP B.

High Resolution Mass Spectrometry (HRMS)

Performed by matrix-assisted laser ionisation time-of-flight mass spectrometry (MALDI-TOF). Analysis was performed in positive ion mode with MALDI ionization on a Thermo QExactive Orbitrap mass spectrometer (Thermo Scientific, Bremen, Germany) equipped with an AP-SMALDI 10 ion source (TransmitMIT, Giessen, Germany) and operated with mass resolving power 140,000 at m/z 200. 2,5-Dihydroxybenzoic acid was used as matrix and lock-mass for internal mass calibration, providing a mass accuracy of 3 ppm or better. Samples were prepared using 2,5-dihydroxybenzoic acid as the matrix.

Melting Point (MP)

Melting point was measured for recrystallized compounds on a Stanford Research System OptiMelt capillary melting point apparatus with visual inspection and the values are reported in a range rounded to the nearest 0.5° C.

Nuclear Magnetic Resonance Spectroscopy (NMR)

NMR experiments were performed on a 300, 400 or 600 MHz Bruker instrument or a Varian Mercury (400 MHz) instrument. The obtained spectra were analysed using MestReNova 11.0 software typically using Whittaker smoother baseline correction. Chemical shifts are reported in ppm (δ) with reference to the deuterated solvent used. Coupling constants (0.1) are reported in Hertz (Hz). Multiplet patterns are designated the following abbreviations or combinations thereof: br (broad), m (multiplet), s (singlet), d (doublet), t (triplet), q (quartet), p (pentet), sex (sextet) and hep (heptet).

General Procedures

Hydrogenation Procedure A. Hydrogenantion of Phenylpyridines Using Parr Apparatus The phenylpyridine (1 eq.) was dissolved in glacial AcOH (1.0 M) in a hydrogenation flask. $PtO_2$ (0.1 eq.) was added and the reaction vessel was shaken under $H_2$ atmosphere (50-60 psi) on a Parr-apparatus for 24 h. Upon completion, the reaction mixture was washed through a pad of Celite with EtOAc (25 mL) and the filtrate was basified using 35% aq. NaOH solution. The phases were separated isolated and the aqueous layer further extracted with EtOAc (2×50 mL). The combined organic phases were dried over $MgSO_4$, filtered and evaporated in vacuo.

Hydrogenation Procedure B. Hydrogenantion of Phenylpyridines Using Thalesnano H-Cube The phenylpyridine was dissolved in glacial AcOH (0.01M). Thalesnano H-Cube was loaded with a fresh catalyst cartridge ($Pd(OH)_2$/C). The apparatus was set to run at 100° C. and 80 Barr. The reaction was followed by TLC. Upon complete consumption of starting material, AcOH was removed in vacuo.

General Procedure C the Synthesis of Phenylpyridines

A flame dried round-bottom flask equipped with a stir bar and a cooler, backfilled with N2 gas was charged with the appropriate boronic acid (1 eq.), 3-bromopyridine (1.1 eq.), triphenylphosphine (0.15 eq.) and DME (10 M). 2M aqueous $Na_2CO_3$ (2.7 eq.) was added followed by Pd/C (0.15 mmol). The reaction was stirred at 80° C. for 17 h under N2 atmosphere. The reaction was allowed to cool to ambient temperature, then filtered over a pad of Celite. The filtrate was diluted with $H_2O$ and EtOAc. The phases were separated and the aqueous phase further extracted with EtOAc. The combined organic phases were washed with $H_2O$ and brine before being dried over $MgSO_4$, filtered and evaporated in vacuo. The crude product was purified by flash column chromatography to give the title compound.

General Procedure D. The Separation of Enantiomeric Mixtures of Free-Amines

Analytical amounts of the racemate was dissolved in a mixture of MeOH, EtOH and Diethylamine (10:17:0.1) and separated by Enantiomeric separation method 1, 2 or 3 unless otherwise specified. The hydrochloride salts were prepared by dissolving the products in a minimum amount of $Et_2O$ and treating the solution with 4 M HCl in dioxane. The precipitate was isolated by decantation and redissolved in the minimum amount of MeOH. $Et_2O$ was added dropwise until nucleation was observed and the solution was allowed to crystalize at −4° C. overnight giving the pure title compound as white or off-white solids. Enantiomeric excess (EE) of the desired enantiomer was determined using Chiral HPLC Method 1. (ee>95%). The (S)-enantiomer eluted first. All other analytical data was identical for both enantiomers.

Enantiomeric Separation Method 1.—Chiral HPLC

Analytical amounts of racemate were dissolved in a mixture of MeOH, EtOH and Diethylamine (10:17) and separated on a Thermo Scientific Dionex 3000 UltiMate instrument connected to a Thermo Scientific Dionex 3000 Diode Array Detector by a Phenomenex Lux 5 Amylose-2 (250×10 mm) chiral column with UV detection at 205, 210, 254 and 280 nm. MP A: 0.1% Diethylamine in Heptane (v/v). MP B: 0.1% Diethylamine in EtOH (v/v). Flow rate: 10.0 mL/min. using an isocratic gradient of 30-10% MP B. Loadings were between 1-3 mL per injection (3-5 mg/mL). The (S)-enantiomers eluted at retention times between 2 min and 18 min depending upon loading. Enantiomeric excess (EE) of the desired enantiomers was determined on an identical instrument using a Phenomenex Lux 5 Amylose-2 (250×4.6 mm) chiral column.

Enantiomeric Separation Method 2.—Chiral SFC

Racemic amine as the hydrochloride was dissolved in MeOH and separated by preparative supercritical fluid chromatography (SFC). Separation was performed on a Diacell AD-H chiralpak column (250×21.2 mm) connected to a Berger Multigram II operating at 50 mL/min at 35° C. and 100 bar backpressure using stacked injections. MP: $CO_2$ (75%) and Ethanol+0.1% diethylamine (25%). UV detection at 290 nM Enantiomeric excess (EE) of the enantiomers was determined on a Diacell AD-H chiralpak column 3μ 15 cm (150×4.6 mm) connected to an Aurora Fusion A5/Agilent SFC system operating at 4 mL/min at 40° C. and 150 bar backpressure. MP: $CO_2$ (75%) and Ethanol+0.1% diethylamine (25%).

Enantiomeric Separation Method 3.—Resolution by Chiral Salt Formation and Crystallization Racemic amine (1 eq.) was dissolved in MeOH (0.5 M) at room temperature and added over 5 minutes to a boiling solution of L(+)tartaric acid (1 eq.) in MeOH (70 mM). Upon complete addition, the reaction was left to cool to room temperature for 48 h yielding white crystalline solids which were isolated by filtration. The filtrate was left at 4° C. overnight giving a second crop of solids, isolated by filtration. Crops were combined and redissolved in boiling MeOH (40 mL) and allowed to cool to room temperature giving white solids which were again subjected to recrystallization from boiling MeOH (20 mL) eventually giving clear prismatic crystals (5% total yield, 96% enantiomeric excess)

Enantiomeric excess (EE) of the desired enantiomer was determined using a Thermo Scientific Dionex 3000 UltiMate instrument connected to a Thermo Scientific Dionex 3000 Diode Array Detector by a Phenomenex Lux 5 Amylose-2 (250×4.6 mm) chiral column with UV detection at 205, 210, 254 and 280 nm. MP A: 0.1% Diethylamine in Heptane (v/v). MP B: 0.1% Diethylamine in EtOH (v/v). Flow rate: 10.0 mL/min. using an isocratic gradient of 30-10% MP B.

General Procedure E. The Coupling of Functionalized Sulfonyl Hydrazines with Boronic Acid to Give Phenyl Azetidines and Phenyl Pyrrolidines.

A flame dried microwave vial, backfilled with argon gas, was charged with sulfonylhydrazone (1 eq.), boronic acid (2 eq.) and dry $Cs_2CO_3$ (1.1 eq.). The contents of the vial were sealed and subjected to high vacuum for 2 h before re-establishing argon atmosphere. The contents of the vial were suspended in anhydrous 1,4 Dioxane (0.12 M). The suspension was thoroughly de-gassed before capping the vial. The reaction was heated to 110° C. under vigorous stirring. After 18 h the reaction was allowed to cool to ambient temperature and filtered over a plug of celite. The filtrate was concentrated in vacuo and immediately subjected to purification by flash column chromatography (1:2 EtOAc/Heptane) giving the desired compound with minor impurities as a clear oil.

The crude carboxylate was dissolved in 4 M HCl in dioxane (1 mL) and stirred at ambient temperature for 24 h. The pure amine hydrochloride was precipitated out by the addition of $Et_2O$ (25 mL) and isolated by decantation giving the title compound.

General Procedure F. Coupling of Pyridyl Boronic Acids with Aryl Bromides.

A flame dried microwave vial equipped with a stir-bar and backfilled with argon gas was charged with the corresponding boronic acid (1 eq.) and [1,1'-Bis(di-tert-butylphosphino)ferrocene]dichloropalladium(II) (5 mol %) within a glove box and tightly sealed. Aqueous degassed $K_3PO_4$ solution (0.9 M, 1.5 eq.) was added, followed by addition of the corresponding aryl bromide (1 eq) in degassed dioxane (0.3 M). The resulting mixture was heated by microwave irradiation at 100° C. for 1 h, then allowed to cool to ambient temperature, filtered through a silica pad and further eluted with EtOAc, then evaporated in vacuo. The residue was purified by flash-column chromatography using mobile phase mixtures of Petroleum ether/EtOAc.

General Procedure G. Bromination of Phenols.

A flame dried round-bottom flask, equipped with a stir bar and a rubber septum, backfilled with argon gas, was charged with the corresponding phenol (1 eq.) in DCM and AcOH (2:1, 0.1 M) elemental bromine was added (1.05 eq.) dropwise at 0° C. The reaction mixture was slowly warmed to ambient temperature overnight, then evaporated directly in vacuo. The residue was purified by flash-column chromatography using mobile phase mixtures of Petroleum ether/EtOAc.

General Procedure H. Methylation of Phenols

A flame dried microwave vial equipped with a stir bar and backfilled with argon gas, was charged with the corresponding phenol (1 eq.) in acetone (0.25 M). $K_2CO_3$, (8 eq.) was added followed by methyl iodide (6 eq.). The vial was sealed and the reaction mixture was stirred for 5 h at 60° C. then evaporated directly in vacuo and partitioned between DCM and $H_2O$. Phases were separated and the aqueous phase further extracted with DCM. Combined organic extracts were dried over $Na_2SO_4$, filtered, and evaporated in vacuo. The residue was purified by flash-column chromatography using mobile phase mixtures of Petroleum ether/EtOAc.

General Procedure J. Ethylation of Phenols

A flame dried microwave vial equipped with a stir bar and backfilled with argon gas, was charged with the corresponding phenol (1 eq.) in acetone (0.25M) $K_2CO_3$, (8 eq) was added followed by bromoethane (5 eq.). The vial was sealed and the reaction mixture was stirred for 5 h at 60° C. then evaporated directly in vacuo and partitioned between DCM and $H_2O$. Phases were separated and the aqueous phase further extracted with DCM. Combined organic extracts were dried over $Na_2SO_4$, filtered, and evaporated in vacuo. The residue was purified by flash-column chromatography using mobile phase mixtures of Petroleum ether/EtOAc.

General Procedure I. Hydrogenation of Pyridines Using Pressure Reactor.

To a stirred solution of the substrate (1 eq.) in glacial AcOH (0.25 M) was added $PtO_2$ (15 mol %). The reaction mixture was hydrogenated at ambient temperature under 10 Bar $H_2$ pressure in a Buchi tinyclave steel pressure reactor. After 16 h the reaction mixture was filtered through a syringe filter and evaporated in vacuo. The residue was partitioned between DCM and aq. sat. $NaHCO_3$. The organic phase was separated, the aqueous phase was further extracted with DCM. Combined organic extracts were dried over $Na_2SO_4$, filtered, and evaporated in vacuo. The residue was used in the next step without further purification.

General Procedure K. Introduction of Boc Protecting Group.

A round-bottom flask was charged with the amine (1 eq.), $Boc_2O$ (1.5 eq.) and $Et_3N$ (2 eq.) was added. The resulting mixture was stirred for 1 h at ambient temperature then evaporated to dryness in vacuo. The residue was purified by flash-column chromatography using mobile phase mixtures of Petroleum ether/EtOAc.

General Procedure L. Cleavage of Boc Protecting Group.

A round-bottom flask was charged with the carboxylate (1 eq.) and etheral HCl (40 eq.) was added. The solution was stirred for 3-7 days at ambient temperature to achieve full conversion eventually giving the desired product as a white precipitate. The slurry was centrifuged and the etheral layer discarded. The resulting solids were washed with $Et_2O$ and evaporated to dryness in vacuo.

General Procedure M. Reductive Amination.

A flame dried round-bottom flask equipped with a stirr bar and a rubber septum was charged with the amine (1 eq.) and MeOH (61.5 mM). The corresponding aldehyde (5 eq.) was added, followed by one drop of AcOH. The resulting mixture was cooled to 0° C., then $NaCNBH_3$ (3 eq.) was added. The reaction mixture was allowed to warm up to room temperature overnight. DCM was added and the mixture was washed with 1 M NaOH and brine. The organic phase was dried over anhydrous $Na_2SO_4$, filtered and evaporated. The residue was taken up in $Et_2O$ and treated with ethereal 2M HCl (5 eq.). The resulting suspension was centrifugated. The supernatant was discarded, the solid washed with ether, and evaporated to dryness in vacuo.

General Procedure N. Thioanisole Derivative Synthesis from Bromobenzenes

A flame dried round-bottom flask equipped with a stirr bar and a rubber septum, backfilled with argon gas, was charged with 1,4-Dibromo-2,5-dimethoxybenzene (1 eq.) in dry THF (0.4 M). The resulting solution was cooled to −78° C. and 2.5 M n-BuLi in Hexanes (1.1 eq.) was added dropwise. The reaction mixture was stirred at this temperature for 1 h before the dropwise addition of the appropriate disulfide (1.1 eq.). The mixture was allowed to warm to ambient temperature and stirred for 1 h then quenched with 1 M HCl. The mixture was concentrated under reduced pressure to half of the initial volume. $Et_2O$ was added and phases separated. The organic phase was washed with $H_2O$ and $NaHCO_3$, then concentrated in vacuo. The residue was purified by flash-column chromatography using mobile phase mixtures of Petroleum ether/EtOAc.

General Procedure O. Thioanisole Derivative Synthesis from Fluorobenzenes

A flame dried round-bottom flask equipped with a stirr bar and a cooler, backfilled with argon gas, was charged with 3-(5-fluoro-2-methoxy-4-(trifluoromethyl)phenyl)pyridine (1 eq) and anhydrous DMF (233 M). To this suspension was added the appropriate sodium thiolate (1.5 eq). The resulting mixture was heated to 50° C. for 24 h. After cooling to ambient temperature, the reaction mixture was concentrated in vacuo and the resulting crude residue was partitioned between $Et_2O$ and $H_2O$. The organic phase was isolated and the aqueous phase further extracted with $Et_2O$. Combined organic extracts were dried over anhydrous $Na_2SO_4$, filtered, and evaporated in vacuo. The residue was purified by flash-column chromatography using mobile phase mixtures of Petroleum ether/EtOAc.

Synthesis of Compound 1 and 2

4-methoxybenzenesulfonohydrazide

A round bottom flask equipped with a stir bar and a rubber septum was charged with 4-methoxybenzenesulfonyl chloride (5.17 g, 25 mmol) in THF (125 mL) and cooled to 0° C. 50% aq. hydrazine solution (3.90 mL, 62.5 mmol) was added via dropwise addition. The reaction mixture was stirred at 0° C. for 1 h before being evaporated in vacuo. The crude residue was partitioned between $H_2O$ (50 mL) and EtOAc (100 mL) and phases were separated. The aqueous phase was further extracted with EtOAc (2×100 mL). Combined organic phases were washed with $H_2O$ water (50 mL) and brine (50 mL), dried over $Na_2SO_4$, filtered and evaporated in vacuo to yield the title compound as a colorless amorphous solid (3.79 g, 75%). $^1$H-NMR (600 MHz, $CDCl_3$) δ 7.85 (d, J=8.9 Hz, 2H), 7.02 (d, J=8.9 Hz, 2H), 5.55 (s, 1H), 3.89 (s, 3H), 3.59 (s, 2H); $^{13}$C-NMR (151 MHz, $CDCl_3$) δ 163.86, 130.63, 127.64, 114.68, 55.86.

tert-butyl 3-(2-((4-methoxyphenyl)sulfonyl)hydrazineylidene)azetidine-1-carboxylate To a flame dried microwave vial, backfilled with argon gas, was added 4-methoxybenzenesulfonohydrazide (3.83 g, 18.91 mmol) and tert-butyl 3-oxoazetidine-1-carboxylate (3.24 g, 18.93 mmol). The contents of the vial were dissolved in anhydrous DMSO (13 mL). The vial was capped and heated to 60° C. The reaction was followed by H-NMR. Upon completion, the reaction mixture was poured into H$_2$O (350 mL) and the aqueous mixture extracted with Et$_2$O (3×100 mL). Combined organic phases were washed with H$_2$O (5×50 mL) and brine (50 mL), dried over Na$_2$SO$_4$, filtered and evaporated in vacuo to give the crude compound, in quantitative yields, as an off-white solid with minor impurities. The product was deemed of sufficient purity for use in the subsequent reactions without further purification. TLC Rf=0.1 (33% EtOAc in Heptane v/v); $^1$H-NMR (400 MHz, DMSO-d$_6$) δ 7.70 (dd, J=8.9, 3.4 Hz, 3H), 7.08 (dd, J=8.8, 4.2 Hz, 3H), 4.48-4.34 (m, 3H), 3.80 (d, J=3.1 Hz, 4H), 1.33 (bs, 9H); $^{13}$C-NMR (101 MHz, DMSO-d$_6$) δ 163.13, 156.17, 148.44, 130.86, 130.00, 114.85, 79.96, 56.16, 28.38.

(4-bromo-2,5-dimethoxyphenyl)boronic acid

To a flame dried vessel, backfilled with argon gas, was added 1,4-dibromo-2,5-dimethoxybenzene (2.22 g, 7.5 mmol) and anhydrous THF (75 mL). the reaction was cooled to −78° C. before the slow, dropwise addition of n-BuLi solution (2.17 M, 7.5 mmol). The solution was stirred at −78° C. for 20 minutes before the addition of Triisopropyl borate (5.19 mL, 22.5 mmol). The cooling source was removed and the reaction was allowed to reach ambient temperature and stirred on for an additional 20 h before quenching by careful addition of 2 M aq. HCl solution (15 mL). The aqueous mixture was diluted with Et$_2$O (100 mL) and phases were separated. The aqueous phase was further extracted with Et$_2$O (2×100 mL). Combined organic phases were washed with H$_2$O (50 mL), dried over Na$_2$SO$_4$, filtered through a plug of silica and evaporated to give the title compound as a crude white solid with minor impurities. The product was deemed of sufficient purity for use in the subsequent reactions without further purification.

(2,5-dimethoxy-4-(trifluoromethyl)phenyl)boronic acid

A flame dried vessel, backfilled with argon gas, was charged with 1-bromo-2,5-dimethoxy-4-(trifluoromethyl) benzene (1.00 g, 3.52 mmol) and anhydrous THF (75 mL) and cooled (−78° C.) before the slow, dropwise addition of n-BuLi (2.3 M, 7.04 mmol). The solution was stirred at −78° C. for 20 minutes before the addition of triisopropyl borate (5.19 mL, 22.5 mmol). The cooling source was removed and the reaction was allowed to reach ambient temperature and stirred on for an additional 20 h before quenching the reaction by careful addition of 0.5 M aq. HCl solution (25 mL) followed by H$_2$O (50 mL). The reaction was concentrated in vacuo and the remaining aqueous mixture was diluted with DCM (50 mL) and phases were separated. The aqueous phase was further extracted with DCM (2×50 mL). Combined organic phases were washed with H$_2$O (50 mL), dried over MgSO$_4$, filtered through a silica plug and evaporated to give the crude compound as an off-white solid in quantitative yields with minor impurities. The product was deemed of sufficient quality for use in the subsequent reactions without further purification.

3-(4-bromo-2,5-dimethoxyphenyl)azetidine hydrochloride (1)

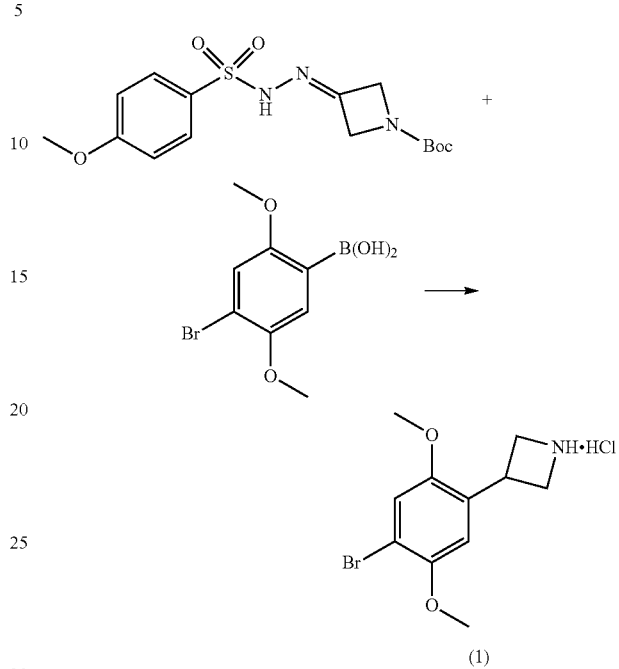

Synthesized according to general procedure E using tert-butyl 3-(2-((4-methoxyphenyl)sulfonyl)hydrazineylidene) azetidine-1-carboxylate (249 mg, 0.70 mmol), (4-bromo-2, 5-dimethoxyphenyl)boronic acid (365 mg, 1.40 mmol). The title compound was isolated as a colorless crystalline solid (26 mg, 12%). TLC Rf=0.1 (33% EtOAc in Heptane v/v); $^1$H-NMR (600 MHz, MeOD) δ 7.22 (s, 1H), 6.91 (s, 1H), 4.35 (d, J=3.3 Hz, 2H), 4.33 (s, 2H), 4.30-4.25 (m, 1H), 3.85 (s, 6H); $^{13}$C-NMR (151 MHz, MeOD) δ 153.17, 151.74, 127.91, 117.33, 113.85, 112.06, 57.57, 56.69, 52.50, 34.73; HRMS m/z calculated for [C$_{11}$H$_{15}$BrNO$_2$]$^+$ (M$_{free\ base}$+H) 272.0281; found: 272.0282.

3-(2,5-dimethoxy-4-(trifluoromethyl)phenyl)azetidine hydrochloride (2)

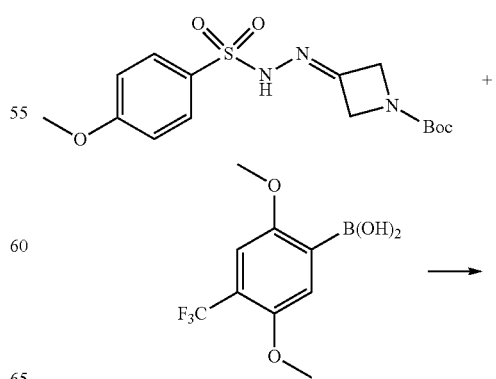

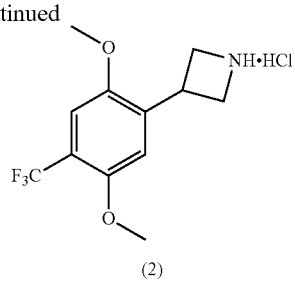

(2)

Synthesized according to general procedure E using tert-butyl 3-(2-((4-methoxyphenyl)sulfonyl)hydrazineylidene)azetidine-1-carboxylate (257 mg, 0.72 mmol), (2,5-dimethoxy-4-(trifluoromethyl)phenyl)boronic acid (362 mg, 1.45 mmol). The title compound was isolated as a colorless crystalline solid (15.3 mg, 7%). ¹H-NMR (600 MHz, MeOD) δ 7.19 (s, 1H), 7.04 (s, 1H), 4.39-4.34 (m, 5H), 3.89 (s, 6H); ¹³C-NMR (151 MHz, MeOD) δ 151.61, 150.72, 131.66, 124.36, 112.79, 109.08, 109.04, 55.81, 55.20, 51.00, 33.38; HRMS m/z calculated for $[C_{12}H_{15}F_3NO_2]^+$ ($M_{free\ base}$+H) 262.1049; found: 262.1051.

Synthesis of Compound 3 and 4 tert-butyl (E)-3-(((4-methoxyphenyl)sulfonyl)diazenyl)pyrrolidine-1-carboxylate

A flame dried microwave vial, backfilled with argon gas, was charged with 4-methoxybenzenesulfonohydrazide (1.6 g, 7.9 mmol) and tert-butyl 3-oxopyrrolidine-1-carboxylate (1.46 g, 7.9 mmol) and anhydrous MeOH (35 mL). The vial was capped and heated to 60° C. for 18 h. The reaction was followed by ¹H-NMR. Upon completion, the reaction mixture was poured into H₂O (350 mL) and extracted with Et₂O (3×100 mL). Combined organic phases were washed with H₂O (5×50 mL) and brine (50 mL), dried over Na₂SO₄, filtered and evaporated in vacuo to give the crude compound, in quantitative yields, as an off-white solid with minor impurities. The product was deemed of sufficient quality for use in the subsequent reactions without further purification. ¹H-NMR (400 MHz, CDCl₃) δ 7.88 (d, J=8.9 Hz, 2H), 7.04-6.92 (m, 2H), 3.99 (bs, 1H), 3.92 (bs, 1H), 3.87 (bs, 3H), 3.80 (bs, 1H), 3.75 (bs, 1H), 2.68 (m, 2H), 2.54 (s, 1H), 1.44 (s, 10H); ¹³C-NMR (101 MHz, CDCl₃) δ 26.3 (br), 28.4, 30.6 (br), 43.9 (br), 46.5 (br), 49.5 (br), 55.6, 80.1, 80.4, 114.3, 129.6, 131.3, 154.1, 159.9, 163.5.

tert-butyl 3-(2,5-dimethoxyphenyl)pyrrolidine-1-carboxylate

Synthesized according to general procedure E tert-butyl (E)-3-(((4-methoxyphenyl) sulfinyl)diazenyl)pyrrolidine-1-carboxylate (369.4 mg, 1 mmol), (2,5-dimethoxyphenyl)boronic acid (363.9 mg, 2 mmol). The title compound was isolated as a brown oil (42.6 mg, 13%). TLC Rf 0.3 (20% EtOAc in Heptane v/v); ¹H-NMR (400 MHz, CDCl₃) δ 6.83-6.66 (m, 3H), 3.79 (s, 4H), 3.76 (s, 4H), 3.64 (tt, J=9.7, 6.9 Hz, 1H), 3.56 (ddd, J=11.2, 8.1, 3.3 Hz, 1H), 3.38 (ddd, J=10.7, 9.0, 6.9 Hz, 1H), 3.25 (dd, J=10.5, 8.6 Hz, 1H), 2.17 (dtd, J=12.8, 6.6, 3.3 Hz, 1H), 2.05-1.92 (m, 1H), 1.47 (s, 9H). ¹³C-NMR (151 MHz, CDCl₃) δ 154.74, 153.79, 151.88, 131.10, 113.78, 111.45, 111.40, 79.19, 56.08, 51.13, 45.66, 37.71, 31.34, 28.71.

3-(2,5-dimethoxyphenyl)pyrrolidine hydrochloride

To a round bottom flask, equipped with a stir bar, charged with tert-butyl 3-(2,5-dimethoxyphenyl)pyrrolidine-1-carboxylate (72 mg, 0.23 mmol) and MeOH (2 mL), was added 4 M HCl in dioxane (0.5 mL). The reaction was stirred at ambient temperature for 2 h giving precipitation of the hydrochloride. The precipitate was isolated by decantation and dissolved in the minimum amount of MeOH. Et₂O was added dropwise until nucleation was observed and the solution was allowed to crystalize at −4° C. overnight giving the pure title compound as a white solid (54 mg, 94%). ¹H-NMR (600 MHz, MeOD) δ 6.97 (dd, J=8.4, 0.9 Hz, 1H), 6.88-6.85 (m, 2H), 3.86 (s, 3H), 3.78 (s, 3H), 3.77-3.70 (m, 1H), 3.72-3.66 (m, 1H), 3.58 (ddd, J=11.8, 8.4, 3.6 Hz, 1H), 3.38 (ddd, J=11.6, 9.7, 7.2 Hz, 1H), 3.26 (dd, J=11.0, 9.3 Hz, 1H), 2.40 (dh, J=14.1, 3.6, 3.2 Hz, 1H), 2.22 (dtd, J=13.0, 9.7, 8.4 Hz, 1H); ¹³C-NMR (151 MHz, MeOD) 155.30, 152.98, 129.00, 115.59, 113.43, 112.93, 56.30, 56.15, 50.73, 46.84, 40.06, 30.92; HPLC $t_R$=9.88 (Method B).

(R)-3-(4-bromo-2,5-dimethoxyphenyl)pyrrolidine (3) hydrobromide and (S)-3-(4-bromo-2,5-dimethoxyphenyl)pyrrolidine hydrobromide (4)

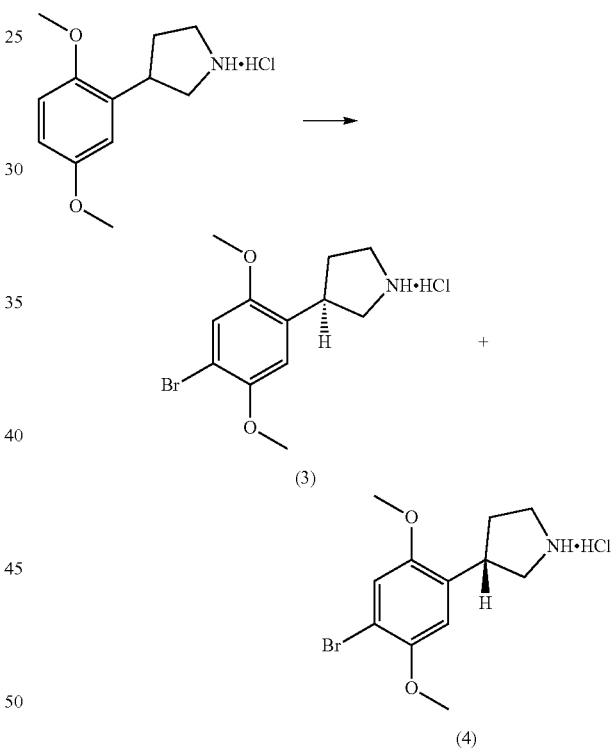

A flame dried vessel, backfilled with argon gas, was charged with 3-(2,5-dimethoxyphenyl)pyrrolidine hydrochloride (63.3 mg, 0.26 mmol), and glacial AcOH (1 mL). A solution of elemental bromine (14 μL, 0.28 mmol) in glacial AcOH (1 mL) was added dropwise. The reaction was shielded from light and stirred at ambient temperature. The reaction was monitored by TLC. Upon completion, the reaction was diluted with H₂O (5 mL) and washed with Et₂O (10 mL). The aqueous mixture was basified with 10% aq. NaOH solution and extracted with EtOAc (15 mL) followed by a mixture of EtOH and Chloroform (1:2) (2×15 mL). The combined organics were dried over MgSO4, filtered and evaporated in vacuo giving the crude hydrobromide as a brown solid in high purity (59 mg, 62%). Analytical amounts of the racemic mixture was separated and isolated as the two individual enantiomers as their hydrochloride salts using general procedure D using an isocratic gradient of 25% MP B. Enantiomer 1 (compound 4): Rt 18.03, Enantiomer 2 (compound 3): Rt 2=26.02; $^1$H-NMR (600 MHz, DMSO-d6) δ 8.88 (s, 2H), 7.25 (s, 1H), 7.06 (s, 1H), 3.84 (s, 3H), 3.80 (s, 3H), 3.64 (tt, J=9.7, 7.8 Hz, 1H), 3.53 (dd, J=11.3, 8.2 Hz, 1H), 3.41 (ddd, J=11.9, 8.4, 3.8 Hz, 1H), 3.25 (ddd, J=11.5, 9.3, 7.2 Hz, 1H), 3.13 (dd, J=11.3, 9.7 Hz, 1H), 2.26 (dtd, J=12.5, 7.3, 3.8 Hz, 1H), 2.08-1.99 (dtd, 1H); $^{13}$C-NMR (151 MHz, DMSO-d6) δ 151.42, 149.60, 127.90, 116.11, 112.57, 109.15, 56.88, 56.39, 48.85, 44.88, 36.98, 29.92; HPLC $t_R$=18.30 (Method A); HRMS m/z calculated for $[C_{12}H_{16}BrNO_2]+(M_{free\ base}+H)$ 286.0437, found 286.0439.

Synthesis of Compound 5 and 6

(R)-3-(2,5-dimethoxy-4-(trifluoromethyl)phenyl)pyrrolidine (5) and (S)-3-(2,5-dimethoxy-4-(trifluoromethyl)phenyl)pyrrolidine (6)

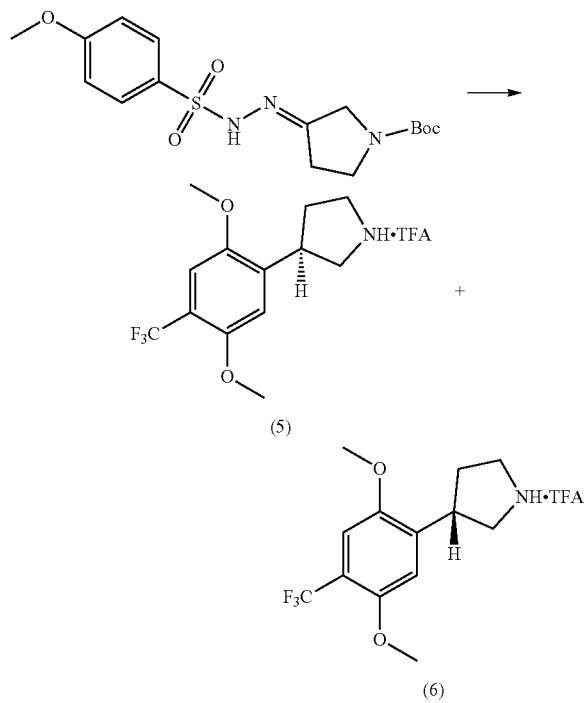

A flame dried microwave vial, backfilled with argon gas, was charged with tert-butyl (E)-3-(((4-methoxyphenyl)sulfonyl)diazenyl)pyrrolidine-1-carboxylate (841 mg, 2.27 mmol), (2,5-dimethoxy-4-(trifluoromethyl)phenyl)boronic acid (860 mg, 3.45 mmol) and dry Cs$_2$CO$_3$ (1.12 g, 3.45 mmol). The contents of the vial were sealed and subjected to high vacuum for 1 h before reestablishing argon atmosphere. The contents of the vial were suspended in anhydrous 1,4 Dioxane (0.12 M). The suspension was thoroughly degassed before capping the vial. The reaction was heated to 150° C. by microwave irradiation under vigorous stirring. After 1 h, the reaction was allowed to cool to ambient temperature and filtered over a plug of Celite and washed through with EtOAc (20 mL). The filtrate was washed with H$_2$O (20 mL) and brine (20 mL), dried over MgSO$_4$, evaporated in vacuo and subjected to purification by flash column chromatography (1:2 EtOAc/Heptane), removing major impurities giving the boc-protected amine with minor impurities as a brown oil. The crude product was further purified by Prep HPLC (HPLC Method C) giving the pure racemic mixture as white solids (69.9 mg, 6%). Analytical amounts of the racemic mixture were separated and the two individual enantiomers isolated as their hydrochloride salts using general procedure D using an isocratic gradient of 15% MP B. Enantiomer 1 (compound 6): Rt 6.16, Enantiomer 2 (compound 5): Rt 7.36. Both compounds were re-purified by preparative HPLC (HPLC Method C) finally isolating the title compounds as their trifluoroacetate salts in analytical amounts. $^1$H-NMR (600 MHz, MeOD) δ 7.20 (s, 1H), 7.12 (s, 1H), 3.91 (s, 3H), 3.91 (s, 3H), 3.82 (tt, =9.1 Hz, 1H), 3.72 (dd, =11.4, 8.4 Hz, 1H), 3.61 (ddd, =11.8, 8.4, 3.6 Hz, 1H), 3.44-3.37 (ddd, 1H), 3.36-3.35 (m, 1H), 2.45 (dtd, J=14.0, 7.3, 3.5 Hz, 1H), 2.27 (dtd, J=12.9, 9.8, 8.3 Hz, 1H); $^{13}$C-NMR (151 MHz, MeOD) δ 151.63, 150.83, 132.34, 126.20 (q), 117.95 (q), 112.99, 109.30 (q), 55.77, 55.20, 48.96, 45.47, 38.80, 29.44; HPLC=19.87 (Method A); HRMS m/z calculated for $[C_{13}H_{17}F_3NO_2]+(M_{free\ base}+H)$ 276.1206, found 276.1206.

Synthesis of Compound 7 and 8

1,4-Dimethoxy-2-(trifluoromethyl)benzene

To a flame dried round-bottom flask, backfilled with argon gas, containing a solution a solution of sodium methoxide (40.52 g, 750 mmol) in anhydrous degassed DMSO (150 mL) was added 1-fluoro-4-methoxy-2-(trifluromethyl)benzene (14.56 g, 75 mmol). The reaction was stirred at 120° C. for 19 h until full consumption of starting material was observed by NMR. The reaction was quenched with ice H$_2$O (700 mL) and organics were extracted with Et$_2$O (3×200 mL). The combined organic phases were washed with H$_2$O (2×200 mL), followed by brine (200 mL), then dried over MgSO$_4$, filtered and concentrated in vacuo to give the desired dimethoxy benzene as a clear oil. The oil crystalized into a solid over the course of several days and was of sufficiently high purity to use without further purification (15.21 g, 98%). TLC Rf=0.45 (20% EtOAc in Heptane v/v); $^1$H-NMR (400 MHz, CDCl$_3$) δ 7.12 (d, J=3.1 Hz, 1H), 7.02 (dd, J=9.0, 3.1 Hz, 1H), 6.94 (d, J=9.0 Hz, 1H), 3.86 (s, 3H), 3.80 (s, 3H); $^{13}$C-NMR (151 MHz, CDCl$_3$) δ 153.12, 151.70, 126.27, 124.47, 122.66, 120.85, 119.90, 119.69, 119.49, 119.28, 118.27, 113.77, 113.00, 112.96, 56.75, 56.06; HPLC tR=26.79 min (Method A)

1-Bromo-2,5-dimethoxy-4-(trifluoromethyl)benzene

A flame dried round-bottom flask, backfilled with argon gas, was charged with 1,4-dimethoxy-2-(trifluoromethyl)benzene (5.15 g, 25 mmol) and anhydrous DCM (50 mL). The reaction was shielded from light and cooled on an ice-bath before addition of TfOH (4.43 mL, 50 mmol). The reaction mixture was stirred for 2 minutes followed by the addition of 1,3-Dibromo-5,5-dimethylhydantoin (3.57 g, 12.5 mmol) in one portion. The reaction mixture was stirred on for additional 5 minutes before being allowed to warm to ambient temperature and stirred on for a total of 3 h. The reaction was then quenched by careful addition of sat. aq. Na$_2$S$_2$O$_3$ (7 mL) followed by sat. aq. NaHCO$_3$ (30 mL). The resulting biphasic system was separated and the aqueous phase further extracted with DCM (2×50 mL). The combined organic phases were washed with brine (50 mL), dried over Na$_2$SO$_4$, then filtered and concentrated in vacuo to give a crude off-white solid that was dissolved in boiling isopropanol and allowed to cool to ambient temperature. Et$_2$O was added dropwise until turbidity was observed then the reaction was allowed to stand at 4° C. overnight giving the desired bromide (4.63 g, 65%) as a colorless crystalline solid. TLC Rf=0.6 (10% EtOAc in Heptane v/v) $^1$H-NMR (400 MHz, CDCl$_3$) δ 7.23 (s, 1H), 7.09 (s, 1H), 3.87 (d, J=10.6 Hz, 6H); $^{13}$C-NMR (151 MHz, CDCl$_3$)) δ 151.77, 149.86, 123.21 (q, J$_{CF}$=270.9 Hz), 118.51 (q, J$_{CF}$=31.3), 118.23, 116.37, 110.86 (q, J$_{CF}$=3.6 Hz), 57.16, 56.95. HPLC tR=28.64 min (Method A)

3-(2,5-Dimethoxy-4-(trifluoromethyl)phenyl)pyridine

To a flame dried 20 mL microwave vial, backfilled with argon gas, was added 1-Bromo-2,5-dimethoxy-4-(trifluoromethyl)benzene (909 mg, 3.1 mmol) followed by pyridin-3-ylboronic acid (762 mg, 6.2 mmol) and anhydrous, degassed 1,4 dioxane (3.5 mL). The mixture was further degassed for 10 minutes before addition of Bis(triphenylphosphine)palladium(II) dichloride (109 mg, 0.155 mmol, 5 mol %) followed by 1M solution of tri-tert-butylphosphine in toluene (0.155 mL, 0.155 mmol). Finally, a degassed 2M aq. solution of Na$_2$CO$_3$ (3.1 mL, 6.2 mmol) was added before sealing the reaction vial. The reaction was heated to 120° C. using microwave irradiation for 80 minutes. The reaction was monitored by TLC. Upon complete consumption of the bromide. The reaction mixture was diluted with EtOAc (7 mL) and transferred to a separation funnel containing EtOAc (10 mL) and H$_2$O (20 mL). Phases were separated and the aqueous phase further extracted with EtOAc (10 mL). The combined organic phases were washed with brine (20 mL), dried over MgSO$_4$, filtered and concentrated in vacuo to mixed wet solids. The crude product was immediately purified by flash column chromatography (2:5, EtOAc in Heptane). Giving the desired phenyl pyridine as an off-white solid. TLC Rf=0.18 (40% EtOAc in Heptane v/v); $^1$H-NMR (400 MHz, CDCl$_3$)) δ 8.75 (d, J=2.1 Hz, 1H), 8.60 (dd, J=4.9, 1.7 Hz, 1H), 7.86 (dt, J=7.9, 2.0 Hz, 1H), 7.40-7.31 (m, 1H), 7.19 (s, 1H), 6.97 (s, 1H), 3.90 (s, 3H), 3.80 (s, 3H); $^{13}$C-NMR (151 MHz, CDCl$_3$) δ 151.76, 150.14, 150.05, 148.88, 136.88, 133.22, 131.63, 123.49 (q, J$_{CF}$=273.6 Hz), 123.13, 118.99 (q, J$_{CF}$=31.3 Hz), 115.28, 110.76 (q, J$_{CF}$=5.4 Hz), 56.85, 56.49; HPLC tR=20.23 (Method A)

(R)-3-(2,5-Dimethoxy-4-(trifluoromethyl)phenyl)piperidine hydrochloride (7) and (S)-3-(2,5-Dimethoxy-4-(trifluoromethyl)phenyl)piperidine hydrochloride (8)

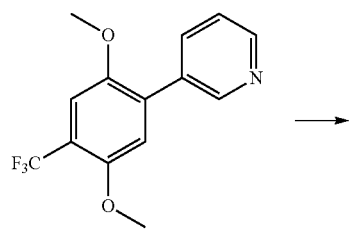

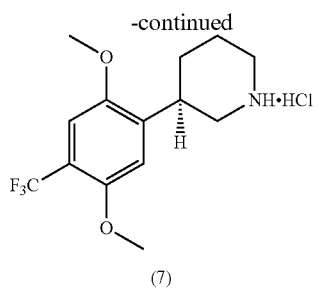

(7)

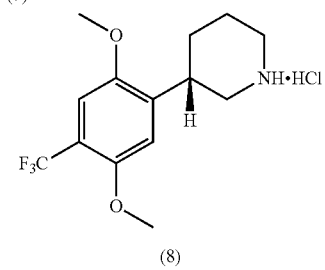

(8)

Synthesized according to Hydrogenation procedure A or B using 3-(2,5-Dimethoxy-4-(trifluoromethyl)phenyl)pyridine (4 g, 14.12 mmol). The hydrochloride salt was prepared by dissolving the product in a minimum amount of Et$_2$O and treating the solution with 4 M dioxanal HCl. The precipitate was isolated by decantation and redissolved in the minimum amount of MeOH. Et$_2$O was added dropwise until nucleation was observed and the solution was allowed to crystalize at −4° C. overnight giving the pure title compound as a white solid (2.82 g, 69%). The racemic mixture was separated and isolated as the two individual enantiomers as their hydrochloride salts using general procedure D using an isocratic gradient of 10% MP B. Enantiomer 1 (compound 8): Rt 7.22, Enantiomer 2 (compound 7): Rt 11.247. Chiral resolution was also achieved using enantiomeric separation method 2 and 3. MP 239-241° C.; TLC Rf=0.3 (5% TEA and 10% MeOH in EtOAc v/v/v); $^1$H-NMR (400 MHz, CDCl$_3$)) δ 7.19 (s, 1H), 7.12 (s, 1H), 3.92 (s, 3H), 3.90 (s, 3H), 3.59-3.42 (m, 3H), 3.20 (t, J=12.3 Hz, 1H), 3.15-3.04 (m, 1H), 2.16-2.07 (m, 1H), 2.05-1.88 (m, 3H); $^{13}$C-NMR (151 MHz, CDCl3)) δ 153.18, 151.73, 135.59, 124.92 (q, J=271.6 Hz), 118.81 (q, J=31.3 Hz), 113.75, 110.62 (q, J=5.4 Hz), 57.22, 56.73, 45.19, 35.41, 28.84, 23.98; HPLC t$_R$=11.75 (Method A); HRMS m/z calculated for [C$_{14}$H$_{19}$F$_3$NO$_2$]+ (M$_{free\ base}$+H) 290.1362, found 290.1377.

Synthesis of Compounds 9 and 10

3-(2,5-Dimethoxyphenyl)pyridine

Synthesized according to general procedure C. using (2,5-Dimethoxyphenyl)boronic acid (2.184 g, 2.3 mmol). The crude product was purified by flash column chromatography (40% EtOAc in Heptane v/v) to give the title compound in quantative yield as a clear oil with minor impurities. The product was deemed of sufficient purity and was used in subsequent reactions without further purification. TLC Rf=0.3 (40% EtOAc in Heptane v/v); $^1$H-NMR (400 MHz, CDCl$_3$) δ 8.77 (d, J=1.8 Hz, 1H), 8.54 (dd, J=4.7, 1.6 Hz, 1H), 7.84 (dt, J=7.9, 1.9 Hz, 1H), 7.30 (ddd, J=7.9, 4.8, 0.9 Hz, 1H), 6.92-6.85 (m, 3H), 3.78 (s, 3H), 3.73 (s, 3H); $^{13}$C-NMR (101 MHz, CDCl$_3$) δ 153.89, 150.83, 150.16, 148.03, 136.77, 134.10, 127.91, 122.90, 116.56, 113.92, 112.66, 56.19, 55.79; HPLC t$_R$=9.88 (Method B).

3-(2,5-Dimethoxyphenyl)piperidine

Synthesized according to general procedure B using 3-(2,5-Dimethoxyphenyl)pyridine (6.012 g, 27.93 mmol). The hydrochloride salt was prepared by dissolving the product in a minimum amount of Et$_2$O and treating the solution with 4 M HCl in dioxane. The precipitate was isolated by decantation and redissolved in the minimum amount of MeOH. Et$_2$O was added dropwise until nucleation was observed and the solution was allowed to crystalize at −4° C. overnight giving the pure title compound as large white crystals (3.44 g, 48%). TLC Rf=0.2 (5% TEA and 10% MeOH in EtOAc v/v/v); $^1$H-NMR (400 MHz, CDCl3) δ 9.84 (s, 1H), 9.44 (s, 1H), 6.80-6.63 (m, 3H), 3.75 (s, 3H), 3.74 (s, 3H), 3.59-3.39 (m, 3H), 3.06 (q, J=11.4 Hz, 1H), 2.85 (q, J=12.1, 11.6 Hz, 1H), 2.24-2.05 (m, 1H), 1.96 (q, J=13.4, 12.3 Hz, 3H), 1.83-1.65 (m, 1H); $^{13}$C-NMR (101 MHz, CDCl$_3$) δ 153.66, 151.38, 129.72, 114.23, 112.32, 111.65, 55.78, 55.75, 47.57, 44.08, 35.35, 28.28, 22.85; HPLC t$_R$=17.04 (Method A).

(R)-3-(4-Chloro-2,5-dimethoxyphenyl)piperidine (9) and (S)-3-(4-Chloro-2,5-dimethoxyphenyl)piperidine (10)

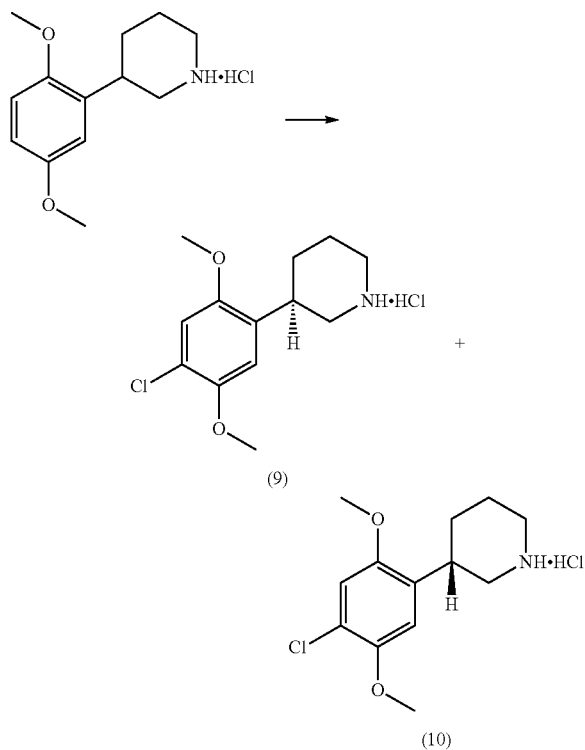

To a flame dried round-bottom flask, backfilled with argon gas, was charged with 3-(2,5-dimethoxyphenyl)piperidine (500 mg, 1.93 mmol), N-Chlorosuccinimide (310 mg, 2.32 mmol) and MeCN. The solution was cooled (0° C.), TiCl$_4$ (0.2 mL, 1.93 mmol) was slowly added and the reaction was stirred for 10 min. The cooling source was removed and the reaction was stirred on for an additional 5 min before being quenched with MeOH (8 mL). The reaction was allowed to warm to ambient temperature then basified (≈pH 9) with aq. NaOH solution (10% v/v) under precipitation of white solid. The solution was clarified by filtration over a fritted glass funnel and washed through with EtOAc (50 mL). The filtrate was washed with sat. aq. Na$_2$CO$_3$ (50 mL) and brine (50 mL), dried over MgSO$_4$, filtered and concentrated in vacuo to give the crude free-base with minimal impurities as a yellow solid (529 mg, 94% crude yield). Analytical amounts of the racemic mixture was separated and isolated as the two individual enantiomers as their hydrochloride salts with minor impurities using general Procedure D using an isocratic gradient of 30% MP B. Enantiomer 1 (compound 10): Rt 6.943, Enantiomer 2 (compound 9): Rt 13.493. Both enantiomers were recrystallized again from mixture of EtOAc, Isopropanol and Et$_2$O giving both enantiomers in high purity. MP 235-236° C.; TLC Rf=0.2 (5% TEA and 10% MeOH in EtOAc v/v/v); $^1$H-NMR (400 MHz, CDCl$_3$) δ 7.07 (s, 1H), 6.99 (s, 1H), 3.88 (s, 3H), 3.85 (s, 3H), 3.49-3.38 (m, 3H), 3.15-3.09 (m, 1H), 3.06 (td, J=12.8, 3.5 Hz, 1H), 2.15-2.04 (m, 1H), 2.01-1.86 (m, 3H); $^{13}$C-NMR (101 MHz, CDCl3) δ 152.55, 150.87, 129.61, 122.80, 114.52, 113.63, 57.50, 56.74, 49.05, 45.18, 35.17, 28.95, 24.05; HPLC tR=18.54 (Method A); HRMS m/z calculated for [C13H18ClNO2]+(Mfree base+H) 256.1099, found 256.1102.

Synthesis of Compounds 11 and 12

(R)-3-(4-bromo-2,5-dimethoxyphenyl)piperidine (11) and (S)-3-(4-bromo-2,5-dimethoxyphenyl)piperidine (12)

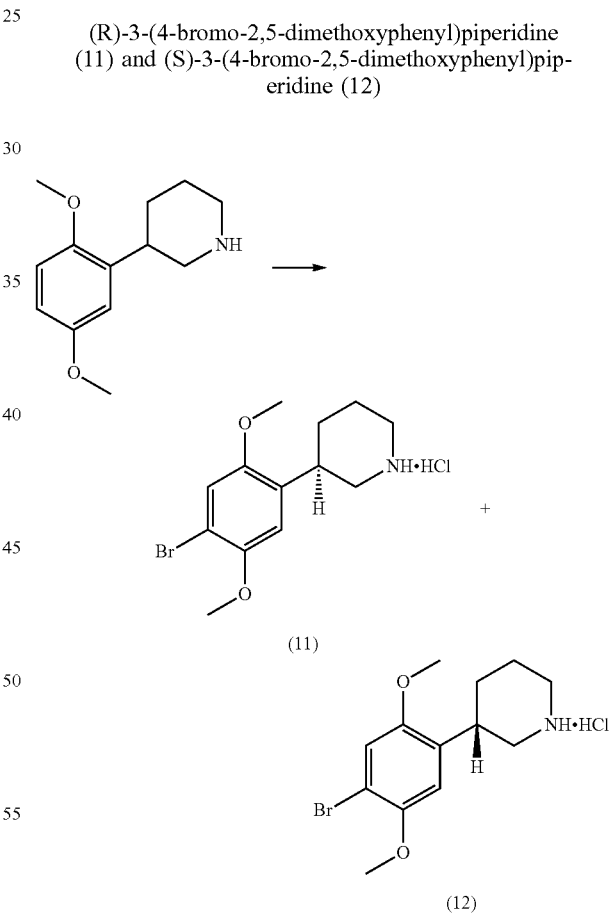

A round-bottom flask, equipped with a stir bar, was charged with 3-(2,5-dimethoxyphenyl)piperidine (1 g, 3.87 mmol) and glacial AcOH (19 mL). A solution of elemental bromine (0.19 mL, 3.87 mmol) in glacial AcOH (10 mL) was added dropwise. The mixture was stirred for 30 min until complete precipitation of product as a white solid. The reaction was diluted with Et$_2$O (20 mL) and solids were isolated by filtration. Product was recrystallized from a mixture of boiling MeOH, Isopropanol and Et$_2$O to give the product as a white solid (853.5 mg, 58%). Analytical amounts of the racemic mixture were separated and isolated as the two individual enantiomers as their hydrochloride salts using general procedure D using an isocratic gradient of 25% MP B. Enantiomer 1 (compound 12): Rt 7.200, Enantiomer 2 (compound 11): Rt 12.160. MP 253-254 OC; TLC Rf=0.15 (0.01% TEA and 25% MeOH in EtOAc v/v/v); $^1$H-NMR (400 MHz, MeOD) δ 7.22 (s, 1H), 6.97 (s, 1H), 3.87 (d, J=9.6 Hz, 6H), 3.45 (t, J=12.9 Hz, 3H), 3.22-2.99 (m, 2H), 2.11 (d, J=10.7 Hz, 1H), 2.04-1.84 (m, 3H); $^{13}$C-NMR (101 MHz, MeOD) δ 152.76, 151.94, 130.33, 117.44, 113.33, 111.54, 57.61, 56.79, 45.23, 35.27, 28.90, 24.06. HPLC tR=14.07 (Method A); HRMS m/z calculated for [C13H18BrNO2]+(Mfree base+H) 300.0594, found 300.0588.

Synthesis of Compounds 13 and 14

(R)-3-(4-Iodo-2,5-dimethoxyphenyl)piperidine (13) and (S)-3-(4-Iodo-2,5-dimethoxyphenyl)piperidine (14)

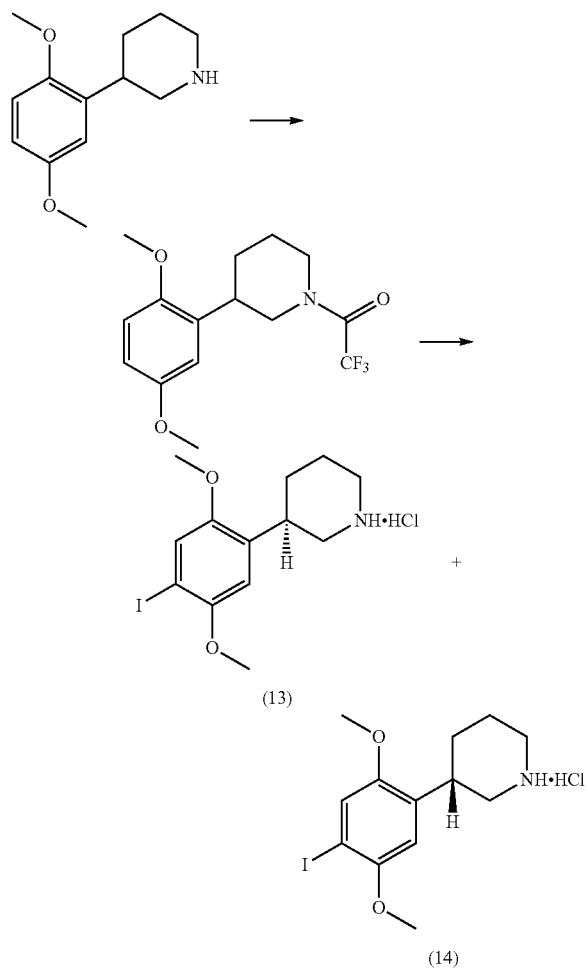

A flame dried round-bottom flask, equipped with a stir bar, backfilled with argon gas, was charged with 3-(2,5-Dimethoxyphenyl)piperidine) (500 mg, 1.9 mmol), TEA (0.53 mL, 3.8 mmol) and DCM. The reaction mixture was cooled to 0° C. over an ice bath and trifluoroacetic anhydride (483.06 mg, 2.3 mmol) was carefully added under vigorous stirring. The reaction was stirred for 5 minutes at 0° C. before being allowed to warm to ambient temperature and stirred for 40 min. The reaction was monitored by TLC. Upon completion the reaction was quenched with H$_2$O (20 mL) and phases were separated. The aqueous layer was further extracted with EtOAc (2×50 mL). The combined organic layers were washed with H$_2$O (50 mL) and brine (50 mL) then dried over MgSO$_4$, filtered and concentrated in vacuo to give the crude triflouroacetamide in quantative yield. TLC Rf=0.5 (33% EtOAc in Heptane v/v). The crude product was dissolved in MeOH (20 mL) and purged with a flow of argon gas. The reaction was cooled to 0° C. over an ice bath and shielded from light with aluminium foil. AgNO$_3$ (355 mg, 2.09 mmol) was added in one portion followed by I$_2$ (578 mg, 2.28 mmol) in several small portions. The reaction was stirred at 0° C. for 1.75 h, then washed over a plug of celite into a mixture of ice and sat. aq. NaHSO$_3$. The mixture was allowed to warm to ambient temperature and organics were evaporated in vacuo. The remaining aqueous mixture was extracted with EtOAc (3×50 mL). The combined organic phases were washed with H$_2$O (50 mL) and brine (50 mL), dried over MgSO$_4$, filtered and concentrated in vacuo, giving the crude iodide as a yellow oil. Major impurities were removed by flash column chromatography (33% EtOAc in Heptane v/v). The protected iodide was suspended in MeOH (15 mL) and 25% aq. NaOH solution (2 ml) was added. The reaction was gently warmed with a heat gun until complete solution and left to stir until TLC showed complete deprotection of the amine. The reaction was concentrated in vacuo and partitioned between a mixture of EtOAc, DCM and H$_2$O (1:1:2, v/v). The aqueous phase was further extracted with DCM (2×50 mL). The combined organic phases were washed with H$_2$O (50 mL) and brine (50 mL), dried over MgSO$_4$, filtered and concentrated in vacuo to give the pure iodide (471 mg, 71%) as clear oil. Analytical amounts of the racemic mixture was separated and isolated as the two individual enantiomers as their hydrochloride salts using general procedure D using an isocratic gradient of 30% MP B. Enantiomer 1 (compound 14): Rt 6.95, Enantiomer 2 (compound 13): Rt 10.163. MP 252-255° C.; TLC Rf=0.15 (5% TEA and 10% MeOH in EtOAc v/v/v)$^1$H-NMR (400 MHz, CDCl$_3$) δ 7.38 (s, 1H), 6.87 (s, 1H), 3.85 (s, 3H), 3.84 (s, 3H), 3.48-3.38 (m, 3H), 3.12 (t, J=13.0 Hz, 1H), 3.06 (td, J=11.2, 9.9, 2.2 Hz, 1H), 2.14-2.06 (m, 1H), 2.02-1.87 (m, 3H); $^{13}$C-NMR (101 MHz, CDCl$_3$) δ 154.58, 152.99, 131.38, 123.26, 111.92, 84.88, 57.66, 56.78, 48.94, 45.18, 35.40, 28.85, 24.03; HPLC tR=18.96 (Method A); HRMS m/z calculated for [C$_{13}$H$_{18}$INO$_2$]+(Mfree base+H) 348.0455 found 348.0453.

Synthesis of Compounds 15 and 16 tert-Butyl 3-(2,5-dimethoxyphenyl)piperidine-1-carboxylate

A flame dried round-bottom flask, equipped with a stir bar, backfilled with argon gas, was charged with 3-(2,5-dimethoxyphenyl)piperidine (1 g, 3.87 mmol) and di-tert-butyl dicarbonate (931.39 mg, 4.26 mmol). The contents of the vessel were suspended in a mixture of TEA in DCM (1:10 v/v) (12 mL). The reaction was stirred at room temperature for 18 h. The reaction was monitored by TLC. Upon complete conversion to the carboxylate, the reaction was concentrated in vacuo. Major impurities were removed by flash column chromatography (20% EtOAc in Heptane v/v) to give the protected amine as a clear oil in quantative yield. The product was deemed of sufficient purity for use in subsequent reactions and was not further purified. TLC Rf=0.35 (20% EtOAc in Heptane v/v); $^1$H-NMR (400 MHz, CDCl$_3$) δ 6.80 (d, J=8.7 Hz, 1H), 6.75 (d, J=3.0 Hz, 1H), 6.71 (dd, J=8.7, 3.0 Hz, 1H), 4.17 (s, 2H), 3.80 (s, 3H), 3.77 (s, 3H), 3.11-2.96 (m, 1H), 2.70 (dd, J=12.8, 11.2 Hz, 2H), 1.94 (d, J=8.2 Hz, 1H), 1.80-1.68 (m, 1H), 1.67-1.53 (m, 2H), 1.46 (s, 9H); $^{13}$C-NMR (101 MHz, CDCl$_3$) δ 155.00, 153.79, 151.60, 133.33, 114.11, 111.58, 110.98, 79.34, 56.19, 55.85, 36.07, 32.04, 28.66, 25.75, 22.84, 14.26; HPLC tR=17.04 (Method A).

tert-Butyl 3-(4-formyl-2,5-dimethoxyphenyl)piperidine-1-carboxylate

A flame dried round-bottom flask, equipped with a stir bar, backfilled with argon gas, was charged with tert-Butyl 3-(2,5-dimethoxyphenyl)piperidine-1-carboxylate (1.03 g, 3.2 mmol) and anhyd. DCM (7 mL). The reaction was cooled (−78° C.) and TiCl$_4$ (0.87 mL, 8.0 mmol) was added followed by Dichloromethyl methyl ether (1103.50 g, 9.6 mmol) and monitored by TLC. Upon completion the reaction was allowed to warm to 0° C. under stirring, then poured into ice (50 mL). Ice was allowed to melt before the mixture was basified with sat. aq. NaHCO$_3$ (100 mL) and drops of concentrated NaOH and phases were separated. The aqueous layer was further extracted with a mixture of EtOH and CHCl$_3$ (1:2 v/v)(3×150 mL). The combined organic layers were dried over MgSO$_4$, filtered and concentrated in vacuo to give the crude product as a yellow solid. To ensure full protection of the amine, the crude product was suspended in a mixture of TEA in DCM (1:10 v/v) (10 mL) and di-tert-butyl dicarbonate (769 mg, 3.5 mmol) was added. The mixture was left to stir for 16 h. The reaction mixture was concentrated in vacuo and purified by repeated flash column chromatography (25% EtOAc in Heptane). Two purifications gave the pure title compound as a clear oil (786 mg, 70%). TLC Rf=0.3 (25% EtOAc in Heptane v/v) (Delvelopment: Ninhydrine); $^1$H-NMR (400 MHz, CDCl$_3$) δ 10.40 (s, 1H), 7.29 (s, 1H), 6.82 (s, 1H), 4.26-4.01 (m, 2H), 3.89 (s, 3H), 3.83 (s, 3H), 3.12 (tt, =10.8, 3.7 Hz, 1H), 2.81 (s, 2H), 2.01-1.90 (m, 1H), 1.75 (d, J=10.6 Hz, 1H), 1.67-1.56 (m, 2H), 1.46 (s, 9H); $^{13}$C-NMR (101 MHz, CDCl$_3$) δ 189.12, 156.77, 154.78, 151.40, 141.08, 123.14, 108.41, 79.46, 56.24, 55.85, 36.67, 31.87, 29.00, 28.47, 25.25, 22.68, 14.10.

tert-Butyl 3-(4-cyano-2,5-dimethoxyphenyl)piperidine-1-carboxylate

A flame dried round-bottom flask, equipped with a stir bar, backfilled with argon gas, was charged with of tert-Butyl 3-(4-formyl-2,5-dimethoxyphenyl)piperidine-1-carboxylate (786 mg, 2.24 mmol), NaN$_3$ (219 mg, 3.38 mmol) and MeCN (5 mL). Trifluoromethanesulfonic acid (0.59 mL, 6.75 mmol) was added dropwise over approximately 1 min. The reaction was stirred at room temperature for 3 min before being concentrated in vacuo and diluted with H$_2$O (2 mL). The aqueous mixture was basified with sat. aq. NaHCO$_3$ (5 mL) and drops of NaOH (≈pH 10). The basic aqueous suspension was extracted with a mixture of EtOH in CHCl3 (1:2)(3×50 mL). The combined organic phases were dried over MgSO$_4$, filtered and concentrated in vacuo to a brown gum. To ensure full protection of the amine the crude product was suspended in a mixture of TEA in DCM (11 mL, 1:10 v/v) and di-tert-butyl dicarbonate (540 mg, 2.47 mmol) was added. The mixture was left to stir for 16 h. The reaction mixture was concentrated in vacuo and purified by flash column chromatography (25% EtOAc in Heptane) to give the pure nitrile as a white solid (298 mg, 38%). TLC Rf=0.3 (25% EtOAc in Heptane v/v)(Delvelopment: Ninhydrine); $^1$H-NMR (400 MHz, CDCl$_3$) δ 6.97 (s, 1H), 6.79 (s, 1H), 4.30-3.96 (m, 2H), 3.89 (s, 3H), 3.81 (s, 3H), 3.09 (ddt, J=10.7, 7.3, 3.7 Hz, 1H), 2.80 (s, 2H), 1.98-1.88 (m, 1H), 1.74 (s, 1H), 1.69-1.54 (m, 3H), 1.46 (s, 10H); $^{13}$C-NMR (101 MHz, CDCl$_3$) δ 156.08, 154.89, 151.07, 139.55, 116.77, 114.55, 111.13, 99.27, 79.67, 56.62, 56.20, 36.61, 28.61, 27.56, 25.33

(R)-2,5-dimethoxy-4-(piperidin-3-yl)benzonitrile (15) and (S)-2,5-dimethoxy-4-(piperidin-3-yl)benzonitrile (16)

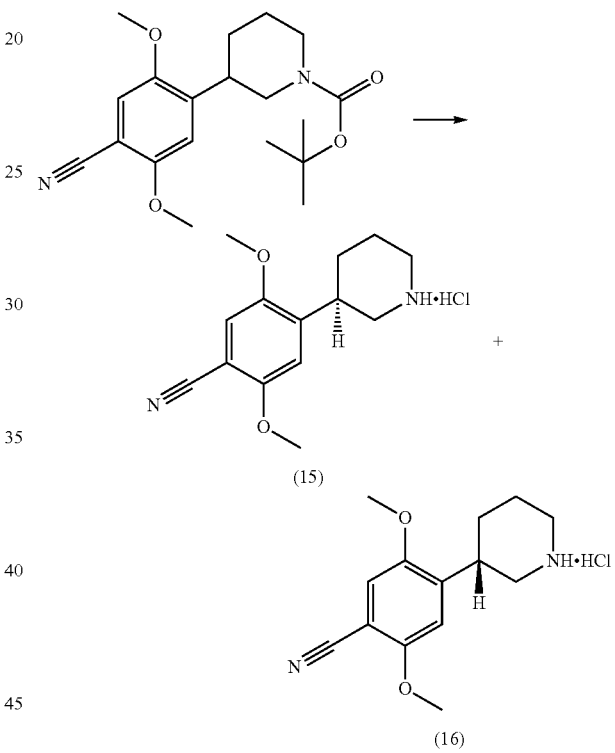

A round-bottom flask, equipped with a stir bar, was charged with tert-Butyl 3-(4-cyano-2,5-dimethoxyphenyl) piperidine-1-carboxylate (150 mg. 0.44 mmol) and MeOH (5 mL). 4 M Dioxanal HCl was gradually added over 2 h (1.7 mL, 6.8 mmol). The reaction was monitored by TLC. Upon full conversion additional Et$_2$O was added until nucleation was observed and reaction was left to crystalize at −4° C. overnight yielding the pure nitrile as the hydrochloride salt as off green crystals, which were isolated by decantation then stripped of remaining solvent traces in vacuo and further dried under reduced pressure (78 mg, 62%). Analytical amounts of the racemic mixture was separated and isolated as the two individual enantiomers as their hydrochloride salts in quantitative yields using general procedure D using an isocratic gradient of 30% MP B. Enantiomer 1 (compound 16): Rt 8.527, Enantiomer 2 (compound 15): Rt 11.860. MP 252-254° C. TLC Rf=0.1 (25% EtOAc in Heptane v/v)(Delvelopment: Ninhydrine)$^1$H-NMR (400 MHz, CDCl$_3$) δ 7.27 (s, 1H), 7.10 (s, 1H), 3.97 (s, 3H), 3.90

(s, 3H), 3.61-3.41 (m, 3H), 3.19 (t, J=12.3 Hz, 1H), 3.15-3.03 (m, 1H), 2.13 (dd, J=10.0, 3.4 Hz, 1H), 1.98 (tdd, J=16.3, 15.0, 6.7, 3.4 Hz, 3H); $^{13}$C-NMR (101 MHz, CDCl$_3$) δ 156.13, 150.75, 136.30, 115.68, 114.75, 111.26, 99.60, 55.83, 55.42, 43.77, 34.24, 27.30, 22.52; HPLC tR=9.75 (Method B); IR vmax (neat)/cm-1 2225.11 (CN); HRMS m/z calculated for [C18H14N2O2]+(Mfree base+H) 247.1441, found 247.1446.

Synthesis of Compounds 17 and 18

(4-bromo-2,5-dimethoxyphenyl)(methyl)sulfane

The title compound was prepared according to the general Procedure N starting from 1,4-dibromo-2,5-dimethoxybenzene (500 mg, 1.689 mmol). 860 mg (49%) of the title compound were prepared. $^1$H-NMR (300 MHz, CDCl$_3$) δ 7.01 (s, 1H), 6.78 (s, 1H), 3.87 (s, 3H), 3.85 (s, 3H), 2.44 (s, 3H).

3-(2,5-dimethoxy-4-(methylthio)phenyl)pyridine

The title compound was prepared according to the general procedure F starting from (4-bromo-2,5-dimethoxyphenyl)(methyl)sulfane (568 mg, 2.158 mmol). 351 mg (62%) of the title compound were prepared. $^1$H-NMR (400 MHz, CDCl$_3$) δ: 8.76 (dd, J=2.3, 0.9 Hz, 1H); 8.55 (dd, J=4.8, 1.7 Hz, 1H); 7.85 (ddd, J=7.9, 2.3, 1.7 Hz, 1H); 7.32 (ddd, J=7.9, 4.8, 0.9 Hz, 1H); 6.86 (s, 1H); 6.80 (s, 1H); 3.90 (s, 3H); 3.79 (s, 3H); 2.50 (s, 3H). MS: m/z 262 [M+H]$^+$.

(R)-3-(2,5-dimethoxy-4-(methylthio)phenyl)piperidine hydrochloride (17) and (S)-3-(2,5-dimethoxy-4-(methylthio)phenyl)piperidine hydrochloride (18)

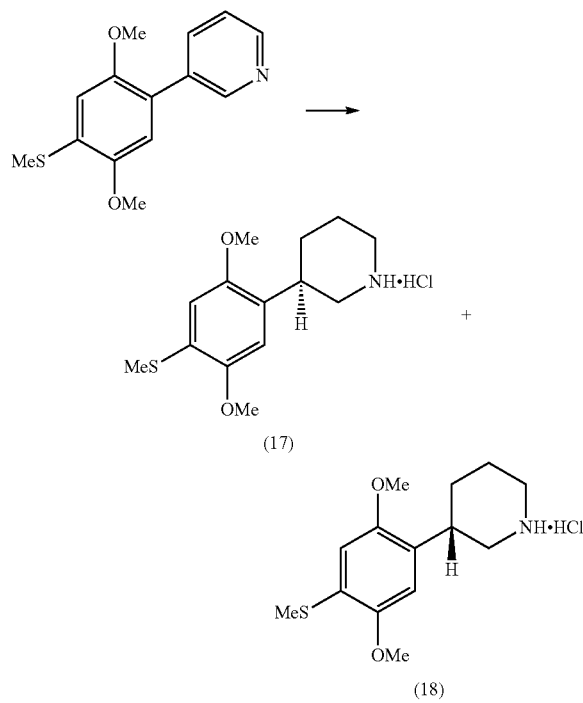

The title compounds were prepared according to the general procedure I starting from 3-(2,5-dimethoxy-4-(methylthio)phenyl)pyridine (350 mg, 1.339 mmol). The material obtained after filtration of the catalyst and evaporation. The compound was purified by flash-column chromatography with MeOH/EtOAc (+5% Et$_3$N) mobile phase. The enantiomers were separated on Daicel Chiralpak IG 250×30 mm, 5 μm; mobile phase: 30% Isopropanol/70% Heptane (+0.1% diethylamine); elution: isocratic; detection: UV 210 nm; flow rate: 40 mL/min. Analytical column: Chiralpak IG 250×4.6 mm, 5 μm; mobile phase: 30% Isopropanol/70% Heptane (+0.1% diethylamine); elution: isocratic; detection: UV 210 nm; flow rate: 1 mL/min. Enantiomer 1: Rt 16.70 min (35 mg, 10%). Enantiomer 2: Rt 21.75 min (35 mg, 10%). Both enantiomers were further converted to the corresponding hydrochlorides using general procedure L in quantitative yields. $^1$H-NMR (400 MHz, MeOD) δ: 6.83 (s, 1H), 6.81 (s, 1H), 3.85 (s, 3H), 3.82 (s, 3H), 3.45-3.34 (m, 3H), 3.10-2.98 (m, 2H), 2.41 (s, 3H), 2.10-2.03 (m, 1H), 1.97-1.84 (m, 3H). $^{13}$C-NMR (100 MHz, MeOD) δ 152.9, 152.3, 128.5, 127.1, 111.6, 111.2, 57.2, 56.7, 49.3, 45.2, 35.1, 29.1, 24.1, 14.8. MS: m/z 268 [M+H]$^+$ Synthesis of Compounds 19 and 20

2-bromo-4-ethoxy-5-(trifluoromethyl)phenol

The title compound was prepared according to the general procedure G. starting from commercially available 4-ethoxy-3-(trifluoromethyl)phenol (2.00 g, 9.701 mmol). 2.60 g (94%) of the title compound were prepared. $^1$H-NMR (400 MHz, CDCl$_3$) δ 7.23 (s, 1H), 7.10 (s, 1H), 4.04 (q, J=7.2 Hz, 2H), 1.42 (t, J=7.2 Hz, 3H).

1-bromo-5-ethoxy-2-methoxy-4-(trifluoromethyl)benzene

The title compound was prepared according to the general procedure H starting from 2-bromo-4-ethoxy-5-(trifluoromethyl)phenol (1.14 g, 4.013 mmol). 1.07 g (89%) of the title compound were prepared. $^1$H-NMR (400 MHz, CDCl$_3$) δ: 7.22 (s, 1H), 7.08 (s, 1H), 4.07 (q, J=6.8 Hz, 2H), 3.88 (s, 3H), 1.42 (t, J=6.8 Hz, 3H).

3-(5-ethoxy-2-methoxy-4-(trifluoromethyl)phenyl)pyridine

The title compound was prepared according to the general procedure F starting from 1-bromo-5-ethoxy-2-methoxy-4-(trifluoromethyl)benzene (1.00 mg, 3.343 mmol). 801 mg (81%) of the title compound were prepared. $^1$H-NMR (400 MHz, CDCl$_3$) δ 8.75 (s, 1H), 8.61 (s, 1H), 7.87 (dt, J=8.0, 1.8 Hz, 1H), 7.38 (dd, J=7.9, 4.8 Hz, 1H), 7.18 (s, 1H), 6.97 (s, 1H), 4.12 (q, J=7.0 Hz, 2H), 3.80 (s, 3H), 1.44 (t, J=7.0 Hz, 3H). MS: m/z 298 [M+H]$^+$.

(R)-3-(5-ethoxy-2-methoxy-4-(trifluoromethyl)phenyl)piperidine hydrochloride (19) and (S)-3-(5-ethoxy-2-methoxy-4-(trifluoromethyl)phenyl)piperidine hydrochloride (20)

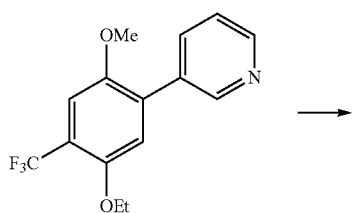

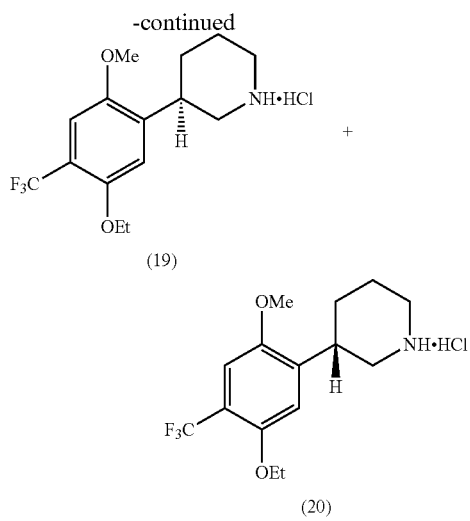

(19)

(20)

The title compounds were prepared according to the general procedure L starting from from 3-(5-ethoxy-2-methoxy-4-(trifluoromethyl)phenyl)pyridine. The enantiomers were transformed to the corresponding ter-butyl carboxylates using general procedure K and separated using a Daicel Chiralpak IG 250×30 mm, 5 μm; mobile phase: 5% Isopropanol/95% Heptane; elution: isocratic; detection: UV 210 nm; flow rate: 40 mL/min. Enantiomer 1 (compound 19): Rt 15.35 min (95 mg, 74%), Enantiomer 2 (compound 20): Rt 26.79 min (90 mg, 77%). The carboxylates were liberated as the corresponding hydrochlorides using general procedure L. giving the titles compounds in quantative yields. The hydrochlorides were further analyzed using a Thermo Scientific Dionex 3000 UltiMate instrument connected to a Thermo Scientific Dionex 3000 Diode Array Detector by a Phenomenex Lux 5 Amylose-2 (250×4.6 mm) chiral column with UV detection at 205, 210, 254 and 280 nm. MP A: 0.1% Diethylamine in Heptane (v/v). MP B: 0.1% Diethylamine in EtOH (v/v). Flow rate: 10.0 mL/min. using an isocratic gradient of 10% MP B to ensure correct stereochemistry. Enantiomer 1 (compound 20): Rt 5.300, Enantiomer 2 (compound 19): Rt 5.970. $^1$H-NMR (400 MHz, MeOD) δ: 7.15 (s, 1H); 7.05 (s, 1H); 4.12 (q, 2H, J=7.0 Hz); 3.86 (s, 3H); 3.52-3.36 (m, 3H); 3.17-2.98 (m, 2H); 2.13-2.03 (m, 1H); 2.02-1.84 (m, 3H); 1.39 (t, 3H, J=7.0 Hz). $^{13}$C-NMR (100 MHz, MeOD; one signal overlapping with CD$_3$OD) δ: 152.6, 151.7, 135.5, 124.9 (q, J=271.6 Hz), 119.3 (q, J=31.0 Hz), 114.8, 110.4 (q, J=5.5 Hz), 66.5, 56.7, 45.2, 35.3, 28.8, 24.0, 15.1. MS: m/z 304 [M+H]$^+$.

Synthesis of Compounds 21 and 22

1-bromo-2,5-diethoxy-4-(trifluoromethyl)benzene

The title compound was prepared according to the general procedure J starting from 2-bromo-4-ethoxy-5-(trifluoromethyl)phenol (1.14 mg, 4.013 mmol). 1.18 mg (94%) of the title compound were prepared. $^1$H NMR (400 MHz, CDCl$_3$) δ: 7.20 (s, 1H), 7.08 (s, 1H), 4.07 (qd, J=7.0, 2.7 Hz, 4H) 1.44 (dt, J=14.8, 7.0 Hz, 6H).

3-(2,5-diethoxy-4-(trifluoromethyl)phenyl)pyridine

The title compound was prepared according to the general procedure E starting from 1-bromo-2,5-diethoxy-4-(trifluoromethyl)benzene (1.12 mg, 3.577 mmol). 768 mg (69%) of the title compound were prepared. $^1$H-NMR (400 MHz, CDCl$_3$) δ: 8.78 (s, 1H), 8.60 (s, 1H), 7.90 (dt, J=7.9, 1.9 Hz, 1H), 7.38 (dd, J=7.9, 4.9 Hz, 1H), 7.18 (s, 1H), 6.97 (m, 1H), 4.12 (q, J=7.0 Hz, 2H), 4.01 (q, J=7.0 Hz, 2H), 1.43 (t, J=7.0 Hz, 3H), 1.32 (t, J=6.9 Hz, 3H). MS: m/z 312 [M+H]$^+$ (R)-3-(2,5-diethoxy-4-(trifluoromethyl)phenyl)piperidine hydrochloride (21) and (S)-3-(2,5-diethoxy-4-(trifluoromethyl)phenyl)piperidine hydrochloride (22)

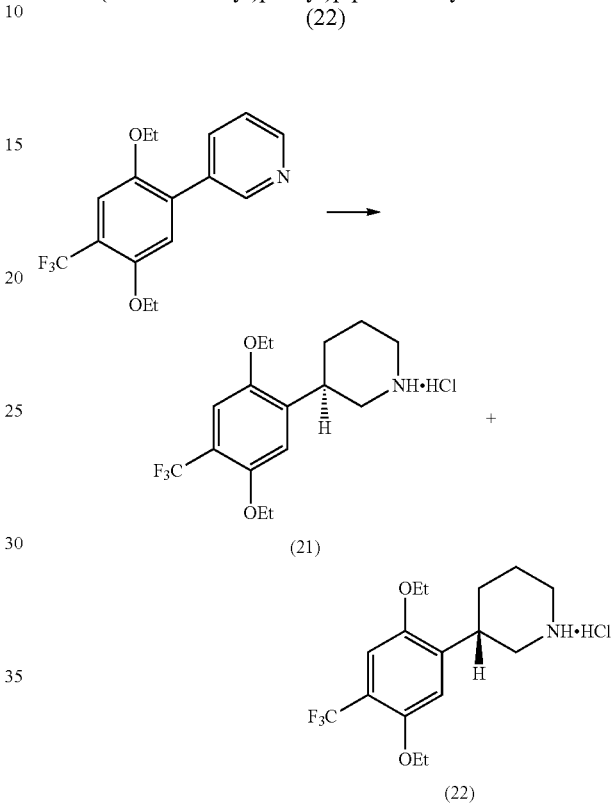

(21)

(22)

The title compounds were prepared according to the general procedure L starting from from 3-(2,5-diethoxy-4-(trifluoromethyl)phenyl)pyridine. The enantiomers were transformed to the corresponding ter-butyl carboxylates using general procedure K and seperated using a Daicel Chiralpak IG 250×30 mm, 5 μm; mobile phase: 5% Isopropanol/95% Heptane; elution: isocratic; detection: UV 210 nm; flow rate: 40 mL/min. Enantiomer 1 (compound 21): Rt 7.03 min (45 mg, 34%), Enantiomer 2 (compound 22): Rt 8.69 min (30 mg, 34%). The carboxylates were liberated as the corresponding hydrochlorides using general procedure L giving the titles compounds in quantative yields. The hydrochlorides were further analyzed using a Thermo Scientific Dionex 3000 UltiMate instrument connected to a Thermo Scientific Dionex 3000 Diode Array Detector by a Phenomenex Lux 5 Amylose-2 (250×4.6 mm) chiral column with UV detection at 205, 210, 254 and 280 nm. MP A: 0.1% Diethylamine in Heptane (v/v). MP B: 0.1% Diethylamine in EtOH (v/v). Flow rate: 10.0 mL/min. using an isocratic gradient of 10% MP B to ensure correct stereochemistry. Enantiomer 1 (compound 22): Rt 5.850, Enantiomer 2 (compound 21): Rt 6.490. $^1$H-NMR (400 MHz, MeOD) δ: 7.13 (s, 1H); 7.05 (s, 1H); 4.17-4.03 (m, 4H); 3.54-3.38 (m, 3H); 3.19-2.98 (m, 2H); 2.15-2.03 (m, 1H); 2.02-1.85 (m, 3H); 1.44 (t, 3H, J=7.0 Hz); 1.39 (t, 3H, J=7.0 Hz). $^{13}$C-NMR (100 MHz, MeOD; one signal overlapping with CD₃OD) δ: 152.5, 151.0, 135.6, 125.0 (q, J=271.6 Hz), 119.3 (q, J=31.0 Hz), 114.8, 111.5 (q, J=5.4 Hz), 66.5, 65.9, 45.2, 35.4, 28.9, 24.0, 15.2, 15.1. MS: m/z 318 [M+H]⁺.

Synthesis of Compounds 23 and 24

3-(2,5-dimethoxy-4-methylphenyl)pyridine

The title compound was prepared according to the general procedure E starting from 1-bromo-2,5-dimethoxy-4-methylbenzene (277 mg, 1.20 mmol). 263 mg (95%) of the title compound were prepared.

¹H-NMR (300 MHz, CDCl₃) δ: 8.77 (s, 1H); 8.54 (d, J=4.8 Hz, 1H); 7.87 (dt, J=7.9, 1.9 Hz, 1H); 7.33 (dd, J=7.9, 4.8 Hz, 1H); 6.84 (s, 1H); 6.80 (s, 1H); 3.83 (s, 3H); 3.76 (s, 3H), 2.28 (s, 3H). MS: m/z 230 [M+H]⁺

(R)-3-(2,5-dimethoxy-4-methylphenyl)piperidine hydrochloride (23) and (S)-3-(2,5-dimethoxy-4-methylphenyl)piperidine hydrochloride (24)

The title compounds were prepared according to the general procedure I starting from 3-(2,5-dimethoxy-4-methylphenyl)pyridine. The enantiomers were transformed to the corresponding ter-butyl carboxylates using general procedure K and separated using a Daicel Chiralpak IG 250×30 mm, 5 µm; mobile phase: 5% Isopropanol/95% Heptane; elution: isocratic; detection: UV 210 nm; flow rate: 40 mL/min. Enantiomer 1 (compound 24): Rt 9.38 min (50 mg, 39%), Enantiomer 2 (compound 23): Rt 12.84 min (40 mg, 45%). The carboxylates were liberated as the corresponding hydrochlorides using general procedure L giving the titles compounds in quantitative yields. ¹H-NMR (400 MHz, CD₃OD) 6.81 (s, 1H); 6.76 (s, 1H); 3.80 (s, 3H); 3.79 (s, 3H); 3.45-3.33 (m, 3H); 3.10-2.97 (m, 2H); 2.17 (s, 3H); 2.10-2.02 (m, 1H); 1.98-1.84 (m, 3H). ¹³C-NMR (100 MHz, CD₃OD, one signal overlapping with CD₃OD) δ: 153.4, 152.0, 127.6, 127.5, 115.2, 110.9, 56.6, 56.5, 45.2, 35.3, 29.1, 24.1, 16.2. MS: m/z 336 [M+H]⁺

Synthesis of Compounds 25 and 26

(4-bromo-2,5-dimethoxyphenyl)(isopropyl)sulfane

The title compound was prepared according to the general procedure N starting from 1,4-dibromo-2,5-dimethoxybenzene (1.50 mg, 5.068 mmol). 794 mg (54%) of the title compound were prepared. MS: m/z 232 [M+H]⁺

3-(4-(isopropylthio)-2,5-dimethoxyphenyl)pyridine

The title compound was prepared according to the general procedure F starting from (4-bromo-2,5-dimethoxyphenyl)(isopropyl)sulfane (789 mg, 2.709 mmol) 589 mg (75%) of the title compound were prepared. MS: m/z 290 [M+H]⁺

(R)-3-(4-(isopropylthio)-2,5-dimethoxyphenyl)piperidine (25) and (S)-3-(4-(isopropylthio)-2,5-dimethoxyphenyl)piperidine (26)

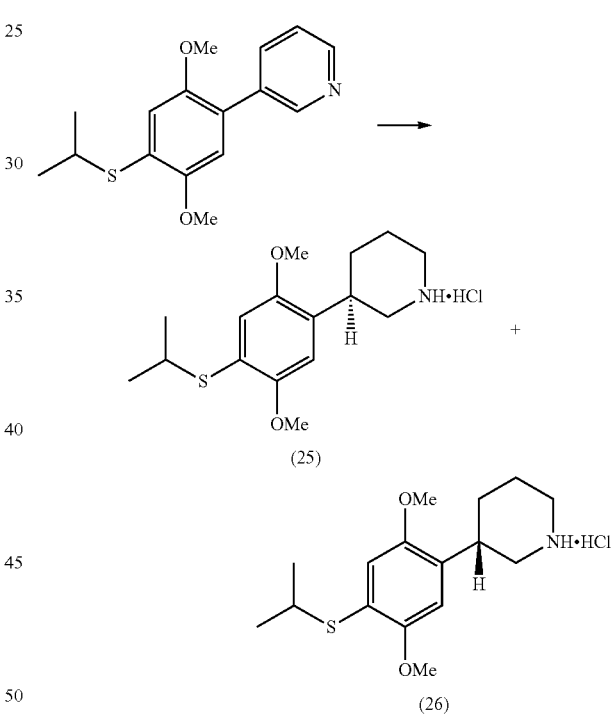

The title compounds were prepared according to the general procedure I starting from 3-(4-(isopropylthio)-2,5-dimethoxyphenyl)pyridine (590 mg, 2.039 mmol). The material obtained after filtration of the catalyst and evaporation was purified by flash-column chromatography with MeOH/EtOAc (+5% Et₃N) mobile phase. The enantiomers were separated on Daicel Chiralpak IG 250×30 mm, 5 µm; mobile phase: 15% Isopropanol/85% Heptane (+0.1% diethylamine); elution: isocratic; detection: UV 210 nm; flow rate: 40 mL/min. Analytical column: Chiralpak IG 250×4.6 mm, 5 µm; mobile phase: 15% Isopropanol/85% Heptane (+0.1% diethylamine); elution: isocratic; detection: UV 210 nm; flow rate: 1 mL/min. Enantiomer 1 (compound 26): Rt 13.01 min (41 mg, 7%). Enantiomer 2 (compound 25): Rt 18.13 min (40 mg, 7%). Both enantiomers were further converted to the corresponding hydrochlorides using general procedure L giving the title compounds in quantitative yields. $^1$H-NMR (400 MHz, MeOD) δ 6.97 (s, 1H), 6.85 (s, 1H), 3.82 (s, 3H), 3.81 (s, 3H), 3.49 (p, J=6.6 Hz, 1H), 3.44-3.31 (m, 3H), 3.12-2.96 (m, 2H), 2.10-2.01 (m, 1H), 1.99-1.82 (m, 3H), 1.22 (s, 3H), 1.21 (s, 3H). $^{13}$C-NMR (100 MHz, MeOD, one signal overlapping with CD$_3$OD) δ 154.6, 152.2, 129.8, 124.6, 117.2, 112.3, 57.2, 56.6, 45.2, 37.4, 35.2, 29.0, 24.1, 23.3. MS: m/z 296 [M+H]$^+$.

Synthesis of compounds 27 and 28

(4-bromo-2,5-dimethoxyphenyl)(ethyl)sulfane

The title compound was prepared according to the general procedure N starting from 1,4-dibromo-2,5-dimethoxybenzene (1.50 mg, 5.068 mmol). 610 mg (43%) of the title compound were prepared.

3-(4-(ethylthio)-2,5-dimethoxyphenyl)pyridine

The title compound was prepared according to the general procedure F starting from (4-bromo-2,5-dimethoxyphenyl)(ethyl)sulfane (589 mg, 2.125 mmol). 407 mg (69%) of the title compound were prepared. MS: m/z 276 [M+H]$^+$ (R)-3-(2,5-dimethoxy-4-(ethylthio)phenyl)piperidine hydrochloride (27) and (S)-3-(2,5-dimethoxy-4-(ethylthio)phenyl)piperidine hydrochloride (28)

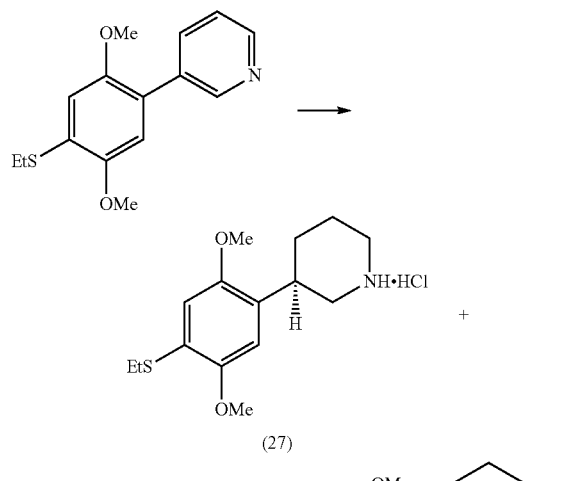

The title compounds were prepared according to the general procedure I starting from 3-(2,5-dimethoxy-4-(ethylthio)phenyl)pyridine (407 mg, 1.478 mmol). The material obtained after filtration of the catalyst and evaporation was purified by flash-column chromatography with MeOH/EtOAc (+5% Et$_3$N) mobile phase. The enantiomers were separated on Daicel Chiralpak IG 250×30 mm, 5 μm; mobile phase: 15% Isopropanol/85% Heptane (+0.1% diethylamine); elution: isocratic; detection: UV 210 nm; flow rate: 40 mL/min. Analytical column: Chiralpak IG 250×4.6 mm, 5 μm; mobile phase: 150% Isopropanol/85% Heptane (+0.1% diethylamine); elution: isocratic; detection: UV 210 nm; flow rate: 1 mL/min. The enantiomer with a Enantiomer 1 (compound 28): Rt 14.92 min (45 mg, 11%). Enantiomer 2 (compound 27): Rt 19.30 (59 mg, 14%). Both enantiomers were further converted to the corresponding hydrochlorides using general procedure L in quantitative yields. $^1$H-NMR (400 MHz, MeOD) δ 6.91 (s, 1H), 6.83 (s, 1H), 3.83 (s, 3H), 3.83 (s, 3H), 3.45-3.33 (m, 3H), 3.12-2.97 (m, 2H), 2.91 (q, J=7.4 Hz, 2H), 2.11-2.02 (m, 1H), 1.99-1.82 (m, 3H), 1.26 (t, J=7.4 Hz, 3H). $^{13}$C-NMR (100 MHz, MeOD, one signal overlapping with CD$_3$OD) δ 153.4, 152.5, 128.4, 125.9, 114.1, 112.1, 57.1, 56.7, 45.2, 35.2, 29.0, 27.0, 24.1, 14.69. MS: m/z 282 [M+H]$^+$ Synthesis of Compounds 29 and 30

1-bromo-2-ethoxy-5-methoxy-4-(trifluoromethyl)benzene

The title compound was prepared according to the general procedure J starting from 2-bromo-4-methoxy-5-(trifluoromethyl)phenol (700 mg, 2.583 mmol). 767 mg (99%) of the title compound were prepared. $^1$H-NMR (400 MHz, CDCl$_3$) δ: 7.21 (s, 1H), 7.09 (s, 1H), 4.05 (q, J=6.0 Hz), 1.46 (t, J=6.0 Hz).

3-(2-ethoxy-5-methoxy-4-(trifluoromethyl)phenyl)pyridine

The title compound was prepared according to the general procedure F starting from 1-bromo-2-ethoxy-5-methoxy-4-(trifluoromethyl)benzene (755 mg, 2.52 mmol). 540 mg (72%) of the title compound were prepared. $^1$H-NMR (300 MHz, CDCl$_3$) δ: 8.78 (dd, J=2.3, 0.9 Hz, 1H), 8.60 (dd, J=4.8, 1.7 Hz, 1H), 7.89 (ddd, J=7.9, 2.3, 1.7 Hz, 1H), 7.36 (ddd, J=7.9, 4.9, 0.9 Hz, 1H), 7.19 (s, 1H), 6.98 (s, 1H), 4.01 (q, J=7.0 Hz, 2H), 3.90 (s, 3H), 1.32 (t, J=7.0 Hz, 3H). MS: m/z 298 [M+H]$^+$.

(R)-3-(2-ethoxy-5-methoxy-4-(trifluoromethyl)phenyl)piperidine hydrochloride (29) and (S)-3-(2-ethoxy-5-methoxy-4-(trifluoromethyl)phenyl)piperidine hydrochloride (30)

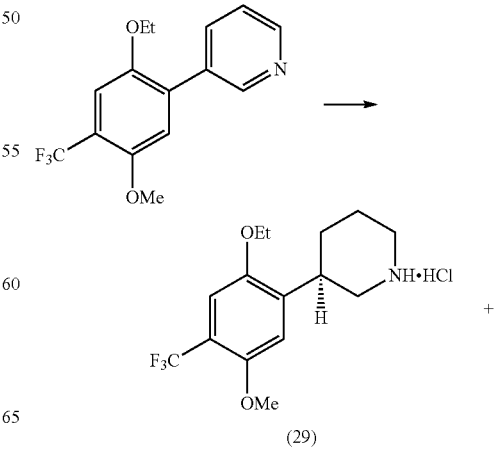

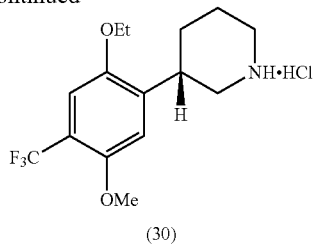

(30)

The title compounds were prepared according to the general procedure L starting from 3-(2-ethoxy-5-methoxy-4-(trifluoromethyl)phenyl)pyridine. The enantiomers were transformed to the corresponding ter-butyl carboxylates using general procedure K and separated using Daicel Chiralpak IG 250×30 mm, 5 μm; mobile phase: 2% Isopropanol/98% Heptane; elution: isocratic; detection: UV 210 nm; flow rate: 40 mL/min. Enantiomer 1 (compound 29): Rt 8.65 min (85 mg, 32%), Enantiomer 2 (compound 30): Rt 9.43 min (91 mg, 32%). The carboxylates were liberated as the corresponding hydrochlorides using general procedure L giving the titles compounds in quantitative yields. The hydrochlorides were further analyzed using a Thermo Scientific Dionex 3000 UltiMate instrument connected to a Thermo Scientific Dionex 3000 Diode Array Detector by a Phenomenex Lux 5 Amylose-2 (250×4.6 mm) chiral column with UV detection at 205, 210, 254 and 280 nm. MP A: 0.1% Diethylamine in Heptane (v/v). MP B: 0.1% Diethylamine in EtOH (v/v). Flow rate: 10.0 mL/min. using an isocratic gradient of 10% MP B to ensure correct stereochemistry. Enantiomer 1 (compound 30): Rt 5.600, Enantiomer 2 (compound 29): Rt 6.31. $^{1}$H-NMR (400 MHz, MeOD) δ 7.14 (s, 1H), 7.07 (s, 1H), 4.08 (q, J=7.0 Hz, 2H), 3.88 (s, 3H), 3.55-3.39 (m, 3H), 3.17 (t, J=12.3 Hz, 1H), 3.11-2.98 (m, 1H), 2.14-2.03 (m, 1H), 2.02-1.86 (m, 3H), 1.44 (t, J=7.0 Hz, 3H). $^{13}$C-NMR (100 MHz, MeOD; one signal overlapping with CD$_3$OD) δ 153.1, 151.0, 135.8, 124.9 (q, J=271.5 Hz), 118.8 (q, J=31.0 Hz), 113.6, 111.7 (q, J=5.4 Hz), 65.9, 57.2, 45.2, 35.4, 28.9, 24.0, 15.2. MS: m/z 304 [M+H]$^+$.

Synthesis of Compounds 31 and 32

2-bromo-5-ethyl-4-methoxyphenol

The title compound was prepared according to the general procedure G starting from known 3-ethyl-4-methoxyphenol (2.083 g, 13.687 mmol). 1.810 g (57%) of the title compound were prepared. $^{1}$H-NMR (300 MHz, CDCl$_3$) δ: 6.88 (s, 1H), 6.84 (s, 1H), 3.76 (s, 3H), 2.55 (q, J=6.1 Hz, 2H), 1.16 (t, J=6.1 Hz, 1H).

1-bromo-4-ethyl-2,5-dimethoxybenzene

The title compound was prepared according to the general procedure H starting from 2-bromo-5-ethyl-4-methoxyphenol (1.46 g, 6.318 mmol). 400 g (26%) of the title compound were prepared. $^{1}$H-NMR (300 MHz, CDCl$_3$) δ: 7.04 (s, 1H), 6.78 (s, 1H), 3.88 (s, 3H), 3.81 (s, 3H), 2.62 (q, J=6.1 Hz, 2H), 1.21 (t, J=6.1 Hz, 3H).

3-(4-ethyl-2,5-dimethoxyphenyl)pyridine

The title compound was prepared according to the general procedure F starting from 1-bromo-4-ethyl-2,5-dimethoxybenzene (400 mg, 1.632 mmol). 163 mg (41%) of the title compound were prepared. $^{1}$H-NMR (300 MHz, CDCl$_3$) δ: 8.78 (s, 1H); 8.55 (s, 1H); 7.87 (d, J=8.0 Hz, 1H); 7.39-7.28 (m, 1H); 6.85 (s, 1H); 6.82 (s, 1H); 3.83 (s, 3H); 3.77 (s, 3H); 2.69 (q, J=7.5 Hz, 2H); 1.24 (t, J=7.5 Hz, 3H). MS: m/z 244 [M+H]$^+$ (R)-3-(4-ethyl-2,5-dimethoxyphenyl)piperidine hydrochloride (31) and (S)-3-(4-ethyl-2,5-dimethoxyphenyl)piperidine hydrochloride (32)

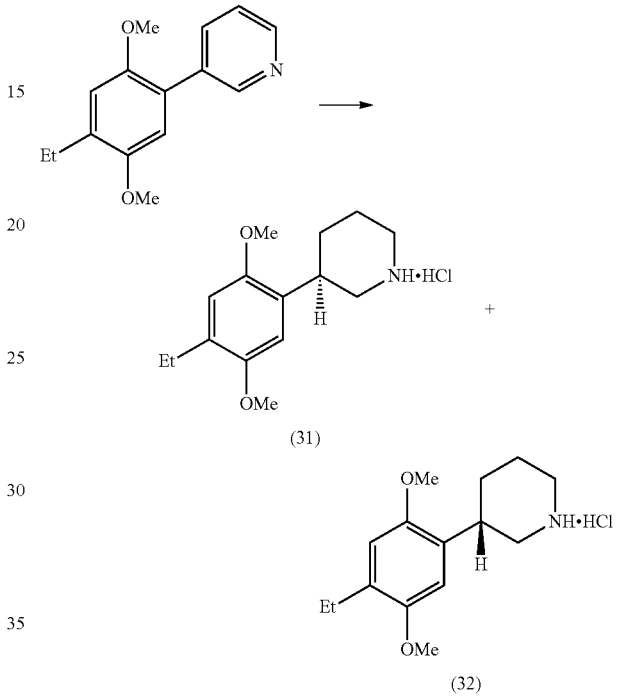

The title compounds was prepared according to the general procedure L starting from 3-(4-ethyl-2,5-dimethoxyphenyl)pyridine. The enantiomers were transformed to the corresponding ter-butyl carboxylates using general procedure K and separated using a Daicel Chiralpak IG 250×30 mm, 5 μm; mobile phase: 2% Isopropanol/98% Heptane; elution: isocratic; detection: UV 210 nm; flow rate: 40 mL/min. Enantiomer 1 (compound 32): Rt 11.35 min (32 mg, 49% mg), Enantiomer 2 (compound 31): Rt 14.10 min (32 mg, 49%). The carboxylates were liberated as the corresponding hydrochlorides using general procedure L giving the titles compounds in quantative yields. $^{1}$H-NMR (400 MHz, MeOD) δ 6.80 (s, 1H), 6.78 (s, 1H), 3.81 (s, 3H), 3.79 (s, 3H), 3.46-3.33 (m, 3H), 3.12-2.97 (m, 2H), 2.60 (q, J=7.5 Hz, 2H), 2.11-2.01 (m, 1H), 1.98-1.83 (m, 3H), 1.15 (t, J=7.5 Hz, 3H). $^{13}$C-NMR (100 MHz, MeOD; one signal overlapping with CD$_3$OD) δ 153.0, 152.2, 133.7, 127.7, 113.8, 111.3, 56.6, 56.5, 45.2, 35.3, 29.1, 24.4, 24.1, 14.9. MS: m/z 250 [M+H]$^+$ Synthesis of Compounds 33 and 34

2-bromo-4-ethoxy-5-ethyl phenol

The title compound was prepared according to the general procedure G starting from known 3-ethyl-4-ethoxyphenol (1.96 g, 11.792 mmol). 930 mg (32%) of the title compound were prepared. $^{1}$H-NMR (300 MHz, CDCl$_3$) δ: 6.88 (s, 1H), 6.84 (s, 1H), 3.94 (q, J=6.4 Hz, 2H), 2.57 (q, J=6.3 Hz, 2H), 1.39 (t, J=6.4 Hz, 3H), 1.16 (t, J=6.3 Hz, 3H).

1-bromo-5-ethoxy-4-ethyl-2-methoxybenzene

The title compound was prepared according to the general procedure H starting from 2-bromo-4-ethoxy-5-ethylphenol (950 mg, 3.876 mmol). 860 g (86%) of the title compound were prepared. $^1$H-NMR (300 MHz, CDCl$_3$) δ: 7.00 (s, 1H), 6.75 (s, 1H), 3.97 (q, J=6.3 Hz, 2H), 3.85 (s, 3H) 2.60 (q, J=6.2 Hz, 2H), 1.39 (t, J=6.3 Hz, 3H), 1.18 (t, J=6.2 Hz, 3H).

3-(5-ethoxy-4-ethyl-2-methoxyphenyl)pyridine

The title compound was prepared according to the general procedure F starting from 1-bromo-5-ethoxy-4-ethyl-2-methoxybenzene (860 mg, 3.139 mmol). 380 mg (44%) of the title compound were prepared.
$^1$H-NMR (300 MHz, CDCl$_3$) δ: 8.76 (d, J=1.8 Hz, 1H); 8.53 (dd, J=4.9, 1.7 Hz, 1H); 7.86 (ddd, J=7.9, 2.3, 1.6 Hz, 1H); 7.31 (ddd, J=7.9, 4.8, 0.9 Hz, 1H); 6.84 (s, 1H); 6.81 (s, 1H); 4.03 (q, J=7.0 Hz, 2H); 3.77 (s, 3H); 2.70 (q, J=7.5 Hz, 2H); 1.42 (t, J=7.0 Hz, 3H); 1.25 (t, J=7.5 Hz, 3H). MS: m/z 258 [M+H]$^+$ (R)-3-(5-ethoxy-4-ethyl-2-methoxyphenyl)piperidine hydrochloride (33) and (S)-3-(5-ethoxy-4-ethyl-2-methoxyphenyl)piperidine hydrochloride (34)

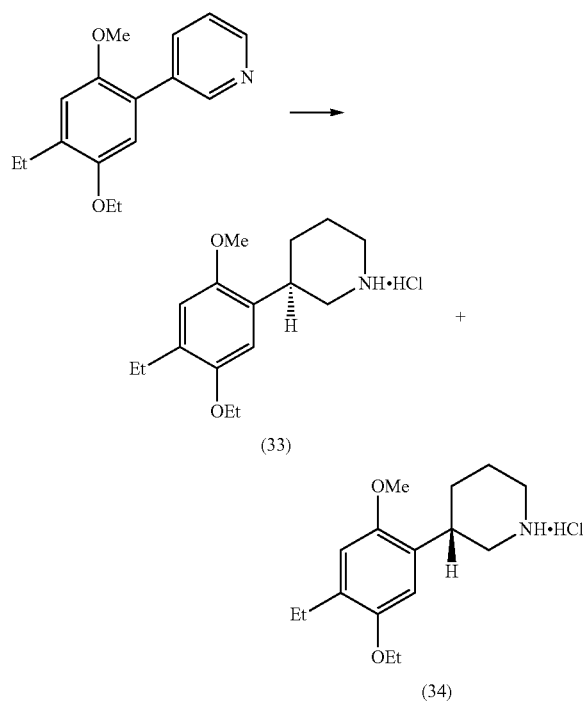

The title compounds was prepared according to the general procedure L starting from 3-(5-ethoxy-4-ethyl-2-methoxyphenyl)pyridine. The enantiomers were transformed to the corresponding ter-butyl carboxylates using general procedure K and separated using a Daicel Chiralpak IG 250×30 mm, 5 μm; mobile phase: 2% Isopropanol/98% Heptane; elution: isocratic; detection: UV 210 nm; flow rate: 40 mL/min. Enantiomer 1 (compound 34): Rt 10.06 min (22 mg, 13%), Enantiomer 2 (compound 33): Rt 14.35 min (20 mg, 11%). The carboxylates were liberated as the corresponding hydrochlorides using general procedure L giving the titles compounds in quantative yields. $^1$H-NMR (400 MHz, MeOD) δ 6.79 (s, 1H), 6.77 (s, 1H), 4.00 (q, J=7.0 Hz, 2H), 3.80 (s, 3H), 3.45-3.32 (m, 3H), 3.10-2.97 (m, 2H), 2.61 (q, J=7.5 Hz, 2H), 2.10-1.99 (m, 1H), 1.97-1.84 (m, 3H), 1.38 (t, J=7.0 Hz, 3H), 1.16 (t, J=7.5 Hz, 3H). $^{13}$C-NMR (100 MHz, MeOD) δ 152.2, 152.2, 134.1, 127.7, 113.7, 112.8, 65.7, 56.5, 49.4, 45.2, 35.2, 29.2, 24.4, 24.1, 15.4, 15.0. MS: m/z 264 [M+H]$^+$ Synthesis of Compound 35

3-(2,5-dimethoxy-4-(trifluoromethyl)phenyl)-2-methylpyridine

The title compound was prepared according to the general procedure F starting from 1-bromo-2,5-dimethoxy-4-(trifluoromethyl)benzene (500 mg, 1.75 mmol). 521 mg (99%) of the title compound were prepared. $^1$H-NMR (300 MHz, CDCl$_3$) δ: 8.54 (dd, J=5.0, 1.8 Hz, 1H); 7.47 (dd, J=7.6, 1.8 Hz, 1H); 7.20 (ddd, J=7.6, 4.9, 0.7 Hz, 1H); 7.17 (s, 1H); 6.82 (s, 1H); 3.87 (s, 3H); 3.76 (s, 3H); 2.38 (s, 3H). MS: m/z 298 [M+H]$^+$ 3-(2,5-dimethoxy-4-(trifluoromethyl)phenyl)-2-methylpiperidine hydrochloride (35)

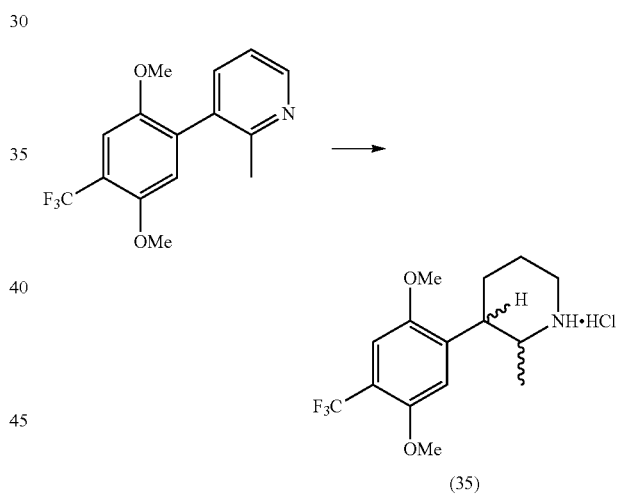

The title compound was prepared according to the general procedure I starting from 3-(2,5-dimethoxy-4-(trifluoromethyl)phenyl)-2-methylpyridine (515 mg, 1.732 mmol). The title compound was purified on preparative HPLC: Xbridge Peptide BEH C18 250×19 mm, 10 μm; mobile phase: H$_2$O/MeOH+0.1% HCOOH; elution: gradient 30% to 50% MeOH (+0.1% HCOOH), 45 min; detection: UV 210 nm; flow rate: 20 mL/min. yielding a single diastereomer. Minor fractions were discarded. The product containing fractions were evaporated. Aq. NaHCO$_3$ (50 mL) and Et$_2$O (50 mL) were added to the residue, Et$_2$O layer separated, aqueous phase extracted with Et$_2$O (2×50 mL). Combined organic extracts was dried over anhydrous Na$_2$SO$_4$, filtered and evaporated. The residue was taken up in Et$_2$O and treated with ethereal HCl (2M, 2 mL). The resulting suspension was centrifugated. Supernatant was discarded, the solid washed with ether and dried under reduced pressure. 83 mg (14%) of the title compound were prepared. Relative stereochemistry was not elucidated for the isolated diastereomer (i.e. either cis or trans). The enantiomers of the diastereomer could not be separated. $^1$H-NMR (400 MHz, MeOD) δ 7.16 (s, 1H), 6.97 (s, 1H), 4.07-3.97 (m, 1H), 3.88 (s, 3H), 3.88 (s, 3H), 3.66 (dt, J=13.2, 3.7 Hz, 1H), 3.25-3.18 (m, 2H), 2.31 (qd, J=13.1, J=3.8 Hz, 1H), 2.16-2.08 (m, 1H), 1.96-1.84 (m, 1H), 1.82-1.75 (m, 1H), 1.11 (d, J=7.1 Hz, 3H). $^{13}$C-NMR (100 MHz, MeOD) δ 153.0, 151.7, 134.8, 124.9 (q, J=271.5 Hz), 118.9 (q, J=31.1 Hz), 114.3, 110.2 (q, J=5.4 Hz), 57.2, 56.6, 51.3, 38.9, 38.4, 24.0, 21.7, 10.3. MS: m/z 304 [M+H]$^+$.

Synthesis of Compound 36

3-(2,5-dimethoxy-4-(trifluoromethyl)phenyl)-5-methylpyridine

The title compound was prepared according to the general procedure F starting from 1-bromo-2,5-dimethoxy-4-(trifluoromethyl)benzene (500 mg, 1.75 mmol). 308 mg (59%) of the title compound were prepared. $^1$H-NMR (300 MHz, CDCl$_3$) δ: 8.55 (s, 1H); 8.44 (s, 1H); 7.66 (s, 1H); 7.19 (s, 1H); 6.95 (s, 1H); 3.90 (s, 3H); 3.80 (s, 3H); 2.41 (s, 3H). MS: m/z 298 [M+H]$^+$ cis or trans 3-(2,5-dimethoxy-4-(trifluoromethyl) phenyl)-5-methylpiperidine hydrochloride (36)

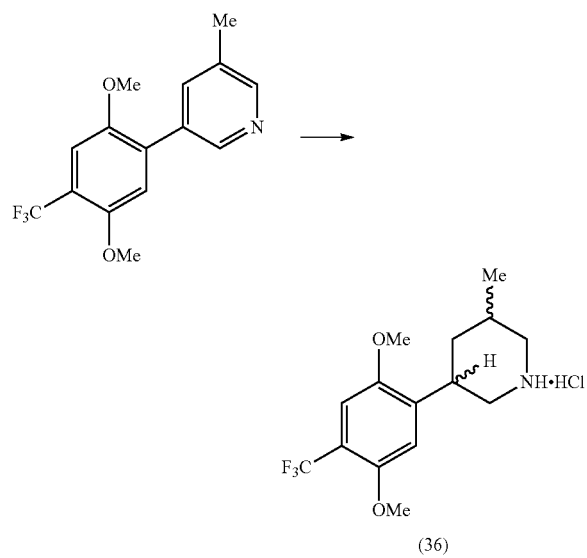

(36)

The title compound was prepared according to the general procedure L starting from 3-(2,5-dimethoxy-4-(trifluoromethyl)phenyl)-5-methylpyridine. The diastereomers were transformed to the corresponding ter-butyl carboxylates using general procedure K and separated using a Daicel Chiralpak IG 250×30 mm, 5 μm; mobile phase: 2% Isopropanol/98% Heptane; elution: isocratic; detection: UV 210 nm; flow rate: 40 mL/min. A single diastereomer was isolated. Diastereomer 1: Rt 19.07 min (17 mg, 11%). The carboxylate was liberated as the corresponding hydrochloride using general procedure L giving the title compound in quantitative yields. Relative stereochemistry was not elucidated for the isolated diastereomer (i.e. either cis or trans). The enantiomers of the diastereomer could not be separated. $^1$H-NMR (400 MHz, MeOD) δ: 7.16 (s, 1H), 7.07 (s, 1H), 3.88 (s, 3H), 3.86 (s, 3H), 3.52 (tt, J=12.4, 3.5 Hz, 1H), 3.44-3.34 (m, 2H), 3.06 (t, J=12.3 Hz, 1H), 2.70 (t, J=12.3 Hz, 1H), 2.09-1.95 (m, 2H), 1.64 (q, J=12.4 Hz, 1H), 1.08 (d, J=6.6 Hz, 3H). $^{13}$C-NMR (100 MHz, MeOD) δ: 153.2, 151.7, 135.3, 124.9 (q, J=271.5 Hz), 118.8 (q, J=31.0 Hz), 113.6, 110.6 (q, J=5.4 Hz), 57.1, 56.7, 50.7, 48.2, 37.4, 35.1, 30.6, 18.9. MS: m/z 304 [M+H]$^+$.

Synthesis of Compounds 37 and 38

5-(2,5-dimethoxy-4-(trifluoromethyl)phenyl)-2-methylpyridine

The title compound was prepared according to the general procedure F starting from 1-bromo-2,5-dimethoxy-4-(trifluoromethyl)benzene (500 mg, 1.75 mmol). 335 mg (64%) of the title compound were prepared. $^1$H-NMR (300 MHz, CDCl$_3$) δ: 8.64 (dd, J=2.3, 0.8 Hz, 1H), 7.76 (dd, J=8.0, 2.3 Hz, 1H), 7.23 (d, J=8.0 Hz, 1H), 7.18 (s, 1H), 6.96 (s, 1H), 3.90 (s, 3H), 3.80 (s, 3H), 2.62 (s, 3H). MS: m/z 298 [M+H]$^+$ 5-(2,5-dimethoxy-4-(trifluoromethyl)phenyl)-2-methylpiperidine The title compound was prepared according to the general procedure I starting from 5-(2,5-dimethoxy-4-(trifluoromethyl)phenyl)-2-methylpyridine (335 mg, 1.127 mmol). 315 mg (92%) of the title compound were prepared. MS: m/z 304 [M+H]$^+$ Cis and trans 5-(2,5-dimethoxy-4-(trifluoromethyl) phenyl)-2-methylpiperidine hydrochloride

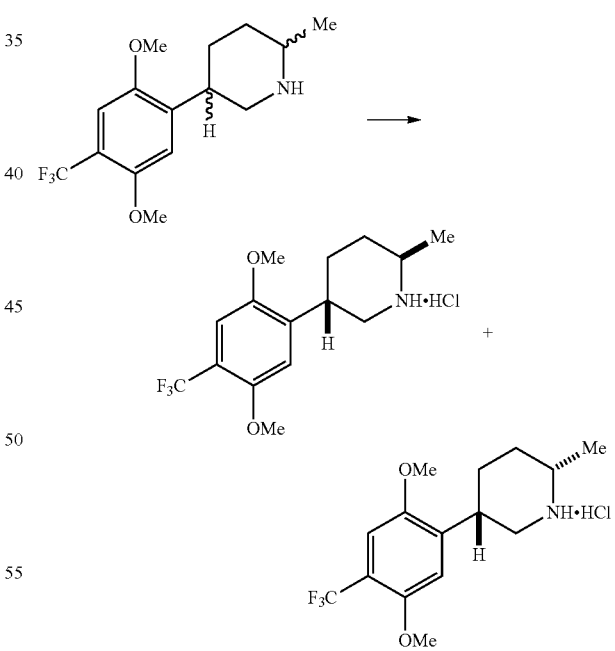

Boc protection was performed according to the general procedure K starting from 5-(2,5-dimethoxy-4-(trifluoromethyl)phenyl)-2-methylpiperidine (181 mg, 0.597 mmol). 213 mg (88%) of the protected title compound were prepared. The Boc-protected diastereomers were separated on Daicel Chiralpak IF 250×30 mm, 5 μm; mobile phase: 2% Isopropanol/98% Heptane; elution: isocratic; detection: UV 210 nm; flow rate: 40 mL/min. Two fractions were isolated.

Boc-Diasteromer 1: Rt 8.89 (69 mg, 31%) and Boc-Diasteromer 2: Rt 16.99 (65 mg, 30%). Boc-diastereomer 1 was deprotected according to the general procedure L starting from tert-butyl 5-(2,5-dimethoxy-4-(trifluoromethyl)phenyl)-2-methylpiperidine-1-carboxylate (Boc-diastereomer 1, 69 mg, 0.171 mmol). 32 mg (55%) of the title compound were prepared. Relative stereochemistry was not further elucidated. $^1$H-NMR (400 MHz, MeOD) δ 7.16 (s, 1H), 7.11 (s, 1H), 3.90 (s, 3H), 3.88 (s, 3H), 3.82-3.75 (m, 1H), 3.44-3.35 (m, 2H), 3.27-3.18 (m, 1H), 2.24-2.05 (m, 2H), 1.95-1.92 (m, 1H), 1.85-1.78 (m, 1H), 1.50 (d, J=7.0 Hz, 3H). $^{13}$C-NMR (100 MHz, MeOD) δ 153.2, 151.8, 135.4, 124.9 (q, J=271.5 Hz), 118.8 (q, J=31.0 Hz), 114.1, 110.59 (q, J=5.4 Hz), 57.2, 56.6, 49.2, 42.6, 36.2, 28.9, 23.2, 14.6. MS: m/z 304 [M+H]$^+$ Boc-diastereomer 2 was deprotected according to the general procedure L starting from tert-butyl 5-(2,5-dimethoxy-4-(trifluoromethyl)phenyl)-2-methylpiperidine-1-carboxylate (Boc-Diastereomer 2, 65 mg, 0.161 mmol). 27 mg (50%) of the title compound were prepared. Relative stereochemistry was not further elucidated for the isolated diastereomer. $^1$H-NMR (400 MHz, MeOD) δ 8.72 (s, 1H), 8.67 (s, 1H), 5.46 (s, 3H), 5.44 (s, 3H), 5.38-5.30 (m, 1H), 5.01-4.90 (m, 2H), 4.83-4.73 (m, 1H), 3.80-3.60 (m, 2H), 3.51-3.44 (m, 1H), 3.41-3.34 (m, 1H), 3.06 (d, J=7.0 Hz, 3H). $^{13}$C-NMR (100 MHz, MeOD) δ 153.2, 151.8, 135.4, 124.9 (q, J=271.5 Hz), 118.90 (q, J=31.1 Hz), 114.1, 110.6 (q, J=5.4 Hz), 57.2, 56.6, 49.2, 42.6, 36.2, 28.9, 23.2, 14.6. MS: m/z 304 [M+H]$^+$.

Synthesis of Compounds 39

1-bromo-2-(fluoromethoxy)-5-methoxy-4-(trifluoromethyl)benzene

A flame dried, round-bottom flask, equipped with a stir bar, backfilled with argon gas, was charged with 2-bromo-4-methoxy-5-(trifluoromethyl)phenol (700 mg, 2.583 mmol) and dry MeCN (4 mL). Cs$_2$CO$_3$ (1.262 g, 3.874 mmol) was added and the flask was tightly sealed before addition of ICH$_2$F (0.186 mL, 2.767 mmol) through the septum using a syringe. The resulting mixture was stirred overnight at ambient temperature. Upon completion the reaction mixture was poured into H$_2$O (20 mL) and extracted into Et$_2$O (3×20 mL). The combined organic extracts were dried over Na$_2$SO$_4$, filtered and evaporated. The residue was purified by flash-column chromatography using a mobile phase of Petroleum ether/EtOAc. 604 mg (77%) of the title compound were prepared. $^1$H-NMR (300 MHz, CDCl$_3$) δ: 7.40 (s, 1H), 7.22 (s, 1H), 5.67 (d, J=54.1 Hz, 2H), 3.89 (s, 3H).

3-(2-(fluoromethoxy)-5-methoxy-4-(trifluoromethyl)phenyl)pyridine

The title compound was prepared according to the general procedure F starting from 1-bromo-2-(fluoromethoxy)-5-methoxy-4-(trifluoromethyl)benzene (604 mg, 1.993 mmol). 517 mg (86%) of the title compound were prepared. $^1$H-NMR (300 MHz, CDCl$_3$) δ: 8.74 (s, 1H); 8.64 (s, 1H); 7.86 (dt, J=7.9, 1.9 Hz, 1H); 7.48 (s, 1H); 7.40 (dd, J=7.9, 4.8 Hz, 1H); 6.98 (s, 1H); 5.58 (d, J=54.2 Hz, 2H); 3.93 (s, 3H). MS: m/z 302 [M+H]$^+$ (S)-3-(2-(fluoromethoxy)-5-methoxy-4-(trifluoromethyl)phenyl)piperidine (39)

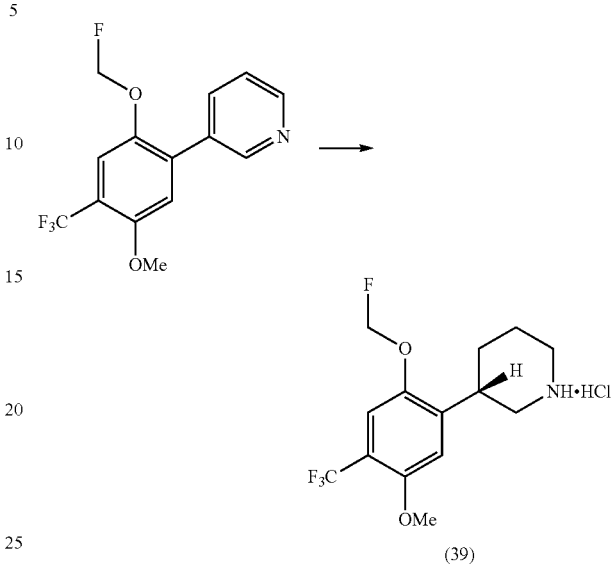

The title compounds was prepared according to the general procedure L starting from 3-(2-(fluoromethoxy)-5-methoxy-4-(trifluoromethyl)phenyl)pyridine. The enantiomers were transformed to the corresponding tert-butyl carboxylates using general procedure K and separated using a Daicel Chiralpak IG 250×30 mm, 5 μm; mobile phase: 2% Isopropanol/98% Heptane; elution: isocratic; detection: UV 210 nm; flow rate: 40 mL/min. Only a single enantiomer was isolated. Enantiomer 1: Rt 16.17 min (30 mg, 33%). The carboxylate was liberated as the corresponding hydrochlorides using general procedure L giving the title compound in quantitative yield. $^1$H-NMR (400 MHz, MeOD) δ 7.40 (s, 1H), 7.14 (s, 1H), 5.78 (d, J=54.3 Hz, 2H), 3.93 (s, 3H), 3.59-3.39 (m, 3H), 3.25-3.03 (m, 2H), 2.13-1.88 (m, 4H). $^{13}$C-NMR (100 MHz, MeOD, one signal overlapping with CD$_3$OD) δ 155.3, 148.6, 137.9, 124.5 (q, J=271.6 Hz), 119.3 (q, J=31.5 Hz), 116.2 (q, J=5.2 Hz), 113.1, 103.4, (d, J=218.3 Hz), 57.1, 45.1, 35.1, 29.1, 23.9. MS: m/z 308 [M+H]$^+$.

Synthesis of Compounds 40 and 41

1-bromo-2,5-diethoxy-4-ethylbenzene

The title compound was prepared according to the general procedure J starting from 2-bromo-5-ethyl-4-ethoxyphenol (930 mg, 3.794 mmol). 407 mg (39%) of the title compound were prepared. $^1$H-NMR (300 MHz, CDCl$_3$) δ: 6.99 (s, 1H), 6.75 (s, 1H), 4.10-3.90 (m, 4H), 2.58 (q, J=7.5 Hz, 2H), 1.47-1.32 (m, 6H), 1.17 (t, J=7.5 Hz, 3H).

3-(2,5-diethoxy-4-ethylphenyl)pyridine

The title compound was prepared according to the general procedure F starting from 1-bromo-2,5-diethoxy-4-ethylbenzene (407 mg, 1.490 mmol). 287 mg (71%) of the title compound were prepared. $^1$H-NMR (300 MHz, CDCl$_3$) δ: 8.81-8.76 (m, 1H); 8.55-8.49 (m, 1H); 7.90 (ddd, J=8.0, 2.3, 1.7 Hz, 1H); 7.32 (ddd, J=7.8, 4.8, 0.8 Hz, 1H); 6.84 (s, 1H);

6.81 (s, 1H); 4.03 (q, J=7.0 Hz, 2H); 3.97 (q, J=6.9 Hz, 2H); 2.68 (q, J=7.5 Hz, 2H); 1.41 (t, J=7.0 Hz, 3H); 1.36-1.21 (m, 6H). MS: m/z 272 [M+H]⁺

(R)-3-(2,5-diethoxy-4-ethylphenyl)piperidine hydrochloride (40) and (R)-3-(2,5-diethoxy-4-ethylphenyl)piperidine hydrochloride (41)

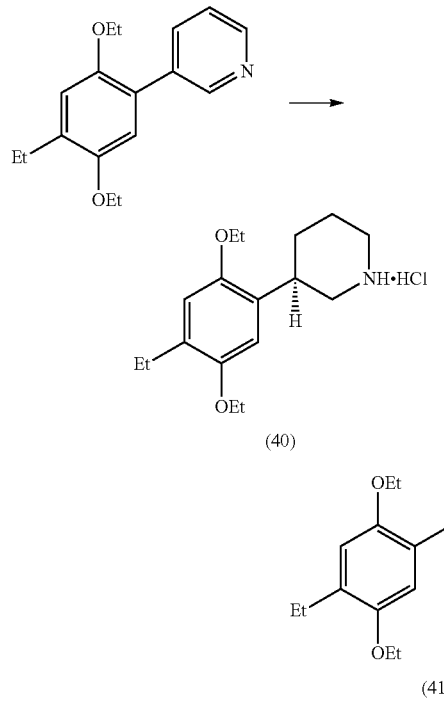

The title compound was prepared according to the general procedure L starting from 3-(2,5-diethoxy-4-ethylphenyl)pyridine. The enantiomers were transformed to the corresponding ter-butyl carboxylates using general procedure K and separated using a Daicel Chiralpak IC 250×30 mm, 5 µm; mobile phase: 2% Isopropanol/98% Heptane; elution: isocratic; detection: UV 210 nm; flow rate: 40 mL/min. Enantiomer 1 (compound 41): Rt 8.04 min (49 mg, 31%), Enantiomer 2 (compound 40): Rt 10.06 min (30 mg, 18%). The carboxylates were liberated as the corresponding hydrochlorides using general procedure L giving the titles compounds in quantative yields. ¹H-NMR (400 MHz, MeOD) δ 6.78 (s, 1H), 6.76 (s, 1H), 4.06-3.97 (m, 4H), 3.43-3.36 (m, 3H), 3.10-2.98 (m, 2H), 2.59 (q, J=7.5 Hz, 2H), 2.07-2.05 (m, 1H), 1.94-1.85 (m, 3H), 1.39 (dt, J=12.4, 7.0 Hz, 6H), 1.15 (t, J=7.5 Hz, 3H). ¹³C-NMR (100 MHz, MeOD; one signal overlapping with CD₃OD) δ 152.3, 151.5, 134.1, 127.9, 114.9, 112.6, 65.7, 65.5, 45.2, 35.3, 29.2, 24.4, 24.1, 15.4, 15.0. MS: m/z 278 [M+H]⁺

Synthesis of Compounds 42 and 43

1-bromo-2-ethoxy-4-ethyl-5-methoxybenzene

The title compound was prepared according to the general procedure J starting from 2-bromo-5-ethyl-4-methoxyphenol (1.00 g, 4.327 mmol). 813 mg (72%) of the title compound were prepared. ¹H-NMR (300 MHz, CDCl₃) δ: 7.00 (s, 1H), 6.76 (s, 1H), 4.05 (q, J=6.4 Hz, 2H), 3.78 (s, 3H), 2.57 (q, J=6.1 Hz, 2H), 1.43 (t, J=6.4 Hz, 3H), 1.16 (q, J=6.1 Hz, 3H).

3-(2-ethoxy-4-ethyl-5-methoxyphenyl)pyridine

The title compound was prepared according to the general procedure F starting from 1-bromo-2-ethoxy-4-ethyl-5-methoxybenzene (813 mg, 3.134 mmol). 543 mg (67%) of the title compound were prepared.

¹H-NMR (300 MHz, CDCl₃) δ: 8.80 (s, 1H); 8.53 (d, J=4.1 Hz, 1H); 7.91 (dt, J=7.9, 1.8 Hz, 1H); 7.33 (dd, J=7.9, 4.8 Hz, 1H); 6.85 (s, 1H); 6.82 (s, 1H); 3.98 (q, J=7.0 Hz, 2H); 3.83 (s, 3H); 2.67 (q, J=7.5 Hz, 2H); 1.30 (t, J=7.0 Hz, 3H); 1.23 (t, J=7.5 Hz, 3H). MS: m/z 258 [M+H]⁺.

(R)-3-(2-ethoxy-4-ethyl-5-methoxyphenyl)piperidine (42) and (S)-3-(2-ethoxy-4-ethyl-5-methoxyphenyl)piperidine (43)

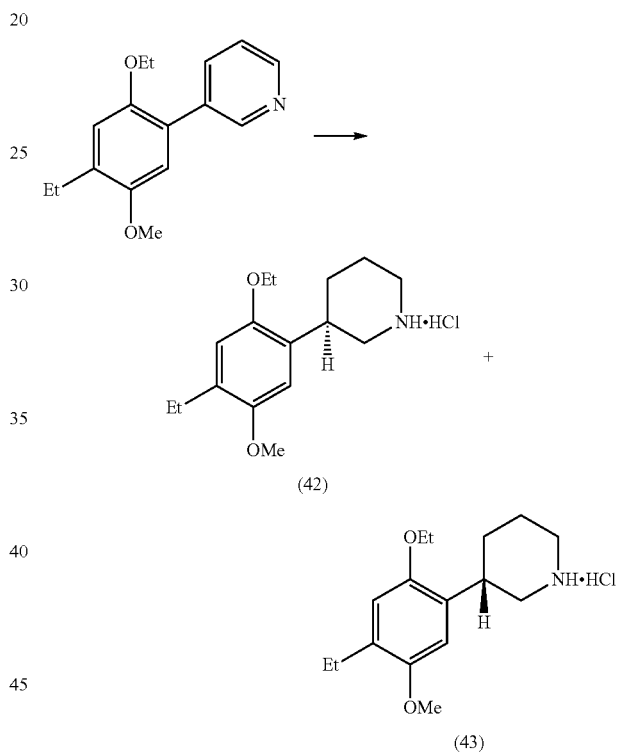

The title compounds was prepared according to the general procedure L starting from 3-(2-ethoxy-4-ethyl-5-methoxyphenyl)pyridine. The enantiomers were transformed to the corresponding tert-butyl carboxylates using general procedure K and separated using a Daicel Chiralpak IC 250×30 mm, 5 µm; mobile phase: 2% Isopropanol/98% Heptane; elution: isocratic; detection: UV 210 nm; flow rate: 40 mL/min. Enantiomer 1 (compound 43): Rt 8.99 min (50 mg, 34%), Enantiomer 2 (compound 42): Rt 11.48 min (49 mg, 36%). The carboxylates were liberated as the corresponding hydrochlorides using general procedure L giving the titles compounds in quantative yields. ¹H-NMR (300 MHz, MeOD) δ 6.81 (s, 1H), 6.79 (s, 1H), 4.05 (q, J=7.0, 2H), 3.81 (s, 3H), 3.46-3.36 (m, 3H), 3.14-3.00 (m, 2H), 2.60 (q, J=7.5, 2H), 2.12-2.06 (m, 1H), 1.99-1.89 (m, 3H), 1.43 (t, J=7.0, 3H), 1.16 (t, J=7.5, 3H). ¹³C-NMR (100 MHz, MeOD; one signal overlapping with CD₃OD) δ 153.0, 151.5, 133.7, 128.0, 115.0, 111.2, 66.5, 56.6, 45.2, 35.3, 29.2, 24.3, 24.1, 15.4, 15.0. MS: m/z 264 [M+H]$^+$.

Synthesis of Compounds 44 and 45

2-bromo-4-fluoro-5-(trifluoromethyl) phenol

The title compound was prepared according to the general procedure G starting from commercially available 4-fluoro-3-(trifluoromethyl)phenol (8.00 g, 44.420 mmol. 5.15 g (45%) of the title compound were prepared. $^1$H-NMR (400 MHz, CDCl$_3$) δ: 7.36 (d, J=6.0 Hz, 1H), 7.24 (d, J=6.0 Hz, 1H). MS: m/z 260 [M+H]$^+$.

1-bromo-5-fluoro-2-methoxy-4-(trifluoromethyl) benzene

The title compound was prepared according to the general procedure H starting from 2-bromo-4-fluoro-5-(trifluoromethyl)phenol (8.67 g, 33.483 mmol). 6.10 g (67%) of the title compound were prepared. $^1$H-NMR (400 MHz, CDCl$_3$) δ: 7.45 (d, J=8.0 Hz, 1H), 7.04 (d, J=8.0 Hz, 1H), 3.92 (s, 3H). MS: m/z 274 [M+H]$^+$

3-(5-fluoro-2-methoxy-4-(trifluoromethyl)phenyl) pyridine

The title compound was prepared according to the general procedure F starting from 1-bromo-5-fluoro-2-methoxy-4-(trifluoromethyl)benzene (2.00 g, 7.325 mmol). 1.51 g (76%) of the title compound were prepared. $^1$H-NMR (300 MHz, CDCl$_3$) δ: 8.75 (d, J=2.2 Hz, 1H); 8.62 (d, J=4.6 Hz, 1H); 7.84 (dt, J=7.9, 1.9 Hz, 1H); 7.37 (dd, J=7.9, 4.9 Hz, 1H); 7.19 (d, J=10.3 Hz, 1H); 7.14 (d, J=5.7 Hz, 1H); 3.85 (s, 3H). MS: m/z 272 [M+H]$^+$

3-(2-methoxy-5-(methylthio)-4-(trifluoromethyl) phenyl)pyridine

The title compound was prepared according to the general Procedure O starting from 3-(5-fluoro-2-methoxy-4-(trifluoromethyl)phenyl)pyridine. (700 mg, 2.581 mmol) 515 mg (67%) of the title compound were prepared. $^1$H-NMR (300 MHz, CDCl$_3$) δ 8.76 (s, 1H), 8.62 (s, 1H), 7.86 (dt, J=7.9, 1.9 Hz, 1H), 7.42 (s, 1H), 7.38 (dd, J=7.7, 4.9 Hz, 1H), 7.27 (s, 1H), 3.86 (s, 3H), 2.50 (s, 3H). MS: m/z 300 [M+H]$^+$

(R)-3-(2-methoxy-5-(methylthio)-4-(trifluoromethyl) phenyl)piperidine hydrochloride (44) and (S)-3-(2-methoxy-5-(methylthio)-4-(trifluoromethyl)phenyl) piperidine hydrochloride (45)

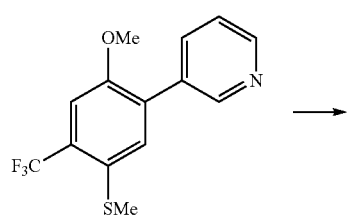

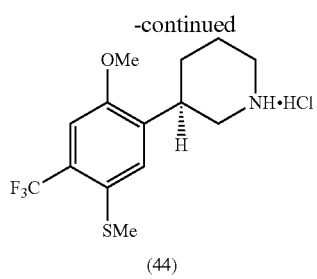

(44)

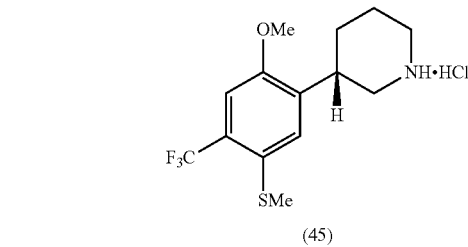

(45)

The title compounds were prepared according to the general procedure L starting 3-(2-methoxy-5-(methylthio)-4-(trifluoromethyl)phenyl)pyridine. The enantiomers were transformed to the corresponding tert-butyl carboxylates using general procedure K and separated using a on Daicel Chiralpak IF 250×30 mm, 5 μm; mobile phase: 2% Isopropanol/98% Heptane; elution: isocratic; detection: UV 210 nm; flow rate: 40 mL/min. Enantiomer 1 (compound 45): Rt 7.94 min (90 mg, 14%), Enantiomer 2 (compound 44): Rt 9.71 min (88 mg, 14%). The carboxylates were liberated as the corresponding hydrochlorides using general procedure L giving the titles compounds in quantative yields. $^1$H-NMR (400 MHz, MeOD) δ 7.46 (s, 1H), 7.26 (s, 1H), 3.92 (s, 3H), 3.51-3.42 (m, 3H), 3.18-3.04 (m, 2H), 2.50 (s, 3H), 2.11-2.06 (m, 1H), 2.00-1.89 (m, 3H). $^{13}$C-NMR (100 MHz, MeOD; one signal overlapping with CD$_3$OD) δ 156.7, 134.8, 131.8, 130.8 (q, J=30.4 Hz), 130.1, 125.1 (q, J=273.1 Hz), 110.4 (q, J=6.0 Hz), 56.5, 45.2, 35.2, 28.7, 24.0, 18.4. MS: m/z 306 [M+H]$^+$.

Synthesis of Compounds 46 and 47

3-(2-methoxy-5-(ethylthio)-4-(trifluoromethyl)phenyl)pyridine

The title compound was prepared according to the general procedure 0 starting from 3-(5-fluoro-2-methoxy-4-(trifluoromethyl)phenyl)pyridine (700 mg, 2.581 mmol). 460 mg (57%) of the title compound were prepared. $^1$H-NMR (300 MHz, CDCl$_3$) δ 8.75 (dd, J=2.3, 0.9 Hz, 1H), 8.61 (dd, J=4.8, 1.7 Hz, 1H), 7.84 (ddd, J=7.9, 2.3, 1.7 Hz, 1H), 7.51 (d, J=0.9 Hz, 1H), 7.37 (ddd, J=7.9, 4.9, 0.9 Hz, 1H), 7.28 (s, 1H), 3.87 (s, 3H), 2.93 (q, J=7.4 Hz, 2H), 1.29 (t, J=7.4 Hz, 3H). MS: m/z 314 [M+H]$^+$.

(R)-3-(2-methoxy-5-(ethylthio)-4-(trifluoromethyl)phenyl)piperidine hydrochloride (46) and (S)-3-(2-methoxy-5-(ethylthio)-4-(trifluoromethyl)phenyl)piperidine hydrochloride (47)

(R)-3-(3-methoxy-4-(trifluoromethyl)phenyl)piperidine hydrochloride (48) and (S)-3-(3-methoxy-4-(trifluoromethyl)phenyl)piperidine hydrochloride (49)

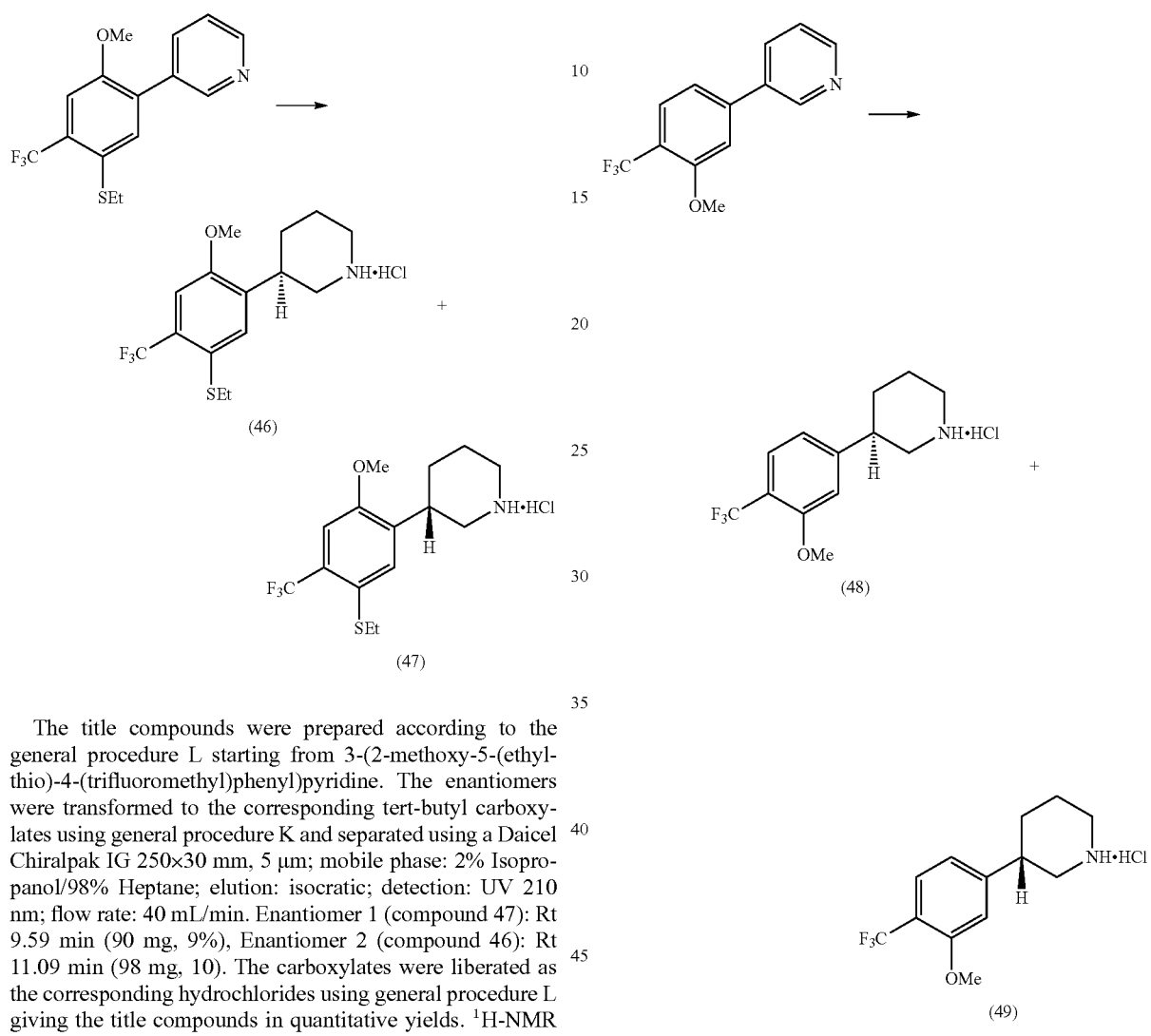

The title compounds were prepared according to the general procedure L starting from 3-(2-methoxy-5-(ethylthio)-4-(trifluoromethyl)phenyl)pyridine. The enantiomers were transformed to the corresponding tert-butyl carboxylates using general procedure K and separated using a Daicel Chiralpak IG 250×30 mm, 5 µm; mobile phase: 2% Isopropanol/98% Heptane; elution: isocratic; detection: UV 210 nm; flow rate: 40 mL/min. Enantiomer 1 (compound 47): Rt 9.59 min (90 mg, 9%), Enantiomer 2 (compound 46): Rt 11.09 min (98 mg, 10). The carboxylates were liberated as the corresponding hydrochlorides using general procedure L giving the title compounds in quantitative yields. $^1$H-NMR (400 MHz, MeOD) δ 7.46 (s, 1H), 7.20 (s, 1H), 3.86 (s, 3H), 3.44-3.36 (m, 3H), 3.10-2.98 (m, 2H), 2.88 (q, J=7.3 Hz, 2H), 2.03-2.01 (m, 1H), 1.92-1.84 (m, 3H), 1.17 (t, J=7.3 Hz, 3H). $^{13}$C-NMR (100 MHz, MeOD; one signal overlapping with CD$_3$OD) δ 157.2, 134.6, 134.5, 132.6 (q, J=29.9 Hz), 127.8, 125.0 (q, J=273.0 Hz), 110.3 (q, J=5.8 Hz), 56.5, 45.1, 35.0, 30.8, 28.8, 23.9, 14.6. MS: m/z 320 [M+H]$^+$.

Synthesis of Compounds 48 and 49

3-(3-methoxy-4-(trifluoromethyl)phenyl)pyridine

The title compound was prepared according to the general procedure F starting from 4-bromo-2-methoxy-1-(trifluoromethyl)benzene (500 mg, 1.96 mmol). 391 mg (79%) of the title compound were prepared. $^1$H-NMR (300 MHz, CDCl$_3$) δ: 8.86 (s, 1H); 8.66 (d, J=4.7 Hz, 1H); 7.90 (d, J=7.9 Hz, 1H); 7.67 (d, J=8.0 Hz, 1H); 7.43 (dd, J=7.9, 4.8 Hz, 1H); 7.20 (d, J=8.1 Hz, 1H); 7.16 (s, 1H); 3.99 (s, 3H). MS: m/z 254 [M+H]$^+$.

The title compounds were prepared according to the general procedure I starting from 3-(3-methoxy-4-(trifluoromethyl)phenyl)piperidine. The enantiomers were transformed to the corresponding tert-butyl carboxylates using general procedure K. and separated using a Daicel Chiralpak IF 250×30 mm, 5 µm; mobile phase: 2% Isopropanol/98% Heptane; elution: isocratic; detection: UV 210 nm; flow rate: 40 mL/min. Enantiomer 1 (compound 49): Rt 10.15 min (131 mg, 49%), Enantiomer 2 (compound 48): Rt 13.22 min (122 mg, 45%). The carboxylates were liberated as the corresponding hydrochlorides using general procedure L giving the titles compounds in quantitative yields. $^1$H-NMR (400 MHz, MeOD) δ 7.54 (d, J=8.0 Hz, 1H), 7.13 (s, 1H), 7.00 (d, J=8.0 Hz, 1H), 3.93 (s, 3H), 3.47-3.43 (m, 2H), 3.19 (t, J=12.1 Hz, 1H), 3.15-3.07 (m, 2H), 2.11-2.06 (m, 2H), 1.99-1.82 (m, 2H). $^{13}$C-NMR (100 MHz, MeOD; one signal overlapping with CD$_3$OD) δ 159.3, 148.9, 128.4 (q, J=5.3

Hz), 125.1 (q, J=271.3 Hz), 119.7, 118.8 (q, J=31.1 Hz), 112.5, 56.6, 45.0, 41.6, 30.6, 23.8. MS: m/z 260 [M+H]$^+$

Synthesis of Compounds 50 and 51

(R)-3-(5-fluoro-2-methoxy-4-(trifluoromethyl)phenyl)piperidine hydrochloride (50) and (S)-3-(5-fluoro-2-methoxy-4-(trifluoromethyl)phenyl)piperidine hydrochloride (51)

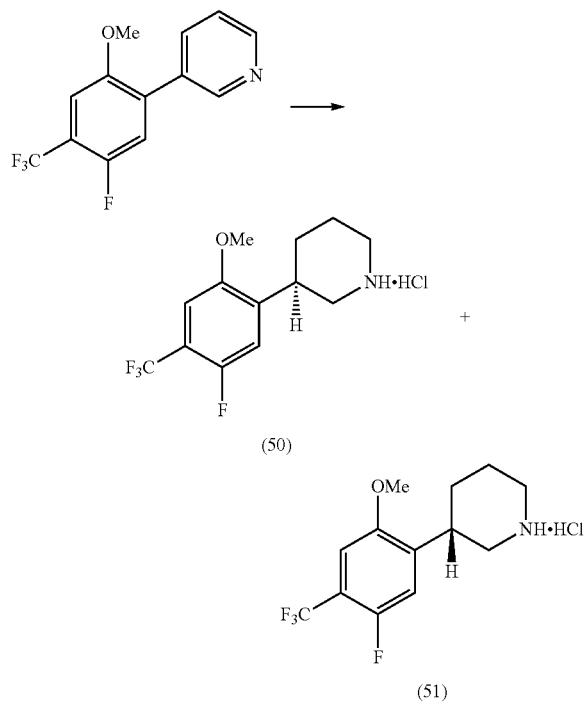

The title compounds was prepared according to the general procedure L starting from 3-(5-fluoro-2-methoxy-4-(trifluoromethyl)phenyl)piperidine. The enantiomers were transformed to the corresponding tert-butyl carboxylates using general procedure K and separated using a Daicel Chiralpak IC 250×30 mm, 5 μm; mobile phase: 2% Isopropanol/98% Heptane; elution: isocratic; detection: UV 210 nm; flow rate: 40 mL/min. Enantiomer 1 (compound 51): Rt 9.38 min (36 mg, 23% mg), Enantiomer 2 (compound 50): Rt 18.16 min (38, 20%). The carboxylates were liberated as the corresponding hydrochlorides using general procedure L giving the titles compounds in quantitative yields. $^1$H-NMR (400 MHz, MeOD) δ 7.29 (d, J=11.2 Hz, 1H), 7.21 (d, J=5.8 Hz, 1H), 3.92 (s, 3H), 3.54-3.43 (m, 3H), 3.10-3.01 (m, 2H), 2.11-2.07 (m, 1H), 2.04-1.81 (m, 3H). $^{13}$C-NMR (100 MHz, MeOD; one signal overlapping with CD$_3$OD) δ 155.2 (d, J=247.6 Hz), 154.5, 137.0 (d, J=7.4 Hz), 124.0 (q, J=271.3 Hz), 118.0 (td, J=33.1, 13.5 Hz), 117.3 (d, J=23.6 Hz), 109.7 (d, J=5.1 Hz), 56.9, 45.1, 34.9, 28.7, 23.8. MS: m/z 278 [M+H]$^+$.

Synthesis of Compounds 52 and 53

3-(2-methoxy-4-(trifluoromethyl)phenyl)pyridine

The title compound was prepared according to the general procedure F starting from 1-bromo-2-methoxy-4-(trifluoromethyl)benzene (500 mg, 1.960 mmol). 392 mg (79%) of the title compound were prepared. MS: m/z 254 [M+H]$^+$ (R)-3-(2-methoxy-4-(trifluoromethyl)phenyl)piperidine hydrochloride (52) and (S)-3-(2-methoxy-4-(trifluoromethyl)phenyl)piperidine hydrochloride (53)

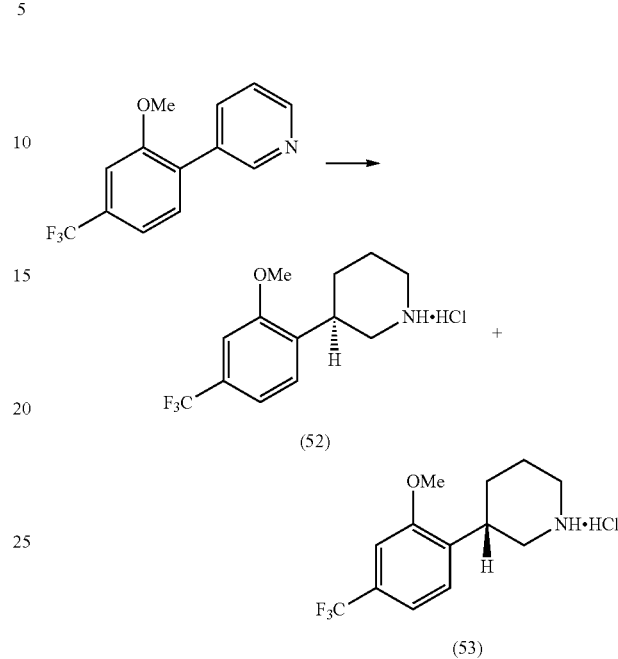

The title compounds were prepared according to the general procedure I starting from 3-(2-methoxy-4-(trifluoromethyl)phenyl)pyridine. The enantiomers were transformed to the corresponding tert-butyl carboxylates using general procedure K and separated using a Daicel Chiralpak IG 250×30 mm, 5 μm; mobile phase: 5% Isopropanol/95% Heptane; elution: isocratic; detection: UV 210 nm; flow rate: 40 mL/min. Enantiomer 1 (compound 53): Rt 9.11 min (22 mg, 31%), Enantiomer 2 (compound 52): Rt 10.31 min (19 mg, 32%). The carboxylates were liberated as the corresponding hydrochlorides using general procedure L giving the titles compounds in quantitative yields. $^1$H-NMR (400 MHz, MeOD) δ 7.44 (d, J=7.9 Hz, 1H), 7.27 (d, J=8.0 Hz, 1H), 7.24 (s, 1H), 3.94 (s, 3H), 3.54-3.42 (m, 3H), 3.12-3.02 (m, 2H), 2.12-2.05 (m, 1H), 2.01-1.88 (m, 3H). $^{13}$C-NMR (100 MHz, MeOD; one signal overlapping with CD$_3$OD) δ 158.7, 134.5, 131.8 (q, J=32.3 Hz), 128.9, 125.5 (q, J=271.4 Hz), 118.7 (q, J=4.0 Hz), 108.5 (q, J=3.7 Hz), 56.4, 45.2, 35.0, 28.9, 24.0. MS: m/z 260 [M+H]$^+$ Synthesis of Compounds 54 and 55

1-bromo-2-cyclopropoxy-5-methoxy-4-(trifluoromethyl)benzene

A flame dried microwave vial, backfilled with argon, was charged with 2-bromo-4-methoxy-5-(trifluoromethyl)phenol (1.00 g, 3.690 mmol), Cs$_2$CO$_3$ (3.606 g, 11.069 mmol), NaI (55 mg, 0.369 mmol, 0.1 eq), bromocyclopropane (1.178 mL, 1.785 g, 14.758 mmol) and dry DMF (6 mL). The reaction was heated for 10 h at 150° C. Upon completion the reaction was allowed to cool to ambient temperature and poured into sat. aq. NH$_4$Cl and extracted with EtOAc (3×20 mL). The combined organic extracts were dried over Na$_2$SO$_4$, filtered, and evaporated. The residue was purified by flash-column chromatography with the Petroleum ether/EtOAc mobile phase. 590 mg (51%) of the title compound were prepared ¹H-NMR (300 MHz, CDCl₃) δ 7.43 (s, 1H), 7.20 (s, 1H), 3.86 (s, 3H), 3.83-3.75 (m, 1H), 0.86-0.81 (m, 4H).

tert-butyl 5-(2-cyclopropoxy-5-methoxy-4-(trifluoromethyl)phenyl)-3,6-dihydropyridine-1(2H)-carboxylate A flame dried microwave vial, backfilled with argon gas, was charged with tert-butyl 5-(4,4,5,5-tetramethyl-1,3,2-dioxaborolan-2-yl)-3,6-dihydropyridine-1(2H)-carboxylate (1.173 g, 3.793 mmol), Pd(dppf)Cl₂*DCM (77 mg, 0.095 mmol, 5 mol %), K₂CO₃ (524 mg, 3.793 mmol) and 1-bromo-2-cyclopropoxy-5-methoxy-4-(trifluoromethyl)benzene (590 mg, 1.896 mmol) in the glove box and tightly sealed. Degassed H₂O (3.5 mL) and dioxane (7 mL) was added and the resulting mixture was heated using microwave irradiation at 100° C. for 16 h, then cooled to ambient temperature. The reaction mixture was filtered through a silica pad, further eluted with EtOAc and evaporated in vacuo. The residue was purified by reversed-phase flash-column chromatography with H₂O/MeOH mobile phase. 735 mg (89%) of the title compound were prepared. ¹H-NMR (300 MHz, CDCl₃) δ 7.40 (s, 1H), 6.81 (s, 1H), 5.94-5.83 (m, 1H), 4.13 (br s, 2H), 3.87 (s, 3H), 3.76-3.68 (m, 1H), 3.55 (t, J=5.8 Hz, 2H), 2.34-2.25 (m, 2H), 1.48 (s, 9H), 0.82-0.72 (m, 4H). MS: m/z 414 [M+H]⁺ tert-butyl 3-(2-cyclopropoxy-5-methoxy-4-(trifluoromethyl)phenyl)piperidine-1-carboxylate A round-bottom flask, equipped with a stir bar was charged with tert-butyl 5-(2-cyclopropoxy-5-methoxy-4-(trifluoromethyl)phenyl)-3,6-dihydropyridine-1(2H)-carboxylate (230 mg, 0.556 mmol, 1 eq) and EtOH (7 mL) then 10% Pd/C (59 mg, 0.056 mmol, 10 mol %) was added. The flask was evacuated and backfilled with H₂ 8 times, then stirred for 16 h under H₂ atmosphere. Upon completion the catalyst was filtered off and volatiles evaporated in vacuo. The residue was purified on prep. HPLC: Xbridge Peptide BEH C18 250×19 mm, 10 µm; mobile phase: H₂O/MeCN+ 0.1% AcOH; elution: gradient 20% to 80% MeCN (+0.1% AcOH), 1 h; detection: UV 210 nm; flow rate: 20 mL/min. ¹H-NMR (300 MHz, CDCl₃) δ 7.40 (s, 1H), 6.82 (s, 1H), 4.22-3.98 (m, 2H), 3.86 (s, 3H), 3.78-3.68 (m, 1H), 3.07-2.94 (m, 1H), 2.86-2.63 (m, 2H), 1.97-1.86 (m, 1H), 1.79-1.52 (m, 3H), 1.46 (s, 9H), 0.87-0.69 (m, 4H). MS: m/z 416 [M+H]⁺

(R)-3-(2-cyclopropoxy-5-methoxy-4-(trifluoromethyl)phenyl)piperidine hydrochloride (54) and (S)-3-(2-cyclopropoxy-5-methoxy-4-(trifluoromethyl)phenyl)piperidine hydrochloride (55)

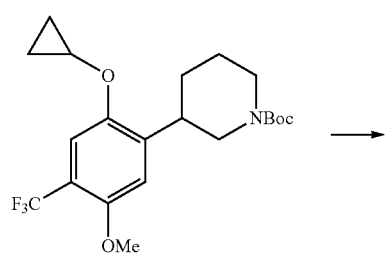

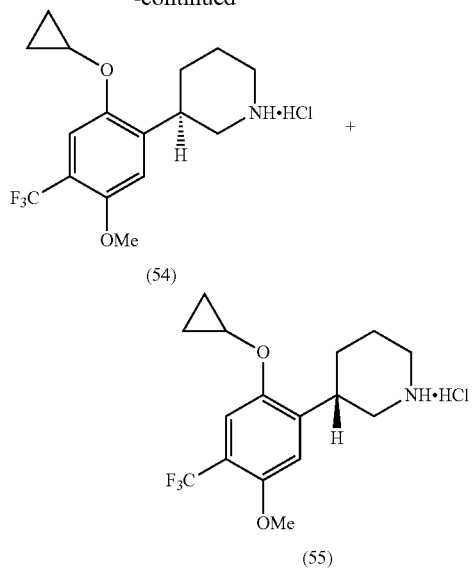

The title compound was prepared according to the general procedure L starting from tert-butyl 3-(2-cyclopropoxy-5-methoxy-4-(trifluoromethyl)phenyl)piperidine-1-carboxylate. The enantiomers were separated using a Daicel Chiralpak IF 250×30 mm, 5 µm; mobile phase: 2% Isopropanol/98% Heptane; elution: isocratic; detection: UV 210 nm; flow rate: 40 mL/min. Compound 55: Rt 7.74 min (35 mg, 53%). Compound 54: Rt 9.85 min (36 mg, 53%). The carboxylates were liberated as the corresponding hydrochlorides using general procedure L giving the titles compounds in quantitative yields. ¹H-NMR (400 MHz, MeOD) δ 7.49 (s, 1H), 7.07 (s, 1H), 3.88 (s, 3H), 3.87-3.82 (m, 1H), 3.47-3.34 (m, 3H), 3.17-3.00 (m, 2H), 2.12-2.02 (m, 1H), 1.99-1.83 (m, 3H), 0.88-0.72 (m, 4H). ¹³C NMR (100 MHz, MeOD) δ 153.4, 150.9, 135.3, 124.9 (q, J=271.6 Hz), 118.8 (q, J=31.0 Hz), 113.5, 112.4 (q, J=5.3 Hz), 57.2, 52.5, 48.7, 45.2, 35.3, 28.8, 23.9, 6.8. MS: m/z 316 [M+H]⁺

Synthesis of Compounds 56 and 57

2-bromo-5-butyl-4-methoxyphenol

The title compound was prepared according to the general procedure G starting from known 3-butyl-4-methoxyphenol (1.15 g, 6.380 mmol) 934 mg (56%) of the title compound were prepared. ¹H-NMR (400 MHz, CDCl₃) δ 6.88 (s, 1H), 6.82 (s, 1H), 3.76 (s, 3H), 2.53 (t, J=10.0 Hz, 2H), 1.58-1.47 (m, 2H), 1.34 (dd, J=15.1, 7.3 Hz, 2H), 0.91 (t, J=8.0 Hz, 3H).

1-bromo-4-butyl-2,5-dimethoxybenzene

The title compound was prepared according to the general procedure H starting from 2-bromo-5-butyl-4-methoxyphenol (934 mg, 3.604 mmol). 343 g (35%) of the title compound were prepared. ¹H-NMR (300 MHz, CDCl₃) δ 7.01 (s, 1H), 6.73 (s, 1H), 3.84 (s, 3H), 3.77 (s, 3H), 2.59-2.53 (m, 2H), 1.59-1.49 (m, 2H), 1.36 (dd, J=15.3, 7.2 Hz, 2H), 0.93 (t, J=7.3 Hz, 3H).

3-(4-butyl-2,5-dimethoxyphenyl)pyridine

The title compound was prepared according to the general procedure F starting from 1-bromo-4-butyl-2,5-dimethoxybenzene (340 mg, 1.245 mmol). 308 mg (91%) of the title compound were prepared. $^1$H-NMR (300 MHz, CDCl$_3$) δ: 8.78 (s, 1H); 8.54 (d, J=4.0 Hz, 1H); 7.92 (d, J=7.9 Hz, 1H); 7.36 (dd, J=7.9, 4.9 Hz, 1H); 6.82 (s, 1H); 6.81 (s, 1H); 3.82 (s, 3H); 3.77 (s, 3H); 2.69-2.60 (m, 2H); 1.67-1.54 (m, 2H); 1.48-1.33 (m, 2H); 0.96 (t, J=7.3 Hz, 3H). MS: m/z 272[M+H]$^+$ (R)-3-(4-butyl-2,5-dimethoxyphenyl)piperidine hydrochloride (56) and (S)-3-(4-butyl-2,5-dimethoxyphenyl)piperidine hydrochloride (57)

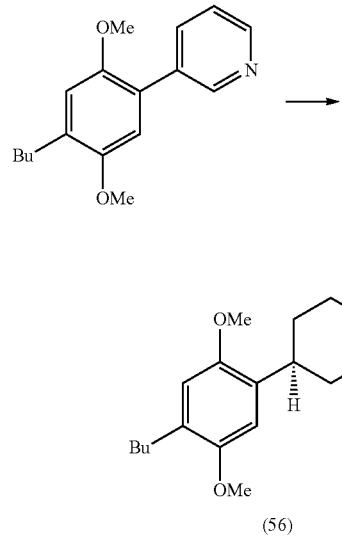

The title compound was prepared according to the general procedure L starting from tert-butyl 3-(4-butyl-2,5-dimethoxyphenyl)piperidine-1-carboxylate. The enantiomers were transformed to the corresponding tert-butyl carboxylates using general procedure K and separated using a Daicel Chiralpak IF 250×30 mm, 5 μm; mobile phase: 2% Isopropanol/98% Heptane; elution: isocratic; detection: UV 210 nm; flow rate: 40 mL/min. Enantiomer 1: Rt 8.08 min (90, 48% mg), Enantiomer 2: Rt 11.15 min (100 mg, 52%). The carboxylates were liberated as the corresponding hydrochlorides using general procedure L. giving the titles compounds in quantitative yields. $^1$H-NMR (400 MHz, MeOD) δ 6.78 (s, 2H), 3.80 (s, 3H), 3.79 (s, 3H), 3.45-3.34 (m, 3H), 3.10-2.99 (m, 2H), 2.60-2.55 (m, 2H), 2.10-2.04 (m, 1H), 1.97-1.85 (m, 2H), 1.57-1.49 (m, 2H), 1.38-1.29 (m, 2H), 0.93 (t, J=7.3 Hz, 3H). $^{13}$C-NMR (100 MHz, MeOD) δ 153.1, 152.0, 132.3, 127.7, 114.4, 111.3, 56.6, 56.5, 45.2, 35.2, 33.5, 30.9, 24.1, 23.6, 14.3. MS: m/z 278 [M+H]$^+$.

(R)-3-(2,5-dimethoxy-4-(trifluoromethyl)phenyl)-1-ethylpiperidine (58)

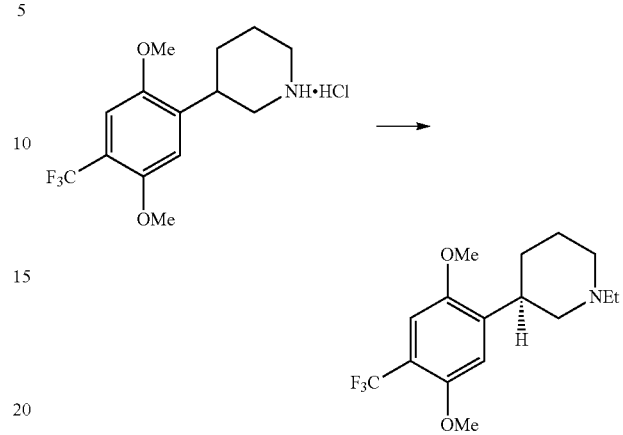

The title compound was prepared according to the general procedure M starting from 3-(2,5-dimethoxy-4-(trifluoromethyl)phenyl)piperidine hydrochloride Enantiomer 2 (60 mg, 0.184 mmol) and acetaldehyde. 54 mg (92%) of the title compound were prepared. $^1$H-NMR (400 MHz, MeOD) δ 7.16 (s, 1H), 7.10 (s, 1H), 3.89 (s, 3H), 3.87 (s, 3H), 3.68-3.52 (m, 3H), 3.23 (q, J=7.3 Hz, 2H), 3.17 (t, J=12.3 Hz, 1H), 3.01 (t, J=12.5 Hz, 1H), 2.19-2.10 (m, 1H), 2.05-1.88 (m, 3H), 1.38 (t, J=7.3 Hz, 3H). $^{13}$C-NMR (100 MHz, MeOD) δ 153.2, 151.7, 135.2, 124.9 (q, J=271.6 Hz), 118.9 (q, J=31.1 Hz), 113.8, 110.7 (q, J=5.3 Hz), 57.2, 56.8, 56.6, 53.7, 53.2, 36.0, 28.6, 24.5, 9.6. MS (m/z): 318 [M+H]$^+$.

(S)-3-(2,5-dimethoxy-4-(trifluoromethyl)phenyl)-1-ethylpiperidine (59)

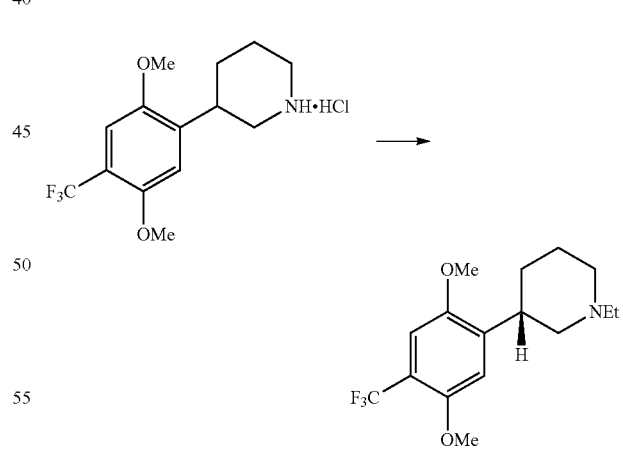

The title compound was prepared according to the general procedure M starting from 3-(2,5-dimethoxy-4-(trifluoromethyl)phenyl)piperidine hydrochloride Enantiomer 1 (60 mg, 0.184 mmol) and acetaldehyde. 57 mg (97%) of the title compound were prepared. $^1$H-NMR (400 MHz, MeOD) δ 7.16 (s, 1H), 7.10 (s, 1H), 3.89 (s, 3H), 3.87 (s, 3H), 3.67-3.52 (m, 3H), 3.23 (q, J=7.3 Hz, 2H), 3.16 (t, J=12.4 Hz, 1H), 3.01 (t, J=12.4 Hz, 1H), 2.19-2.10 (m, 1H), 2.04-1.89 (m, 3H), 1.38 (t, J=7.3 Hz, 3H). $^{13}$C-NMR (100

MHz, MeOD) δ 153.2, 151.7, 135.1, 124.9 (q, J=271.5 Hz), 118.9 (q, J=31.1 Hz), 113.8, 110.7 (q, J=5.3 Hz), 57.2, 56.8, 56.6, 53.7, 53.2, 36.0, 28.6, 24.5, 9.6. MS (m/z): 318 [M+H]$^+$.

(R)3-(2,5-dimethoxy-4-(trifluoromethyl)phenyl)-1-methylpiperidine (60)

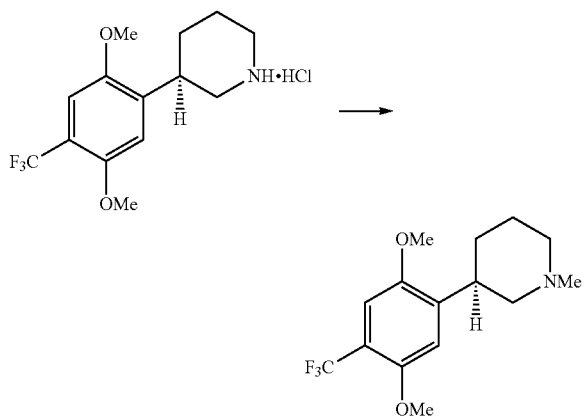

The title compound was prepared according to the general procedure M Starting from 3-(2,5-dimethoxy-4-(trifluoromethyl)phenyl)piperidine hydrochloride Enantiomer 2 (34 mg, 0.104 mmol) and formalin, 27 mg (85%) of the title compound were prepared. $^1$H-NMR (400 MHz, MeOD) δ 7.17 (s, 1H), 7.07 (s, 1H), 3.89 (s, 3H), 3.87 (s, 3H), 3.61-3.47 (m, 3H), 3.20 (t, J=12.8 Hz, 1H), 3.06 (t, J=12.3 Hz, 1H), 2.92 (s, 3H), 2.18-2.08 (m, 1H), 2.02-1.83 (m, 3H). $^{13}$C-NMR (100 MHz, MeOD) δ 153.2, 151.7, 135.0, 124.9 (q, J=271.7 Hz), 119.0 (q, J=31.1 Hz), 113.7, 110.6 (q, J=5.5 Hz), 58.7, 57.2, 56.7, 55.6, 44.3, 36.2, 28.0, 24.7. MS (m/z): 304 [M+H]$^+$.

(S)-3-(2,5-dimethoxy-4-(trifluoromethyl)phenyl)-1-methylpiperidine (61)

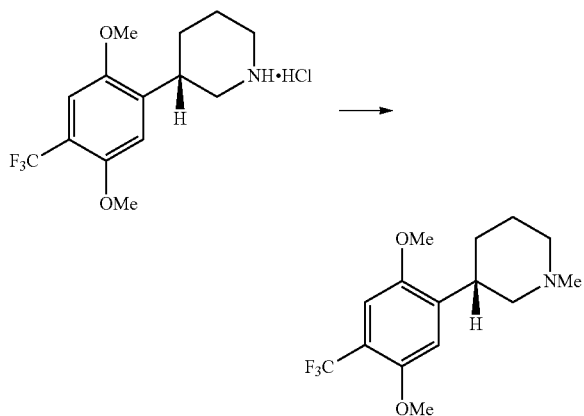

The title compound was prepared according to the general procedure M Starting from 3-(2,5-dimethoxy-4-(trifluoromethyl)phenyl)piperidine hydrochloride Enantiomer 1 (40 mg, 0.123 mmol) and formalin, 35 mg (94%) of the title compound were prepared. $^1$H-NMR (400 MHz, MeOD) δ 7.17 (s, 1H), 7.08 (s, 1H), 3.89 (s, 3H), 3.87 (s, 3H), 3.62-3.47 (m, 3H), 3.21 (t, J=12.6 Hz, 1H), 3.06 (t, J=12.0 Hz, 1H), 2.92 (s, 3H), 2.18-2.08 (m, 1H), 2.03-1.83 (m, 3H). $^{13}$C-NMR (100 MHz, MeOD) δ 153.2, 151.7, 135.0, 124.9 (q, J=271.5 Hz), 119.0 (q, J=31.0 Hz), 113.7, 110.7 (q, J=5.3 Hz), 58.7, 57.2, 56.7, 55.5, 44.3, 36.2, 28.1, 24.7. MS (m/z): 304 [M+H]$^+$.

Enantiomer Identity Elucidation

To elucidate the absolute stereochemistry of the separated enantiomers, an x-ray crystal structure of 59 and 58 was generated as example. Compound 59 (the fastest eluting enantiomer) was determined to be the (S)-enantiomer and compound 58 (the slowest eluting enantiomer) was determined to be the (R)-enantiomer. The stereochemistry of the remaining compounds was assigned based on order of elution (i.e. initial or secondary elution based on retention time).

Preparation of XRD Analysis Suitable Crystals Using Hydrochloride Salts

The substrate (20-40 mg) was dissolved in EtOAc/chloroform (1:1)(3-4 mL) in an 10 mL vial. The vial was sealed with a screw-cap with a rubber septum insert. Samples were allowed to evaporate over 72 h until the formation of prismatic crystals was observed.

Generation of the X-Ray structure of compounds 58 and 59

A suitable crystal 0.18×0.13×0.11 mm3 was selected and mounted on a suitable support and analysed using a Rigaku, XtaLAB Synergy, Dualflex, HyPix diffractometer. The crystal was kept at a steady T=150.0(1) K during data collection. The structure was solved with the help of SheIXT structure solution program[17] using the Intrinsic Phasing solution method. The model was refined with version of the program olex2.refine using Gauss-Newton minimisation[18]

Embodiments of the Invention (Items)

1. A 5-HT$_{2A}$ agonist of the general formula (III)

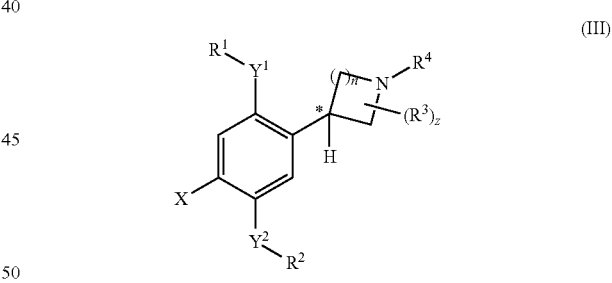

or a pharmaceutically acceptable salt thereof wherein:

X is selected from the group consisting of I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_2$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$ alkyl, $C_1$-$C_3$ fluoroalkyl, or halogen;

$R^2$ is not present when $Y^2$ is H, $C_1$-$C_3$ alkyl, $C_1$-$C_3$ fluoroalkyl, or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl, and $C_3$-$C_5$ fluorocycloalkyl;

* denotes the (R) or (S) stereoisomer or any mixture thereof if a chiral center is present;

n is an integer with a value of 1, 2, 3 or 4 to form an azetidine, pyrrolidine, piperidine or azepane ring system;

z denotes the number of $R^3$ groups and is an integer with a value of 0, 1, 2, 3 or 4 each $R^3$ is independently selected from the group consisting of F, $C_1$-$C_3$ alkyl, $C_1$-$C_3$ fluoroalkyl, $C_2$-$C_3$ alkenyl, and $C_2$-$C_3$ alkynyl;

$R^4$ is H or $CH_3$;

with the proviso that at least one of $Y^1$ or $Y^2$ is selected as O or S.

2. A 5-$HT_{2A}$/5-$HT_{2C}$ agonist according to item 1, wherein n is an integer with a value of 1, 2, 3 or 4 to form an azetidine, pyrrolidine, piperidine or azepane ring system with the proviso that when n=3, * denotes the (R) stereoisomer.

3. A selective 5-$HT_{2A}$ agonist according to item 1, wherein n is an integer with a value 3 to form a piperidine and (*) denotes the (5) stereoisomer of the general formula (II)

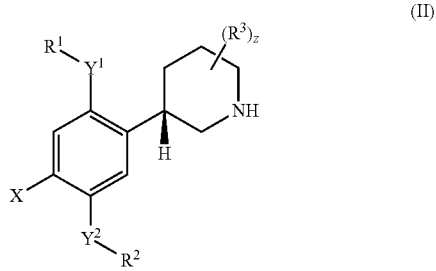

(II)

4. A 5-$HT_{2A}$ agonist according to any of the preceding items, wherein X is selected from the group consisting of I, CN, S—$CH_3$, S—$CF_3$, $C_2$-$C_3$ alkyl, $C_1$-$C_3$ fluoroalkyl, ethynyl, fluoroethynyl, and cyclopropyl, $R^1$ and $R^2$ are independently selected from the group consisting of $C_1$-$C_3$ alkyl, $C_1$-$C_3$ fluoroalkyl, and $C_3$-$C_5$ cycloalkyl; z is 0, 1, 2, or 3; and each $R^3$ is independently selected from F, $C_1$-$C_2$ alkyl, and $C_1$-$C_2$ fluoroalkyl.

5. A 5-$HT_{2A}$ agonist according to any of the preceding items, wherein X is selected from the group consisting of I, CN, S—$CH_3$, S—$CF_3$, $C_2$-$C_3$ alkyl, and $C_1$-$C_3$ fluoroalkyl.

6. A 5-$HT_{2A}$ agonist according to any of the preceding items, wherein X is selected from the group consisting of I, CN, S—$CH_3$, S—$CF_3$, $C_2$-$C_3$ alkyl, and $C_1$-$C_2$ fluoroalkyl.

7. A 5-$HT_{2A}$ agonist according to any of the preceding items, wherein X is selected from the group consisting of I, CN, S—$CH_3$, S—$CF_3$, ethyl, and $CF_3$.

8. A 5-$HT_{2A}$ agonist according to any of the preceding items, wherein X is selected from the group consisting of I, CN, and $CF_3$.

9. A 5-$HT_{2A}$ agonist according to any of the preceding items, wherein X is $CF_3$.

10. A 5-$HT_{2A}$ agonist according to any of the preceding items, wherein $Y^1$ and $Y^2$ are independently selected from the group consisting of O, S, $C_1$-$C_2$ alkyl, and $C_1$-$C_2$ fluoroalkyl.

11. A 5-$HT_{2A}$ agonist according to any of the preceding items, wherein $Y^1$ and $Y^2$ are independently selected from the group consisting of O, S, $CH_3$, and $CF_3$.

12. A 5-$HT_{2A}$ agonist according to any of the preceding items, wherein $Y^1$ and $Y^2$ are independently selected from the group consisting of 0, $CH_3$, and $CF_3$.

13. A 5-$HT_{2A}$ agonist according to any of the preceding items, wherein $Y^1$ and $Y^2$ are independently selected from the group consisting of 0 and $CH_3$.

14. A 5-$HT_{2A}$ agonist according to any of the preceding items, wherein $R^1$ and $R^2$ are independently selected from the group consisting of not present (deleted), $C_1$-$C_3$ alkyl, and $C_1$-$C_3$ fluoroalkyl.

15. A 5-$HT_{2A}$ agonist according to any of the preceding items, wherein $R^1$ and $R^2$ are independently selected from the group consisting of $C_1$-$C_3$ alkyl, $C_1$-$C_3$ and fluoroalkyl, and wherein $Y^1$ and $Y^2$ are O.

16. A 5-$HT_{2A}$ agonist according to any of the preceding items, wherein z is 0, 1, 2 or 3.

17. A 5-$HT_{2A}$ agonist according to any of the preceding items, wherein z is 0, 1 or 2.

18. A 5-$HT_{2A}$ agonist according to any of the preceding items, wherein z is 0 or 1.

19. A 5-$HT_{2A}$ agonist according to any of the preceding items, wherein z is 0.

20. A 5-$HT_{2A}$ agonist according to any of the preceding items 1-18, wherein z is 1, 2, 3, or 4, and each $R^3$ is independently selected from the group consisting of F, $CH_3$, and $CF_3$.

21. A 5-$HT_{2A}$ agonist according to any of the preceding items 1-18, wherein z is 1, 2, 3, or 4, and each $R^3$ is independently selected from F and $CH_3$.

22. A 5-$HT_{2A}$ agonist according to any of the preceding items 1-18, wherein z is 1, 2, 3, or 4, and each $R^3$ is $CH_3$.

23. A 5-$HT_{2A}$ agonist according to any of the preceding items, with a 5-$HT_{2A}$ $EC_{50}$ value below 100 nM when measured in the $Ca^{2+}$/Fluo-4 assay.

24. A method of treating a depressive disorder, comprising:

Administering an effective amount of a medicament comprising a compound of general formula (III) or a pharmaceutically acceptable salt thereof to a subject in need thereof; Wherein general formula (III) has the structure,

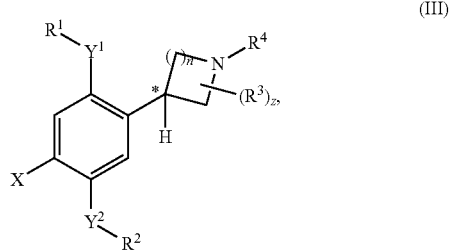

(III)

wherein:

X is selected from the group consisting of F, Cl, Br, I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;

$Y^1$ and $Y^2$ are independently selected from the group consisting of H, O, S, $C_1$-$C_3$ alkyl, $C_1$-$C_3$ fluoroalkyl, and halogen;

$R^1$ is not present when $Y^1$ is H, $C_1$-$C_3$, alkyl, $C_1$-$C_3$ fluoroalkyl or halogen;

$R^2$ is not present when $Y^2$ is H, $C_1$-$C_3$, alkyl, $C_1$-$C_3$ fluoroalkyl or halogen;

when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl, and $C_3$-$C_5$ fluorocycloalkyl;

* denotes the (R) or (S) stereoisomer or any mixture thereof if a chiral center is present;

n is an integer with a value of 1, 2, 3 or 4 to form an azetidine, pyrrolidine, piperidine or azepane ring system;

z denotes the number of $R^3$ groups and is an integer with a value of 0, 1, 2, 3 or 4 each $R^3$ is independently selected from the group consisting of F, $C_1$-$C_3$ alkyl, $C_1$-$C_3$ fluoroalkyl, $C_2$-$C_3$ alkenyl, and $C_2$-$C_3$ alkynyl;

$R^4$ is H or $CH_3$;

with the proviso that at least one of $Y^1$ or $Y^2$ is selected as O or S.

25. A method according to item 24, wherein n is an integer with a value of 1, 2 or 4 to form an azetidine, pyrrolidine or azepane ring system.

26. A method according to item 24, wherein n is an integer with a value 3 to form a piperidine and (*) denotes the (5) stereoisomer of the general formula (II)

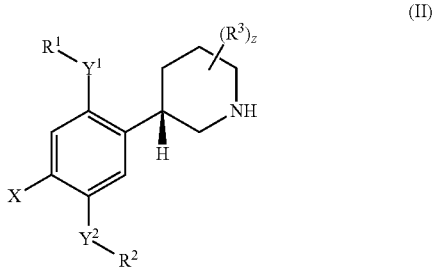

(II)

27. A method according to any of the items 24-26, wherein X is selected from the group consisting of F, Cl, Br, I, CN, S—$CH_3$, S—$CF_3$, $C_1$-$C_3$ alkyl, $C_1$-$C_3$ fluoroalkyl, ethynyl, fluoroethynyl, and cyclopropyl; $R^1$ and $R^2$ are independently selected from the group consisting of $C_1$-$C_3$ alkyl, $C_1$-$C_3$ fluoroalkyl, and $C_3$-$C_5$ cycloalkyl; z is 0, 1 or 2; and each $R^3$ is independently selected from the group consisting of F, $C_1$-$C_2$ alkyl, and $C_1$-$C_2$ fluoroalkyl.

28. A method according to any of the items 24-27, wherein X is selected from the group consisting of F, Cl, Br, I, $CF_3$, CN, S—$CH_3$, S—$CF_3$, $C_1$-$C_3$ alkyl, and $C_2$-$C_3$ fluoroalkyl.

29. A method according to any of the items 24-28, wherein X is selected from the group consisting of F, Cl, Br, I, CN, S—$CH_3$, S—$CF_3$, $C_2$-$C_3$ alkyl, and $C_1$-$C_2$ fluoroalkyl.

30. A method according to any of the items 24-29, wherein X is selected from the group consisting of Br, I, CN, S—$CH_3$, S—$CF_3$, $CH_3$, and $CF_3$.

31. A method according to any of the items 24-30, wherein X is selected from the group consisting of Br, I, and $CF_3$.

32. A method according to any of the items 24-31, wherein X is $CF_3$.

33. A method according to any of the items 24-32, wherein $Y^1$ and $Y^2$ are independently selected from the group consisting of O, S, $C_1$-$C_2$ alkyl, and $C_1$-$C_2$ fluoroalkyl.

34. A method according to any of the items 24-33, wherein $Y^1$ and $Y^2$ are independently selected from the group consisting of O, S, $CH_3$, and $CF_3$.

35. A method according to any of the items 24-34, wherein $Y^1$ and $Y^2$ are independently selected from the group consisting of 0, $CH_3$, and $CF_3$.

36. A method according to any of the items 24-35, wherein $Y^1$ and $Y^2$ are independently selected from the group consisting of 0 and $CH_3$.

37. A method according to any of the items 24-36, wherein $R^1$ and $R^2$ are independently either not present or selected from the group consisting of $C_1$-$C_3$ alkyl, and $C_1$-$C_3$ fluoroalkyl.

38. A method according to any of the items 24-37, wherein $R^1$ and $R^2$ are independently selected from the group consisting of $C_1$-$C_3$ alkyl, and $C_1$-$C_3$ fluoroalkyl; and wherein $Y^1$ and $Y^2$ are O.

39. A method according to any of the items 24-38, wherein z is 0, 1, 2 or 3.

40. A method according to any of the items 24-39, wherein z is 0, 1 or 2.

41. A method according to any of the items 24-40, wherein z is 0 or 1.

42. A method according to any of the items 24-41, wherein z is 0.

43. A method according to any of the items 24-41, wherein z is 1, 2, 3, or 4, and each $R^3$ is independently selected from the group consisting of F, $CH_3$, and $CF_3$.

44. A method according to any of the items 24-41, wherein z is 1, 2, 3, or 4, and each $R^3$ is independently selected from the group consisting of F and $CH_3$.

45. A method according to any of the items 24-41, wherein z is 1, 2, 3, or 4, and $R^3$ is $CH_3$.

46. A method according to any of the items 24-41, wherein the compound of general formula (III) or general formula (II) has a 5-$HT_{2A}$ $EC_{50}$ value below 100 nM when measured in the $Ca^{2+}$/Fluo-4 assay.

47. A method according to any of the items 24-46, in the treatment of depressive disorder.

48. A method according to any of the items 24-47, wherein the depressive disorder is MDD.

49. A method according to any of the items 24-48, wherein the depressive disorder is treatment-resistant depression.

50. A method according to any of the items 24-49, wherein the medicament is administered at a regular interval in a dose range of 0.1 mg to 500 mg.

51. A method according to any of the items 24-50, the regular interval is selected from the group consisting of daily, weekly, biweekly, and monthly.

52. A pharmaceutical composition comprising a compound according to any of the preceding items, a pharmaceutical acceptable carrier and optionally one or more excipients.

The invention claimed is:

1. A method of treating major depressive disorder (MDD) (also known as clinical depression, unipolar depression), melancholia, psychotic depression, antenatal depression, postnatal depression, bipolar disorder, bipolar type I disorder, bipolar type II disorder, cyclothymic disorder, dysthymic disorder or seasonal affective disorder, treatment-resistant depression disorder (TRD), severe treatment-resistant depression disorder, Alzheimer's disease, Parkinson's disease, autism, general anxiety, existential anxiety, end of life anxiety, terminal cancer related end of life anxiety, epilepsy, sleep-wake disorders, neurocognitive disorders, obsessive compulsive disorder (OCD), attention deficit disorder (ADD), attention deficit hyperactivity disorder (ADHD), post-traumatic stress disorder (PTSD), stress, acute stress disorder, Horton's headache, chronic cluster headache, migraine, general local inflammation, muscle inflammation, joint inflammation, pulmonary inflammation, asthma, arthritis, smoking cessation, alcohol cessation, cocaine cessation, heroin cessation, opioid cessation, methamphetamine cessation, general addiction therapy, eating disorders such as compulsive eating disorders, anorexia nervosa, bulimia nervosa, binge eating disorder, Pica, Rumination disorder, avoidant/restrictive food intake disorder, night eating syndrome, other specified feeding or eating disorder (OSFED), body dysmorphic disorder, purging disorder, pain, chronic pain disorders, sleep wake disorders or physical rehabilitation comprising:

administering an effective amount of a pharmaceutical composition comprising a compound of formula (I) or a pharmaceutically acceptable salt thereof to a subject in need thereof;

wherein formula (I) has the structure,

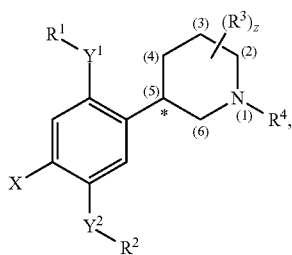

(I)

wherein:
* denotes the (R) or (S) stereoisomer or any mixture thereof;
X is selected from the group consisting of F, Cl, Br, I, CN, S—($C_1$-$C_5$ alkyl), S—($C_1$-$C_5$ fluoroalkyl), S—($C_2$-$C_5$ alkenyl), S—($C_2$-$C_5$ fluoroalkenyl), S—($C_2$-$C_5$ alkynyl), S—($C_2$-$C_5$ fluoroalkynyl), $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, and $C_2$-$C_5$ fluoroalkynyl;
$Y^1$ and $Y^2$ are independently selected from the group consisting of H, O, S, $C_1$-$C_3$ alkyl, $C_1$-$C_3$ fluoroalkyl, and halogen;
$R^1$ is not present when $Y^1$ is H, $C_1$-$C_3$ alkyl, $C_1$-$C_3$ fluoroalkyl, or halogen;
$R^2$ is not present when $Y^2$ is H, $C_1$-$C_3$ alkyl, $C_1$-$C_3$ fluoroalkyl, or halogen;
when present, $R^1$ and $R^2$ are independently selected from the group consisting of $C_1$-$C_5$ alkyl, $C_1$-$C_5$ fluoroalkyl, $C_2$-$C_5$ alkenyl, $C_2$-$C_5$ fluoroalkenyl, $C_2$-$C_5$ alkynyl, $C_2$-$C_5$ fluoroalkynyl, $C_3$-$C_5$ cycloalkyl, and $C_3$-$C_5$ fluorocycloalkyl;
z denotes the number of $R^3$ groups and is an integer with a value of 0, 1, 2, or 3;
each $R^3$ is independently selected from the group consisting of F, $C_1$-$C_3$ alkyl, $C_1$-$C_3$ fluoroalkyl, $C_2$-$C_3$ alkenyl, and $C_1$-$C_3$ alkynyl; and $R^4$ is H or $CH_3$;
with the proviso that at least one of $Y^1$ or $Y^2$ is selected as O or S.

2. The method of claim 1, wherein X is selected from the group consisting of F, Cl, Br, I, CN, S—($C_1$-$C_3$ alkyl), S—($C_1$-$C_3$ fluoroalkyl), $C_1$-$C_4$ alkyl, $C_1$-$C_4$ fluoroalkyl, ethynyl, fluoroethynyl, and cyclopropyl.

3. The method of claim 1, wherein X is selected from the group consisting of F, Cl, Br, I, CN, S—($C_1$-$C_3$ alkyl), S—($C_1$-$C_3$ fluoroalkyl), $C_1$-$C_4$ alkyl, and $C_1$-$C_4$ fluoroalkyl, preferably $CF_3$.

4. The method of claim 1, wherein $Y^1$ and $Y^2$ are independently selected from the group consisting of H, O, S, halogen, and $CH_3$.

5. The method of claim 1, wherein $Y^1$ and $Y^2$ are independently selected from the group consisting of O, S, and H.

6. The method of claim 1, wherein $Y^1$ and $Y^2$ are independently selected from O or S.

7. The method of claim 1, wherein $R^1$ and $R^2$ are independently not present or are independently selected from the group consisting of $C_1$-$C_3$ alkyl, $C_1$-$C_3$ fluoroalkyl, and $C_3$-$C_5$ cycloalkyl.

8. The method of claim 1, wherein $R^1$ and $R^2$ are selected from the group consisting of $C_1$-$C_2$ alkyl, $C_1$-$C_2$ fluoroalkyl and cyclopropyl.

9. The method of claim 1, wherein z is 0 or 1, and $R^3$ is selected from the group consisting of F, $C_1$-$C_2$ alkyl, and $C_1$-$C_2$ fluoroalkyl.

10. The method of claim 1, wherein z is 0 or 1, and $R^3$ is independently selected from the group consisting of F, $CH_3$, and $CF_3$.

11. The method of claim 1, wherein * denotes (S) and $R^4$ is H.

12. The method of claim 1, wherein the one or more $R^3$ groups are present at position 2, 3 or 6 in the piperidine.

13. The method of claim 1, wherein the compound of formula (I) or a pharmaceutically acceptable salt thereof is administered in order to treat a depressive disorder selected from a list consisting of major depressive disorder (MDD) (also known as clinical depression, unipolar depression), melancholia, psychotic depression, antenatal depression, postnatal depression, bipolar disorder, bipolar type I disorder, bipolar type II disorder, cyclothymic disorder, dysthymic disorder or seasonal affective disorder, treatment-resistant depression disorder (TRD) and severe treatment-resistant depression disorder.

14. The method of claim 13, wherein the depressive disorder is major depressive disorder (also known as clinical depression, unipolar depression).

15. The method of claim 13, wherein the depressive disorder is treatment-resistant depression disorder (TRD).

* * * * *

UNITED STATES PATENT AND TRADEMARK OFFICE
CERTIFICATE OF CORRECTION

| | | |
|---|---|---|
| PATENT NO. | : 11,633,390 B2 | Page 1 of 1 |
| APPLICATION NO. | : 17/349255 | |
| DATED | : April 25, 2023 | |
| INVENTOR(S) | : Jesper Langgaard Kristensen et al. | |

It is certified that error appears in the above-identified patent and that said Letters Patent is hereby corrected as shown below:

On the Title Page

Under (71) Applicant, please replace Applicant's city:
From: Copenhagen (DK)
To: Charlottenlund (DK)

Signed and Sealed this
Twenty-second Day of August, 2023

Katherine Kelly Vidal
*Director of the United States Patent and Trademark Office*